US010752611B2

(12) United States Patent
Qiu et al.

(10) Patent No.: US 10,752,611 B2
(45) **Date of Patent: *Aug. 25, 2020**

(54) BENZIMIDAZOLE DERIVATIVES

(71) Applicant: Enanta Pharmaceuticals, Inc., Watertown, MA (US)

(72) Inventors: Yao-Ling Qiu, Andover, MA (US); Ce Wang, Beijing (CN); Xiaowen Peng, Sudbury, MA (US); Lu Ying, Shanghai (CN); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/007,194

(22) Filed: Jun. 13, 2018

(65) Prior Publication Data

US 2020/0002314 A1 Jan. 2, 2020

Related U.S. Application Data

(63) Continuation of application No. 15/339,000, filed on Oct. 31, 2016, now Pat. No. 10,017,499, which is a continuation of application No. 14/155,653, filed on Jan. 15, 2014, now abandoned, which is a continuation of application No. 13/252,924, filed on Oct. 4, 2011, now Pat. No. 8,673,954, which is a continuation-in-part of application No. 12/714,583, filed on Mar. 1, 2010, now Pat. No. 8,101,643.

(60) Provisional application No. 61/156,131, filed on Feb. 27, 2009.

(51) Int. Cl.

| | |
|---|---|
| ***C07D 403/10*** | (2006.01) |
| ***C07D 401/14*** | (2006.01) |
| ***C07D 403/14*** | (2006.01) |
| ***C07D 405/14*** | (2006.01) |
| ***C07D 409/14*** | (2006.01) |
| ***C07D 413/14*** | (2006.01) |
| ***C07D 417/14*** | (2006.01) |
| ***C07D 487/08*** | (2006.01) |
| ***C07F 9/6558*** | (2006.01) |
| ***C07F 7/18*** | (2006.01) |

(52) U.S. Cl.

CPC ......... *C07D 403/10* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 487/08* (2013.01); *C07F 7/1804* (2013.01); *C07F 9/65583* (2013.01)

(58) Field of Classification Search

None

See application file for complete search history.

(56) References Cited

U.S. PATENT DOCUMENTS

| | | | |
|---|---|---|---|
| 8,101,643 | B2 | 1/2012 | Qiu et al. |
| 8,673,954 | B2 | 3/2014 | Ying et al. |
| 8,778,938 | B2 | 7/2014 | Qiu et al. |
| 10,017,499 | B2 | 7/2018 | Qiu et al. |
| 2005/0153877 | A1 | 7/2005 | Miao et al. |
| 2007/0197558 | A1 | 8/2007 | Betebenner et al. |
| 2007/0244148 | A1 | 10/2007 | Bondy et al. |
| 2008/0044379 | A1 | 2/2008 | Bachand et al. |
| 2009/0004140 | A1 | 1/2009 | Qiu et al. |
| 2009/0047247 | A1 | 2/2009 | Qiu et al. |
| 2009/0068140 | A1 | 3/2009 | Bachand et al. |
| 2009/0104149 | A1 | 4/2009 | Lin et al. |
| 2010/0041591 | A1 | 2/2010 | Niu et al. |
| 2010/0081658 | A1 | 4/2010 | Chin et al. |
| 2010/0158860 | A1 | 6/2010 | Steiner et al. |
| 2010/0226879 | A1 | 9/2010 | Abbot et al. |

(Continued)

FOREIGN PATENT DOCUMENTS

| | | | |
|---|---|---|---|
| WO | 2006133326 | A1 | 12/2006 |
| WO | 2007128086 | A2 | 11/2007 |

(Continued)

OTHER PUBLICATIONS

Tellinghuisen, T. L. et al., "Structure of the zinc-binding domain of an essential component of the hepatitis C virus replicase", Nature Letters, 435, May 2005, 374-479.

*Primary Examiner* — Kamal A Saeed

(74) *Attorney, Agent, or Firm* — Elmore Patent Law Group, P.C.; Carolyn Elmore; Edgar Harlan

(57) ABSTRACT

The present invention discloses compounds of Formula (I), or pharmaceutically acceptable salts, esters, or prodrugs thereof:

(I)

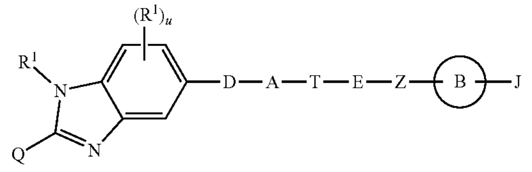

which inhibit RNA-containing virus, particularly the hepatitis C virus (HCV). Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

7 Claims, No Drawings

(56) References Cited

U.S. PATENT DOCUMENTS

| | | | |
|---|---|---|---|
| 2010/0226882 | A1 | 9/2010 | Or et al. |
| 2010/0233122 | A1 | 9/2010 | Qiu et al. |
| 2010/0260715 | A1 | 10/2010 | Or et al. |
| 2010/0316607 | A1 | 12/2010 | Or et al. |
| 2011/0070189 | A1 | 3/2011 | Li et al. |
| 2011/0217261 | A1 | 9/2011 | Or et al. |
| 2014/0193363 | A1 | 7/2014 | Qiu et al. |
| 2014/0341851 | A1 | 11/2014 | Qiu et al. |

FOREIGN PATENT DOCUMENTS

| | | | |
|---|---|---|---|
| WO | 2008021927 | A2 | 2/2008 |
| WO | 2009/079353 | A1 | 6/2009 |
| WO | 2010/132810 | A1 | 11/2010 |
| WO | 2011/002808 | A1 | 1/2011 |
| WO | 2011/153396 | A1 | 12/2011 |
| WO | 2013/059281 | A1 | 4/2013 |

BENZIMIDAZOLE DERIVATIVES

RELATED APPLICATIONS

This application is a continuation application of U.S. application Ser. No. 15/339,000, filed Oct. 31, 2016, which is a continuation application of U.S. application Ser. No. 14/155,653, filed on Jan. 15, 2014, now abandoned, which is a continuation of U.S. application Ser. No. 13/252,924, filed Oct. 4, 2011, now U.S. Pat. No. 8,673,954, issued Mar. 18, 2014, which is a continuation-in-part of U.S. application Ser. No. 12/714,583, filed Mar. 1, 2010, now U.S. Pat. No. 8,101,643, issued Jan. 24, 2012, which claims the benefit of U.S. Provisional Application No. 61/156,131 filed Feb. 27, 2009. The entire teachings of the above applications are incorporated herein by reference.

TECHNICAL FIELD

The present invention relates to novel antiviral agents. More specifically, the present invention relates to compounds which can inhibit the function of the NSSA protein encoded by Hepatitis C virus (HCV), compositions comprising such compounds, methods for inhibiting HCV viral replication, methods for treating or preventing HCV infection, and processes for making the compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

Due to the high degree of variability in the viral surface antigens, existence of multiple viral genotypes, and demonstrated specificity of immunity, the development of a successful vaccine in the near future is unlikely. Alpha-interferon (alone or in combination with ribavirin) has been widely used since its approval for treatment of chronic HCV infection. However, adverse side effects are commonly associated with this treatment: flu-like symptoms, leukopenia, thrombocytopenia, depression from interferon, as well as anemia induced by ribavirin (Lindsay, K. L. (1997) Hepatology 26 (suppl 1): 71S-77S). This therapy remains less effective against infections caused by HCV genotype 1 (which constitutes ~75% of all HCV infections in the developed markets) compared to infections caused by the other 5 major HCV genotypes. Unfortunately, only ~50-80% of the patients respond to this treatment (measured by a reduction in serum HCV RNA levels and normalization of liver enzymes) and, of responders, 50-70% relapse within 6 months of cessation of treatment. Recently, with the introduction of pegylated interferon (Peg-IFN), both initial and sustained response rates have improved substantially, and combination treatment of Peg-IFN with ribavirin constitutes the gold standard for therapy. However, the side effects associated with combination therapy and the impaired response in patients with genotype 1 present opportunities for improvement in the management of this disease.

First identified by molecular cloning in 1989 (Choo, Q-L et al (1989) Science 244:359-362), HCV is now widely accepted as the most common causative agent of post-transfusion non-A, non-B hepatitis (NANBH) (Kuo, G et al (1989) Science 244:362-364). Due to its genome structure and sequence homology, this virus was assigned as a new genus in the Flaviviridae family. Like the other members of the Flaviviridae, such as flaviviruses (e.g. yellow fever virus and Dengue virus types 1-4) and pestiviruses (e.g. bovine viral diarrhea virus, border disease virus, and classic swine fever virus) (Choo, Q-L et al (1989) Science 244:359-362; Miller, R. H. and R. H. Purcell (1990) Proc. Natl. Acad. Sci. USA 87:2057-2061), HCV is an enveloped virus containing a single strand RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang C Y et al 'An RNA pseudoknot is an essential structural element of the internal ribosome entry site located within the hepatitis C virus 5' noncoding region' RNA—A Publication of the RNA Society. 1(5): 526-537, 1995 July). This element is followed by a region which encodes a single long open reading frame (ORF) encoding a polypeptide of ~3000 amino acids comprising both the structural and nonstructural viral proteins.

Upon entry into the cytoplasm of the cell, this RNA is directly translated into a polypeptide of ~3000 amino acids comprising both the structural and nonstructural viral proteins. This large polypeptide is subsequently processed into the individual structural and nonstructural proteins by a combination of host and virally-encoded proteinases (Rice, C. M. (1996) in B. N. Fields, D. M. Knipe and P. M. Howley (eds) Virology 2nd Edition, p 931-960; Raven Press, N.Y.). There are three structural proteins, C, E1 and E2. The P7 protein is of unknown function and is comprised of a highly variable sequence. There are several nonstructural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease. NS5A is a membrane-anchored phosphoprotein that is observed in basally phosphorylated (56 kDa) and hyper-phosphorylated (58 kDa) forms. While its function has not fully been elucidated, NS5A is believed to be important in viral replication. The NSSB protein (591 amino acids, 65 kDa) of HCV (Behrens, S. E. et al (1996) *EMBO J.* 151 2-22) encodes an RNA-dependent RNA polymerase (RdRp) activity and contains canonical motifs present in other RNA viral polymerases. The NSSB protein is fairly well conserved both intra-typically (~95-98% amino acid (aa) identity across 1b isolates) and inter-typically (~85% aa identity between genotype 1a and 1b isolates). The essentiality of the HCV NSSB RdRp activity for the generation of infectious progeny virions has been formally proven in chimpanzees (A. A. Kolykhalov et al. (2000) *Journal of Virology,* 74(4): 2046-2051). Thus, inhibition of NSSB RdRp activity (inhibition of RNA replication) is predicted to be useful to treat HCV infection.

Following the termination codon at the end of the long ORF, there is a 3' NTR which roughly consists of three regions: an ~40 base region which is poorly conserved among various genotypes, a variable length poly(U)/polypyrimidine tract, and a highly conserved 98 base element also called the "3' X-tail" (Kolykhalov, A. et al (1996) J. Virology 70:3363-3371; Tanaka, T. et al (1995) Biochem Biophys. Res. Commun. 215744-749; Tanaka, T. et al (1996) J. Virology 70:3307-3312; Yamada, N. et al (1996) Virology 223:255-261). The 3' NTR is predicted to form a stable secondary structure which is essential for HCV growth in chimps and is believed to function in the initiation and regulation of viral RNA replication.

Compounds useful for treating HCV-infected patients are desired which selectively inhibit HCV viral replication. In particular, compounds which are effective to inhibit the function of the NSSA protein are desired. The HCV NSSA protein is described, for example, in Tan, S.-L., Katzel, M. G. *Virology* 2001, 284, 1; and in Rice, C. M. *Nature* 2005, 435, 374.

Based on the foregoing, there exists a significant need to identify compounds with the ability to inhibit HCV. A general strategy for the development of antiviral agents is to inactivate virally encoded proteins, including NSSA, that are essential for the replication of the virus. The relevant patent disclosures describing the synthesis of HCV NSSA inhibitors are: US 2009/0202478; US 2009/0202483; WO 2009/020828; WO 2009/020825; WO 2009/102318; WO 2009/102325; WO 2009/102694; WO 2008/144380; WO 2008/021927; WO 2008/021928; WO 2008/021936; WO 2006/133326; WO 2004/014852; WO 2008/070447; WO 2009/034390; WO 2006/079833; WO 2007/031791; WO 2007/070556; WO 2007/070600; WO 2008/064218; WO 2008/154601; WO 2007/082554; and WO 2008/048589; the contents of each of which are expressly incorporated by reference herein.

SUMMARY OF THE INVENTION

The present invention relates to novel antiviral compounds represented herein below, pharmaceutical compositions comprising such compounds, and methods for the treatment or prophylaxis of viral (particularly HCV) infection in a subject in need of such therapy with said compounds. Compounds of the present invention interfere with the life cycle of the hepatitis C virus and are also useful as antiviral agents.

In its principal aspect, the present invention provides a compound of Formula (I)

(I)

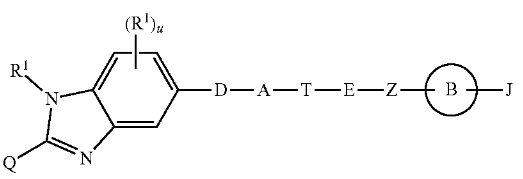

or a pharmaceutically acceptable salt thereof, wherein:

D and Z are each independently absent or optionally substituted linear aliphatic group containing zero to eight carbons;

A and E are each independently absent or a cyclic group independently selected from aryl, heteroaryl, heterocyclic, $C_3$-$C_8$ cycloalkyl, and $C_3$-$C_8$ cycloalkenyl, each optionally substituted;

T is absent or an optionally substituted aliphatic group;

Wherein one to four of A, D, E, T and Z is absent;

Ring B is a five-membered heteroaryl wherein said heteroaryl is optionally substituted; preferably, a five-membered heteroaryl containing one or more nitrogen; more preferably, imidazolyl that is C-attached to group J and one of groups Z, E, T, A and D;

$R^1$ at each occurrence is independently selected from the group consisting of hydrogen, halogen, cyano, optionally substituted $C_1$-$C_4$ alkyl, —$NR^aR^b$, —$C(O)R^{11}$, —$CO_2R^{11}$, and —$C(O)NR^aR^b$; preferably hydrogen, halogen and optionally substituted $C_1$-$C_4$ alkyl;

$R^{11}$ at each occurrence is independently hydrogen or optionally substituted $C_1$-$C_8$ alkyl;

$R^a$ and $R^b$ at each occurrence are each independently selected from the group consisting of hydrogen, optionally substituted $C_1$-$C_8$ alkyl, and optionally substituted $C_2$-$C_8$ alkenyl; or $R^a$ and $R^b$ can be taken together with the nitrogen atom to which they are attached to form an optionally substituted heterocyclic or optionally substituted heteroaryl group;

u is 1, 2, or 3;

Q and J are each independently selected from:

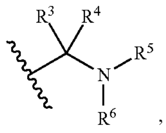
, and
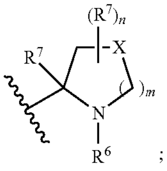
;

$R^3$ and $R^4$ at each occurrence are each independently selected from the group consisting of hydrogen, optionally substituted $C_1$-$C_8$ alkyl, optionally substituted $C_2$-$C_8$ alkenyl, and optionally substituted $C_3$-$C_8$ cycloalkyl; preferably hydrogen or optionally substituted $C_1$-$C_4$ alkyl; or alternatively, $R^3$ and $R^4$ can be taken together with the carbon atom to which they are attached to form optionally substituted $C_3$-$C_8$ cycloalkyl or optionally substituted heterocyclic;

$R^5$ at each occurrence is independently hydrogen, optionally substituted $C_1$-$C_8$ alkyl, or optionally substituted $C_3$-$C_8$ cycloalkyl; preferably hydrogen or optionally substituted $C_1$-$C_4$ alkyl;

$R^6$ at each occurrence is independently selected from the group consisting of —C(O)—$R^{12}$, —C(O)—C(O)—$R^{12}$, $S(O)_2$—$R^{12}$, and —C(S)—$R^{12}$, preferably —C(O)—$R^{12}$, more preferably an optionally substituted amino acid acyl;

$R^{12}$ at each occurrence is independently selected from the group consisting of —O—$R^{11}$, —$NR^aR^b$, —$R^{13}$, and —$NR^cR^d$, preferably optionally substituted $C_1$-$C_8$ alkyl and —O—$R^{11}$;

$R^{13}$ at each occurrence is independently selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably optionally substituted $C_1$-$C_8$ alkyl; more preferably $C_1$-$C_8$ alkyl optionally substituted with amino, hydroxy, optionally substituted phenyl, protected amino, or $O(C_1$-$C_4$ alkyl); and $R^c$ and $R^d$ at each occurrence are each independently selected from the group consisting of hydrogen, —$R^{13}$, —C(O)—$R^{13}$, —C(O)—$OR^{13}$, —$S(O)_2$—$R^{13}$, —C(O)N$(R^{13})_2$, and —$S(O)_2N(R^{13})_2$;

m is 0, 1, or 2, preferably 1;

n is 1, 2, 3, or 4, preferably 1 or 2;

X at each occurrence is independently selected from O, S, S(O), $SO_2$, and $C(R^7)_2$, preferably $CH_2$ or $CHR^7$; provided that when m is 0, X is $C(R^7)_2$; and $R^7$ at each occurrence is independently selected from the group consisting of hydrogen, halogen, cyano, —O—$R^{11}$, —$NR^aR^b$, optionally substituted aryl, optionally substituted heteroaryl, optionally substituted —$C_1$-$C_4$ alkyl; and optionally substituted $C_3$-$C_8$-cycloalkyl, preferably hydrogen, methyl, cyclopropyl or halogen; or two vicinal $R^7$ groups are taken together with the two adjacent atoms to which they are attached to form a fused, optionally substituted $C_3$-$C_8$ cycloalkyl or optionally substituted heterocyclic ring; preferably a fused, optionally substituted cyclopropyl; or alternatively two geminal $R^7$ groups are taken together with the carbon atom to which they are attached to form a spiro, optionally substituted $C_3$-$C_8$ cycloalkyl or optionally substituted heterocyclic ring; preferably a spiro, optionally substituted cyclopropyl.

Each preferred group stated above can be taken in combination with one, any or all other preferred groups.

In another aspect, the present invention provides a pharmaceutical composition comprising a therapeutically effective amount of a compound or combination of compounds of the present invention, or a pharmaceutically acceptable salt thereof, in combination with a pharmaceutically acceptable carrier or excipient.

In yet another aspect, the present invention provides a method of inhibiting the replication of a RNA-containing virus comprising contacting said virus with a therapeutically effective amount of a compound or a combination of compounds of the present invention, or a pharmaceutically acceptable salt thereof. Particularly, this invention is directed to methods of inhibiting the replication of HCV.

In still another aspect, the present invention provides a method of treating or preventing infection caused by an RNA-containing virus comprising administering to a patient in need of such treatment a therapeutically effective amount of a compound or combination of compounds of the present invention, or a pharmaceutically acceptable salt thereof. Particularly, this invention is directed to methods of treating or preventing infection caused by HCV.

Yet another aspect of the present invention provides the use of a compound or combination of compounds of the present invention, or a therapeutically acceptable salt thereof, as defined hereinafter, in the preparation of a medicament for the treatment or prevention of infection caused by RNA-containing virus, specifically HCV.

DETAILED DESCRIPTION OF THE INVENTION

The present invention relates to compounds of Formula (I) as illustrated above, or a pharmaceutically acceptable salt thereof.

The compounds of the invention have utility in inhibiting the replication of RNA-containing virus, including, for example, HCV. Other compounds useful for inhibiting the replication of RNA-containing viruses and/or for the treatment or prophylaxis of HCV infection have been described in copending U.S. application Ser. No. 12/702,673 filed Feb. 9, 2010 entitled "Linked Dibenzimidazole Antivirals"; U.S. application Ser. No. 12/702,692 filed Feb. 9, 2010 entitled "Linked Dibenzimidazole Derivatives"; U.S. application Ser. No. 12/702,802 filed Feb. 9, 2010 entitled "Linked Dibenzimidazole Derivatives"; U.S. application Ser. No. 12/707,190 filed Feb. 17, 2010 entitled "Linked Diimidazole Antivirals"; U.S. application Ser. No. 12/707,200 filed Feb. 17, 2010 entitled "Linked Diimidazole Derivatives"; U.S. application Ser. No. 12/707,210 filed Feb. 17, 2010 entitled "Hepatitis C Virus Inhibitors"; and U.S. Provisional Application Ser. No. 61/158,071 filed Mar. 6, 2009 entitled "Hepatitis C Virus Inhibitors"; the contents of each of which are expressly incorporated by reference herein.

In one embodiment, the present invention relates to compounds of Formula (Ia), or a pharmaceutically acceptable salt thereof:

(Ia)

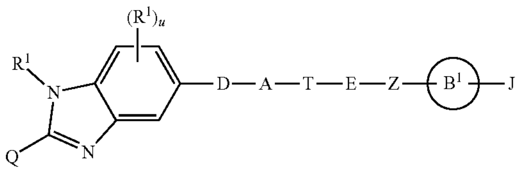

wherein A, D, E, T, Z, Q, J, u, and $R^1$ are as previously defined and Ring $B^1$ is a five-membered heteroaryl that is C-attached to J and to one Z, E, T, A and D.

In another embodiment, the present invention relates to compounds of Formula (Ib), or a pharmaceutically acceptable salt thereof:

(Ib)

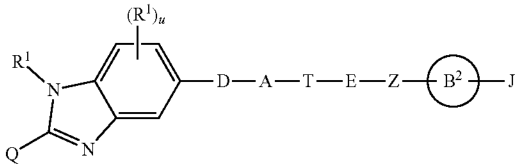

wherein A, D, E, T, Z, Q, J, u, and $R^1$ are as previously defined and Ring $B^2$ is selected from imidazolyl, pyrazolyl, triazolyl, oxadiazolyl, thiazolyl, and isoxazolyl; and $B^2$ is C-attached to J and to one Z, E, T, A and D.

In yet another embodiment, the present invention relates to compounds of Formulae (Ic-1~Ic-4), or a pharmaceutically acceptable salt thereof:

(Ic-1)

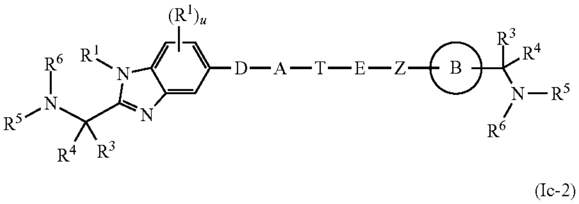

(Ic-2)

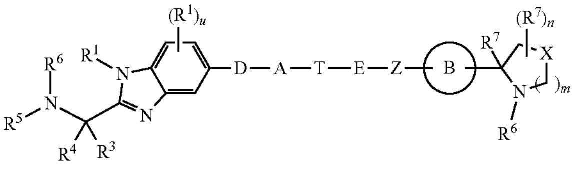

-continued (Ic-3)

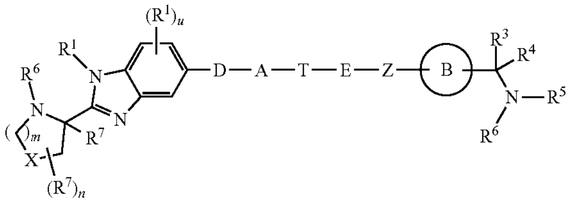

(Ic-4)

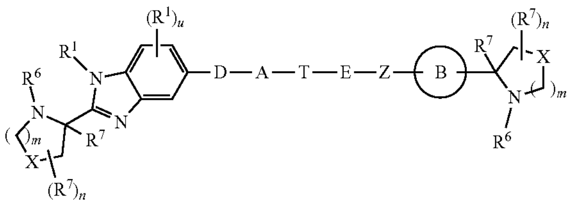

wherein A, D, E, T, Z, Ring B, X, u, m, n, $R^1$, $R^3$, $R^4$, $R^5$, $R^6$ and $R^7$ are as previously defined.

In still another embodiment, the present invention relates to compounds of Formulae (Id-1~Id-4), or a pharmaceutically acceptable salt thereof:

(Id-1)

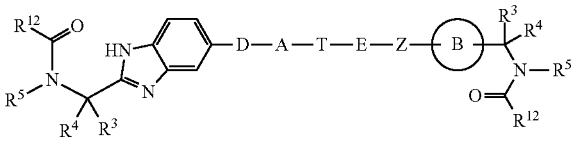

(Id-2)

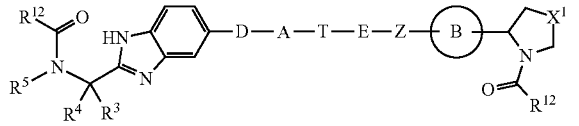

(Id-3)

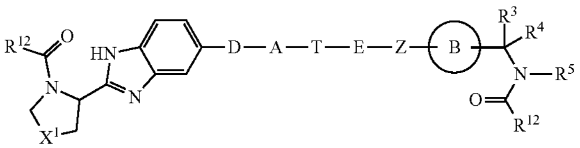

(Id-4)

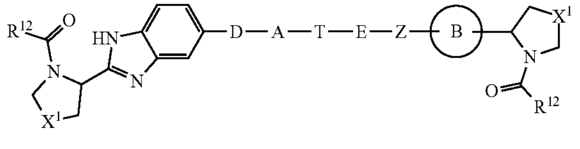

wherein A, D, E, T, Z, Ring B, $R^3$, $R^4$, $R^5$, and $R^{12}$ are as previously defined and $X^1$ is independently $CH_2$, CHF, CH(OH), or $CF_2$.

In still another embodiment of the present invention, the absolute stereochemistry of the pyrrolidine and 2-benzimidazolylmethylamine or five-membered heteroarylmethylamine moiety is represented by Formulae (Ie-1~Ie-4):

(Ie-1)

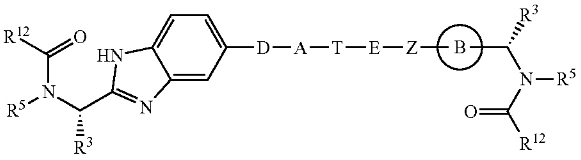

(Ie-2)

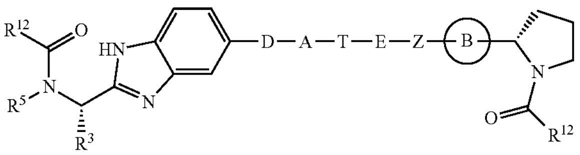

(Ie-3)

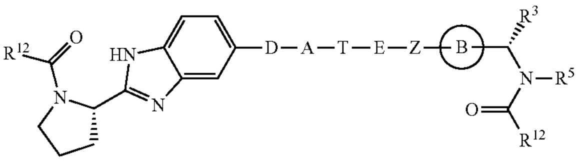

(Ie-4)

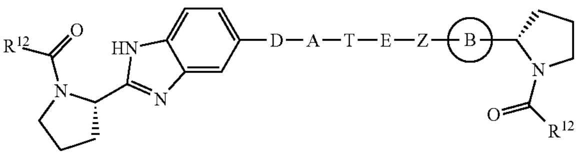

wherein A, D, E, T, Z, Ring B, $R^3$, $R^5$, and $R^{12}$ are as previously defined.

In still another embodiment, the present invention relates to compounds of Formula (If), or a pharmaceutically acceptable salt thereof:

(If)

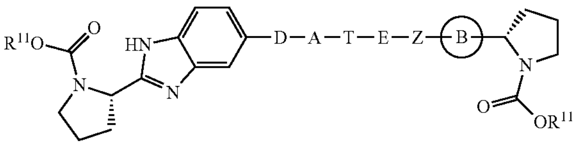

wherein A, D, E, T, Z, Ring B, and $R^{11}$ are as previously defined.

In still another embodiment, the present invention relates to compounds of Formula (Ig), or a pharmaceutically acceptable salt thereof:

(Ig)

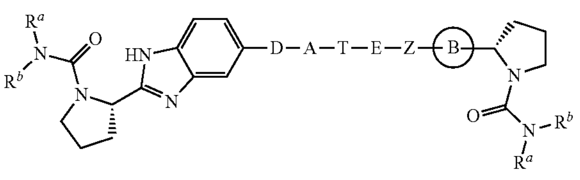

wherein A, D, E, T, Z, Ring B, $R^a$ and $R^b$ are as previously defined.

In still another embodiment, the present invention relates to compounds of Formula (Ih), or a pharmaceutically acceptable salt thereof:

(Ih)

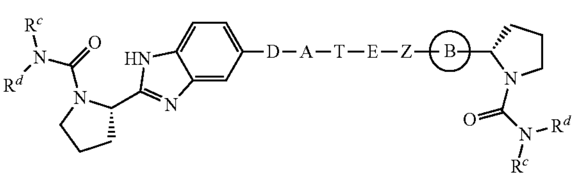

wherein A, D, E, T, Z, Ring B, $R^c$ and $R^d$ are as previously defined.

In still another embodiment, the present invention relates to compounds of Formula (Ii), or a pharmaceutically acceptable salt thereof:

(Ii)

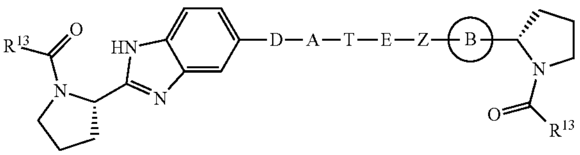

wherein A, D, E, T, Z, Ring B, and $R^{13}$ are as previously defined.

In still another embodiment, the present invention relates to compounds of Formula (Ij), or a pharmaceutically acceptable salt thereof:

(Ij)

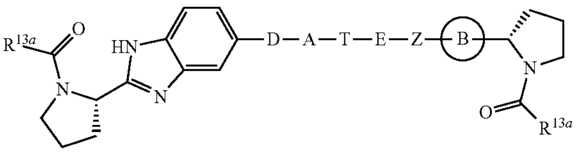

wherein A, D, E, T, Z, Ring B are as previously defined and $R^{13a}$ at each occurrence is independently an optionally substituted $C_1$-$C_8$ alkyl; preferably $C_1$-$C_8$ alkyl optionally substituted with amino, hydroxy, phenyl, protected amino, or $O(C_1$-$C_4$ alkyl); or a pharmaceutically acceptable salt thereof.

In still another embodiment, the present invention relates to compounds of Formula (IIa), or a pharmaceutically acceptable salt thereof:

(IIa)

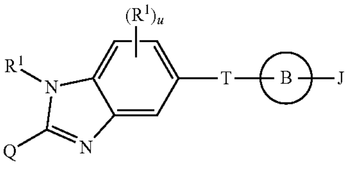

wherein Q, J, Ring B, u, and $R^1$ are as previously defined and T is present and as previously defined.

In still another embodiment, the present invention relates to compounds of Formula (IIb), or a pharmaceutically acceptable salt thereof:

(IIb)

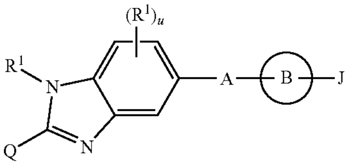

wherein Q, J, Ring B, u, and $R^1$ are as previously defined and A is present and as previously defined.

In still another embodiment, the present invention relates to compounds of Formula (IIc), or a pharmaceutically acceptable salt thereof:

(IIc)

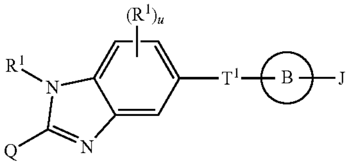

wherein Q, J, Ring B, u, and $R^1$ are as previously defined and $T^1$ is a linear aliphatic group, optionally containing one or more of an olefinic double bond and an alkynic triple bond and further, optionally comprising one or more groups selected from the group consisting of O, $N(R^{11})$, C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ and $C(O)N(R^{11})S(O)_2N(R^{11})$.

In still another embodiment, the present invention relates to compounds of Formula (IId), or a pharmaceutically acceptable salt thereof:

(IId)

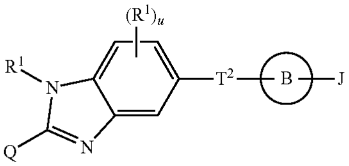

wherein Q, J, Ring B, u, and $R^1$ are as previously defined and $T^2$ is an aliphatic group comprising a $C_3$-$C_8$ cycloalkyl or $C_3$-$C_8$ cycloalkenyl and optionally contains one or more of an olefinic double bond and an alkynic triple bond and further, optionally comprises one or more groups selected from the group consisting of O, $N(R^{11})$, C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{11})C(O)C(O)N(R^{11})$, $N(R^{11})S(O)_2N(R^{11})$, $C(O)N(R^{11})S(O)_2$ and $C(O)N(R^{11})S(O)_2N(R^{11})$.

In still another embodiment, the present invention relates to compounds of Formulae (IIIa-1 and IIIa-2), or a pharmaceutically acceptable salt thereof:

(IIIa-1)

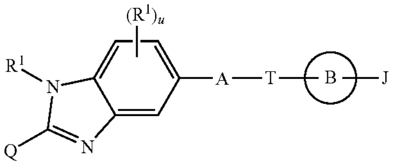

(IIIa-2)

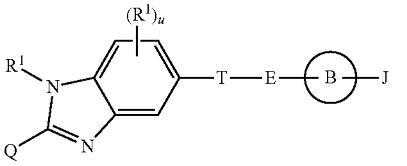

wherein Q, J, Ring B, u, and $R^1$ are as previously defined; in Formula (IIIa-1), A and T are each present and as previously defined; and in Formula (IIIa-2), T and E are each present and as previously defined.

In still another embodiment, the present invention relates to compounds of Formula (IIIa-3), or a pharmaceutically acceptable salt thereof:

(IIIa-3)

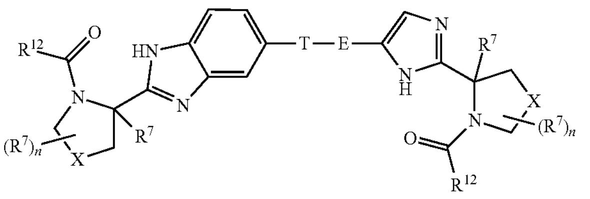

wherein n is 1 or 2; T is absent or optionally substituted $C_2$-$C_4$ alkenyl or optionally substituted $C_2$-$C_4$ alkynyl; E is phenyl, monocyclic heteroaryl, bicyclic aryl, or bicyclic heteroaryl, each optionally substituted; X at each occurrence is independently $CH_2$, CHF, CH(OH), CHMe, $CF_2$, or $C(R^7)_2$; wherein $R^7$ at each occurrence is independently hydrogen or methyl; alternatively, the two geminal $R^7$ groups are taken together with the carbon to which they are attached to form a spiro, optionally substituted $C_3$-$C_8$ cycloalkyl; or yet alternatively, two vicinal $R^7$ groups are taken together with the two adjacent atoms to which they are attached to form a fused, optionally substituted $C_3$-$C_8$ cycloalkyl; and $R^{12}$ at each occurrence is independently optionally substituted $C_1$-$C_8$ alkyl. In certain aspects, the invention is a compound of Formula (IIIa-3), wherein $R^{12}$ at each occurrence is independently $C_1$-$C_8$ alkyl substituted with —$NHCO_2$($C_1$-$C_4$ alkyl) or O($C_1$-$C_4$ alkyl).

In still another embodiment, the present invention relates to compounds of Formula (IIIa-3), or a pharmaceutically acceptable salt thereof; wherein two geminal $R^7$ groups are taken together with the carbon to which they are attached to form a spiro cyclopropyl; and $R^{12}$ at each occurrence is independently $C_1$-$C_8$ alkyl optionally substituted with amino, hydroxy, protected amino, or O($C_1$-$C_4$ alkyl).

In still another embodiment, the present invention relates to compounds of Formula (IIIa-3), or a pharmaceutically acceptable salt thereof; wherein two vicinal $R^7$ groups are taken together with the two adjacent atoms to which they are attached to form a fused cyclopropyl; and $R^{12}$ at each occurrence is independently $C_1$-$C_8$ alkyl optionally substituted with amino, hydroxy, protected amino, or O($C_1$-$C_4$ alkyl).

In still another embodiment, the present invention relates to compounds of Formula (III-a), (III-b), (III-c) or (III-d), or a pharmaceutically acceptable salt thereof:

III-a

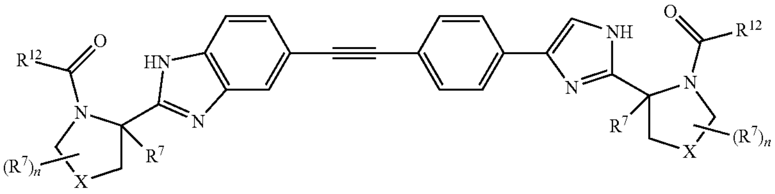

III-b

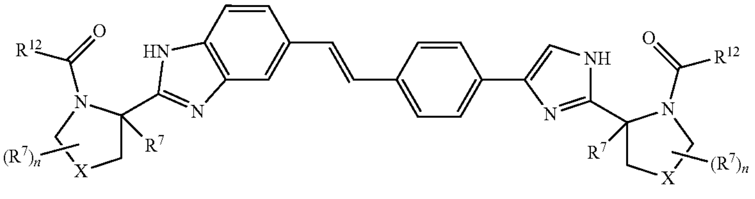

III-c

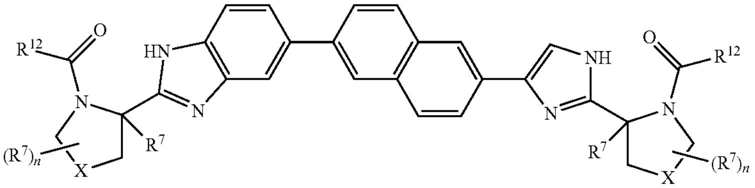

-continued

III-d

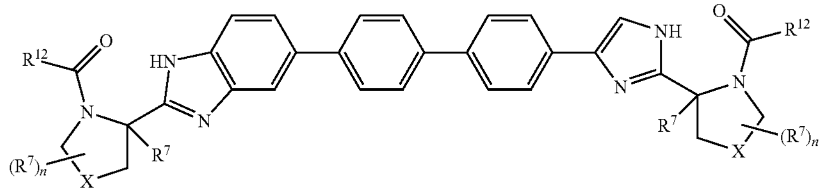

wherein n is 1 or 2; X at each occurrence is each independently $CH_2$, CHF, CH(OH), CHMe, $CF_2$, or $C(R^7)_2$; wherein $R^7$ at each occurrence is independently hydrogen or methyl; alternatively, two geminal $R^7$ groups are taken together with the carbon to which they are attached to form a spiro cyclopropyl; or yet alternatively, two vicinal $R^7$ groups can be taken together with the two adjacent atoms to which they are attached to form a fused cyclopropyl; and $R^{12}$ at each occurrence is independently $C_1$-$C_8$ alkyl optionally substituted with amino, hydroxy, protected amino, or $O(C_1$-$C_4$ alkyl).

In still another embodiment, the present invention relates to compounds of Formula (III-a), (III-b), (III-c) or (III-d); wherein $R^{12}$ at each occurrence is independently $C_1$-$C_8$ alkyl substituted with $—NHCO_2(C_1$-$C_4$ alkyl) or $O(C_1$-$C_4$ alkyl); or a pharmaceutically acceptable salt thereof.

In still another embodiment, the present invention relates to compounds of Formula (IIIb), or a pharmaceutically acceptable salt thereof:

(IIIb)

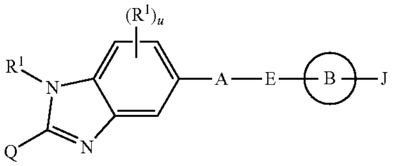

wherein Q, J, Ring B, u, and $R^1$ are as previously defined; A and E are each present and as previously defined.

In still another embodiment, the present invention relates to compounds of Formulae (IVa-1 and IVa-2), or a pharmaceutically acceptable salt thereof:

(IVa-1)

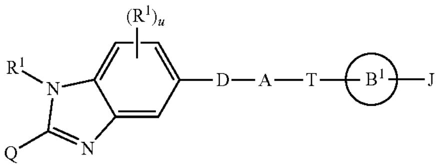

(IVa-2)

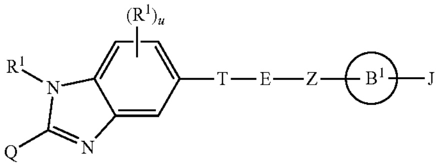

wherein Ring $B^1$, Q, J, u, and $R^1$ are as previously defined; in Formula (IVa-1), A, D, and T are each present and as previously defined; and in Formula (IVa-2), E, T, and Z are each present and as previously defined.

In still another embodiment, the present invention relates to compounds of Formula (IVb), or a pharmaceutically acceptable salt thereof:

(IVb)

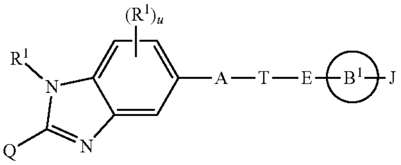

wherein Ring $B^1$, Q, J, u, and $R^1$ are as previously defined; A, E, and T are each present and as previously defined.

In still another embodiment, the present invention relates to compounds of Formulae (Va-1 and Va-2), or a pharmaceutically acceptable salt thereof:

(Va-1)

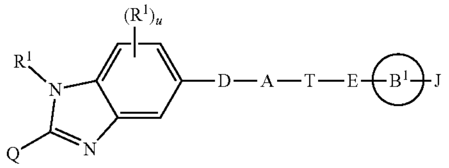

(Va-2)

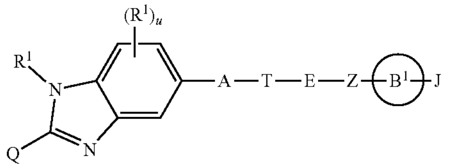

wherein Ring $B^1$, Q, J, u, and $R^1$ are as previously defined; in Formula (Va-1), D, A, T and E are each present and as previously defined; in Formula (Va-2), A, E, T, and Z are each present and as previously defined.

In still another embodiment, the present invention relates to compounds of Formula (I), or a pharmaceutically acceptable salt thereof; wherein

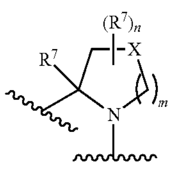

at each occurrence is independently illustrated by one of the following groups:

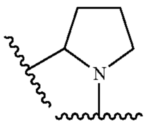
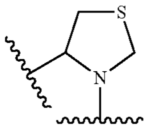
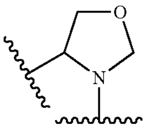
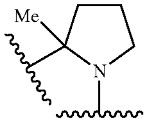
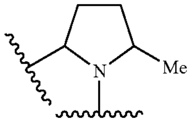
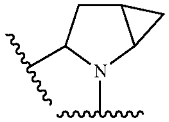
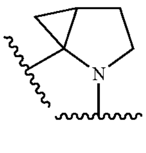
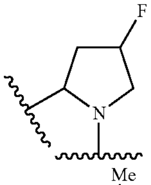
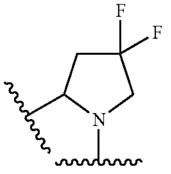
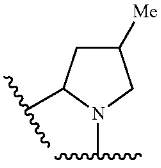
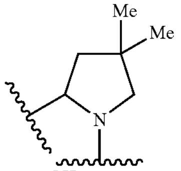
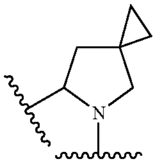
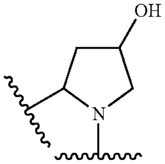
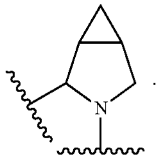
Representative compounds of the present invention are those selected from compounds 1-1, 2-1, and 2-2 (shown below), and compounds 1-545 compiled in Tables 1-9:
TABLE 1
Compounds 1-219.
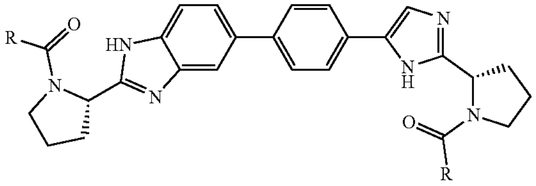
| Entry | 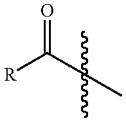 |
|---|---|
| 1 | 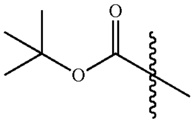 [SMILES: *C(=O)OC(C)(C)C] |
| 2 | 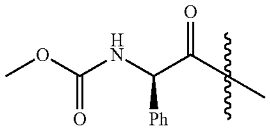 [SMILES: *C(=O)[C@H](NC(=O)OC)c1ccccc1] |
| 3 | 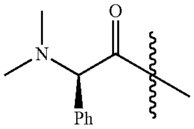 [SMILES: *C(=O)[C@@H](c1ccccc1)N(C)C] |
compound 1-1
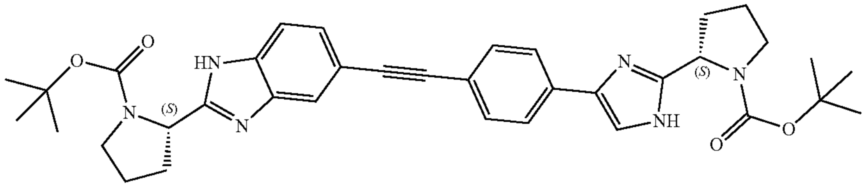
compound 2-1
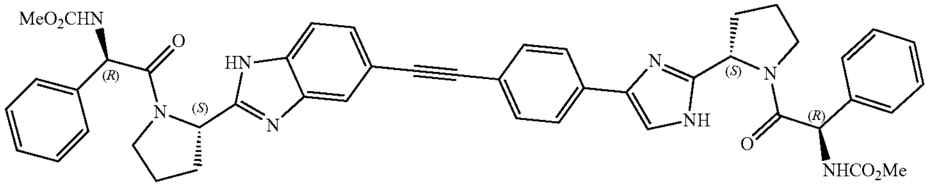
compound 2-2
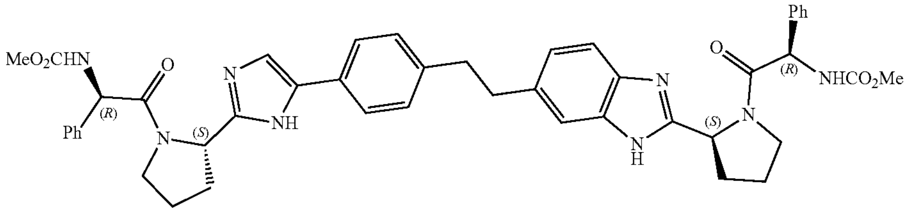

TABLE 1-continued
Compounds 1-219.
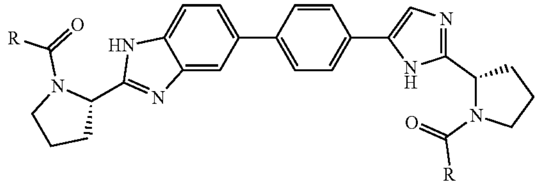
| Entry | 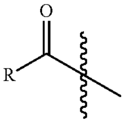 |
| --- | --- |
| 4 | 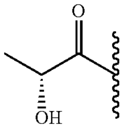 [SMILES: *C(=O)[C@@H](C)O] |
| 5 | 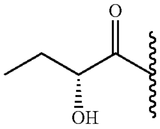 [SMILES: *C(=O)[C@H](O)CC] |
| 6 | 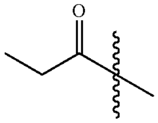 [SMILES: *C(=O)CC] |
| 7 | 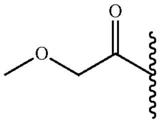 [SMILES: *C(=O)COC] |
| 8 | 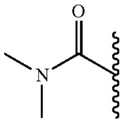 [SMILES: *C(=O)N(C)C] |
| 9 | 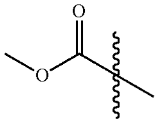 [SMILES: *C(=O)OC] |
| 10 | 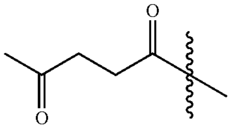 [SMILES: *C(=O)CCC(C)=O] |
| 11 | 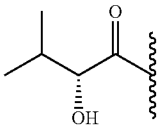 [SMILES: *C(=O)[C@H](O)C(C)C] |
TABLE 1-continued
Compounds 1-219.
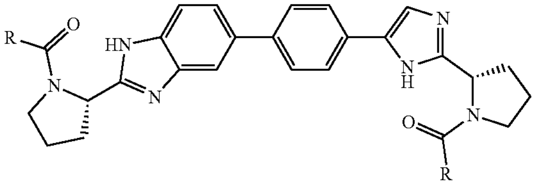
| Entry | 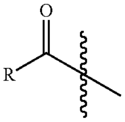 |
| --- | --- |
| 12 | 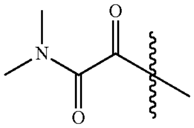 [SMILES: *C(=O)C(=O)N(C)C] |
| 13 | 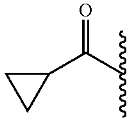 [SMILES: *C(=O)C1CC1] |
| 14 | 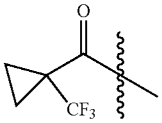 |
| 15 | 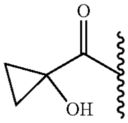 [SMILES: *C(=O)C1(O)CC1] |
| 16 | 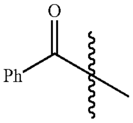 |
| 17 | 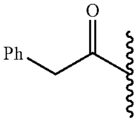 [SMILES: *C(=O)Cc1ccccc1] |
| 18 | 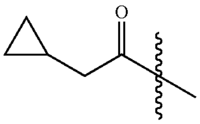 [SMILES: *C(=O)CC1CC1] |
| 19 | 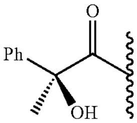 [SMILES: *C(=O)[C@@](C)(O)c1ccccc1] |
| 20 | 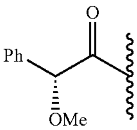 [SMILES: *C(=O)[C@H](OC)c1ccccc1] |

TABLE 1-continued
Compounds 1-219.
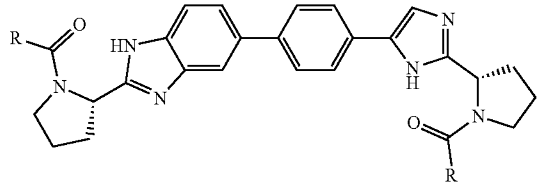
| Entry | 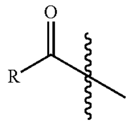 |
|---|---|
| 21 | 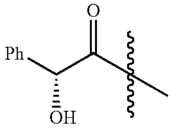 [SMILES: *C(=O)[C@H](O)c1ccccc1] |
| 22 | 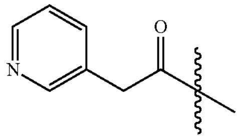 [SMILES: *C(=O)Cc1cccnc1] |
| 23 | 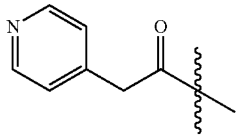 [SMILES: *C(=O)Cc1ccncc1] |
| 24 | 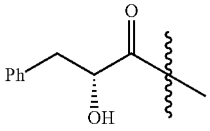 [SMILES: *C(=O)[C@H](O)Cc1ccccc1] |
| 25 | 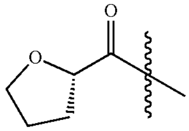 [SMILES: *C(=O)[C@@H]1CCCO1] |
| 26 | 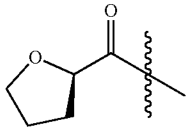 [SMILES: *C(=O)[C@H]1CCCO1] |
| 27 | 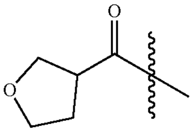 [SMILES: *C(=O)C1CCOC1] |
| 28 | 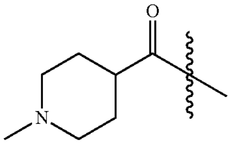 [SMILES: *C(=O)C1CCN(C)CC1] |
TABLE 1-continued
Compounds 1-219.
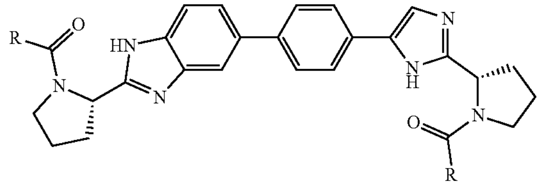
| Entry | 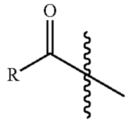 |
|---|---|
| 29 | 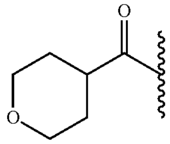 [SMILES: *C(=O)C1CCOCC1] |
| 30 | 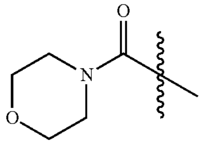 |
| 31 | 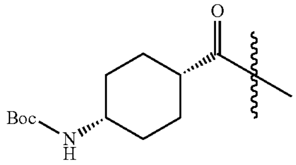 [SMILES: *C(=O)[C@H]1CC[C@@H](NC(=O)OC(C)(C)C)CC1] |
| 32 | 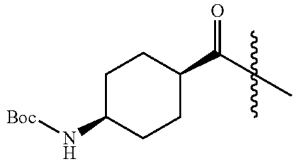 [SMILES: *C(=O)[C@H]1CC[C@@H](NC(=O)OC(C)(C)C)CC1] |
| 33 | 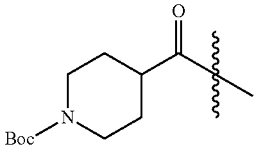 [SMILES: *C(=O)C1CCN(C(=O)OC(C)(C)C)CC1] |
| 34 | 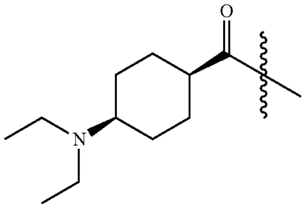 [SMILES: *C(=O)[C@H]1CC[C@@H](N(CC)CC)CC1] |
| 35 | 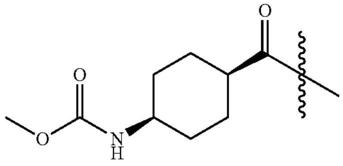 [SMILES: *C(=O)[C@H]1CC[C@@H](NC(=O)OC)CC1] |

TABLE 1-continued
Compounds 1-219.
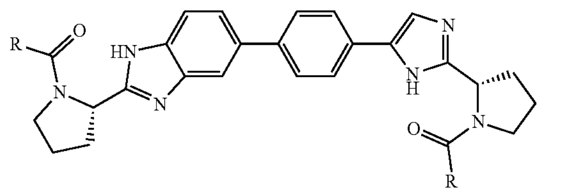
| Entry | 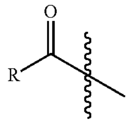 |
| --- | --- |
| 36 | 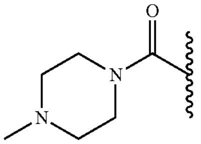 [SMILES: *C(=O)N1CCN(C)CC1] |
| 37 | 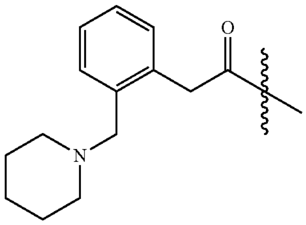 [SMILES: *C(=O)Cc1ccccc1CN1CCCCC1] |
| 38 | 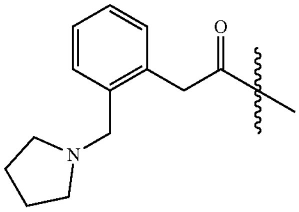 [SMILES: *C(=O)Cc1ccccc1CN1CCCC1] |
| 39 | 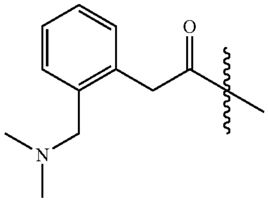 [SMILES: *C(=O)Cc1ccccc1CN(C)C] |
| 40 | 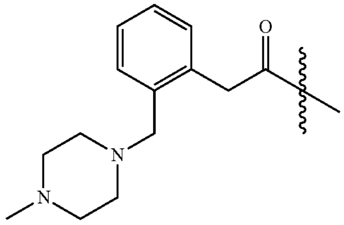 [SMILES: *C(=O)Cc1ccccc1CN1CCN(C)CC1] |
TABLE 1-continued
Compounds 1-219.
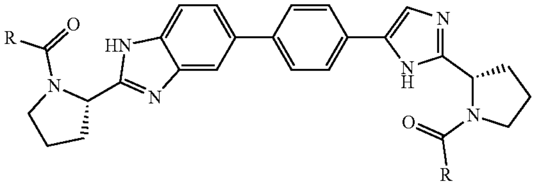
| Entry | 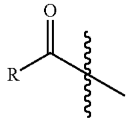 |
| --- | --- |
| 41 | 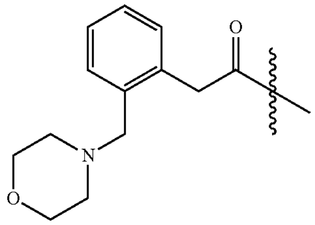 [SMILES: *C(=O)Cc1ccccc1CN1CCOCC1] |
| 42 | 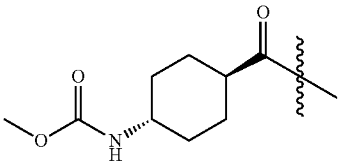 [SMILES: *C(=O)[C@H]1CC[C@H](NC(=O)OC)CC1] |
| 43 | 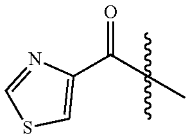 [SMILES: *C(=O)c1cscn1] |
| 44 | 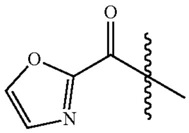 [SMILES: *C(=O)c1ncco1] |
| 45 | 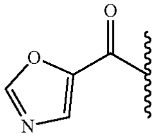 [SMILES: *C(=O)c1cnco1] |
| 46 | 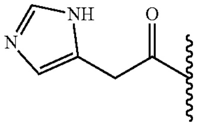 [SMILES: *C(=O)Cc1cnc[nH]1] |
| 47 | 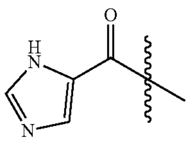 [SMILES: *C(=O)c1cnc[nH]1] |

TABLE 1-continued
Compounds 1-219.
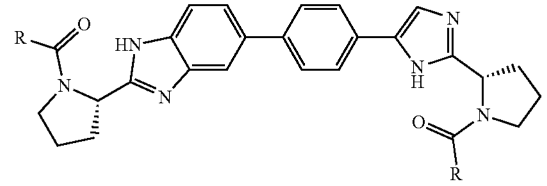
| Entry | 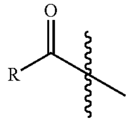 |
|---|---|
| 48 | 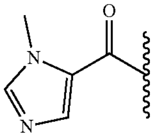 [SMILES: *C(=O)c1cncn1C] |
| 49 | 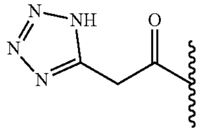 [SMILES: *C(=O)Cc1nnn[nH]1] |
| 50 | 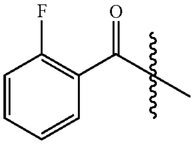 [SMILES: *C(=O)c1ccccc1F] |
| 51 | 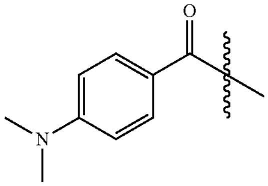 [SMILES: *C(=O)c1ccc(N(C)C)cc1] |
| 52 | 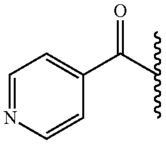 [SMILES: *C(=O)c1ccncc1] |
| 53 | 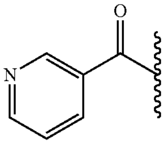 |
| 54 | 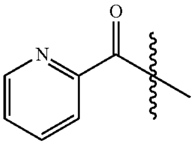 [SMILES: *C(=O)c1ccccn1] |
| 55 | 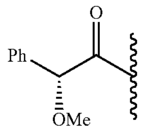 [SMILES: *C(=O)[C@H](OC)c1ccccc1] |
TABLE 1-continued
Compounds 1-219.
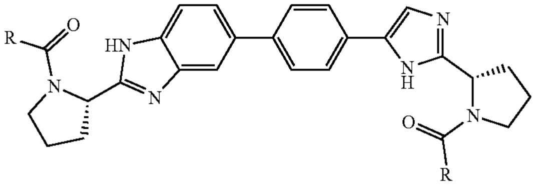
| Entry | 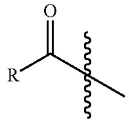 |
|---|---|
| 56 | 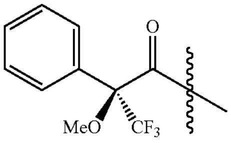 [SMILES: *C(=O)[C@@](OC)(c1ccccc1)C(F)(F)F] |
| 57 | 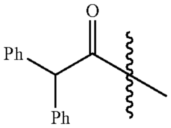 [SMILES: *C(=O)C(c1ccccc1)c1ccccc1] |
| 58 | 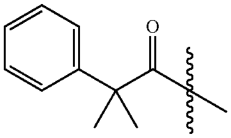 [SMILES: *C(=O)C(C)(C)c1ccccc1] |
| 59 | 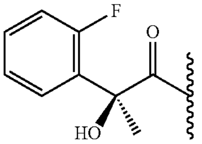 [SMILES: *C(=O)[C@@](C)(O)c1ccccc1F] |
| 60 | 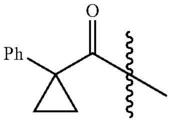 [SMILES: *C(=O)C1(c2ccccc2)CC1] |
| 61 | 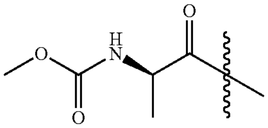 [SMILES: *C(=O)[C@@H](C)NC(=O)OC] |
| 62 | 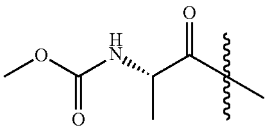 [SMILES: *C(=O)[C@H](C)NC(=O)OC] |
| 63 | 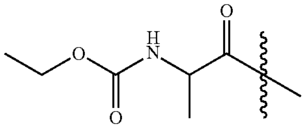 [SMILES: *C(=O)C(C)NC(=O)OCC] |

TABLE 1-continued
Compounds 1-219.
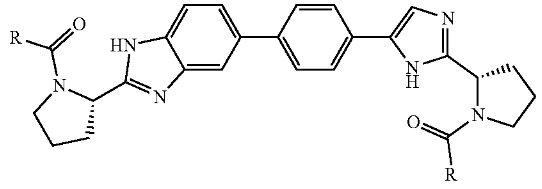
| Entry | 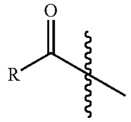 |
|---|---|
| 64 | 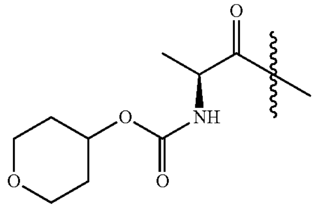 [SMILES: *C(=O)[C@H](C)NC(=O)OC1CCOCC1] |
| 65 | 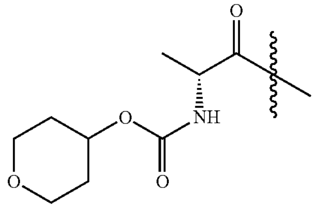 [SMILES: *C(=O)[C@@H](C)NC(=O)OC1CCOCC1] |
| 66 | 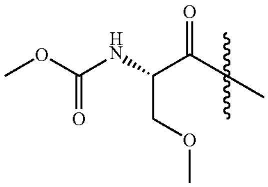 |
| 67 | 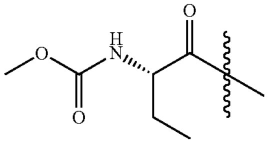 [SMILES: *C(=O)[C@H](CC)NC(=O)OC] |
| 68 | 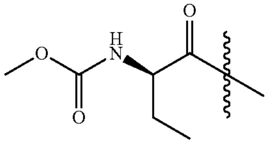 [SMILES: *C(=O)[C@@H](CC)NC(=O)OC] |
| 69 | 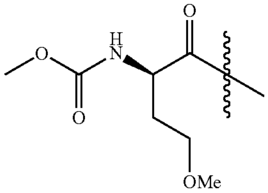 [SMILES: *C(=O)[C@@H](CCOC)NC(=O)OC] |
TABLE 1-continued
Compounds 1-219.
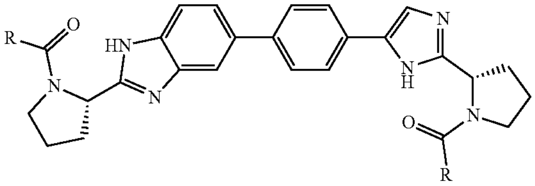
| Entry | 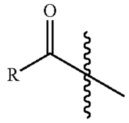 |
|---|---|
| 70 | 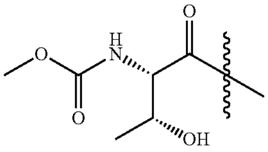 [SMILES: *C(=O)[C@@H](NC(=O)OC)[C@@H](C)O] |
| 71 | 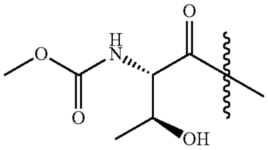 [SMILES: *C(=O)[C@@H](NC(=O)OC)[C@H](C)O] |
| 72 | 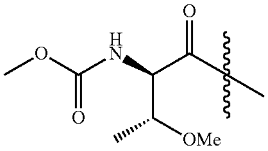 [SMILES: *C(=O)[C@H](NC(=O)OC)[C@@H](C)OC] |
| 73 | 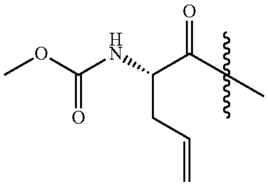 [SMILES: *C(=O)[C@H](CC=C)NC(=O)OC] |
| 74 | 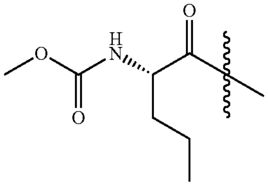 [SMILES: *C(=O)[C@H](CCC)NC(=O)OC] |
| 75 | 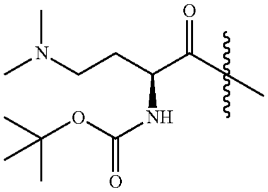 [SMILES: *C(=O)[C@H](CCN(C)C)NC(=O)OC(C)(C)C] |
| 76 | 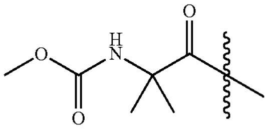 [SMILES: *C(=O)C(C)(C)NC(=O)OC] |

TABLE 1-continued
| Compounds 1-219. | |
| --- | --- |
| | 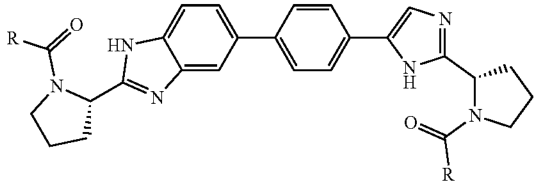 |
| Entry | 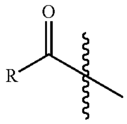 |
| 77 | 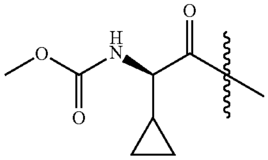 [SMILES: *C(=O)[C@H](NC(=O)OC)C1CC1] |
| 78 | 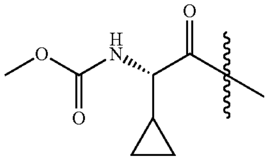 [SMILES: *C(=O)[C@@H](NC(=O)OC)C1CC1] |
| 79 | 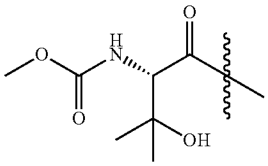 [SMILES: *C(=O)[C@@H](NC(=O)OC)C(C)(C)O] |
| 80 | 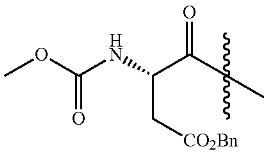 [SMILES: *C(=O)[C@H](CC(=O)OCc1ccccc1)NC(=O)OC] |
| 81 | 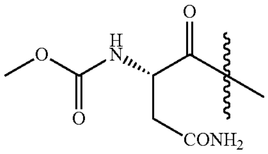 [SMILES: *C(=O)[C@H](CC(N)=O)NC(=O)OC] |
| 82 | 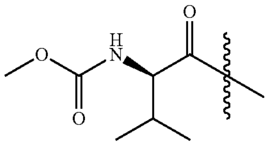 [SMILES: *C(=O)[C@H](NC(=O)OC)C(C)C] |
| 83 | 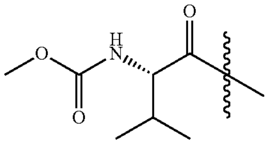 [SMILES: *C(=O)[C@@H](NC(=O)OC)C(C)C] |
TABLE 1-continued
| Compounds 1-219. | |
| --- | --- |
| | 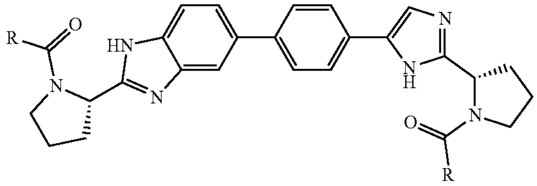 |
| Entry | 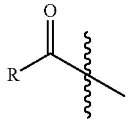 |
| 84 | 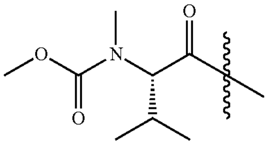 [SMILES: *C(=O)[C@H](C(C)C)N(C)C(=O)OC] |
| 85 | 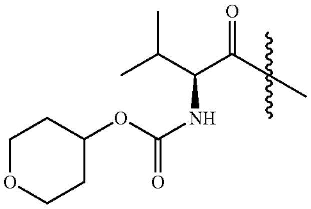 [SMILES: *C(=O)[C@@H](NC(=O)OC1CCOCC1)C(C)C] |
| 86 | 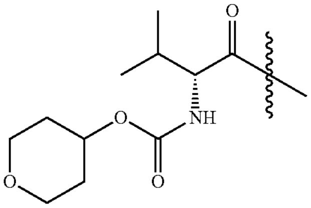 [SMILES: *C(=O)[C@H](NC(=O)OC1CCOCC1)C(C)C] |
| 87 | 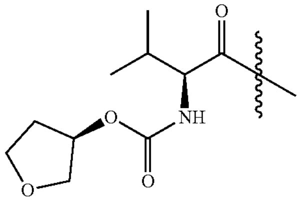 [SMILES: *C(=O)[C@@H](NC(=O)O[C@@H]1CCOC1)C(C)C] |
| 88 | 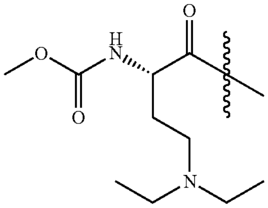 [SMILES: *C(=O)[C@H](CCN(CC)CC)NC(=O)OC] |
| 89 | 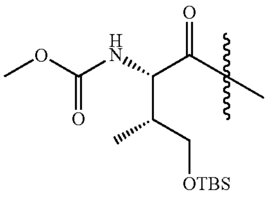 [SMILES: *C(=O)[C@@H](NC(=O)OC)[C@@H](C)CO[Si](C)(C)C(C)(C)C] |

TABLE 1-continued
Compounds 1-219.
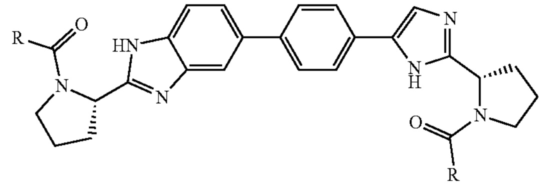
| Entry | 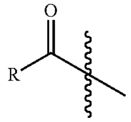 |
| --- | --- |
| 90 | 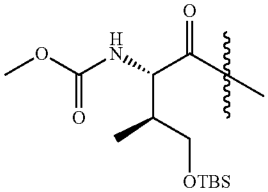 [SMILES: *C(=O)[C@@H](NC(=O)OC)[C@H](C)CO[Si](C)(C)C(C)(C)C] |
| 91 | 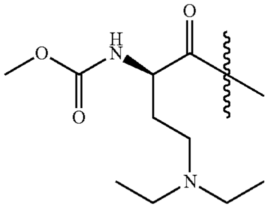 [SMILES: *C(=O)[C@@H](CCN(CC)CC)NC(=O)OC] |
| 92 | 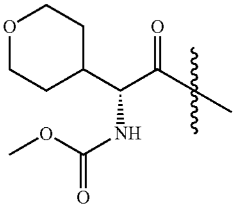 [SMILES: *C(=O)[C@H](NC(=O)OC)C1CCOCC1] |
| 93 | 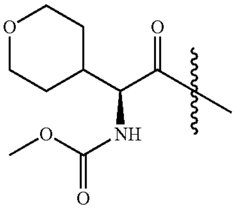 [SMILES: *C(=O)[C@@H](NC(=O)OC)C1CCOCC1] |
| 94 | 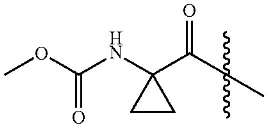 [SMILES: *C(=O)C1(NC(=O)OC)CC1] |
| 95 | 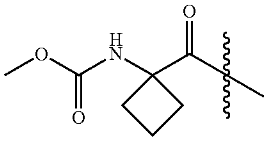 [SMILES: *C(=O)C1(NC(=O)OC)CCC1] |
TABLE 1-continued
Compounds 1-219.
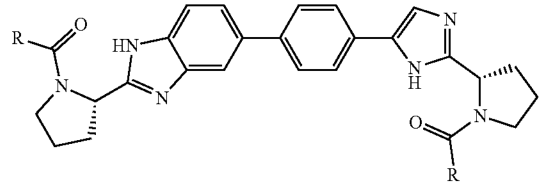
| Entry | 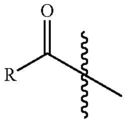 |
| --- | --- |
| 96 | 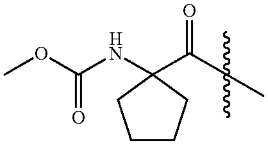 [SMILES: *C(=O)C1(NC(=O)OC)CCCC1] |
| 97 | 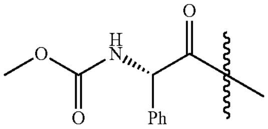 [SMILES: *C(=O)[C@@H](NC(=O)OC)c1ccccc1] |
| 98 | 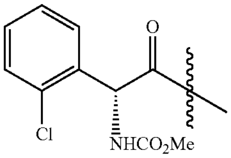 |
| 99 | 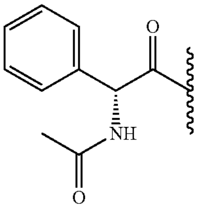 [SMILES: *C(=O)[C@H](NC(C)=O)c1ccccc1] |
| 100 | 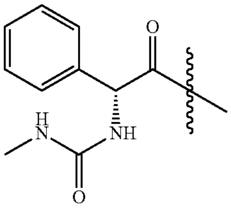 [SMILES: *C(=O)[C@H](NC(=O)NC)c1ccccc1] |
| 101 | 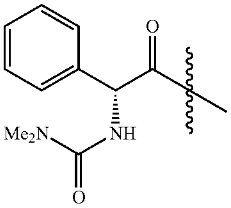 [SMILES: *C(=O)[C@H](NC(=O)N(C)C)c1ccccc1] |

TABLE 1-continued
Compounds 1-219.
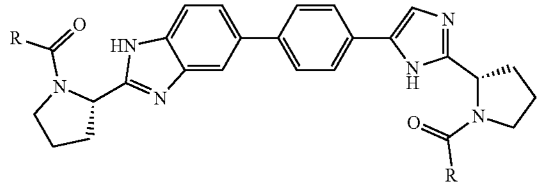
| Entry | 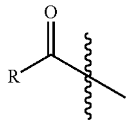 |
|---|---|
| 102 | 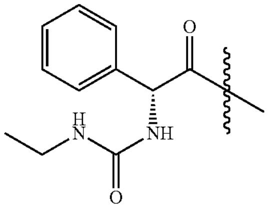 [SMILES: *C(=O)[C@H](NC(=O)NCC)c1ccccc1] |
| 103 | 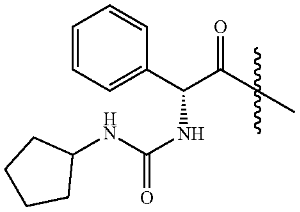 [SMILES: *C(=O)[C@H](NC(=O)NC1CCCC1)c1ccccc1] |
| 104 | 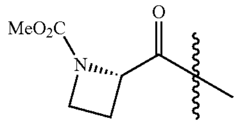 [SMILES: *C(=O)[C@@H]1CCN1C(=O)OC] |
| 105 | 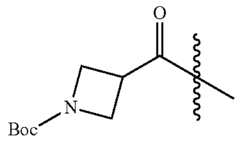 [SMILES: *C(=O)C1CN(C(=O)OC(C)(C)C)C1] |
| 106 | 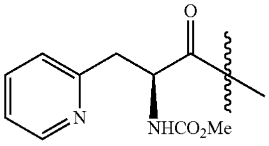 |
| 107 | 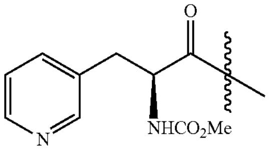 |
| 108 | 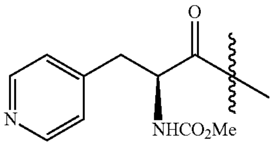 |
TABLE 1-continued
Compounds 1-219.
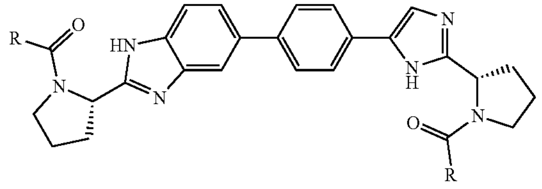
| Entry | 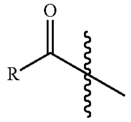 |
|---|---|
| 109 | 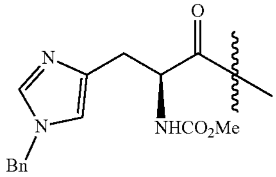 |
| 110 | 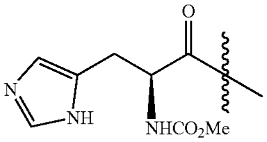 |
| 111 | 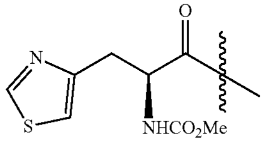 |
| 112 | 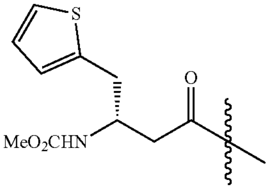 |
| 113 | 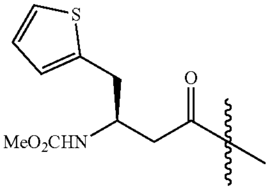 |
| 114 | 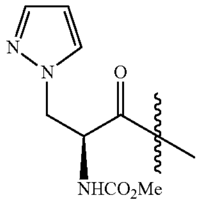 |

TABLE 1-continued
Compounds 1-219.
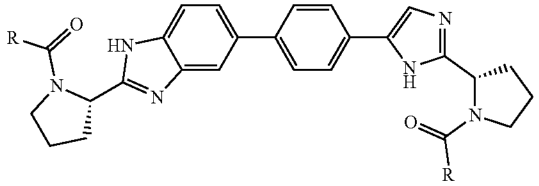
| Entry | 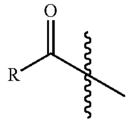 |
|---|---|
| 115 | 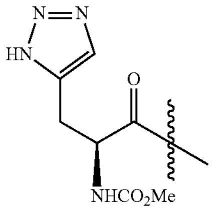 |
| 116 | 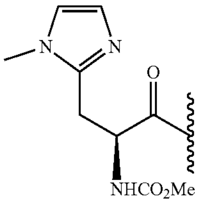 |
| 117 | 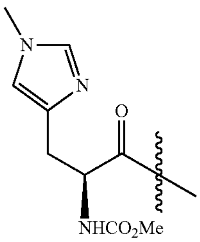 |
| 118 | 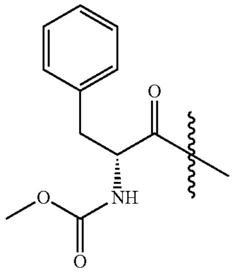 [SMILES: *C(=O)[C@@H](Cc1ccccc1)NC(=O)OC] |
| 119 | 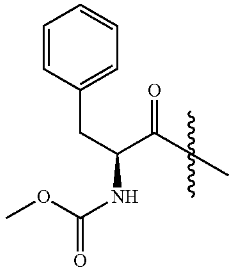 [SMILES: *C(=O)[C@H](Cc1ccccc1)NC(=O)OC] |
TABLE 1-continued
Compounds 1-219.
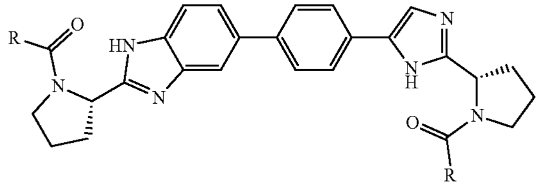
| Entry | 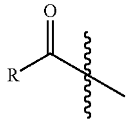 |
|---|---|
| 120 | 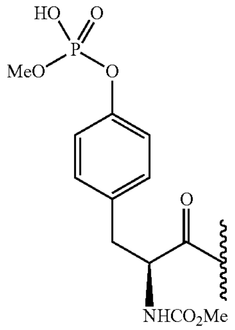 |
| 121 | 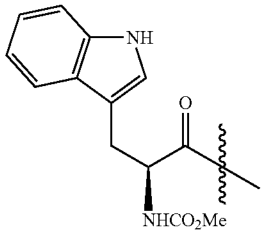 |
| 122 | 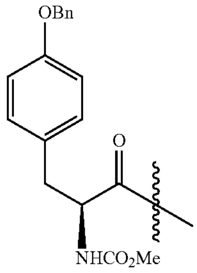 |
| 123 | 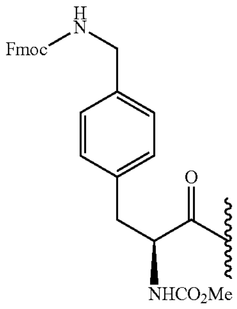 |

TABLE 1-continued
Compounds 1-219.
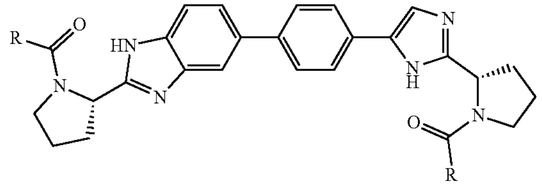
| Entry | 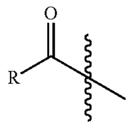 |
| --- | --- |
| 124 | 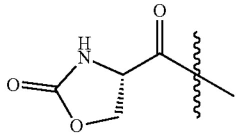 [SMILES: *C(=O)[C@@H]1COC(=O)N1] |
| 125 | 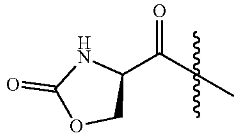 [SMILES: *C(=O)[C@H]1COC(=O)N1] |
| 126 | 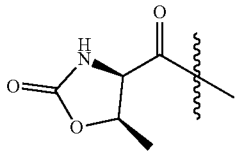 [SMILES: *C(=O)[C@@H]1NC(=O)O[C@@H]1C] |
| 127 | 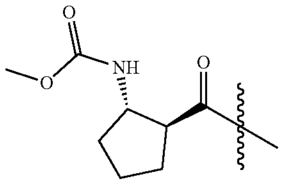 [SMILES: *C(=O)[C@H]1CCC[C@@H]1NC(=O)OC] |
| 128 | 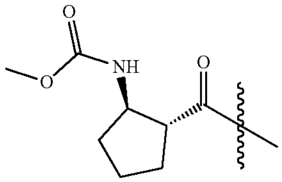 [SMILES: *C(=O)[C@@H]1CCC[C@H]1NC(=O)OC] |
| 129 | 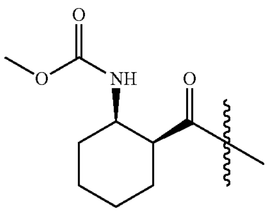 [SMILES: *C(=O)[C@H]1CCCC[C@H]1NC(=O)OC] |
| 130 | 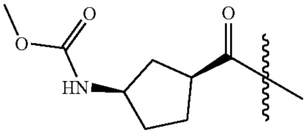 [SMILES: *C(=O)[C@H]1CC[C@@H](NC(=O)OC)C1] |
TABLE 1-continued
Compounds 1-219.
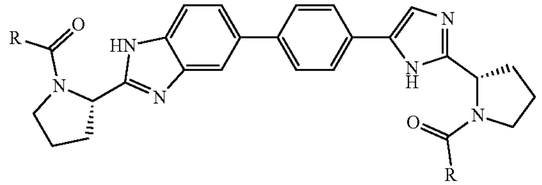
| Entry | 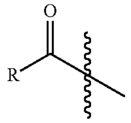 |
| --- | --- |
| 131 | 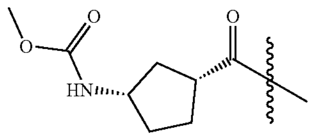 [SMILES: *C(=O)[C@@H]1CC[C@H](NC(=O)OC)C1] |
| 132 | 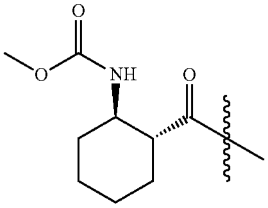 [SMILES: *C(=O)[C@@H]1CCCC[C@H]1NC(=O)OC] |
| 133 | 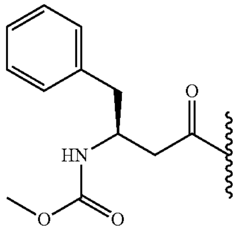 [SMILES: *C(=O)C[C@H](Cc1ccccc1)NC(=O)OC] |
| 134 | 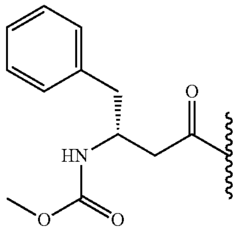 [SMILES: *C(=O)C[C@@H](Cc1ccccc1)NC(=O)OC] |
| 135 | 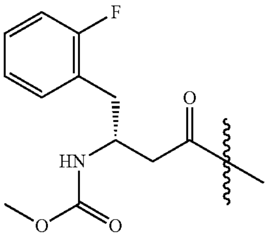 [SMILES: *C(=O)C[C@@H](Cc1ccccc1F)NC(=O)OC] |

TABLE 1-continued
| Compounds 1-219. | |
|---|---|
| 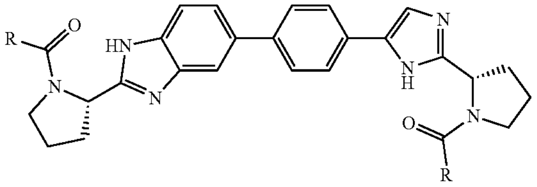 | |
| Entry | 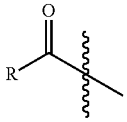 |
| 136 | 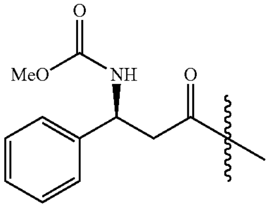 [SMILES: *C(=O)C[C@H](NC(=O)OC)c1ccccc1] |
| 137 | 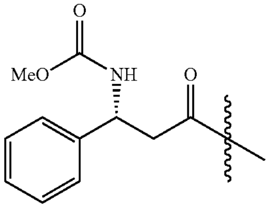 [SMILES: *C(=O)C[C@@H](NC(=O)OC)c1ccccc1] |
| 138 | 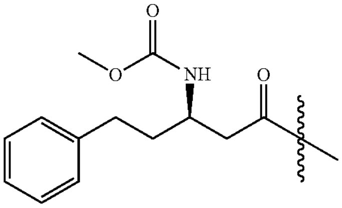 [SMILES: *C(=O)C[C@@H](CCc1ccccc1)NC(=O)OC] |
| 139 | 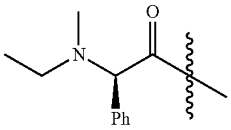 [SMILES: *C(=O)[C@@H](c1ccccc1)N(C)CC] |
| 140 | 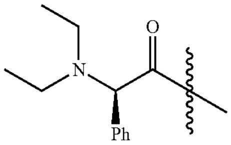 [SMILES: *C(=O)[C@@H](c1ccccc1)N(CC)CC] |
| 141 | 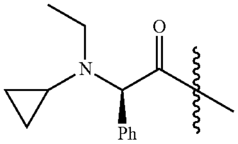 [SMILES: *C(=O)[C@@H](c1ccccc1)N(CC)C1CC1] |
TABLE 1-continued
| Compounds 1-219. | |
|---|---|
| 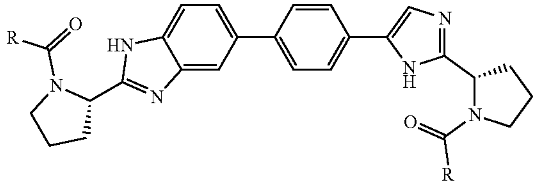 | |
| Entry | 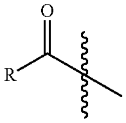 |
| 142 | 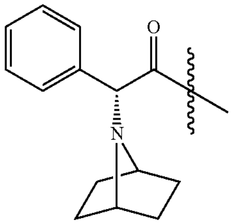 [SMILES: *C(=O)[C@@H](c1ccccc1)N1C2CCC1CC2] |
| 143 | 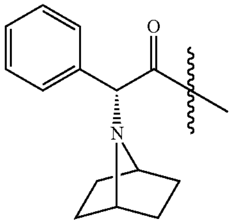 [SMILES: *C(=O)[C@@H](c1ccccc1)N1C2CCC1CC2] |
| 144 | 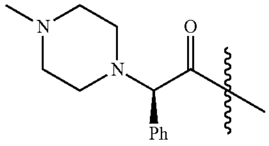 [SMILES: *C(=O)[C@@H](c1ccccc1)N1CCN(C)CC1] |
| 145 | 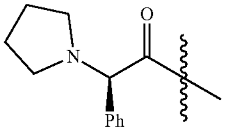 [SMILES: *C(=O)[C@@H](c1ccccc1)N1CCCC1] |
| 146 | 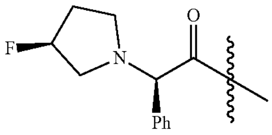 [SMILES: *C(=O)[C@@H](c1ccccc1)N1CC[C@H](F)C1] |
| 147 | 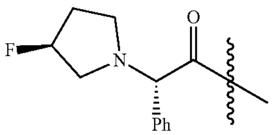 [SMILES: *C(=O)[C@H](c1ccccc1)N1CC[C@H](F)C1] |
| 148 | 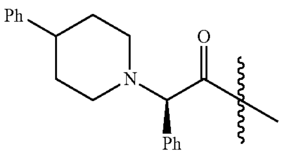 [SMILES: *C(=O)[C@@H](c1ccccc1)N1CCC(c2ccccc2)CC1] |

TABLE 1-continued
Compounds 1-219.
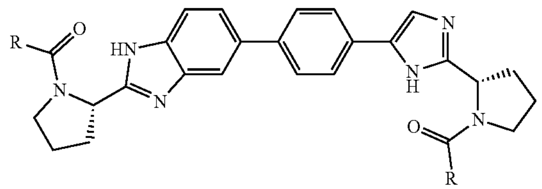
| Entry | 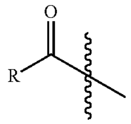 |
|---|---|
| 149 | 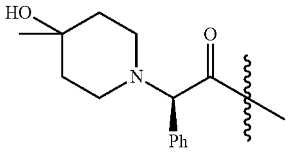 [SMILES: *C(=O)[C@@H](c1ccccc1)N1CCC(C)(O)CC1] |
| 150 | 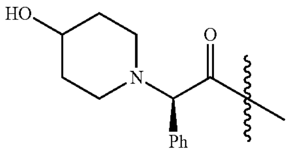 [SMILES: *C(=O)[C@@H](c1ccccc1)N1CCC(O)CC1] |
| 151 | 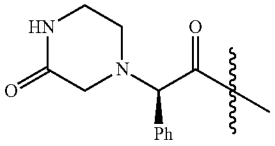 [SMILES: *C(=O)[C@@H](c1ccccc1)N1CCNC(=O)C1] |
| 152 | 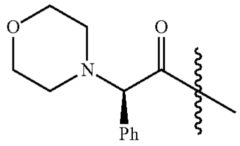 [SMILES: *C(=O)[C@@H](c1ccccc1)N1CCOCC1] |
| 153 | 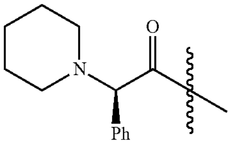 [SMILES: *C(=O)[C@@H](c1ccccc1)N1CCCCC1] |
| 154 | 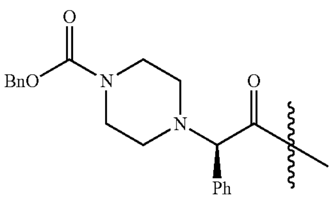 [SMILES: *C(=O)[C@@H](c1ccccc1)N1CCN(C(=O)OCc2ccccc2)CC1] |
| 155 | 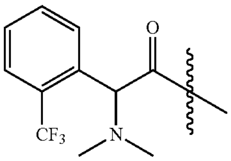 |
TABLE 1-continued
Compounds 1-219.
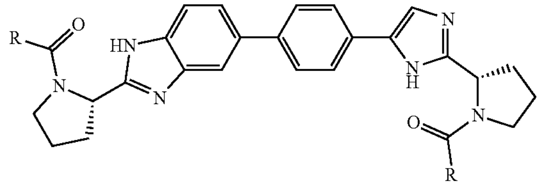
| Entry | 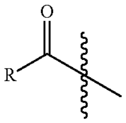 |
|---|---|
| 156 | 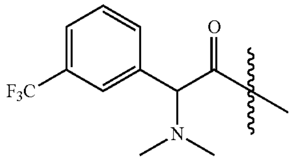 [SMILES: *C(=O)C(c1cccc(C(F)(F)F)c1)N(C)C] |
| 157 | 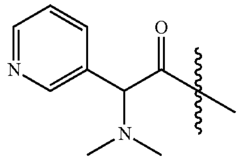 [SMILES: *C(=O)C(c1cccnc1)N(C)C] |
| 158 | 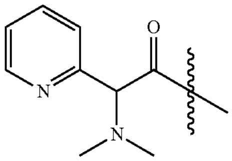 [SMILES: *C(=O)C(c1ccccn1)N(C)C] |
| 159 | 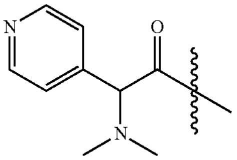 [SMILES: *C(=O)C(c1ccncc1)N(C)C] |
| 160 | 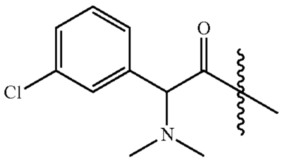 [SMILES: *C(=O)C(c1cccc(Cl)c1)N(C)C] |
| 161 | 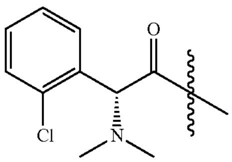 [SMILES: *C(=O)[C@@H](c1ccccc1Cl)N(C)C] |
| 162 | 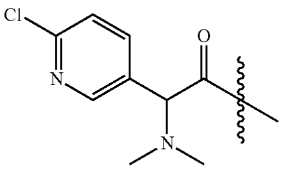 [SMILES: *C(=O)C(c1ccc(Cl)nc1)N(C)C] |

TABLE 1-continued
| Compounds 1-219. | |
|---|---|
| 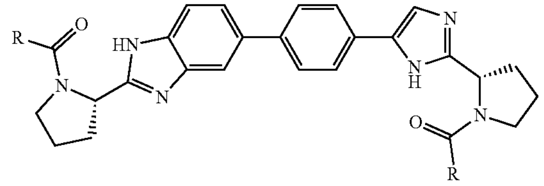 | |
| Entry | 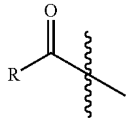 |
| 163 | 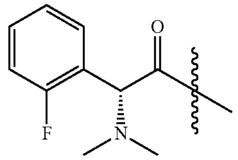 [SMILES: *C(=O)[C@@H](c1ccccc1F)N(C)C] |
| 164 | 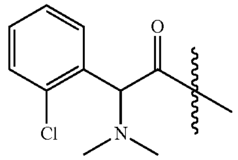 |
| 165 | 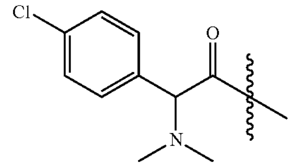 |
| 166 | 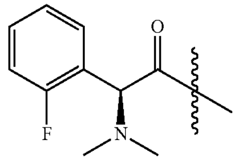 [SMILES: *C(=O)[C@H](c1ccccc1F)N(C)C] |
| 167 | 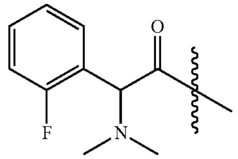 [SMILES: *C(=O)C(c1ccccc1F)N(C)C] |
| 168 | 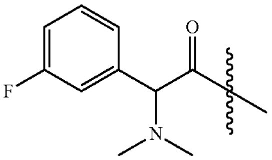 [SMILES: *C(=O)C(c1cccc(F)c1)N(C)C] |
| 169 | 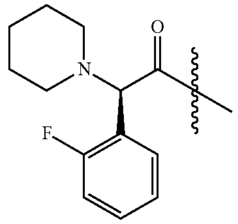 [SMILES: *C(=O)[C@@H](c1ccccc1F)N1CCCCC1] |
TABLE 1-continued
| Compounds 1-219. | |
|---|---|
| 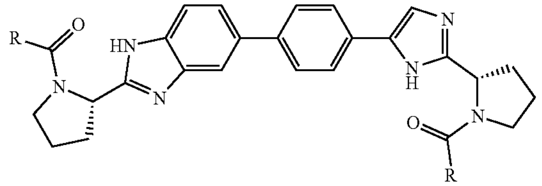 | |
| Entry | 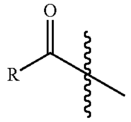 |
| 170 | 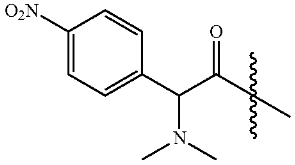 [SMILES: *C(=O)C(c1ccc([N+](=O)[O-])cc1)N(C)C] |
| 171 | 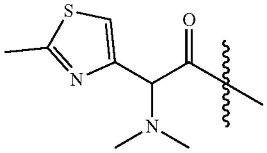 [SMILES: *C(=O)C(c1csc(C)n1)N(C)C] |
| 172 | 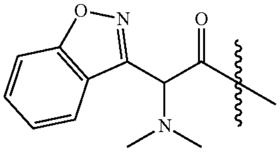 [SMILES: *C(=O)C(c1noc2ccccc12)N(C)C] |
| 173 | 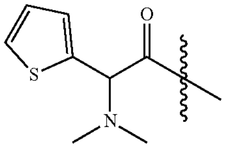 [SMILES: *C(=O)C(c1cccs1)N(C)C] |
| 174 | 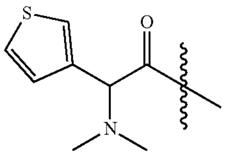 [SMILES: *C(=O)C(c1ccsc1)N(C)C] |
| 175 | 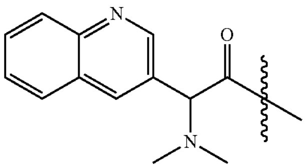 [SMILES: *C(=O)C(c1cnc2ccccc2c1)N(C)C] |
| 176 | 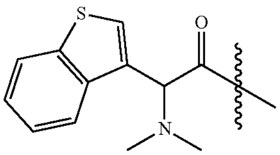 [SMILES: *C(=O)C(c1csc2ccccc12)N(C)C] |

TABLE 1-continued
| Compounds 1-219. | |
|---|---|
| 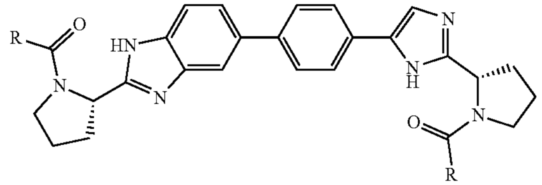 | |
| Entry | 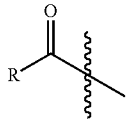 |
| 177 | 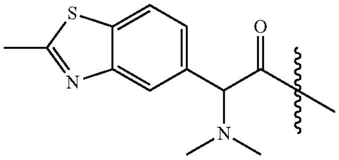 [SMILES: *C(=O)C(c1ccc2sc(C)nc2c1)N(C)C] |
| 178 | 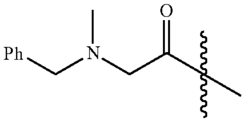 [SMILES: *C(=O)CN(C)Cc1ccccc1] |
| 179 | 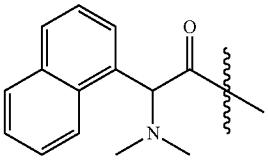 [SMILES: *C(=O)C(c1cccc2ccccc12)N(C)C] |
| 180 | 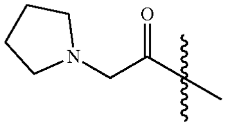 [SMILES: *C(=O)CN1CCCC1] |
| 181 | 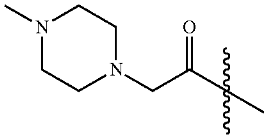 [SMILES: *C(=O)CN1CCN(C)CC1] |
| 182 | 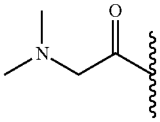 |
| 183 | 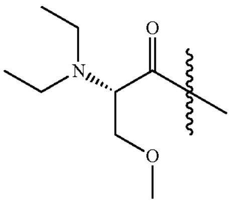 [SMILES: *C(=O)[C@H](COC)N(CC)CC] |
TABLE 1-continued
| Compounds 1-219. | |
|---|---|
| 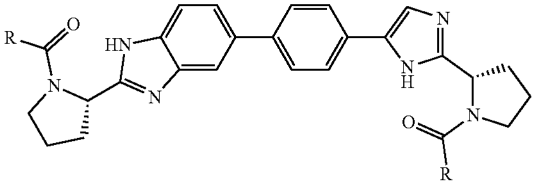 | |
| Entry | 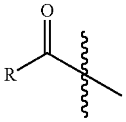 |
| 184 | 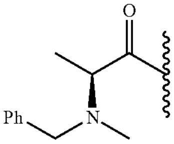 [SMILES: *C(=O)[C@H](C)N(C)Cc1ccccc1] |
| 185 | 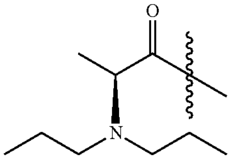 [SMILES: *C(=O)[C@H](C)N(CCC)CCC] |
| 186 | 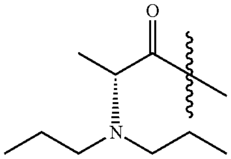 [SMILES: *C(=O)[C@@H](C)N(CCC)CCC] |
| 187 | 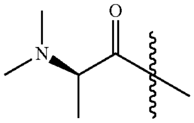 [SMILES: *C(=O)[C@@H](C)N(C)C] |
| 188 | 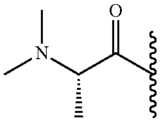 [SMILES: *C(=O)[C@H](C)N(C)C] |
| 189 | 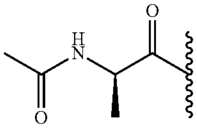 [SMILES: *C(=O)[C@@H](C)NC(C)=O] |
| 190 | 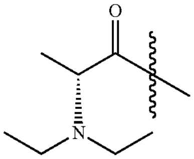 [SMILES: *C(=O)[C@@H](C)N(CC)CC] |
| 191 | 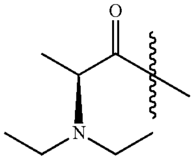 [SMILES: *C(=O)[C@H](C)N(CC)CC] |

TABLE 1-continued
Compounds 1-219.
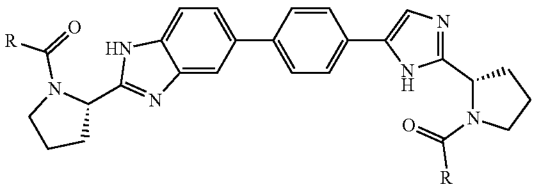
| Entry | 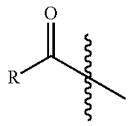 |
|---|---|
| 192 | 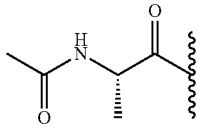 [SMILES: *C(=O)[C@H](C)NC(C)=O] |
| 193 | 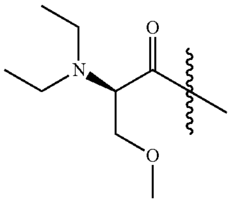 [SMILES: *C(=O)[C@@H](COC)N(CC)CC] |
| 194 | 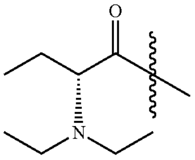 [SMILES: *C(=O)[C@@H](CC)N(CC)CC] |
| 195 | 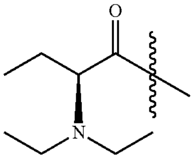 [SMILES: *C(=O)[C@H](CC)N(CC)CC] |
| 196 | 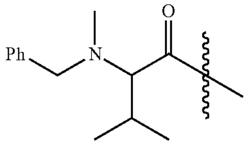 [SMILES: *C(=O)C(C(C)C)N(C)Cc1ccccc1] |
| 197 | 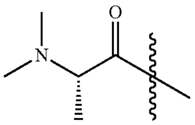 [SMILES: *C(=O)[C@H](C)N(C)C] |
| 198 | 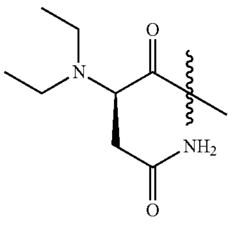 [SMILES: *C(=O)[C@@H](CC(N)=O)N(CC)CC] |
TABLE 1-continued
Compounds 1-219.
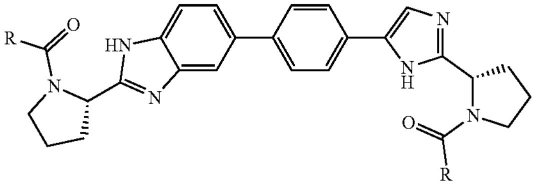
| Entry | 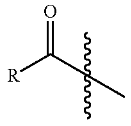 |
|---|---|
| 199 | 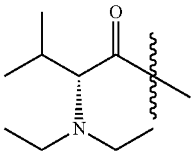 [SMILES: *C(=O)[C@@H](C(C)C)N(CC)CC] |
| 200 | 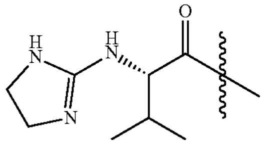 [SMILES: *C(=O)[C@@H](NC1=NCCN1)C(C)C] |
| 201 | 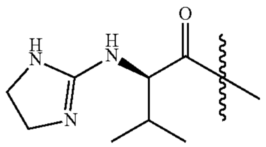 [SMILES: *C(=O)[C@H](NC1=NCCN1)C(C)C] |
| 202 | 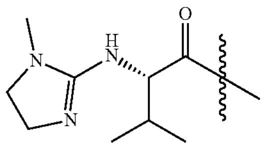 [SMILES: *C(=O)[C@@H](NC1=NCCN1C)C(C)C] |
| 203 | 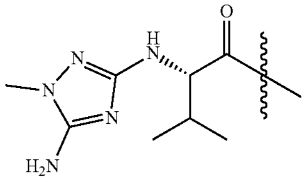 [SMILES: *C(=O)[C@@H](Nc1nc(N)n(C)n1)C(C)C] |
| 204 | 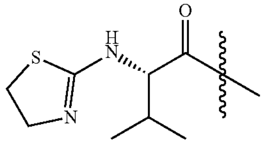 [SMILES: *C(=O)[C@@H](NC1=NCCS1)C(C)C] |
| 205 | 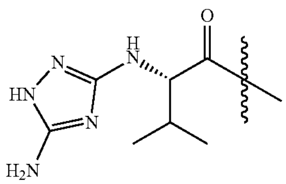 [SMILES: *C(=O)[C@@H](Nc1n[nH]c(N)n1)C(C)C] |

TABLE 1-continued
Compounds 1-219.
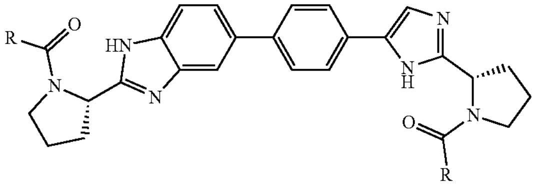
| Entry | 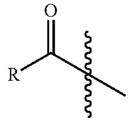 |
|---|---|
| 206 | 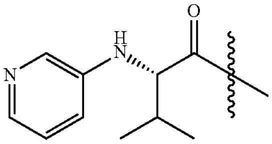 [SMILES: *C(=O)[C@@H](Nc1cccnc1)C(C)C] |
| 207 | 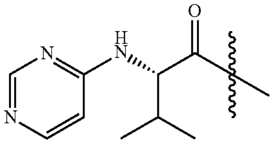 [SMILES: *C(=O)[C@@H](Nc1ccncn1)C(C)C] |
| 208 | 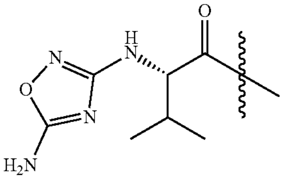 [SMILES: *C(=O)[C@@H](Nc1noc(N)n1)C(C)C] |
| 209 | 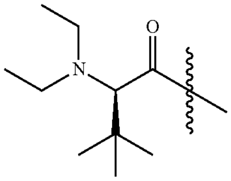 [SMILES: *C(=O)[C@H](N(CC)CC)C(C)(C)C] |
| 210 | 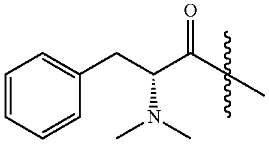 [SMILES: *C(=O)[C@@H](Cc1ccccc1)N(C)C] |
| 211 | 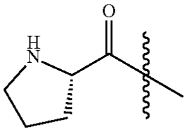 [SMILES: *C(=O)[C@@H]1CCCN1] |
| 212 | 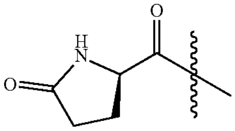 [SMILES: *C(=O)[C@H]1CCC(=O)N1] |
TABLE 1-continued
Compounds 1-219.
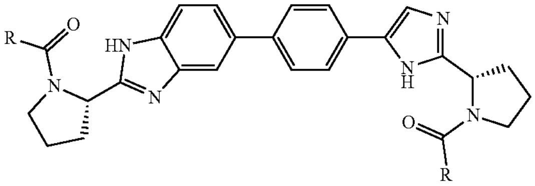
| Entry | 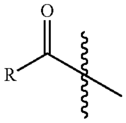 |
|---|---|
| 213 | 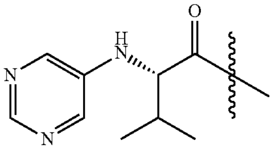 [SMILES: *C(=O)[C@@H](Nc1cncnc1)C(C)C] |
| 214 | 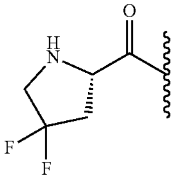 [SMILES: *C(=O)[C@@H]1CC(F)(F)CN1] |
| 215 | 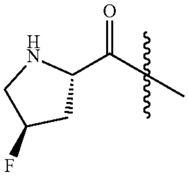 [SMILES: *C(=O)[C@@H]1C[C@@H](F)CN1] |
| 216 | 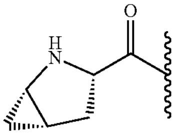 [SMILES: *C(=O)[C@@H]1C[C@@H]2C[C@@H]2N1] |
| 217 | 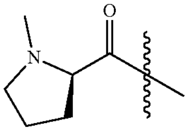 [SMILES: *C(=O)[C@H]1CCCN1C] |
| 218 | 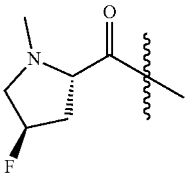 [SMILES: *C(=O)[C@@H]1C[C@@H](F)CN1C] |
| 219 | 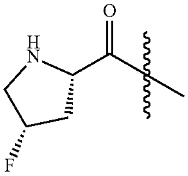 [SMILES: *C(=O)[C@@H]1C[C@H](F)CN1] |

TABLE 2
Compounds 220-219.
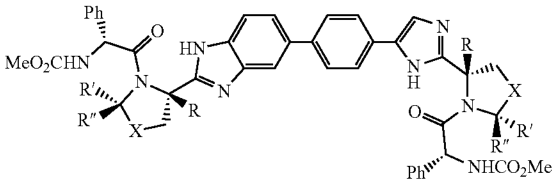
| Entry | R | R' | R" | X |
|---|---|---|---|---|
| 220 | Me | H | H | $CH_2$ |
| 221 | H | H | H | $CF_2$ |
| 222 | Me | H | H | S |
| 223 | H | H | H | 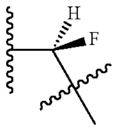 |
| 224 | Me | H | H | O |
| 225 | H | H | H | 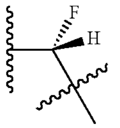 |
TABLE 2-continued
Compounds 220-219.
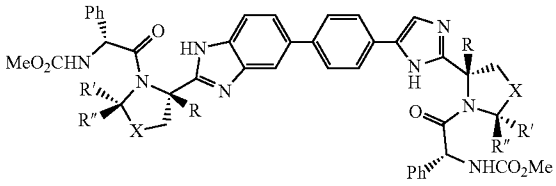
| Entry | R | R' | R" | X |
|---|---|---|---|---|
| 226 | H | Ph | H | $CH_2$ |
| 227 | H | H | H | 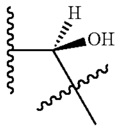 |
| 228 | H | H | Ph | $CH_2$ |
| 229 | H | H | H | 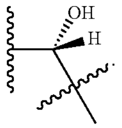 |
Compound 230
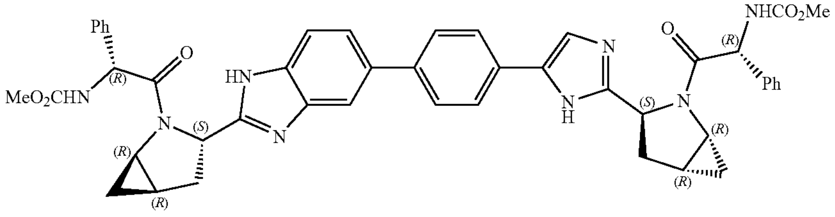
Compound 231
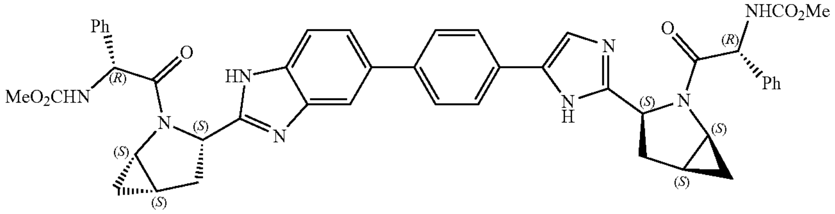
Compound 232
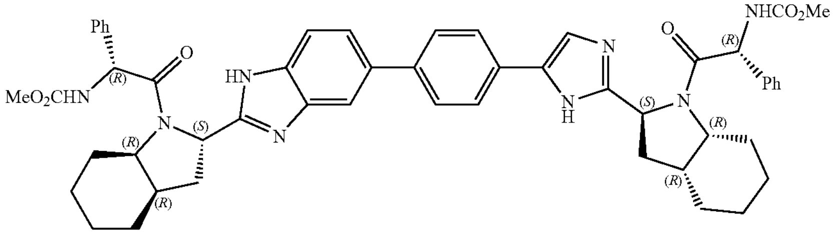

-continued
Compound 233
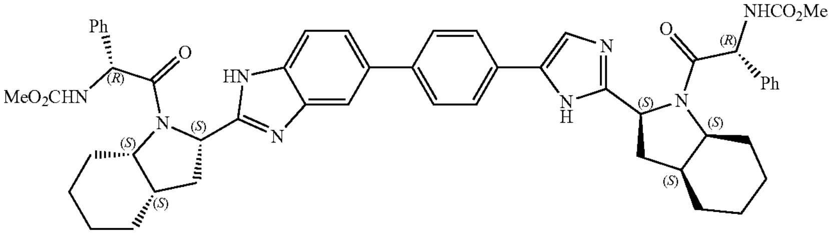
TABLE 3
Compounds 234-243.
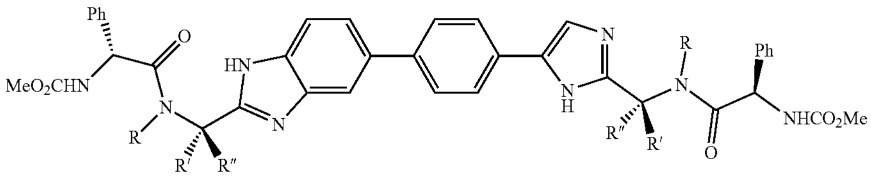
| Entry | R | R' | R'' |
|---|---|---|---|
| 234 | Me | Me | H |
| 235 | H | Me | H |
| 236 | Me | H | Me |
| 237 | cyclopropyl | Me | H |
| 238 | Me | Me | Me |
| 239 | Me | cyclopropyl | H |
| 240 | Me | Allyl | H |
| 241 | Et | Me | H |
| 242 | Me | $CHMe_2$ | H |
| 243 | Me | Et | H. |
TABLE 4
Compounds 244-263.
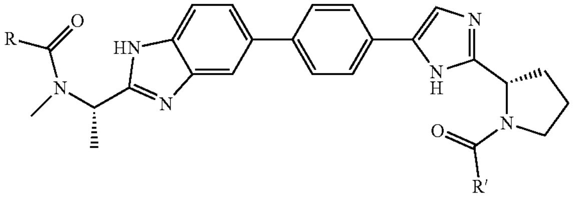
| Entry | R | R' |
|---|---|---|
| 244 | 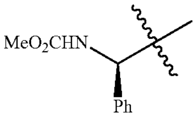 | 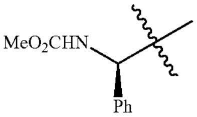 |
| 245 | 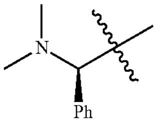 [SMILES: *[C@@H](c1ccccc1)N(C)C] | 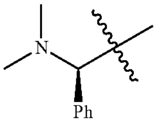 [SMILES: *[C@@H](c1ccccc1)N(C)C] |
| 246 | 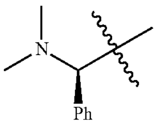 [SMILES: *[C@@H](c1ccccc1)N(C)C] | 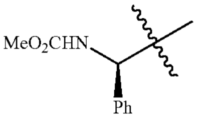 |
TABLE 4-continued
Compounds 244-263.
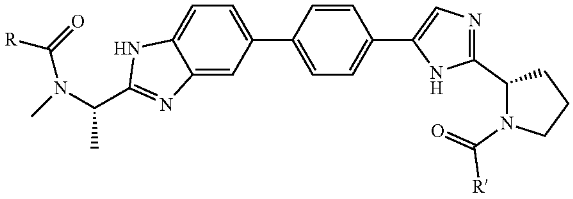
| Entry | R | R' |
|---|---|---|
| 247 | 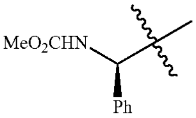 | 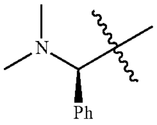 [SMILES: *[C@@H](c1ccccc1)N(C)C] |
| 248 | 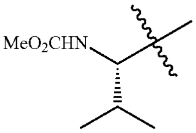 | 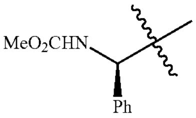 |

TABLE 4-continued
Compounds 244-263.
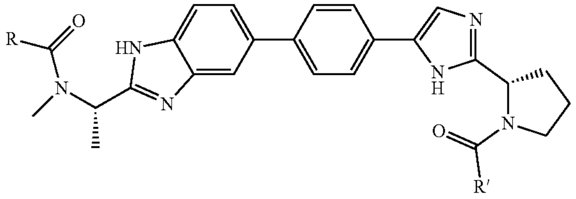
TABLE 4-continued
Compounds 244-263.
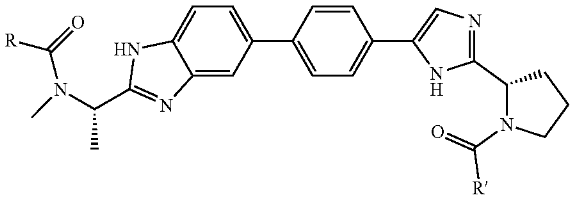
| Entry | R | R' |
|---|---|---|
| 249 | 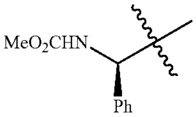 | 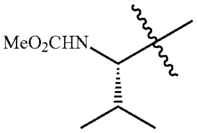 |
| 250 | 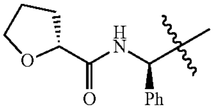 [SMILES: *[C@H](NC(=O)[C@H]1CCCO1)c1ccccc1] | 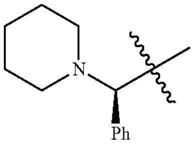 [SMILES: *[C@@H](c1ccccc1)N1CCCCC1] |
| 251 | 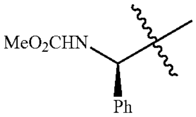 | 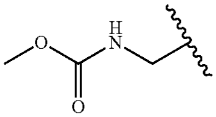 [SMILES: *CNC(=O)OC] |
| 252 | 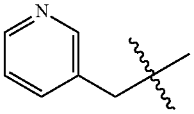 [SMILES: *Cc1cccnc1] | 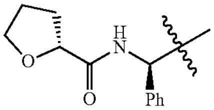 [SMILES: *[C@H](NC(=O)[C@H]1CCCO1)c1ccccc1] |
| 253 | 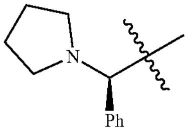 [SMILES: *[C@@H](c1ccccc1)N1CCCC1] | 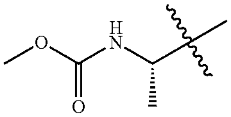 [SMILES: *[C@H](C)NC(=O)OC] |
| 254 | 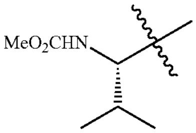 | 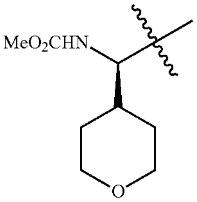 |
| 255 | 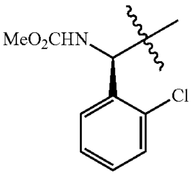 | 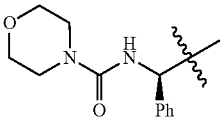 [SMILES: *[C@H](NC(=O)N1CCOCC1)c1ccccc1] |
| 256 | 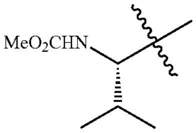 | 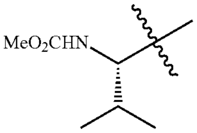 |
| 257 | 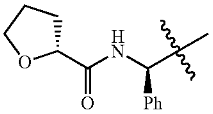 [SMILES: *[C@H](NC(=O)[C@H]1CCCO1)c1ccccc1] | 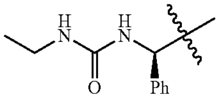 [SMILES: *[C@H](NC(=O)NCC)c1ccccc1] |
| 258 | 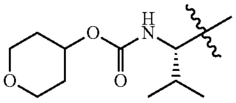 [SMILES: *[C@@H](NC(=O)OC1CCOCC1)C(C)C] | 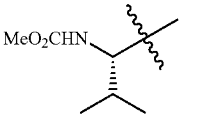 |
| 259 | 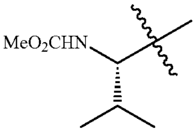 | 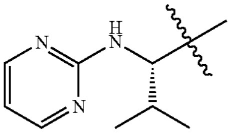 [SMILES: *[C@@H](Nc1ncccn1)C(C)C] |
| 260 | 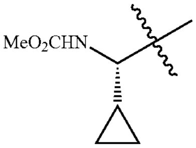 | 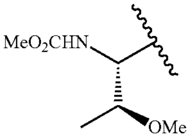 |
| 261 | 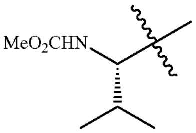 | 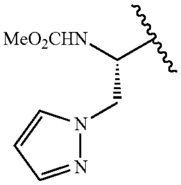 |
| 262 | 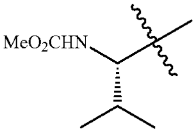 | 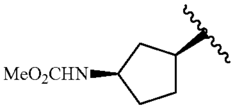 |
| 263 | 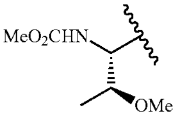 | 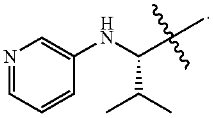 [SMILES: *[C@@H](Nc1cccnc1)C(C)C] |

TABLE 5

Compounds 264-273.

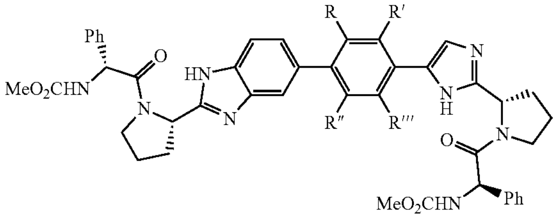

| Entry | R | R' | R'' | R''' |
|---|---|---|---|---|
| 264 | F | H | H | H |
| 265 | F | F | H | H |
| 266 | Me | H | H | H |
| 267 | Me | Me | H | H |
| 268 | H | H | Me | Me |
| 269 | H | H | Et | Et |
| 270 | $CF_3$ | H | H | H |
| 271 | $CF_3$ | H | $CF_3$ | H |
| 272 | Cl | H | H | H |
| 273 | Cl | H | Cl | H. |

TABLE 6

Compounds 274-299.

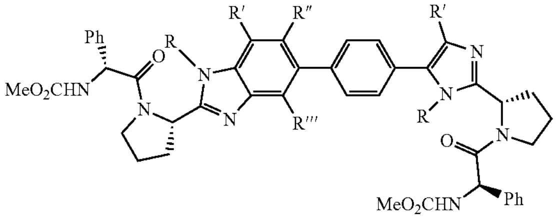

| Entry | R | R' | R'' | R''' |
|---|---|---|---|---|
| 274 | Me | H | H | H |
| 275 | H | $CO_2H$ | H | H |
| 276 | H | F | H | H |
| 277 | H | H | $CO_2H$ | H |
| 278 | H | H | F | H |
| 279 | H | H | H | $CO_2H$ |
| 280 | H | H | H | F |
| 281 | H | $CO_2Me$ | H | H |
| 282 | H | Cl | H | H |
| 283 | H | H | $CO_2Me$ | H |
| 284 | H | H | Cl | H |
| 285 | H | H | H | $CO_2Me$ |
| 286 | H | H | H | Cl |
| 287 | H | $CONH_2$ | H | H |
| 288 | H | Me | H | H |
| 289 | H | H | $CONH_2$ | H |
| 290 | H | H | Me | H |
| 291 | H | H | H | $CONH_2$ |
| 292 | H | H | H | Me |
| 293 | H | OMe | H | H |
| 294 | H | $CF_3$ | H | H |
| 295 | H | H | OMe | H |
| 296 | H | H | $CF_3$ | H |
| 297 | H | H | H | OMe |
| 298 | H | H | H | $CF_3$ |
| 299 | $CO_2Me$ | H | H | H. |

TABLE 7

Compounds 300-434.

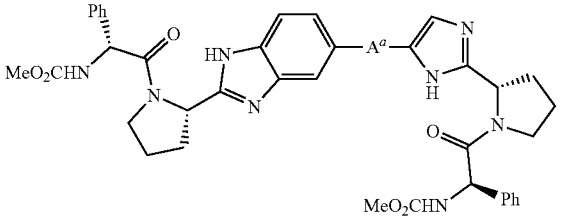

| Entry | $A^a$ |
|---|---|
| 300 | 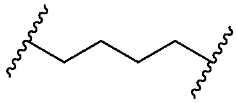 [SMILES: *CCCC*] |
| 301 | 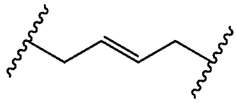 [SMILES: *C/C=C/C*] |
| 302 | 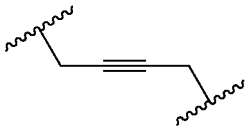 [SMILES: *CC#CC*] |
| 303 | 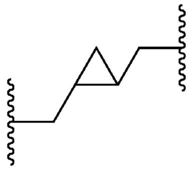 [SMILES: *CC1CC1C*] |
| 304 | 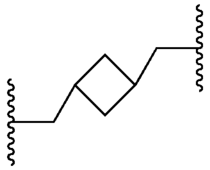 [SMILES: *CC1CC(C*)C1] |
| 305 | 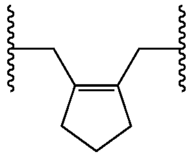 [SMILES: *CC1=C(C*)CCC1] |
| 306 | 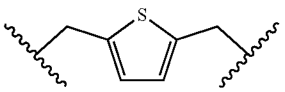 [SMILES: *Cc1ccc(C*)s1] |
| 307 | 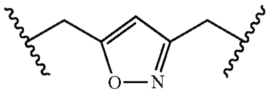 [SMILES: *Cc1cc(C*)on1] |
| 308 | 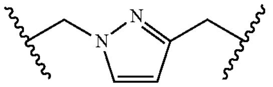 [SMILES: *Cc1ccn(C*)n1] |

TABLE 7-continued
Compounds 300-434.
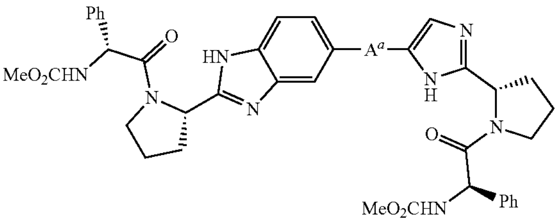
| Entry | $A^a$ |
|---|---|
| 309 | 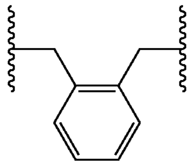 [SMILES: *Cc1ccccc1C*] |
| 310 | 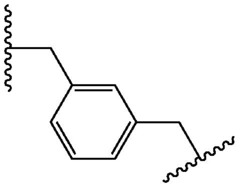 [SMILES: *Cc1cccc(C*)c1] |
| 311 | 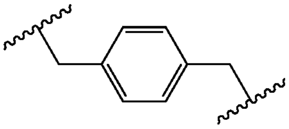 [SMILES: *Cc1ccc(C*)cc1] |
| 312 | 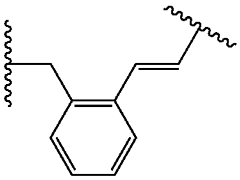 [SMILES: */C=C/c1ccccc1C*] |
| 313 | 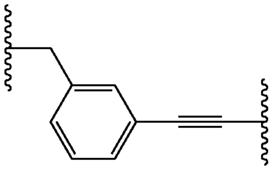 [SMILES: *C#Cc1cccc(C*)c1] |
| 314 | 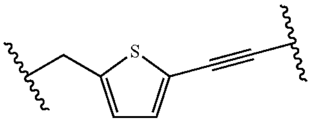 [SMILES: *C#Cc1ccc(C*)s1] |
| 315 | 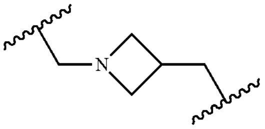 [SMILES: *CC1CN(C*)C1] |
| 316 | 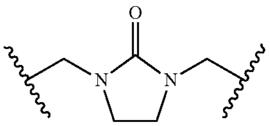 [SMILES: *CN1CCN(C*)C1=O] |
TABLE 7-continued
Compounds 300-434.
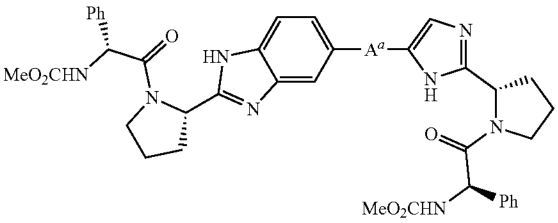
| Entry | $A^a$ |
|---|---|
| 317 | 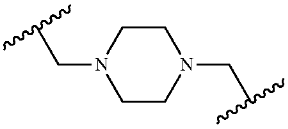 [SMILES: *CN1CCN(C*)CC1] |
| 318 | 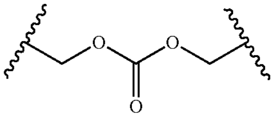 [SMILES: *COC(=O)OC*] |
| 319 | 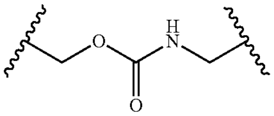 [SMILES: *CNC(=O)OC*] |
| 320 | 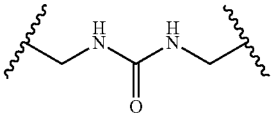 [SMILES: *CNC(=O)NC*] |
| 321 | 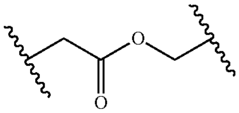 [SMILES: *COC(=O)C*] |
| 322 | 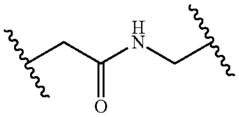 [SMILES: *CNC(=O)C*] |
| 323 | 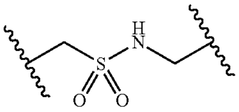 [SMILES: *CNS(=O)(=O)C*] |
| 324 | 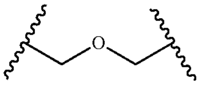 [SMILES: *COC*] |
| 325 | 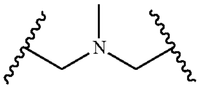 [SMILES: *CN(C)C*] |
| 326 | 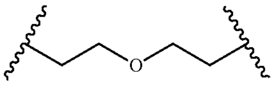 |
| 327 | 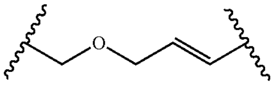 [SMILES: */C=C/COC*] |

TABLE 7-continued
Compounds 300-434.
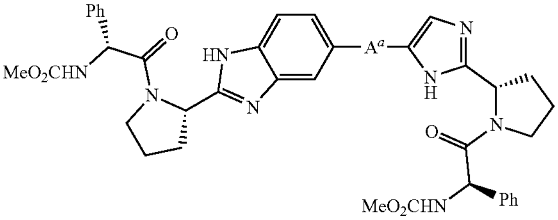
| Entry | $A^a$ |
|---|---|
| 328 | 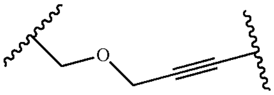 [SMILES: *C#CCOC*] |
| 329 | 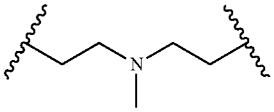 [SMILES: *CCN(C)CC*] |
| 330 | 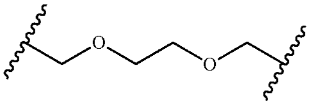 [SMILES: *COCCOC*] |
| 331 | 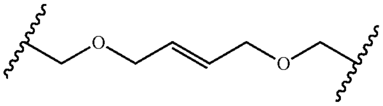 [SMILES: *COC/C=C/COC*] |
| 332 | 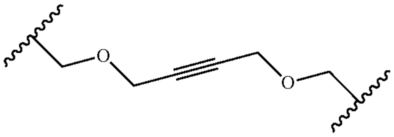 [SMILES: *COCC#CCOC*] |
| 333 | 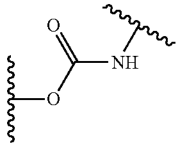 [SMILES: *NC(=O)O*] |
| 334 | 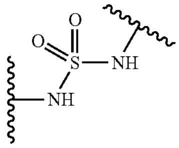 [SMILES: *NS(=O)(=O)N*] |
| 335 | 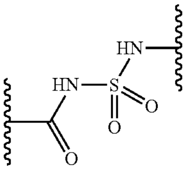 [SMILES: *NS(=O)(=O)NC(*)=O] |
| 336 | 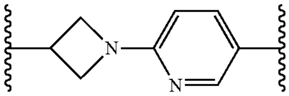 [SMILES: *c1ccc(N2CC(*)C2)nc1] |
TABLE 7-continued
Compounds 300-434.
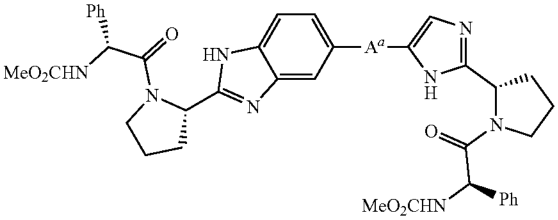
| Entry | $A^a$ |
|---|---|
| 337 | 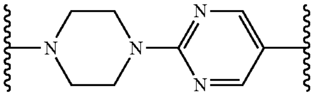 |
| 338 | 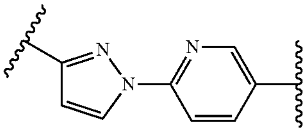 [SMILES: *c1ccc(-n2ccc(*)n2)nc1] |
| 339 | 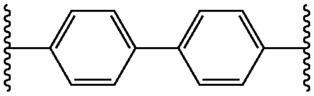 [SMILES: *c1ccc(-c2ccc(*)cc2)cc1] |
| 340 | 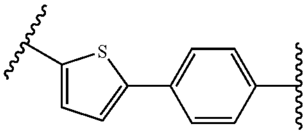 [SMILES: *c1ccc(-c2ccc(*)s2)cc1] |
| 341 | 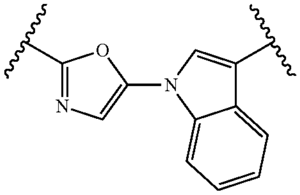 [SMILES: *c1ncc(-n2cc(*)c3ccccc32)o1] |
| 342 | 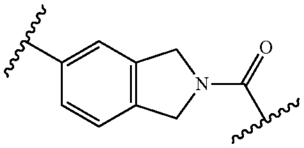 [SMILES: *C(=O)N1Cc2ccc(*)cc2C1] |
| 343 | 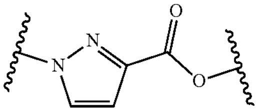 [SMILES: *OC(=O)c1ccn(*)n1] |
| 344 | 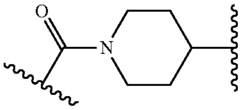 [SMILES: *C(=O)N1CCC(*)CC1] |
| 345 | 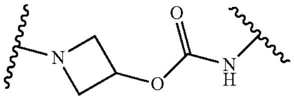 [SMILES: *NC(=O)OC1CN(*)C1] |

TABLE 7-continued
Compounds 300-434.
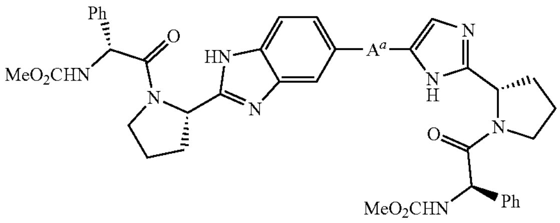
| Entry | $A^a$ |
| --- | --- |
| 346 | 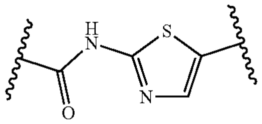 [SMILES: *C(=O)Nc1ncc(*)s1] |
| 347 | 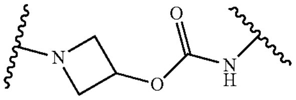 [SMILES: *NC(=O)OC1CN(*)C1] |
| 348 | 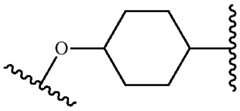 [SMILES: *OC1CCC(*)CC1] |
| 349 | 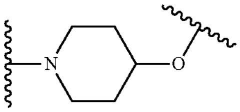 [SMILES: *OC1CCN(*)CC1] |
| 350 | 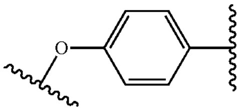 |
| 351 | 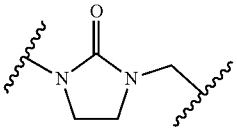 [SMILES: *CN1CCN(*)C1=O] |
| 352 | 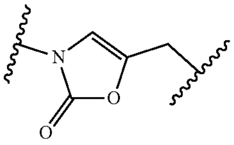 [SMILES: *Cc1cn(*)c(=O)o1] |
| 353 | 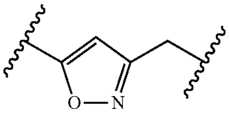 [SMILES: *Cc1cc(*)on1] |
| 354 | 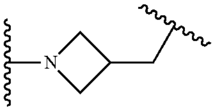 [SMILES: *CC1CN(*)C1] |
| 355 | 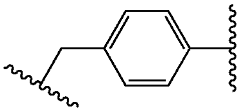 [SMILES: *Cc1ccc(*)cc1] |
TABLE 7-continued
Compounds 300-434.
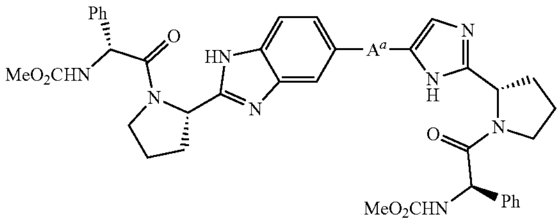
| Entry | $A^a$ |
| --- | --- |
| 356 | 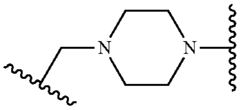 [SMILES: *CN1CCN(*)CC1] |
| 357 | 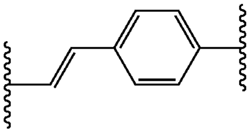 [SMILES: */C=C/c1ccc(*)cc1] |
| 358 | 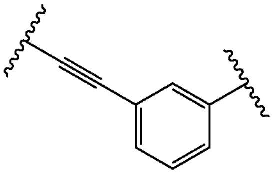 [SMILES: *C#Cc1cccc(*)c1] |
| 359 | 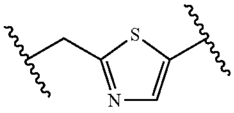 [SMILES: *Cc1ncc(*)s1] |
| 360 | 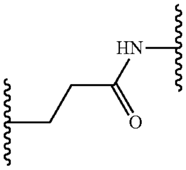 [SMILES: *CCC(=O)N*] |
| 361 | 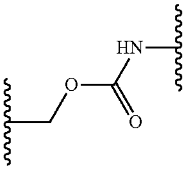 [SMILES: *COC(=O)N*] |
| 362 | 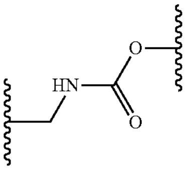 [SMILES: *CNC(=O)O*] |
| 363 | 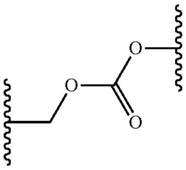 [SMILES: *COC(=O)O*] |

TABLE 7-continued
Compounds 300-434.
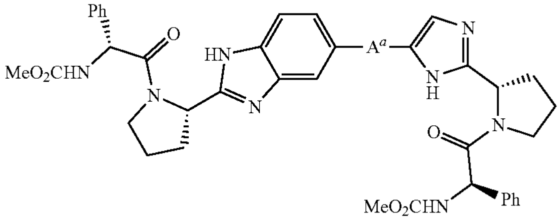
| Entry | $A^a$ |
|---|---|
| 364 | 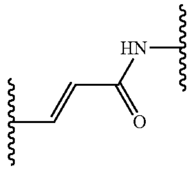 [SMILES: */C=C/C(=O)N*] |
| 365 | 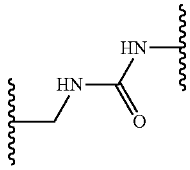 [SMILES: *CNC(=O)N*] |
| 366 | 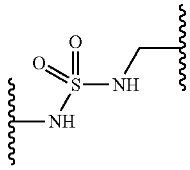 [SMILES: *CNS(=O)(=O)N*] |
| 367 | 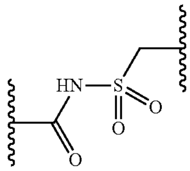 [SMILES: *CS(=O)(=O)NC(*)=O] |
| 368 | 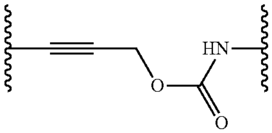 [SMILES: *C#CCOC(=O)N*] |
| 369 | 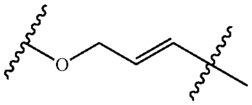 [SMILES: */C=C/CO*] |
| 370 | 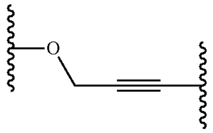 [SMILES: *C#CCO*] |
| 371 | 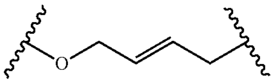 [SMILES: *C/C=C/CO*] |
TABLE 7-continued
Compounds 300-434.
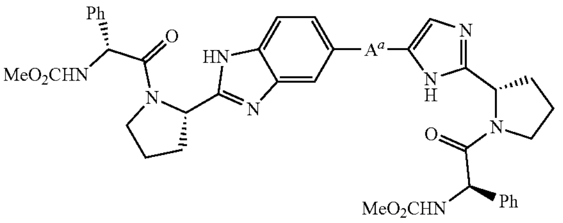
| Entry | $A^a$ |
|---|---|
| 372 | 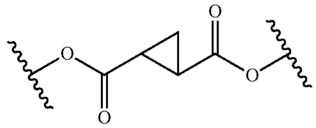 [SMILES: *OC(=O)C1CC1C(=O)O*] |
| 373 | 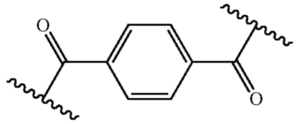 [SMILES: *C(=O)c1ccc(C(*)=O)cc1] |
| 374 | 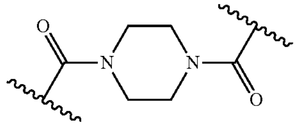 [SMILES: *C(=O)N1CCN(C(*)=O)CC1] |
| 375 | 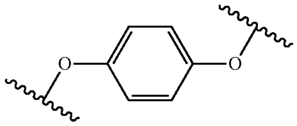 [SMILES: *Oc1ccc(O*)cc1] |
| 376 | 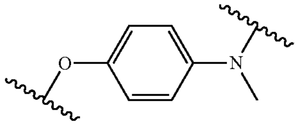 [SMILES: *Oc1ccc(N(*)C)cc1] |
| 377 | 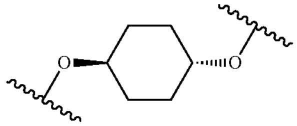 [SMILES: *O[C@H]1CC[C@H](O*)CC1] |
| 378 | 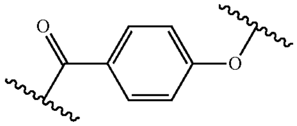 [SMILES: *Oc1ccc(C(*)=O)cc1] |
| 379 | 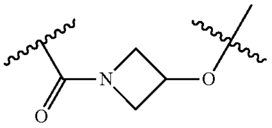 [SMILES: *OC1CN(C(*)=O)C1] |
| 380 | 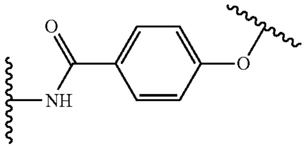 [SMILES: *NC(=O)c1ccc(O*)cc1] |

TABLE 7-continued
Compounds 300-434.
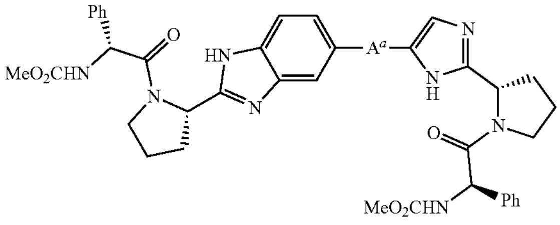
| Entry | $A^a$ |
|---|---|
| 381 | 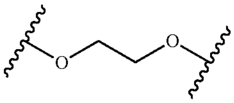 [SMILES: *OCCO*] |
| 382 | 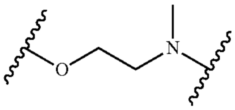 [SMILES: *OCCN(*)C] |
| 383 | 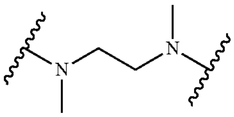 [SMILES: *N(C)CCN(*)C] |
| 384 | 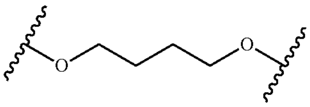 [SMILES: *OCCCCO*] |
| 385 | 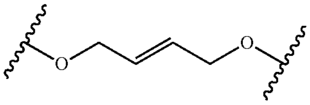 [SMILES: *OC/C=C/CO*] |
| 386 | 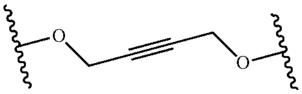 [SMILES: *OCC#CCO*] |
| 387 | 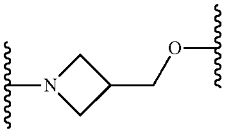 [SMILES: *OCC1CN(*)C1] |
| 388 | 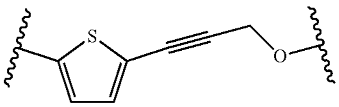 [SMILES: *OCC#Cc1ccc(*)s1] |
| 389 | 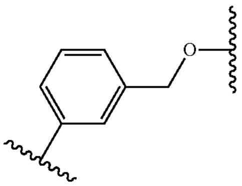 [SMILES: *OCc1cccc(*)c1] |
TABLE 7-continued
Compounds 300-434.
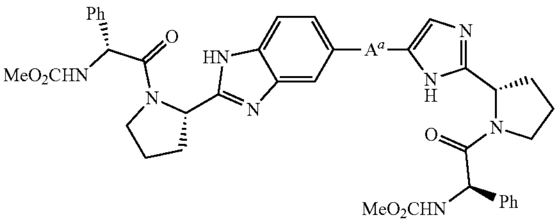
| Entry | $A^a$ |
|---|---|
| 390 | 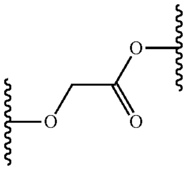 [SMILES: *OCC(=O)O*] |
| 391 | 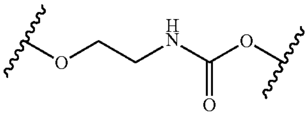 [SMILES: *OCCNC(=O)O*] |
| 392 | 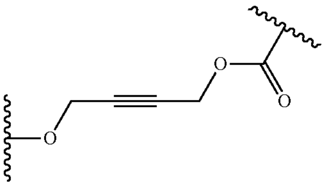 [SMILES: *OCC#CCOC(*)=O] |
| 393 | 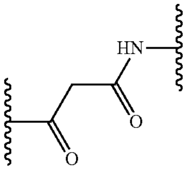 [SMILES: *NC(=O)CC(*)=O] |
| 394 | 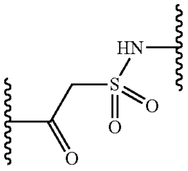 [SMILES: *NS(=O)(=O)CC(*)=O] |
| 395 | 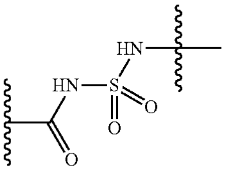 [SMILES: *NS(=O)(=O)NC(*)=O] |
| 396 | 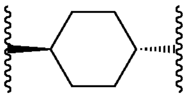 [SMILES: *[C@H]1CC[C@H](*)CC1] |

TABLE 7-continued
Compounds 300-434.
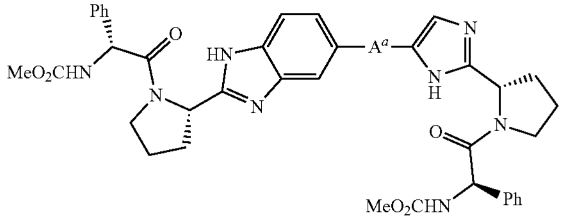
| Entry | $A^a$ |
|---|---|
| 397 | 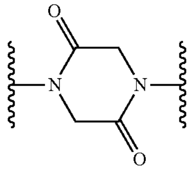 [SMILES: *N1CC(=O)N(*)CC1=O] |
| 398 | 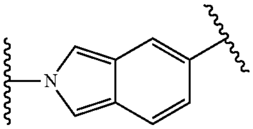 [SMILES: *c1ccc2cn(*)cc2c1] |
| 399 | 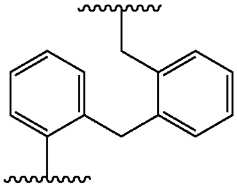 [SMILES: *Cc1ccccc1Cc1ccccc1*] |
| 400 | 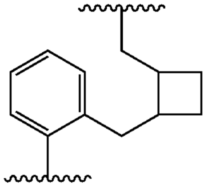 [SMILES: *CC1CCC1Cc1ccccc1*] |
| 401 | 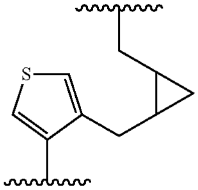 [SMILES: *CC1CC1Cc1cscc1*] |
| 402 | 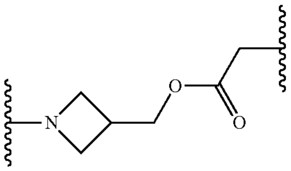 [SMILES: *CC(=O)OCC1CN(*)C1] |
| 403 | 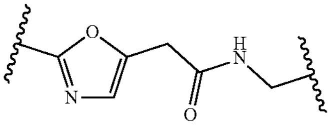 [SMILES: *CNC(=O)Cc1cnc(*)o1] |
TABLE 7-continued
Compounds 300-434.
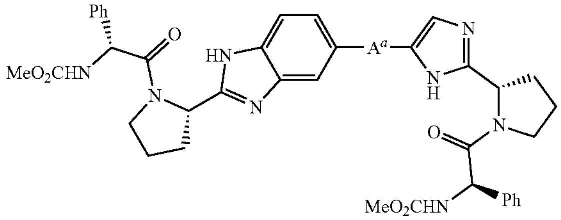
| Entry | $A^a$ |
|---|---|
| 404 | 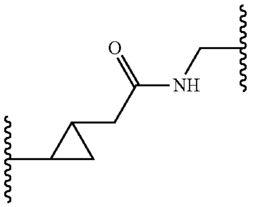 [SMILES: *CNC(=O)CC1CC1*] |
| 405 | 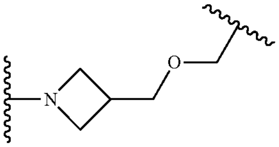 [SMILES: *COCC1CN(*)C1] |
| 406 | 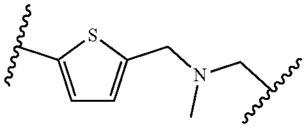 [SMILES: *CN(C)Cc1ccc(*)s1] |
| 407 | 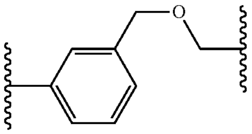 [SMILES: *COCc1cccc(*)c1] |
| 408 | 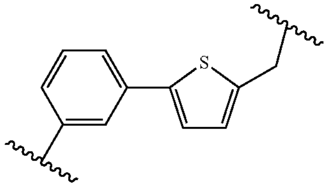 [SMILES: *Cc1ccc(-c2cccc(*)c2)s1] |
| 409 | 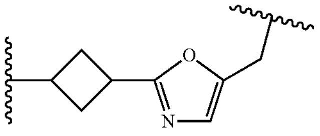 [SMILES: *Cc1cnc(C2CC(*)C2)o1] |
| 410 | 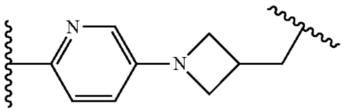 [SMILES: *CC1CN(c2ccc(*)nc2)C1] |

TABLE 7-continued
Compounds 300-434.
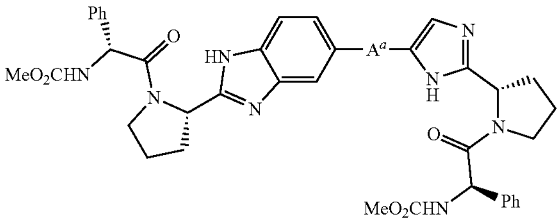
| Entry | $A^a$ |
|---|---|
| 411 | 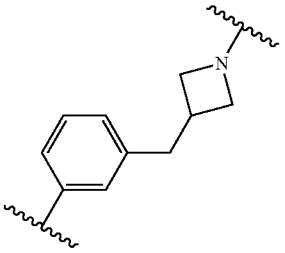 [SMILES: *c1cccc(CC2CN(*)C2)c1] |
| 412 | 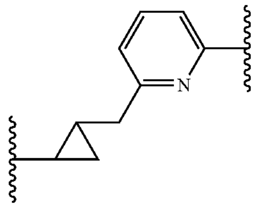 [SMILES: *c1cccc(CC2CC2*)n1] |
| 413 | 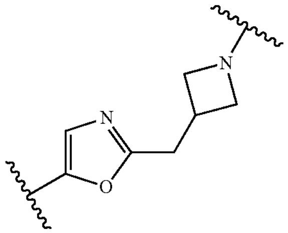 [SMILES: *c1cnc(CC2CN(*)C2)o1] |
| 414 | 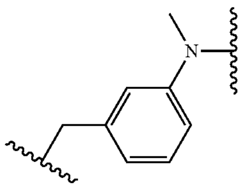 [SMILES: *Cc1cccc(N(*)C)c1] |
| 415 | 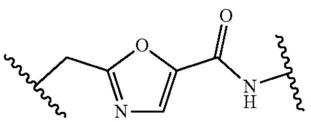 [SMILES: *Cc1ncc(C(=O)N*)o1] |
| 416 | 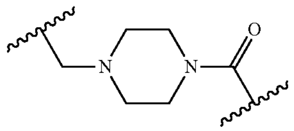 [SMILES: *CN1CCN(C(*)=O)CC1] |
| 417 | 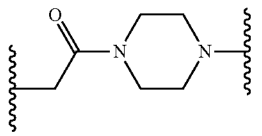 [SMILES: *CC(=O)N1CCN(*)CC1] |
TABLE 7-continued
Compounds 300-434.
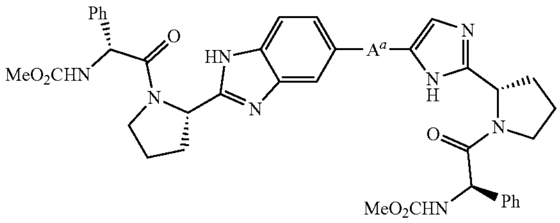
| Entry | $A^a$ |
|---|---|
| 418 | 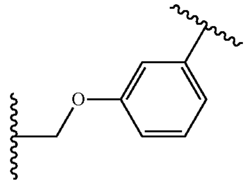 [SMILES: *COc1cccc(*)c1] |
| 419 | 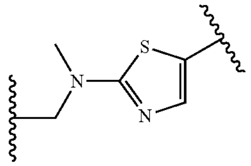 [SMILES: *CN(C)c1ncc(*)s1] |
| 420 | 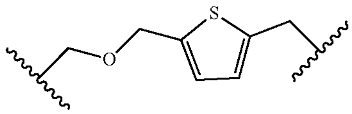 [SMILES: *COCc1ccc(C*)s1] |
| 421 | 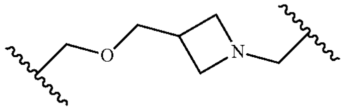 [SMILES: *COCC1CN(C*)C1] |
| 422 | 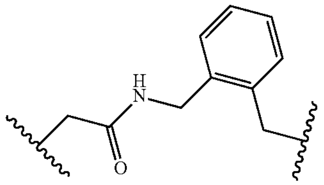 [SMILES: *CC(=O)NCc1ccccc1C*] |
| 423 | 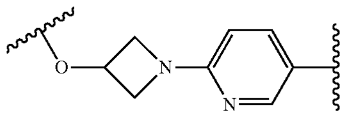 [SMILES: *OC1CN(c2ccc(*)cn2)C1] |
| 424 | 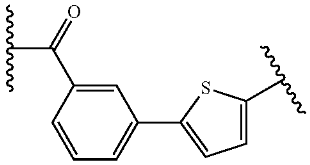 [SMILES: *C(=O)c1cccc(-c2ccc(*)s2)c1] |
| 425 | 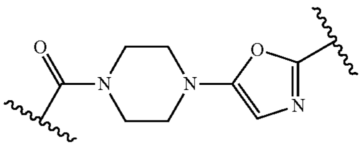 [SMILES: *C(=O)N1CCN(c2cnc(*)o2)CC1] |

TABLE 7-continued
Compounds 300-434.
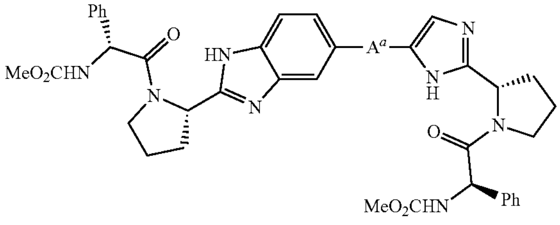
| Entry | $A^a$ |
|---|---|
| 426 | 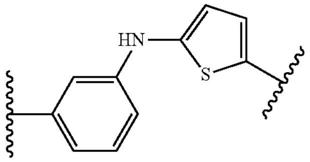 [SMILES: *c1cccc(Nc2ccc(*)s2)c1] |
| 427 | 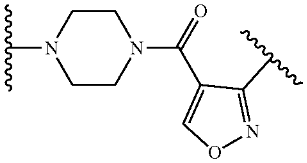 [SMILES: *c1nocc1C(=O)N1CCN(*)CC1] |
| 428 | 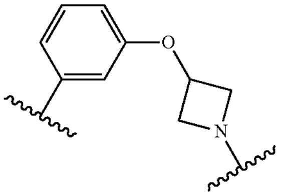 [SMILES: *c1cccc(OC2CN(*)C2)c1] |
| 429 | 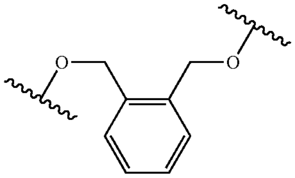 [SMILES: *OCc1ccccc1CO*] |
| 430 | 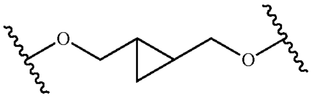 [SMILES: *OCC1CC1CO*] |
| 431 | 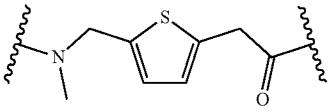 [SMILES: *C(=O)Cc1ccc(CN(*)C)s1] |
| 432 | 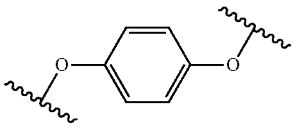 [SMILES: *Oc1ccc(O*)cc1] |
| 433 | 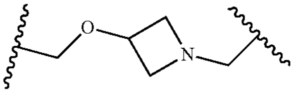 [SMILES: *COC1CN(C*)C1] |
TABLE 7-continued
Compounds 300-434.
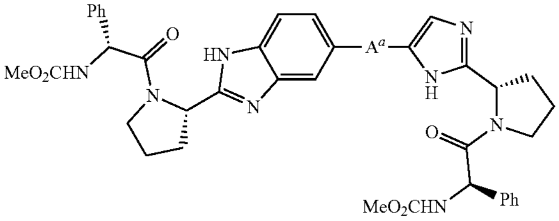
| Entry | $A^a$ |
|---|---|
| 434 | 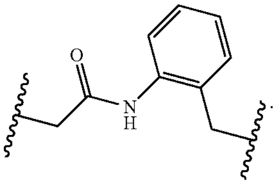 [SMILES: *CC(=O)Nc1ccccc1C*] |
TABLE 8
Compounds 435-440.
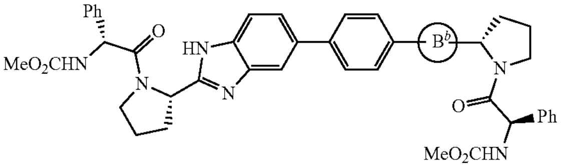
| Entry | $B^b$ |
|---|---|
| 435 | 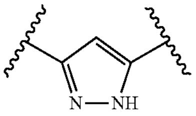 [SMILES: *c1cc(*)[nH]n1] |
| 436 | 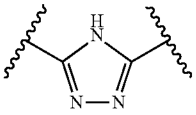 [SMILES: *c1nnc(*)[nH]1] |
| 437 | 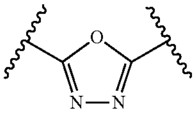 [SMILES: *c1nnc(*)o1] |
| 438 | 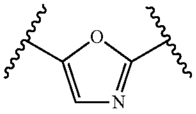 [SMILES: *c1cnc(*)o1] |
| 439 | 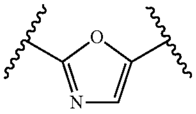 [SMILES: *c1cnc(*)o1] |
| 440 | 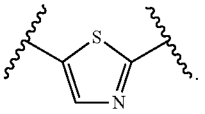 [SMILES: *c1cnc(*)s1] |

TABLE 9
| Compounds 441-545 |
| --- |
441
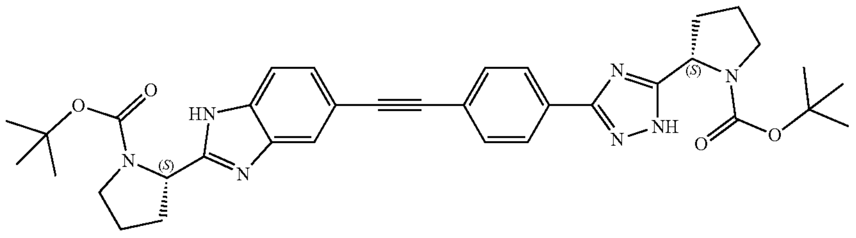
442
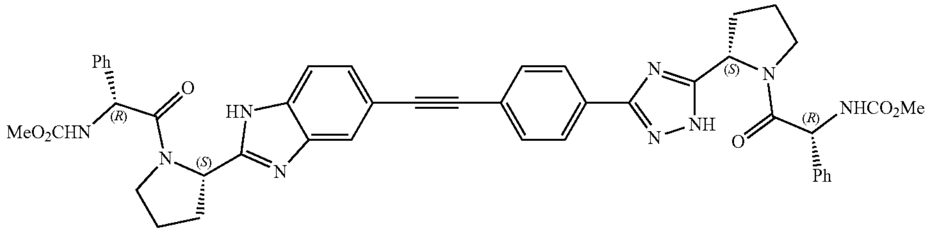
443
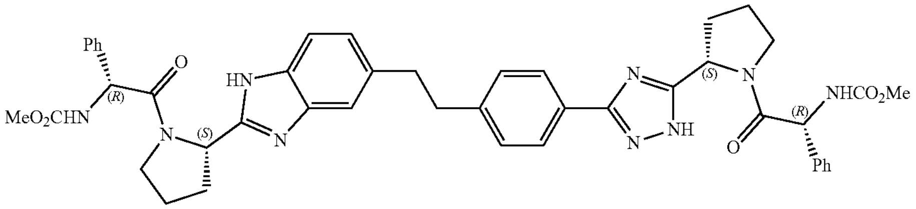
444
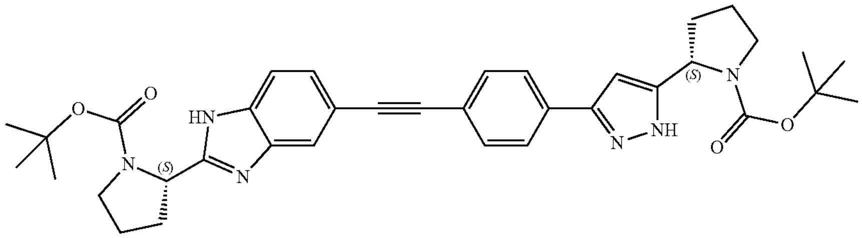
445
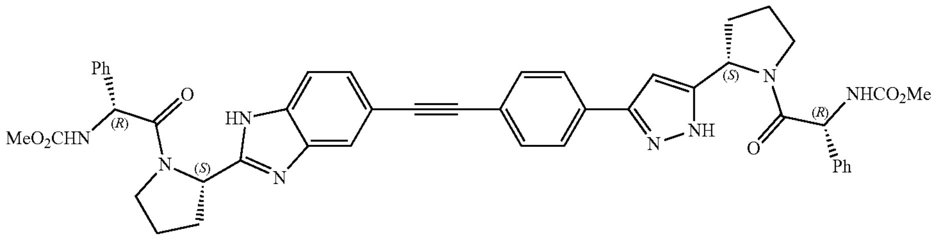
446
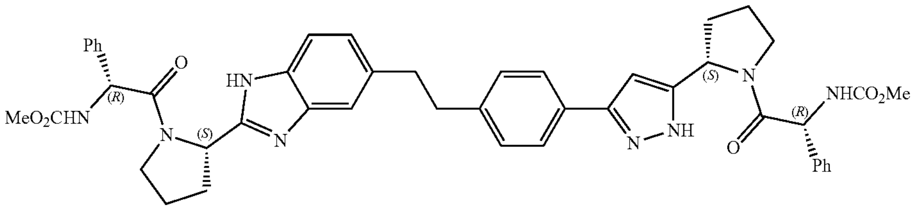

TABLE 9-continued
Compounds 441-545
447
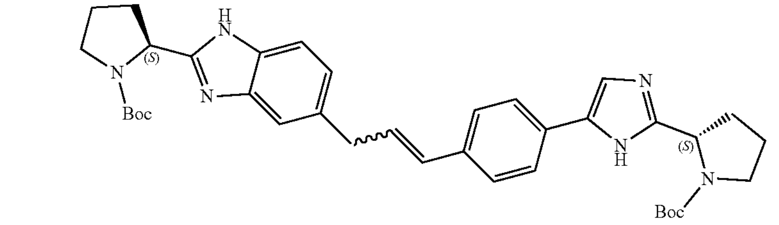
and/or
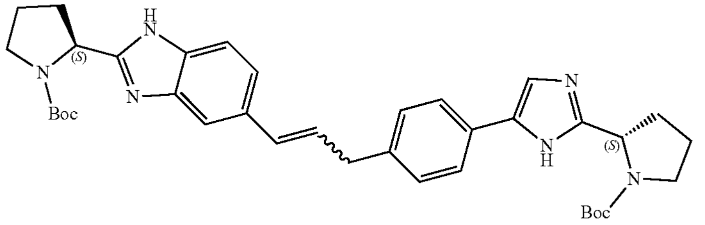
448
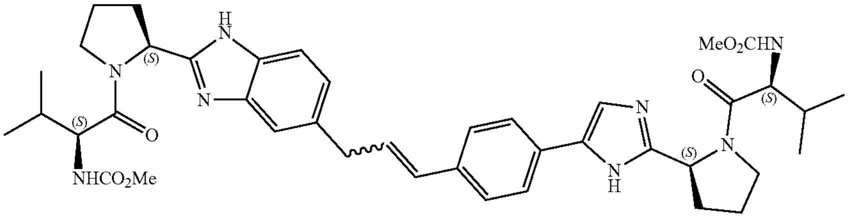
and/or
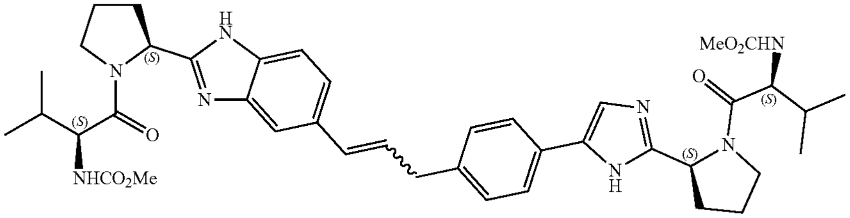
449
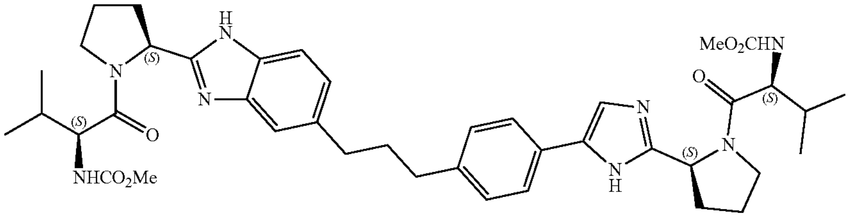
450
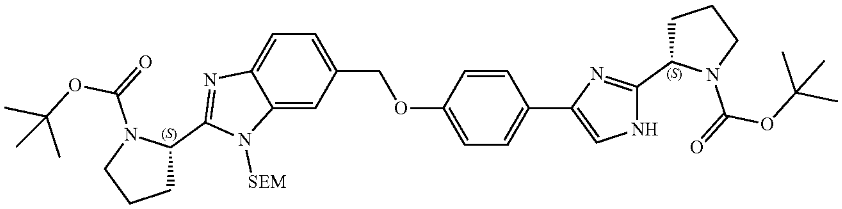
451
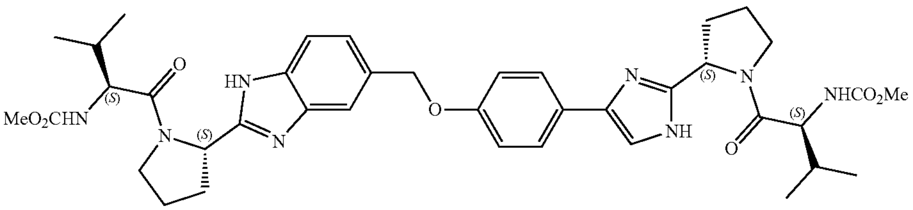

TABLE 9-continued
| Compounds 441-545 | |
|---|---|
| 452 | 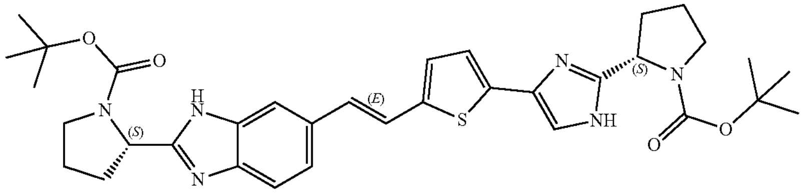 |
| 453 | 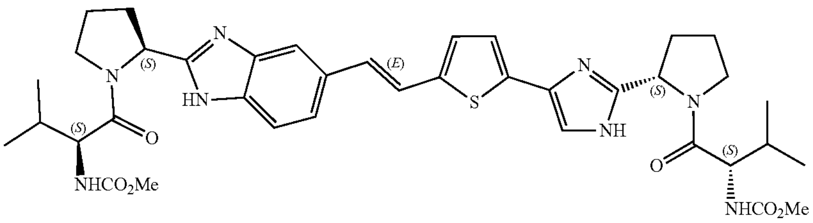 |
| 454 | 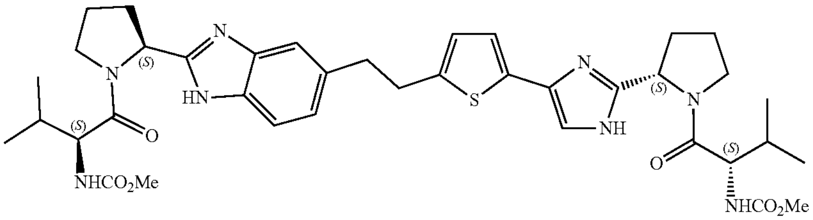 |
| 455 | 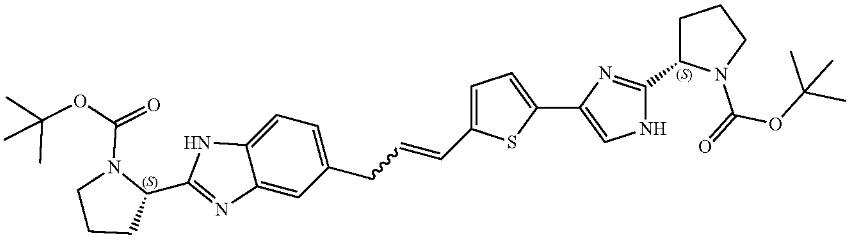 and/or 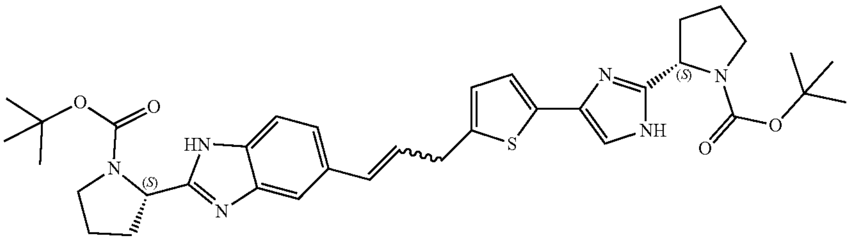 |
| 456 | 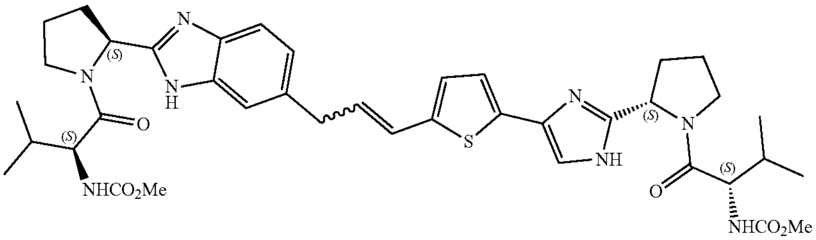 and/or |

TABLE 9-continued
Compounds 441-545
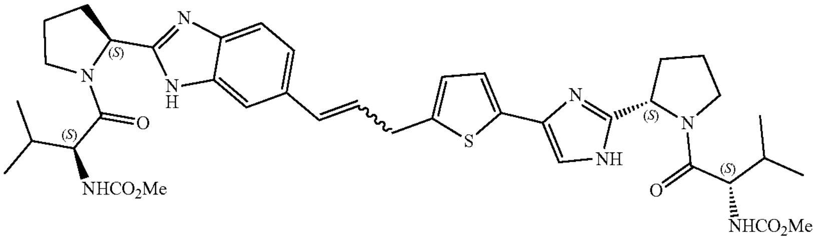
457
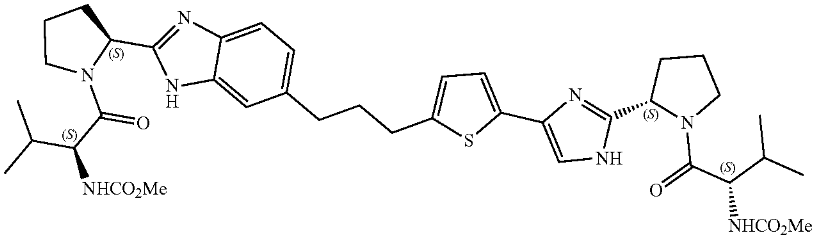
458
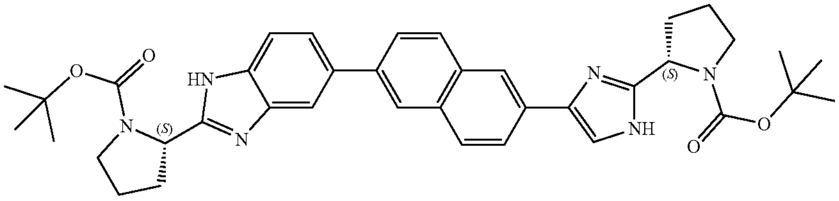
459
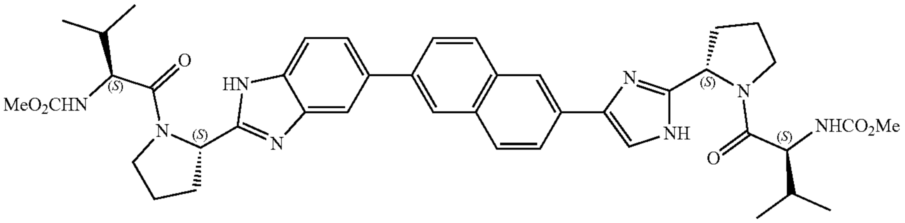
460
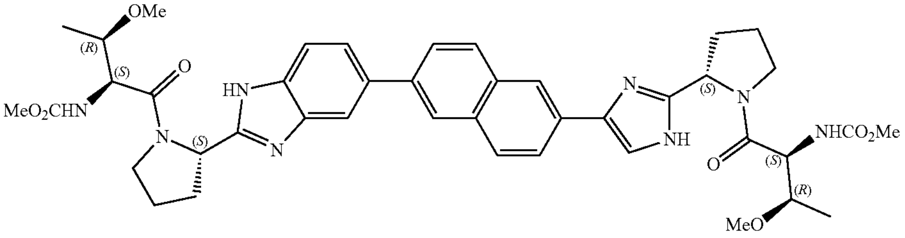
461
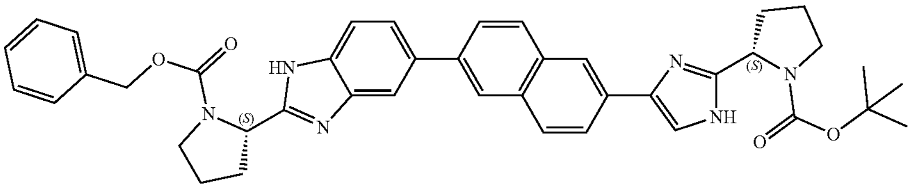
462
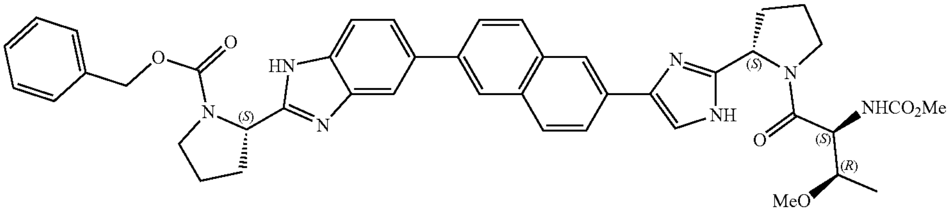

TABLE 9-continued
Compounds 441-545
463
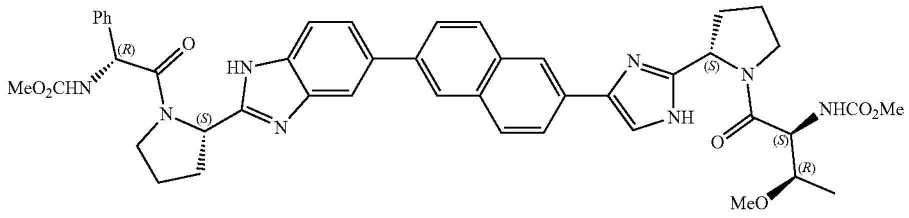
464
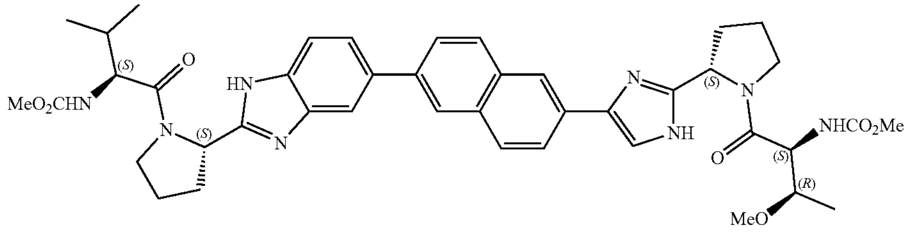
465
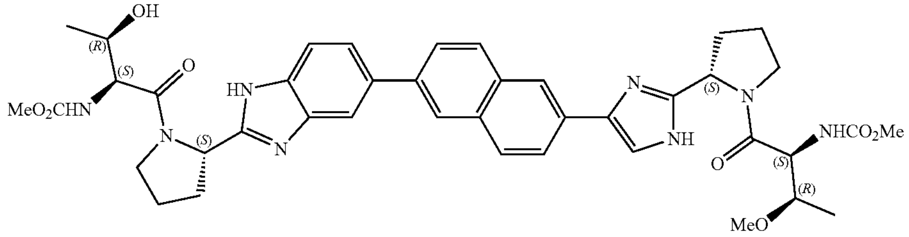
466
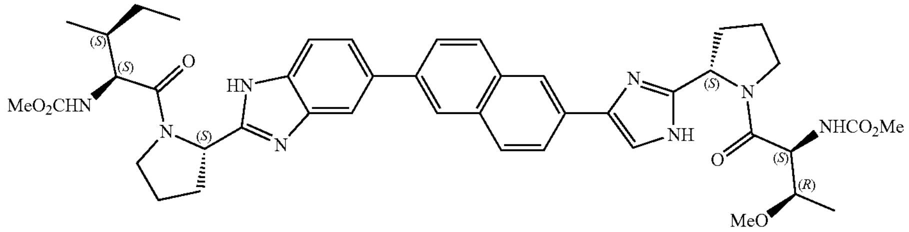
467
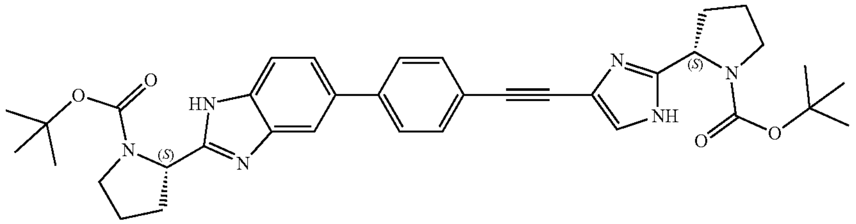
468
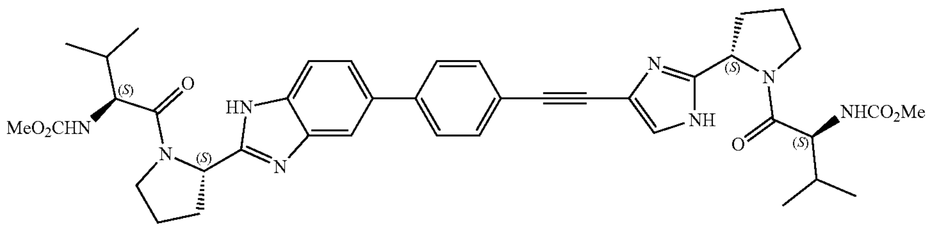

TABLE 9-continued
Compounds 441-545
469
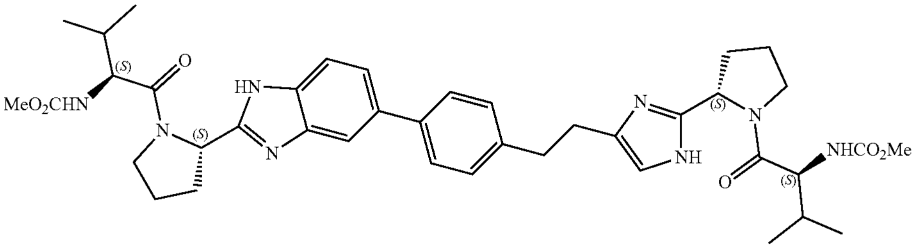
470
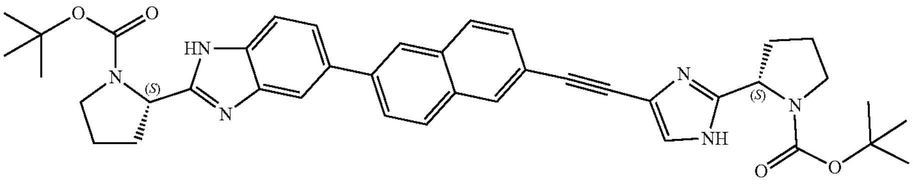
471
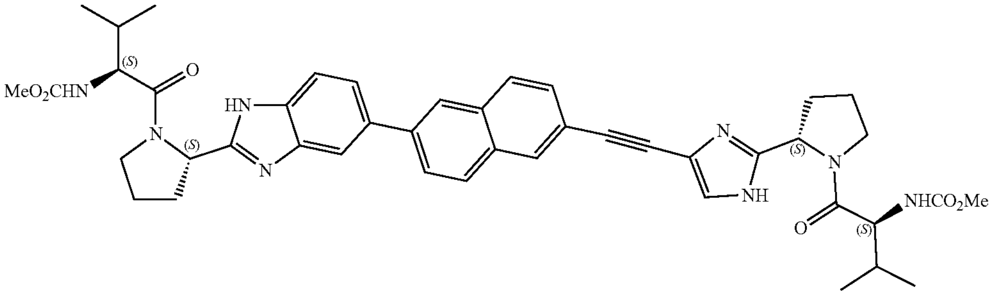
472
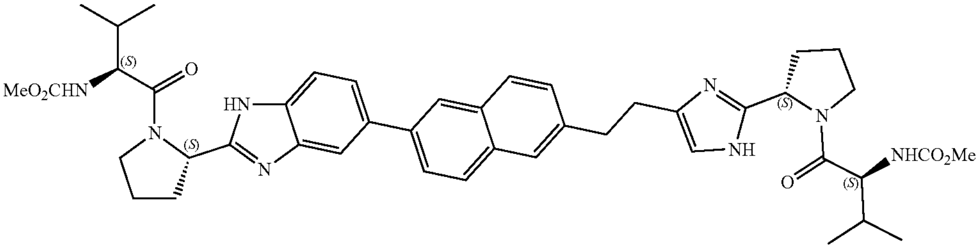
473
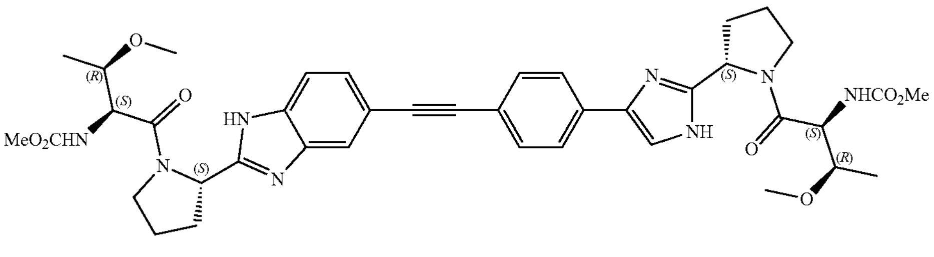
474
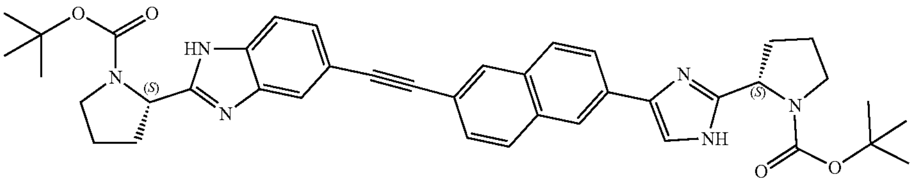

TABLE 9-continued
| Compounds 441-545 | |
|---|---|
| 475 | 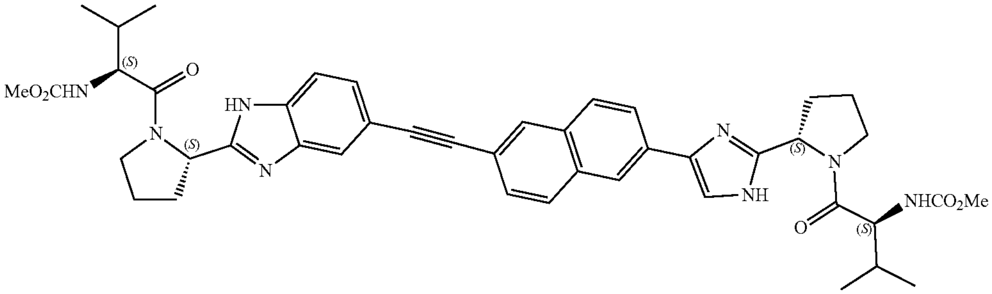 |
| 476 | 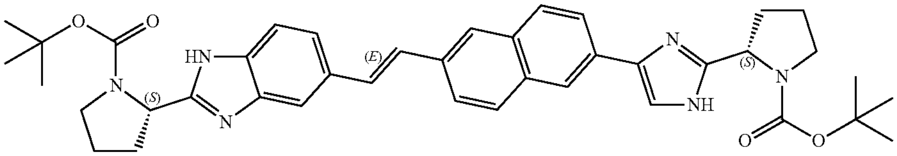 |
| 477 | 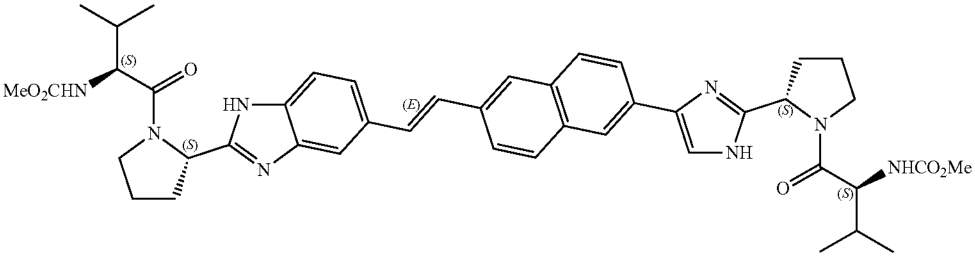 |
| 478 | 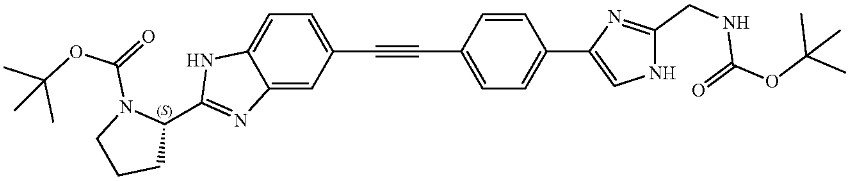 |
| 479 | 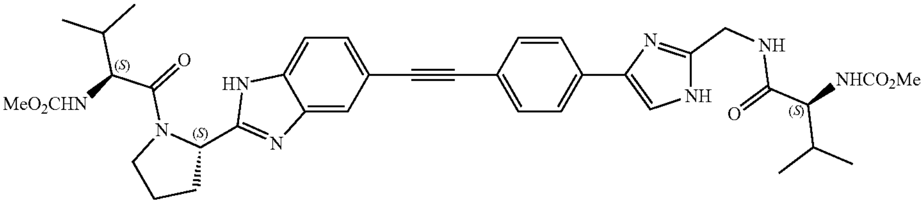 |
| 480 | 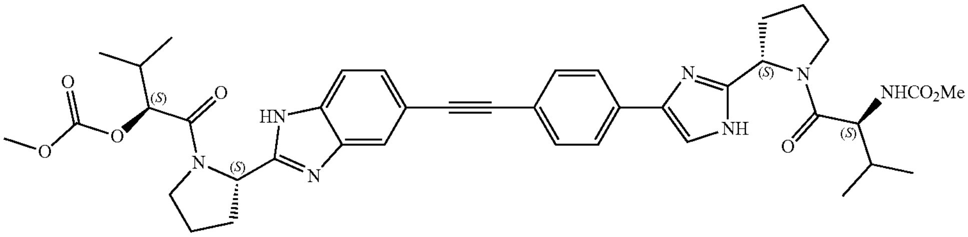 |

TABLE 9-continued
| Compounds 441-545 | |
|---|---|
| 481 | 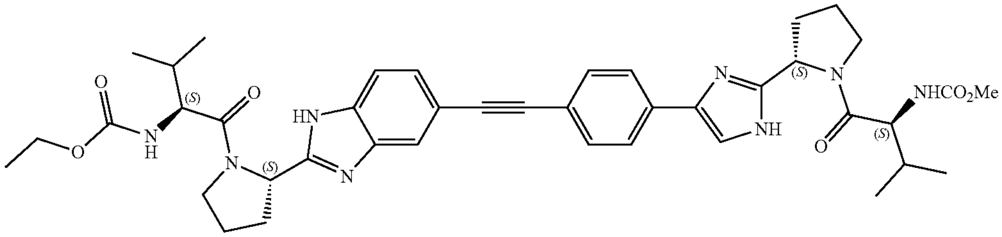 |
| 482 | 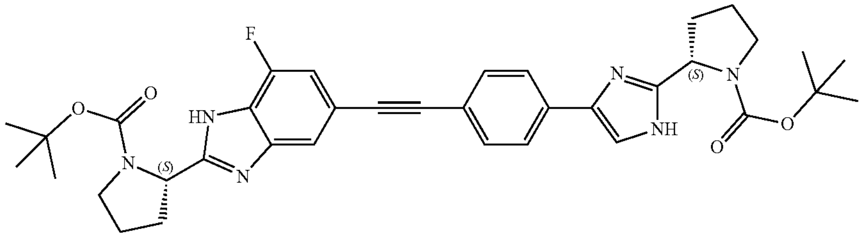 |
| 483 | 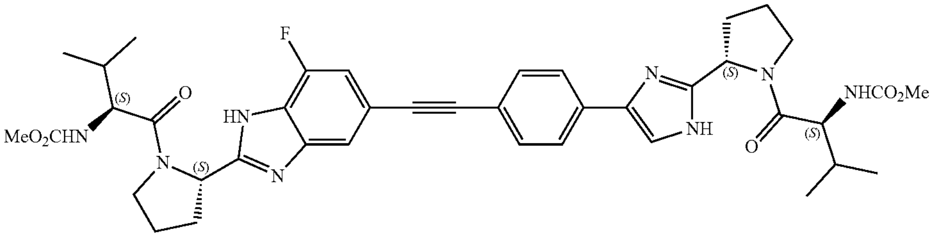 |
| 484 | 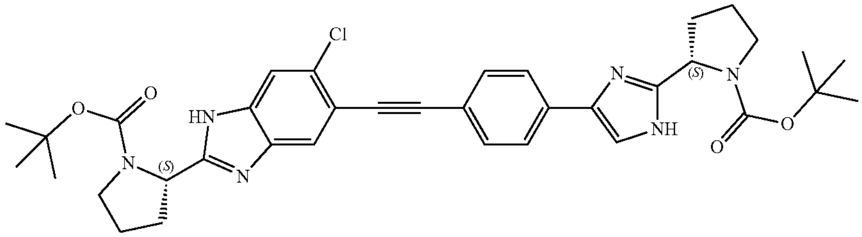 |
| 485 | 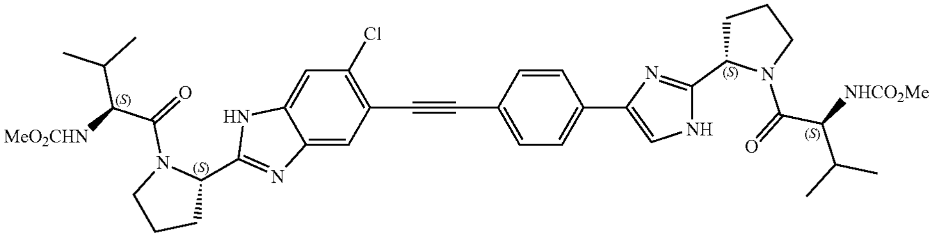 |
| 486 | 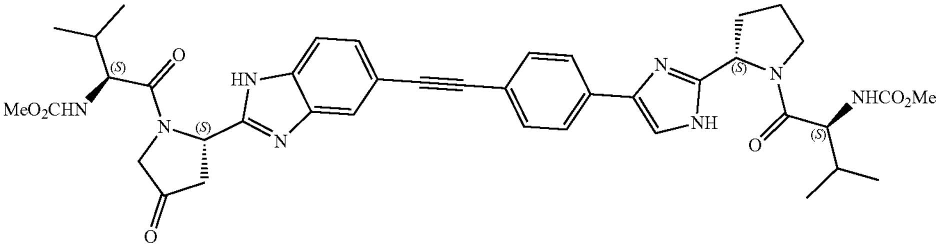 |

TABLE 9-continued
Compounds 441-545
487
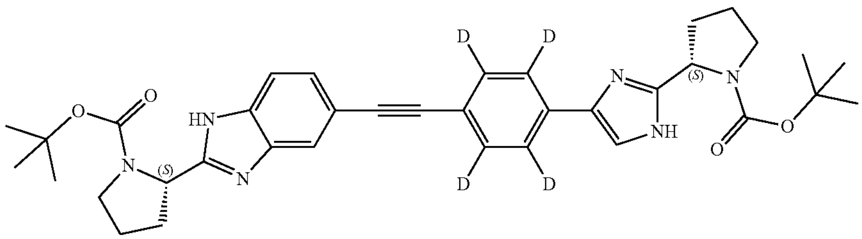
each D is deuterium
488
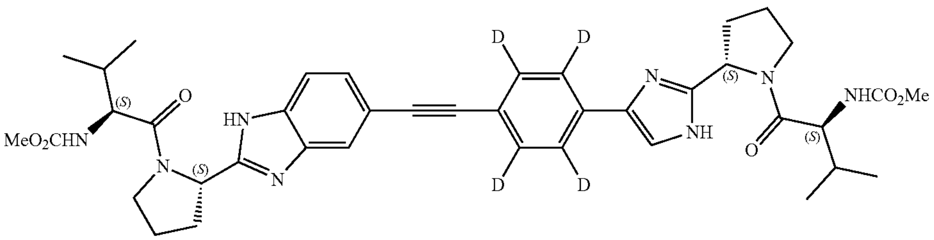
each D is deuterium
489
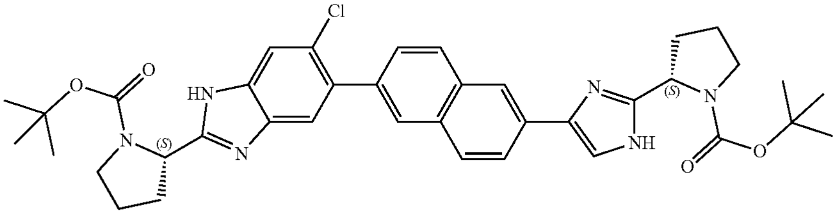
490
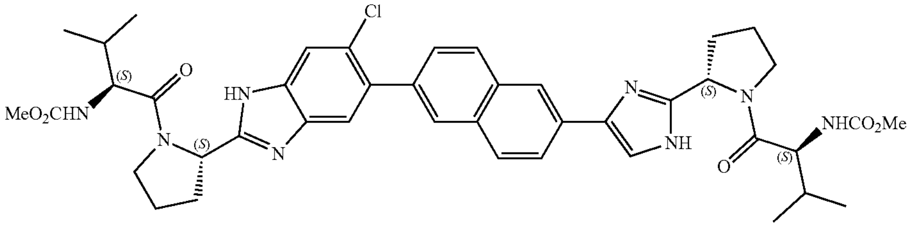
491
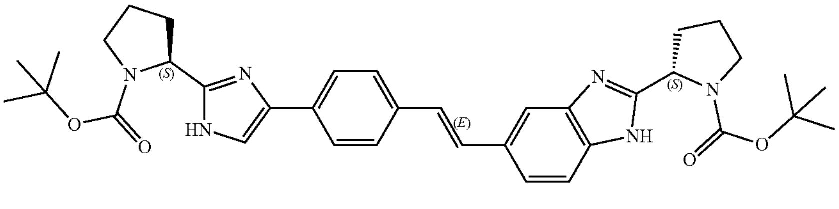
492
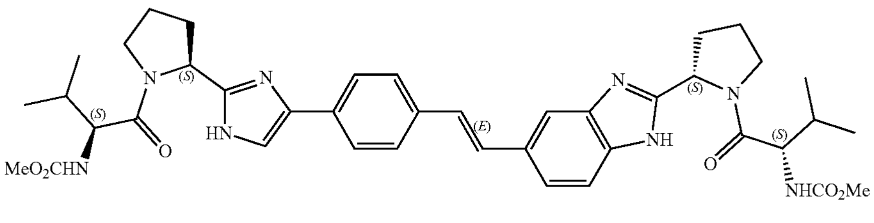

TABLE 9-continued
Compounds 441-545
493
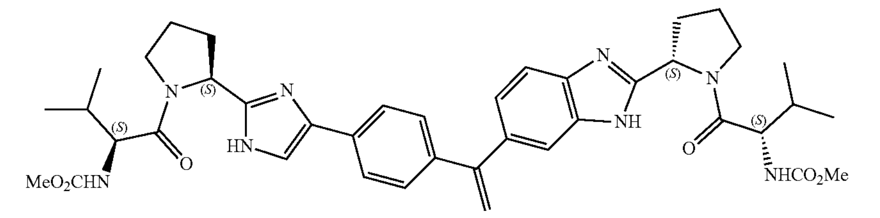
494
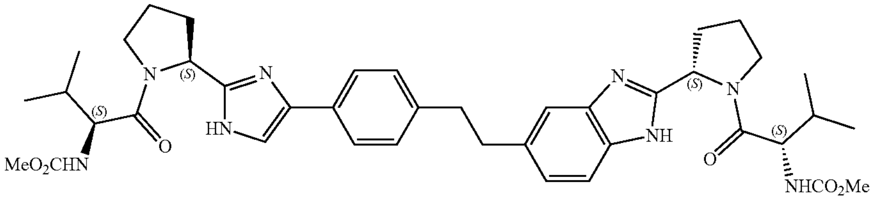
495
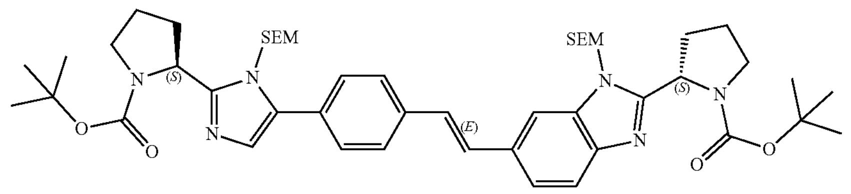
496
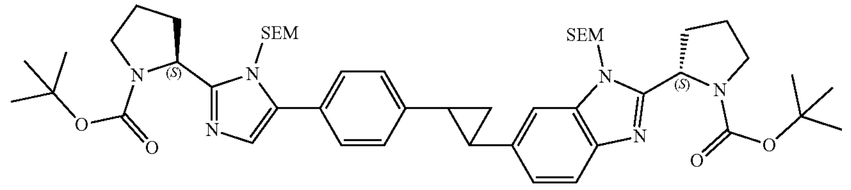
497-a
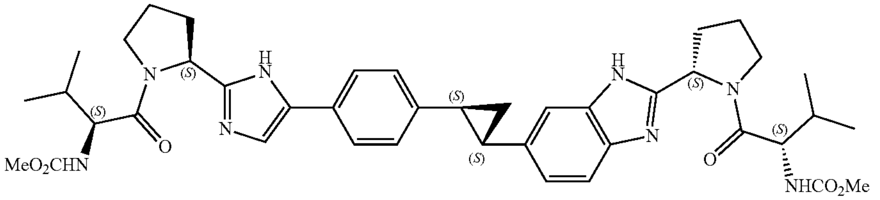
tentative
497-b
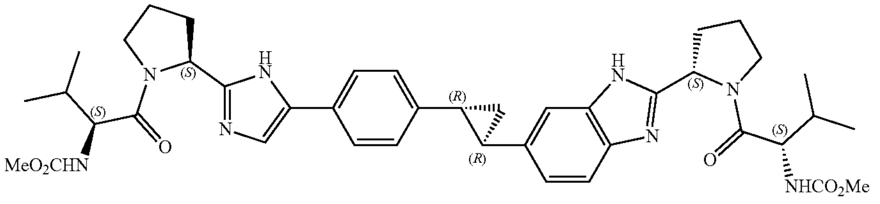
tentative
498
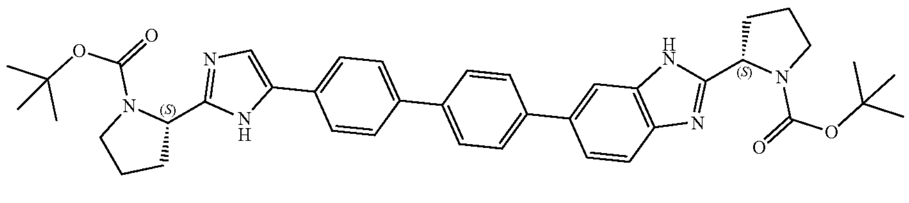

TABLE 9-continued
| Compounds 441-545 | |
|---|---|
| 499 | 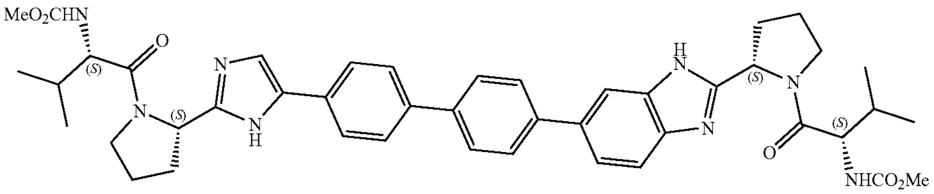 |
| 500 | 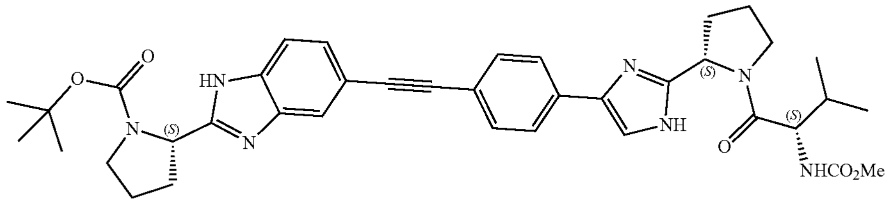 |
| 501 | 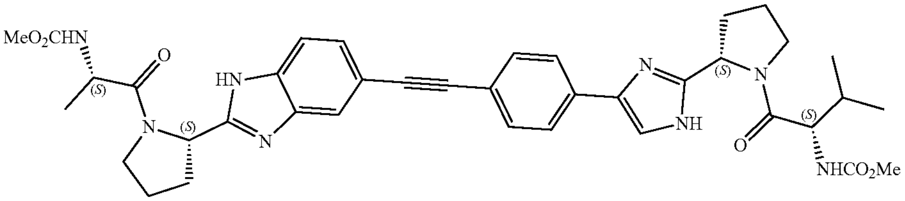 |
| 502 | 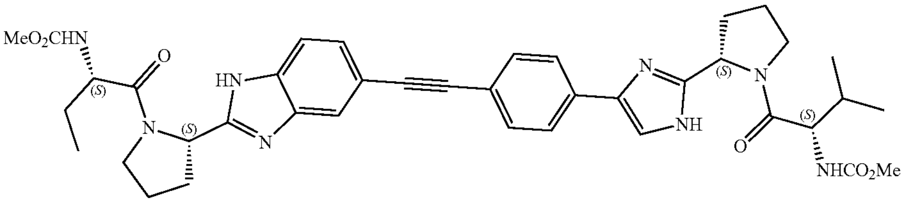 |
| 503 | 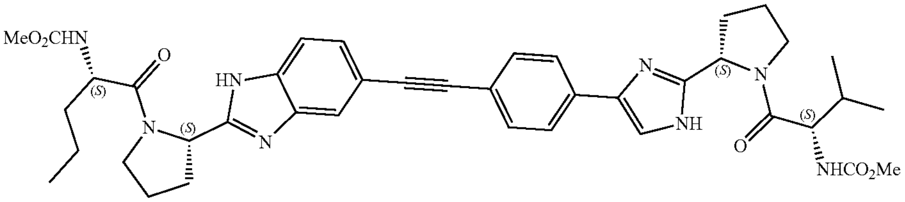 |
| 504 | 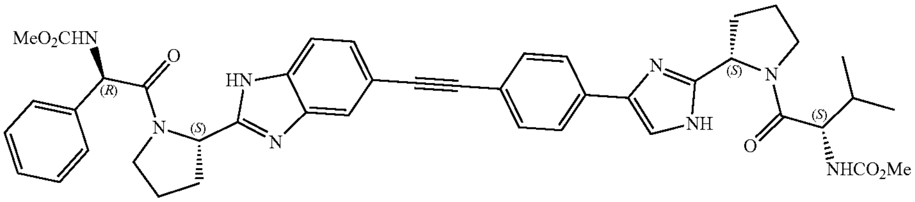 |
| 505 | 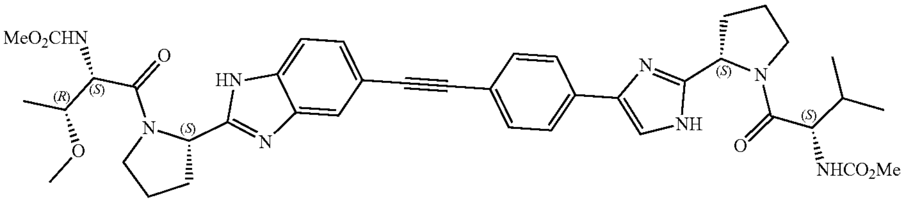 |

TABLE 9-continued
| Compounds 441-545 |
|---|
506
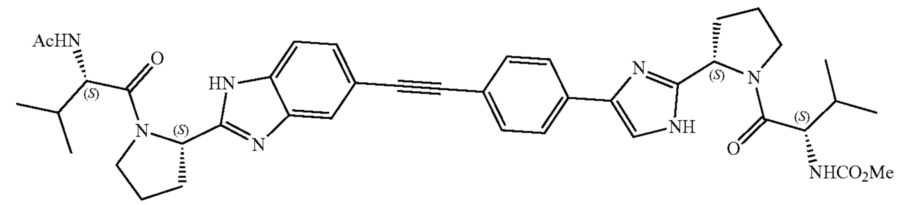
507
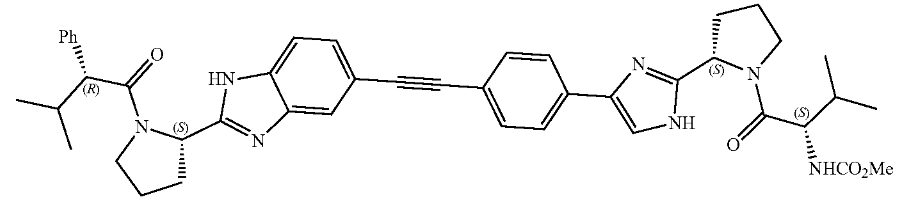
508
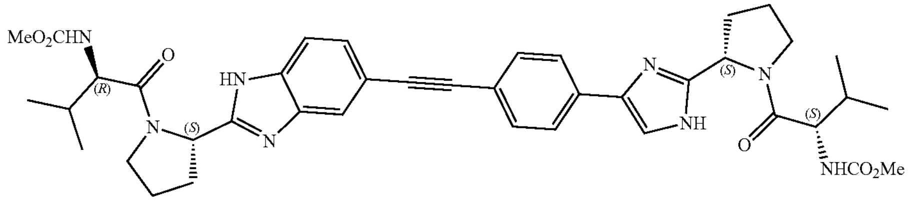
509
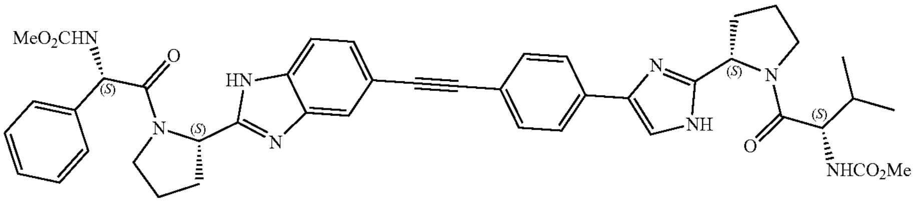
510
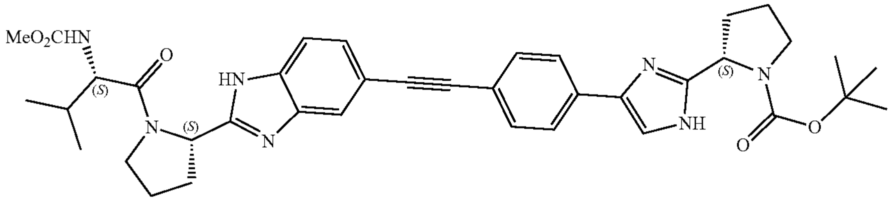
511
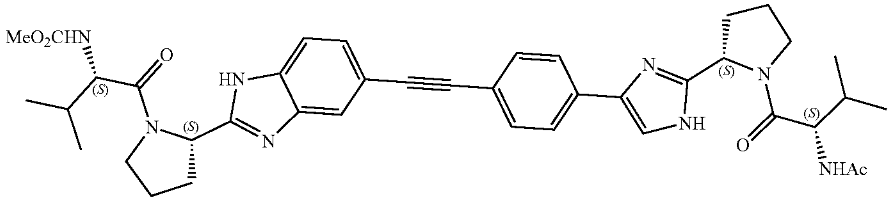
512
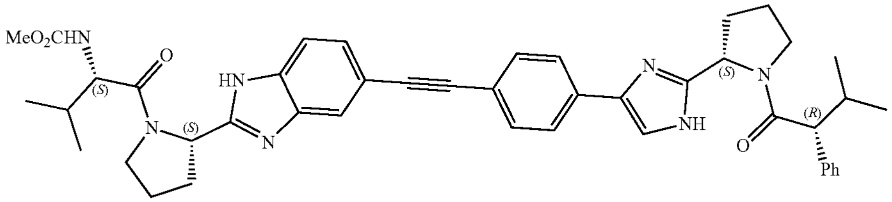

TABLE 9-continued
| Compounds 441-545 | |
|---|---|
| 513 | 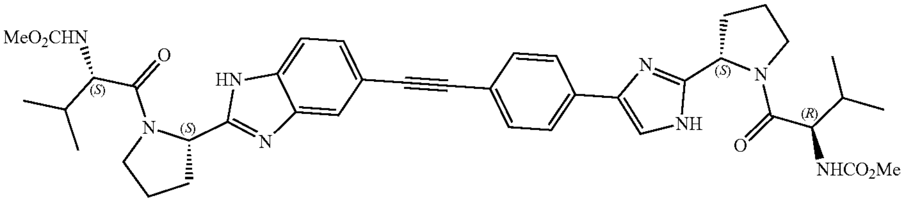 |
| 514 | 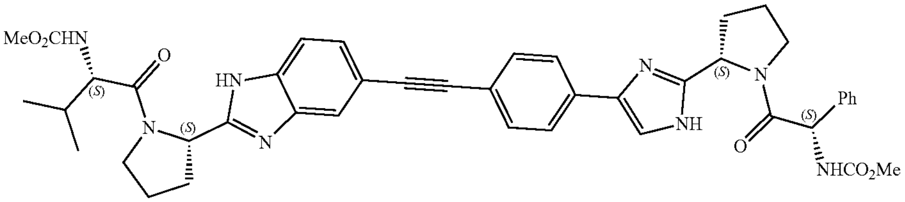 |
| 515 | 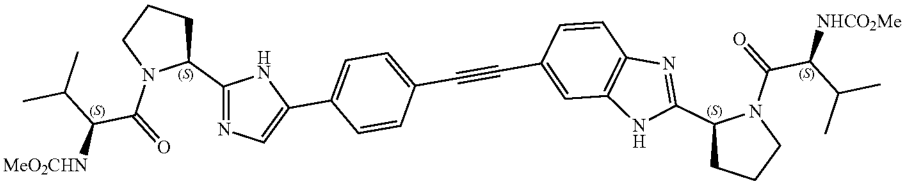 |
| 516 | 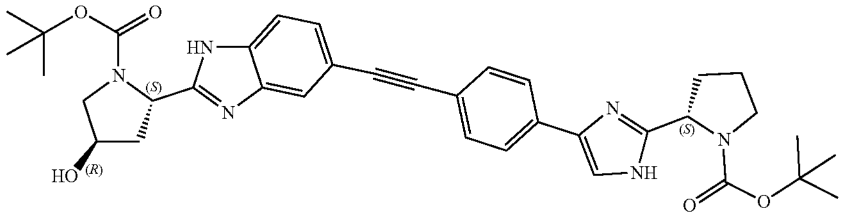 |
| 517 | 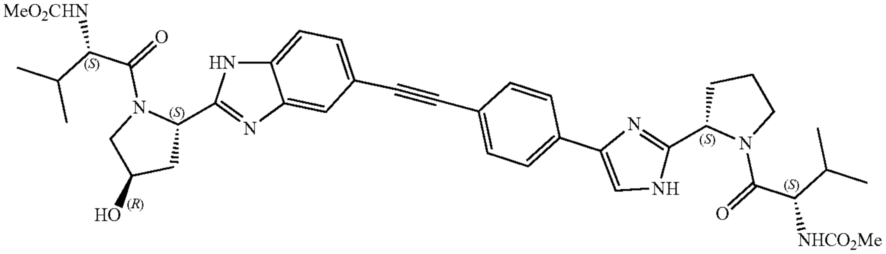 |
| 518 | 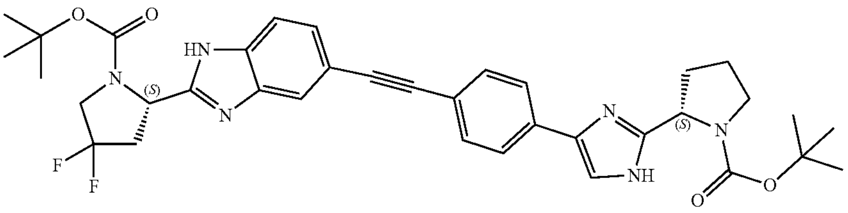 |
| 519 | 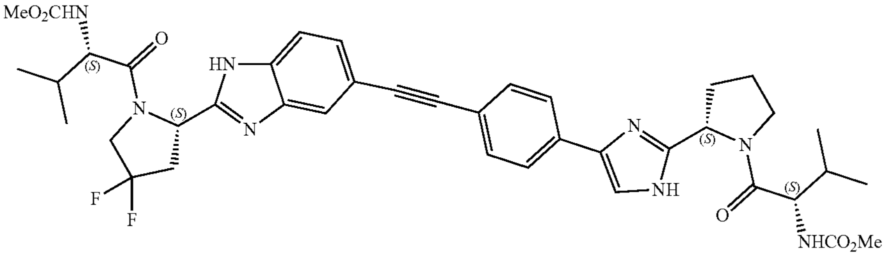 |

TABLE 9-continued
| Compounds 441-545 | |
|---|---|
| 520 | 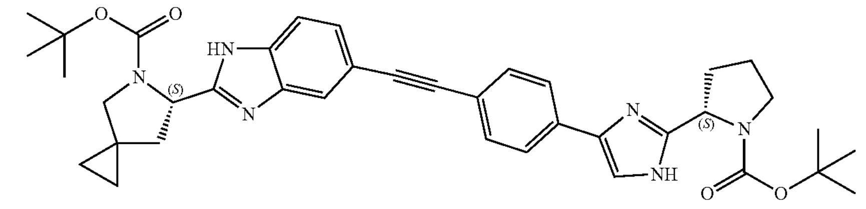 |
| 521 | 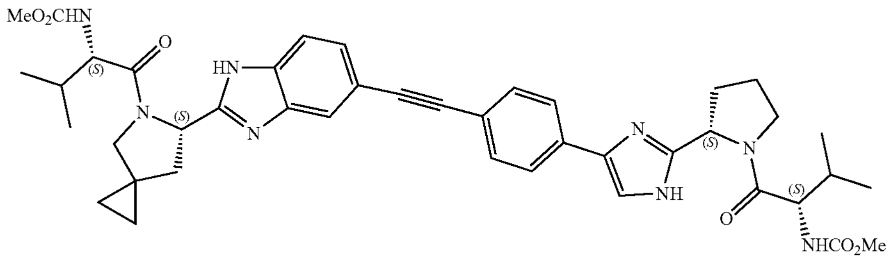 |
| 522 | 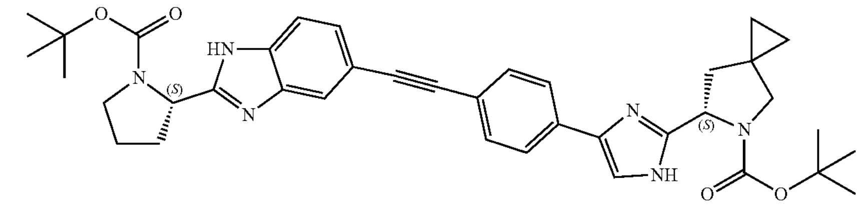 |
| 523 | 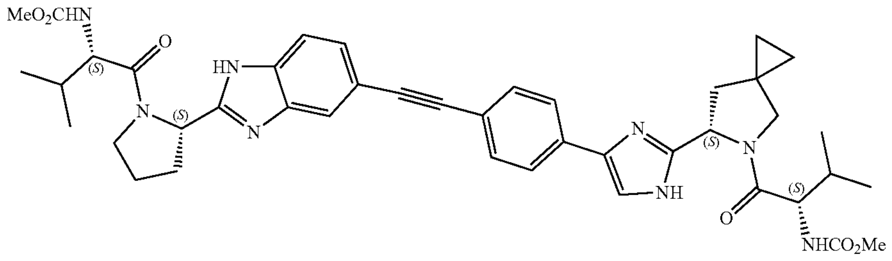 |
| 524 | 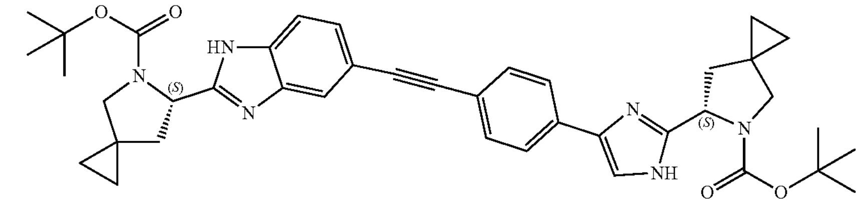 |
| 525 | 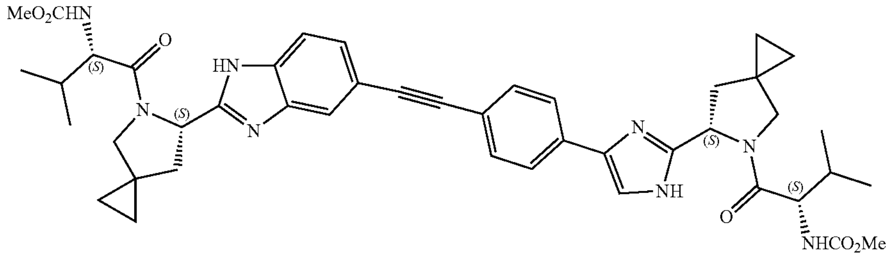 |

TABLE 9-continued
| Compounds 441-545 |
|---|
526
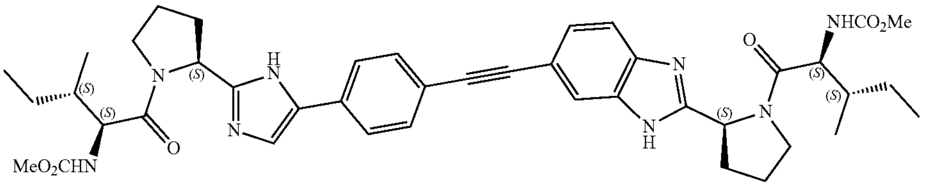
527
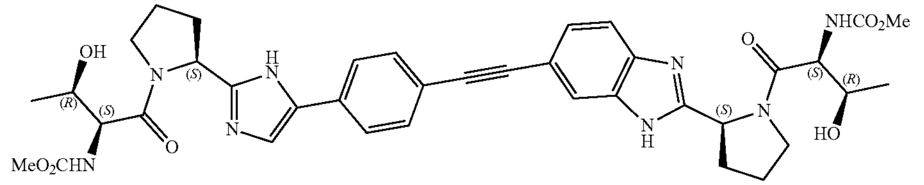
528
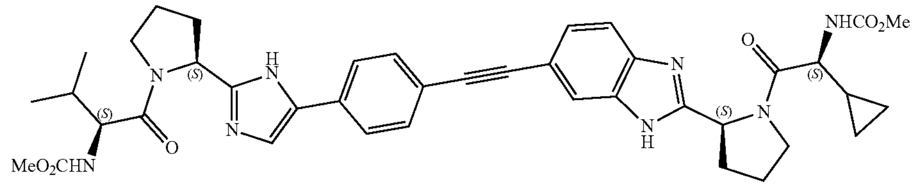
529
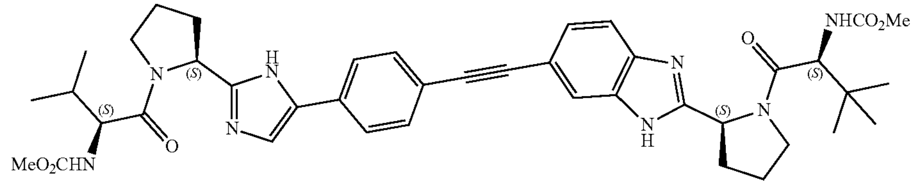
530
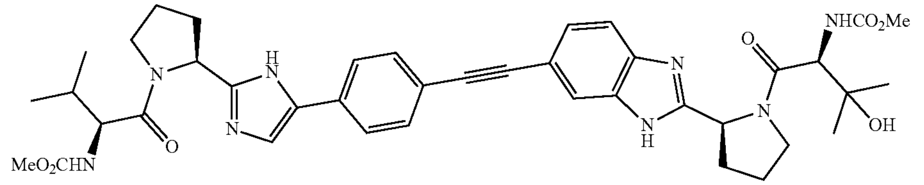
531
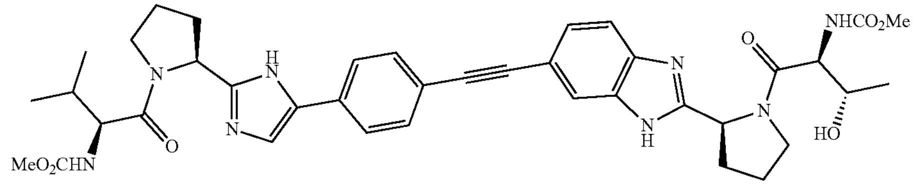
532
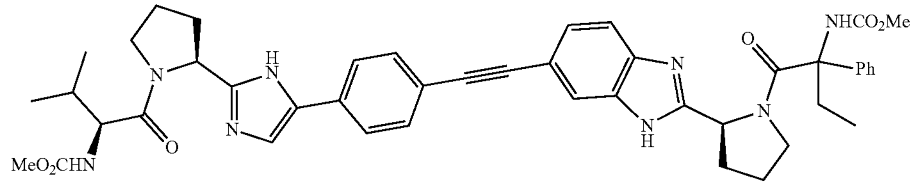
533
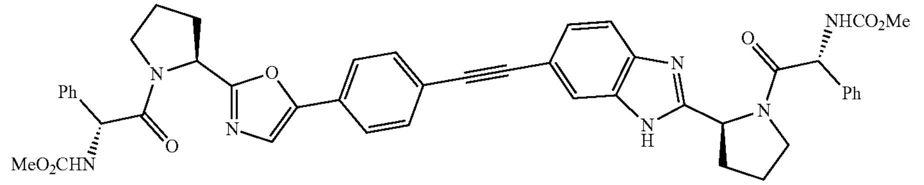

TABLE 9-continued
| Compounds 441-545 | |
|---|---|
| 534 | 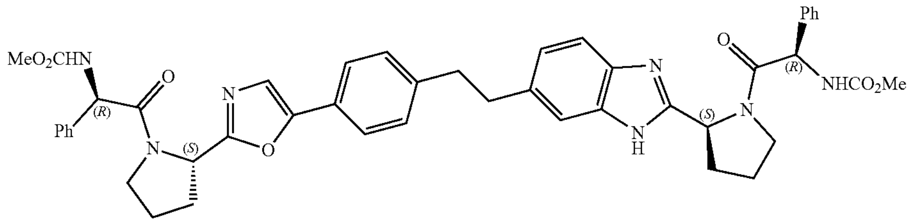 |
| 535 | 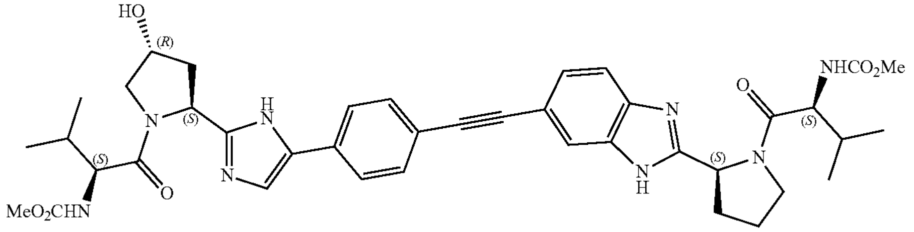 |
| 536 | 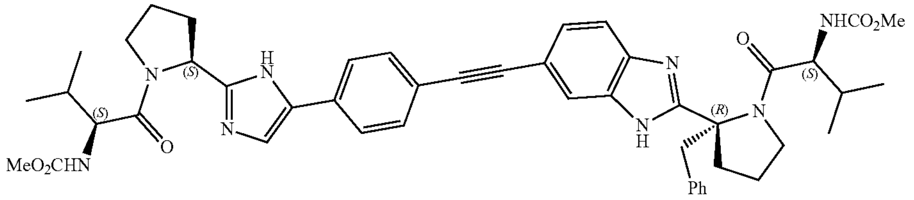 |
| 537 | 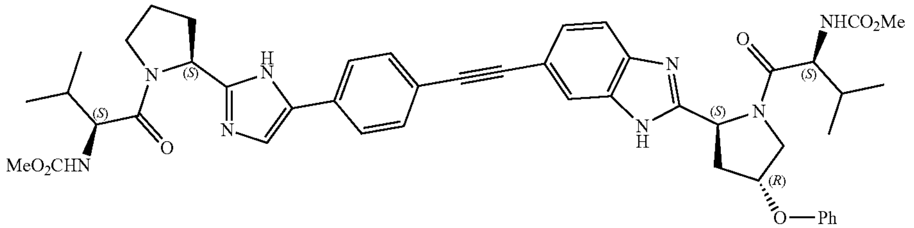 |
| 538 | 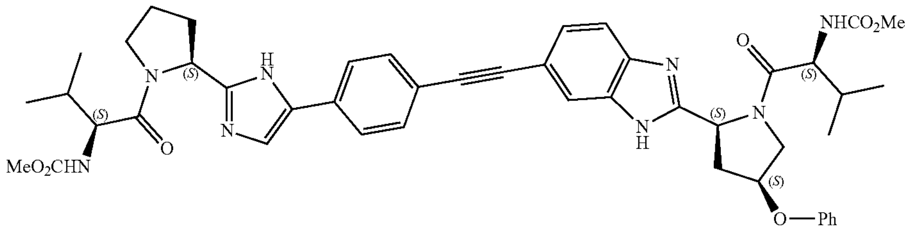 |
| 539 | 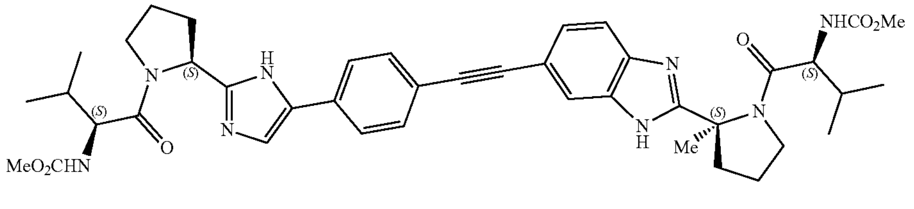 |
| 540 | 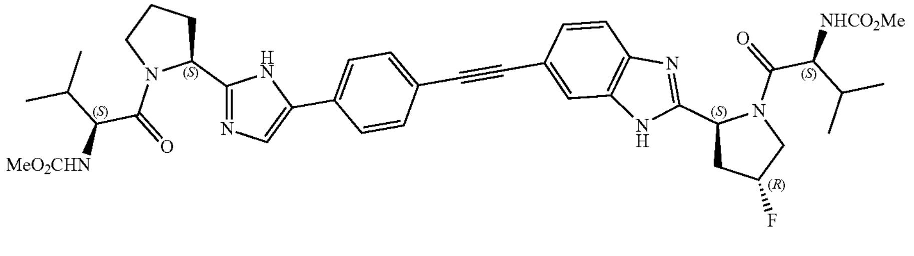 |

TABLE 9-continued
| Compounds 441-545 | |
|---|---|
| 541 | 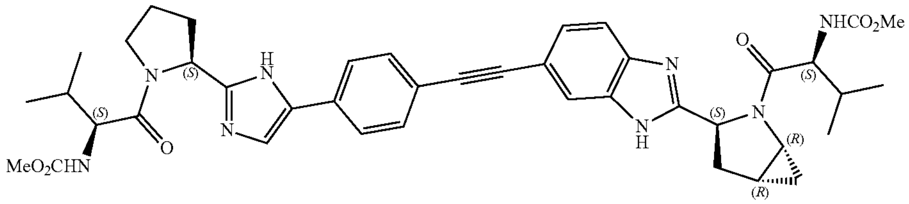 |
| 542 | 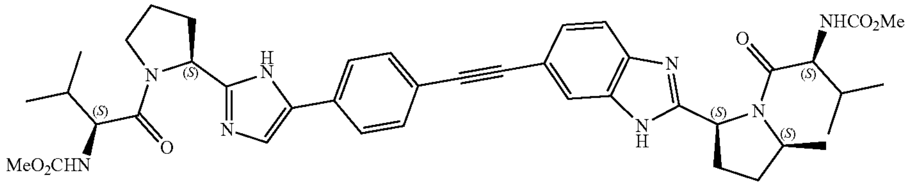 |
| 543 | 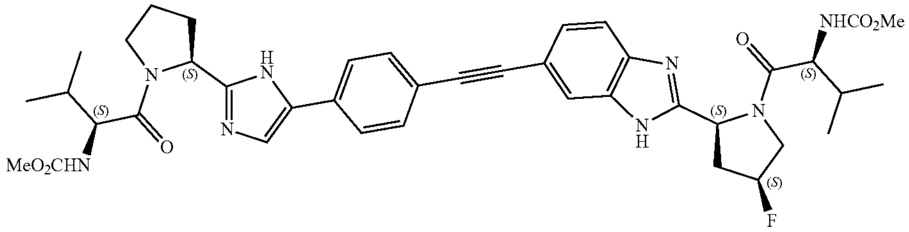 |
| 544 | 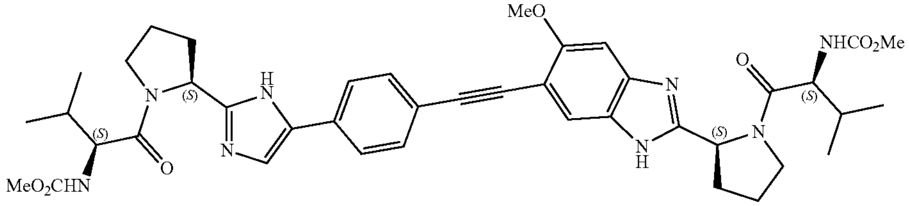 |
| 545 | 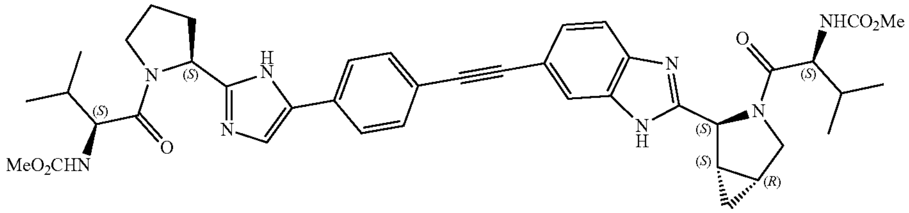 |
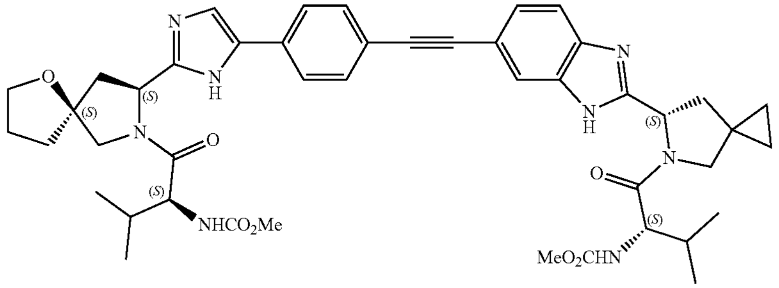

TABLE 9-continued
| Compounds 441-545 |
| --- |
| 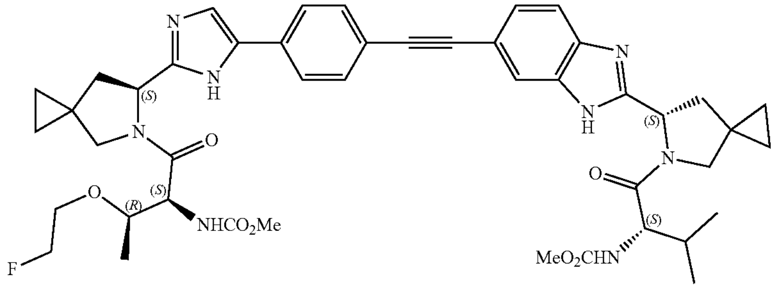 |
| 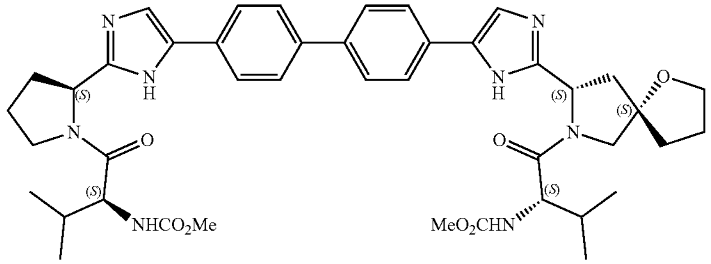 |
| 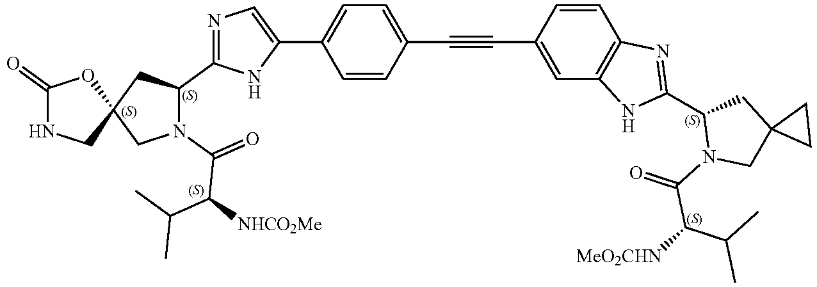 |
| 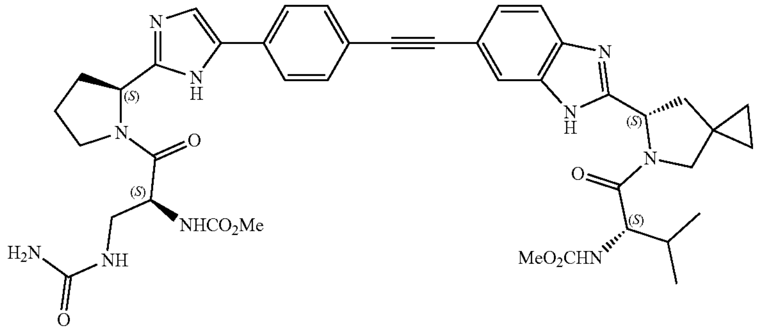 |
| 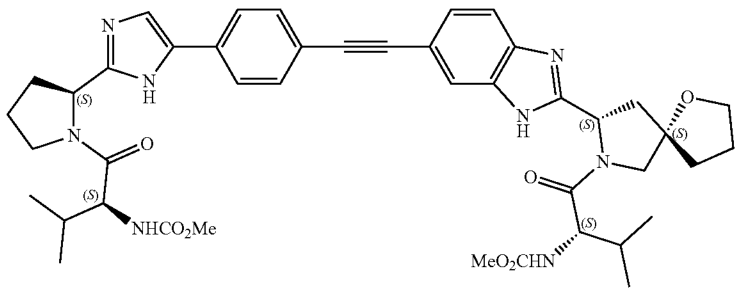 |

TABLE 9-continued
| Compounds 441-545 |
|---|
| 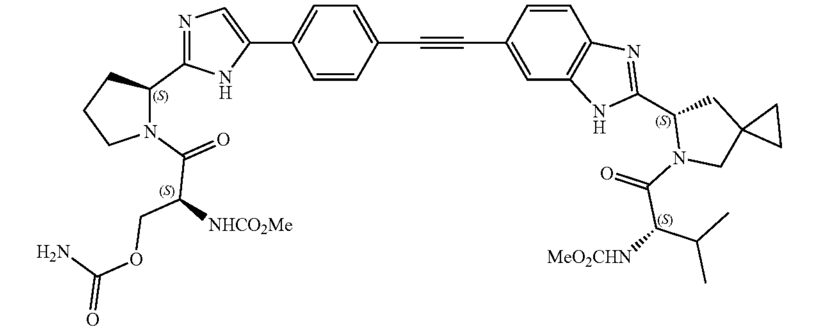 |
| 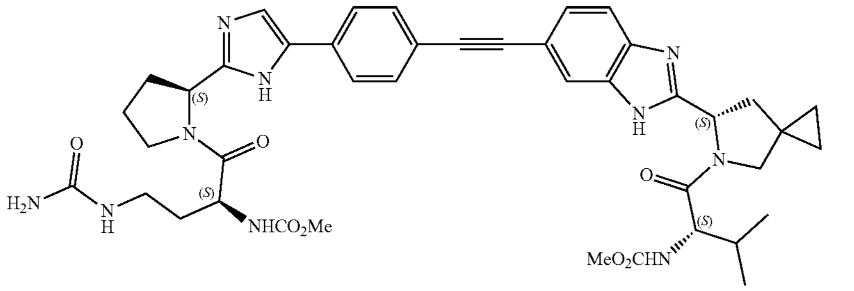 |
| 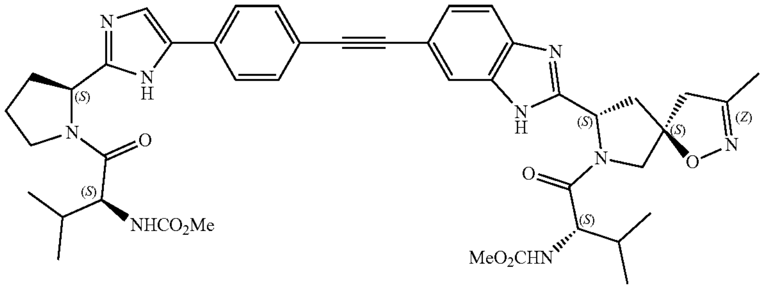 |
| 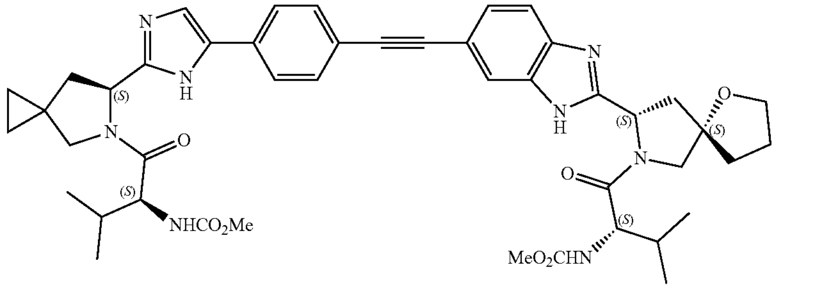 |
| 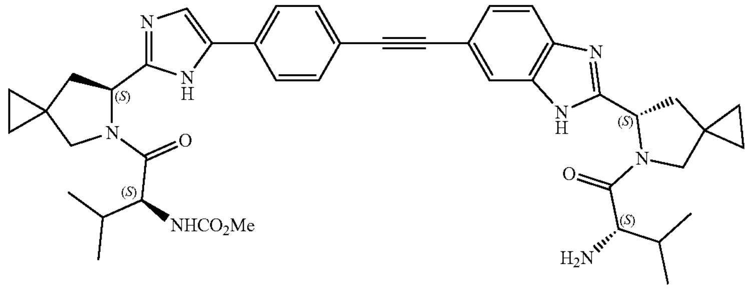 |

TABLE 9-continued
Compounds 441-545
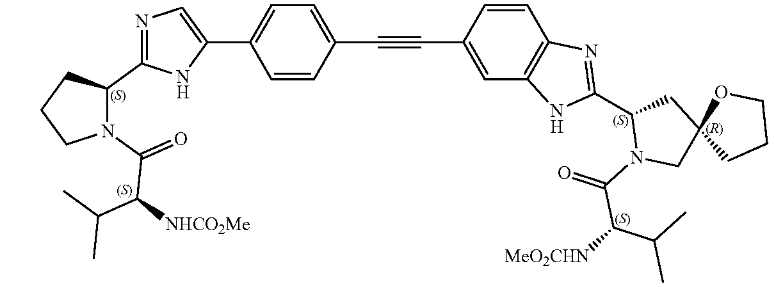
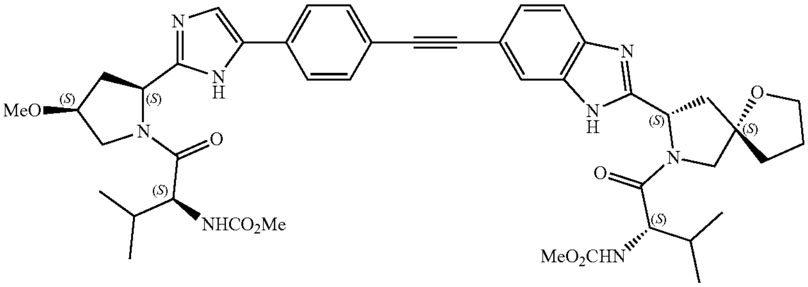
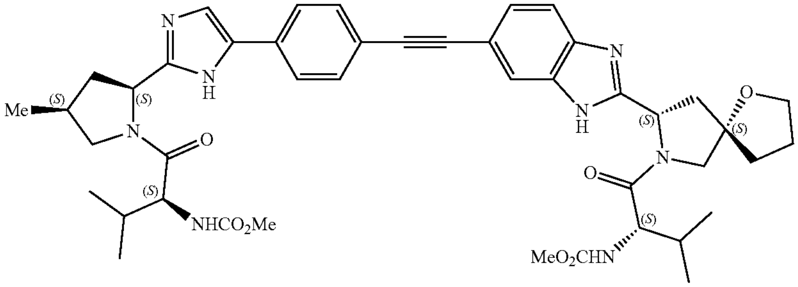
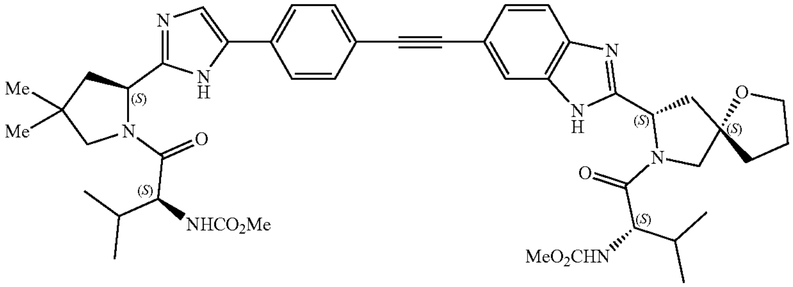
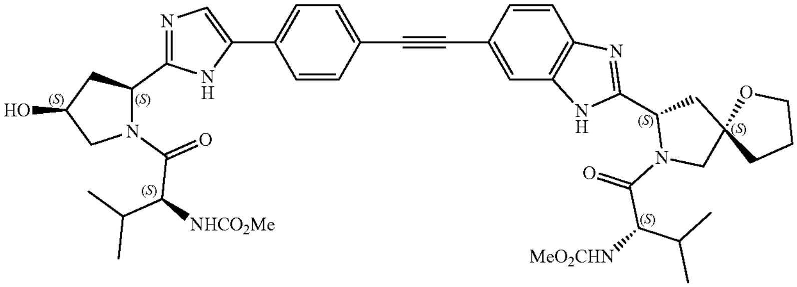

TABLE 9-continued
| Compounds 441-545 |
| --- |
| 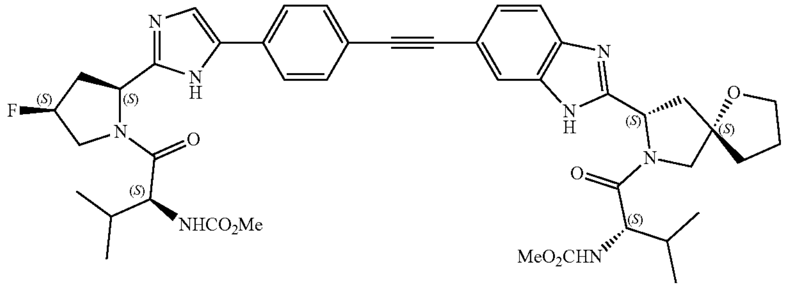 |
| 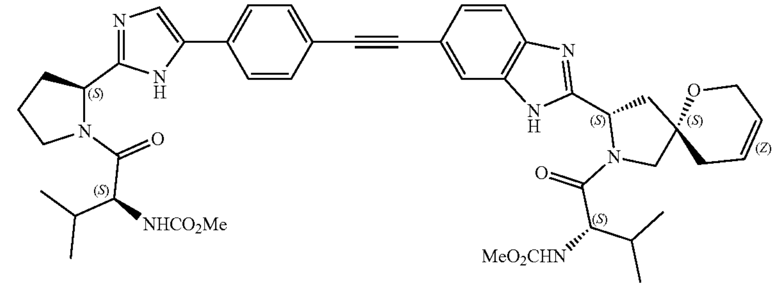 |
| 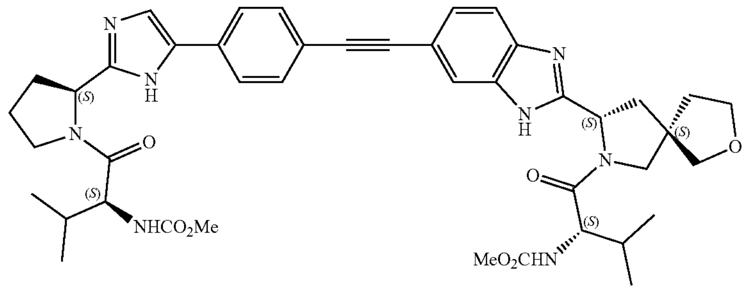 |
| 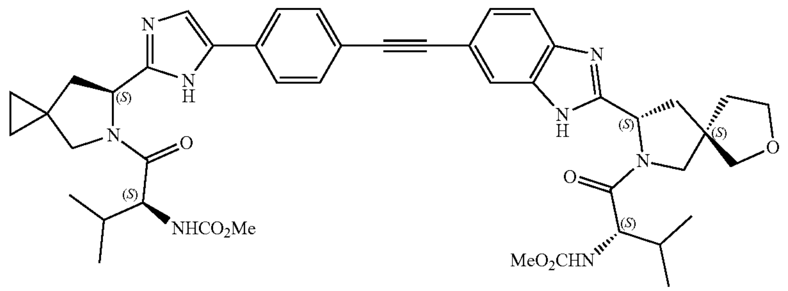 |
| 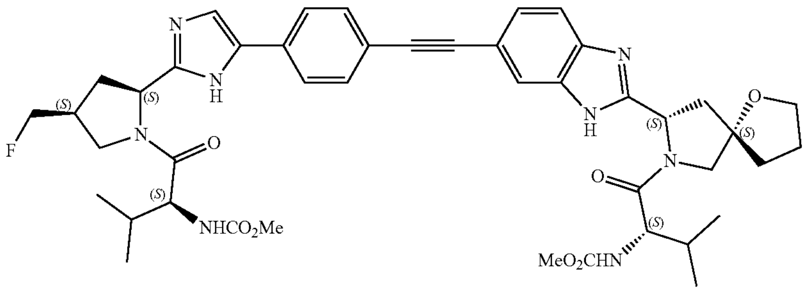 |

TABLE 9-continued
| Compounds 441-545 |
| --- |
| 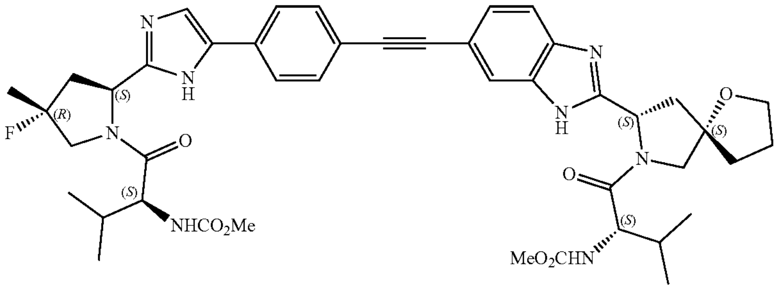 |
| 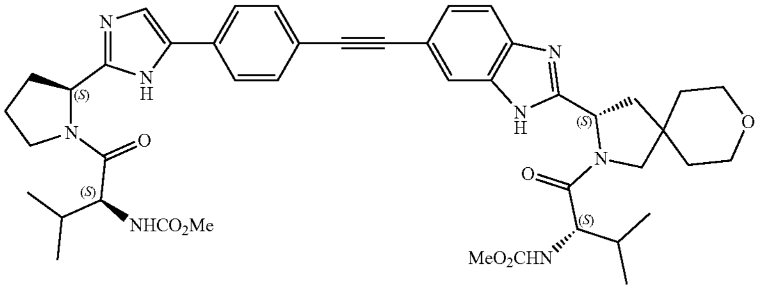 |
| 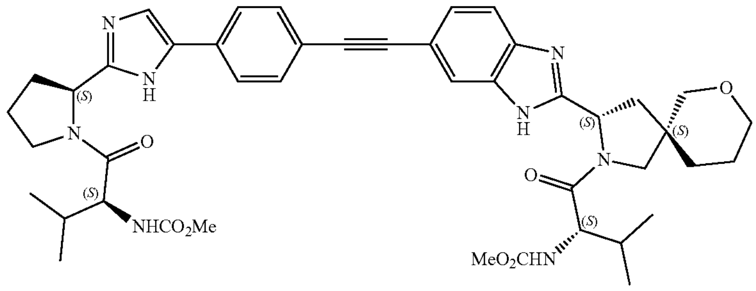 |
| 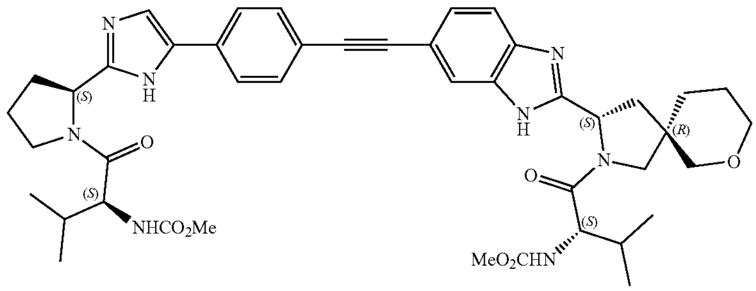 |
| 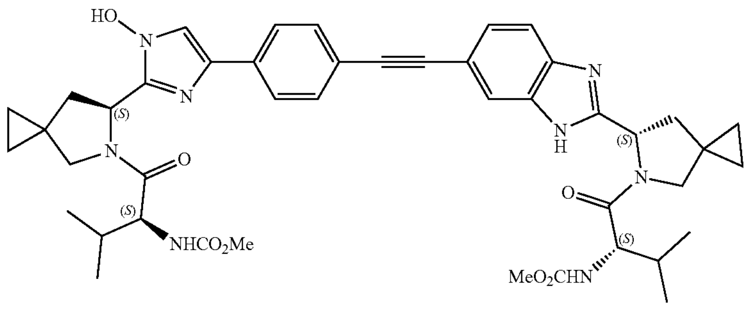 |

TABLE 9-continued
Compounds 441-545
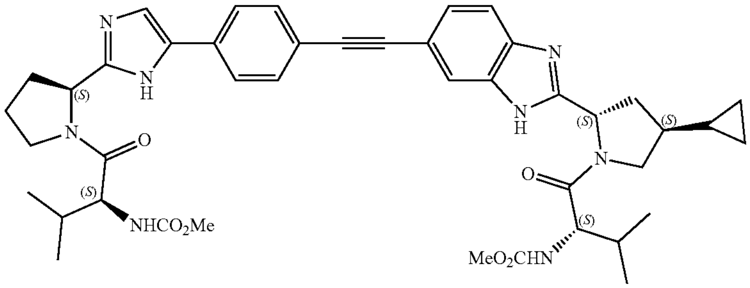
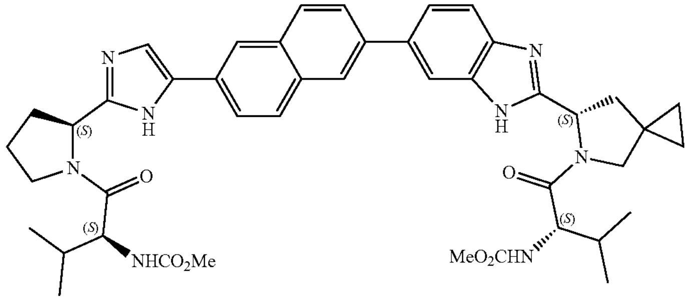
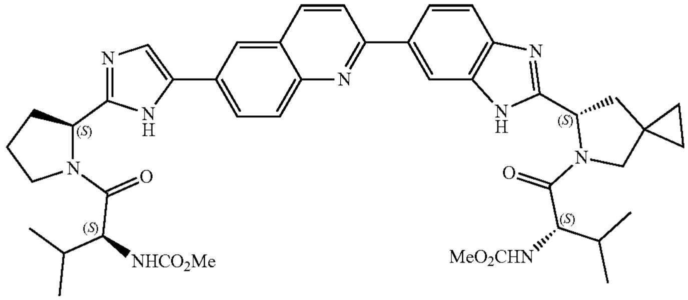
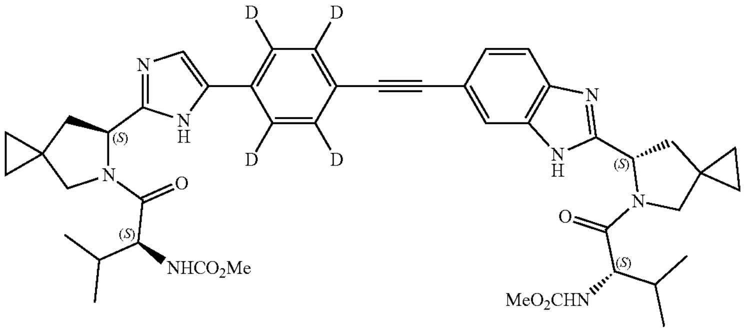
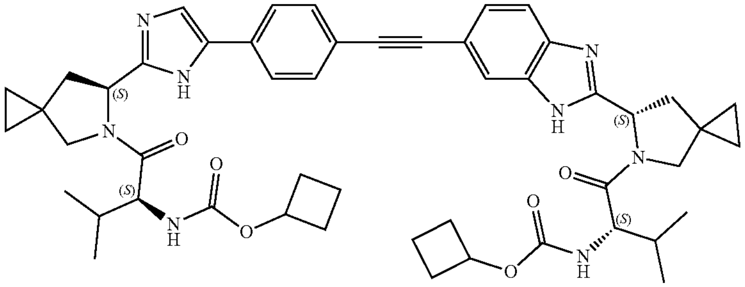

TABLE 9-continued
| Compounds 441-545 |
| --- |
| 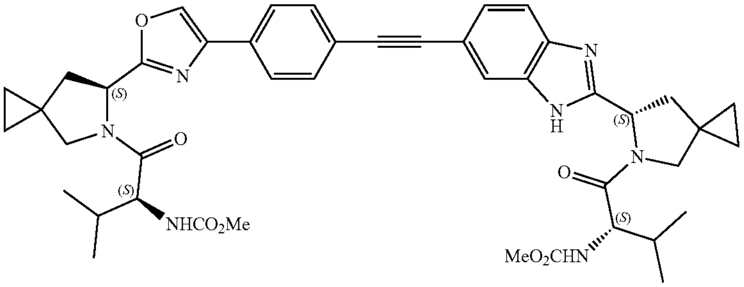 |
| 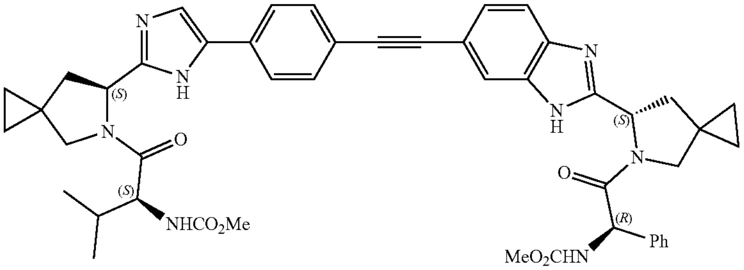 |
| 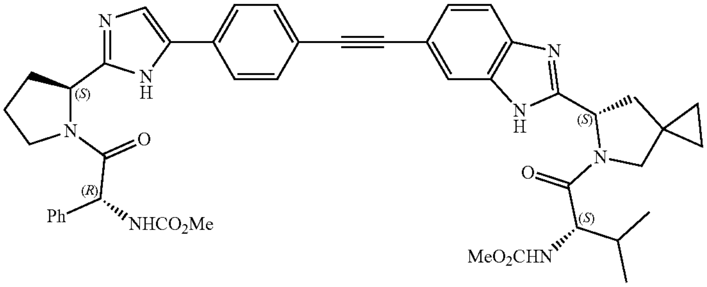 |
| 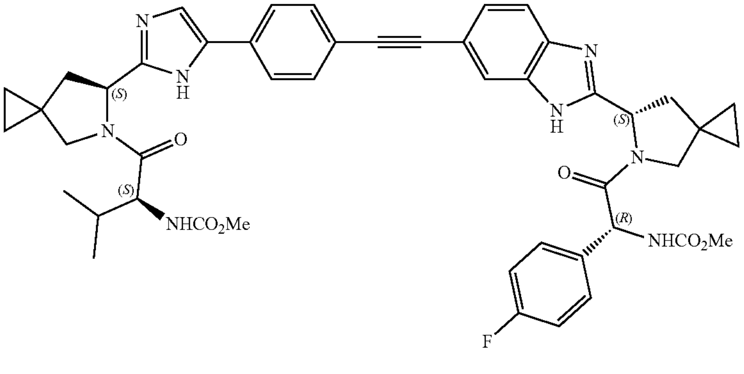 |
| 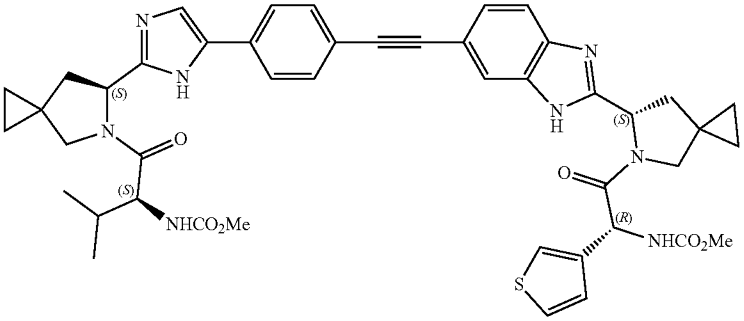 |

TABLE 9-continued
Compounds 441-545
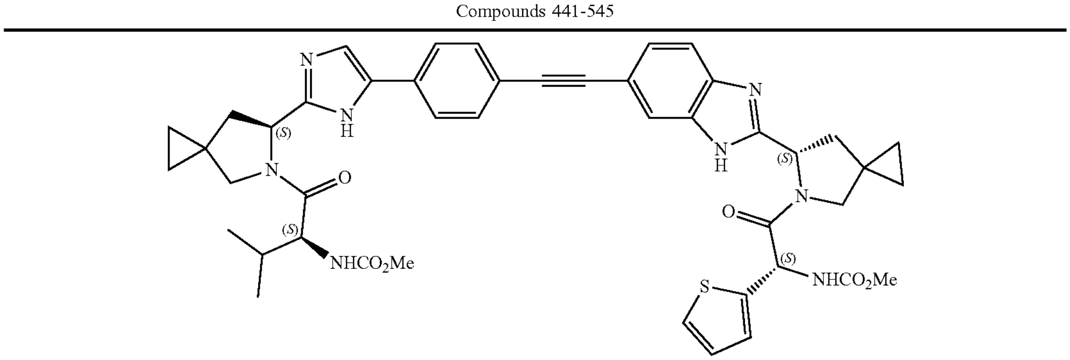
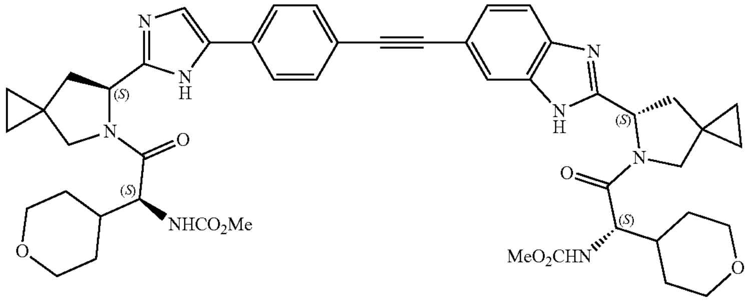
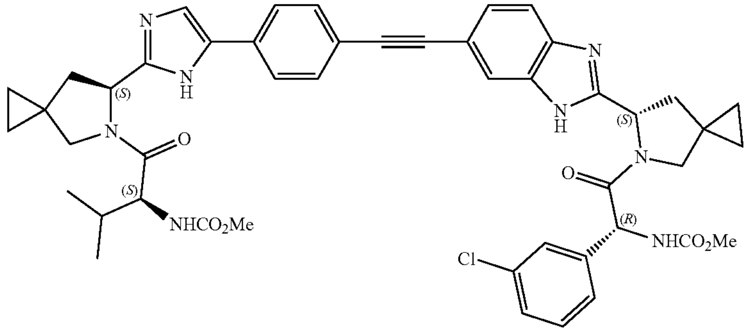
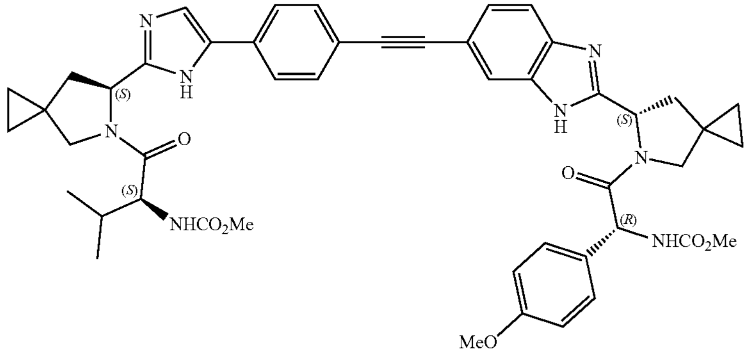
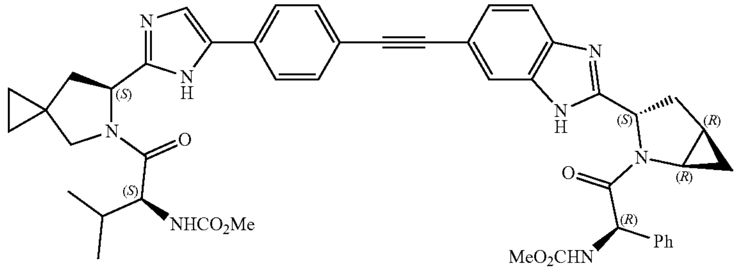

TABLE 9-continued
Compounds 441-545
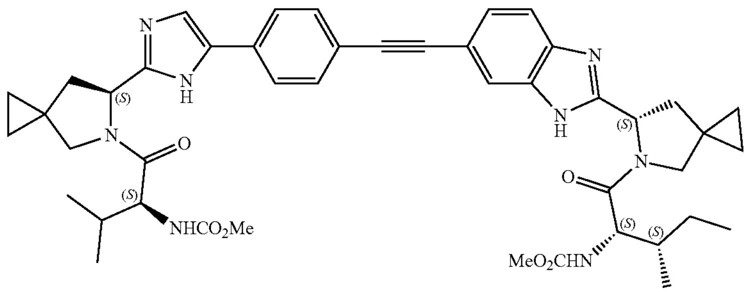
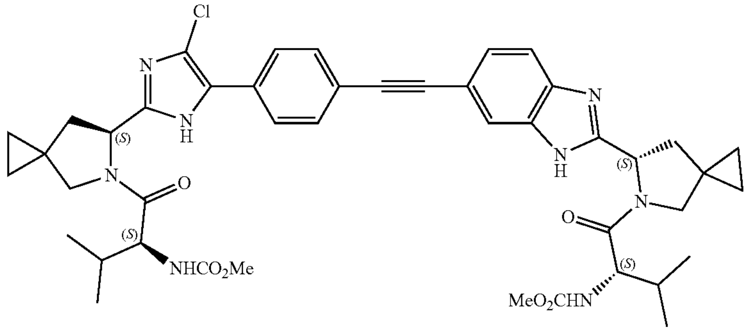
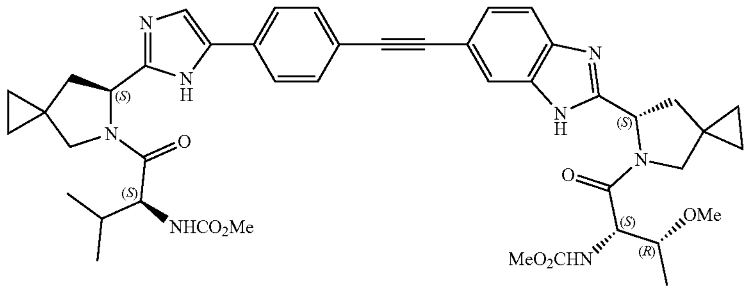
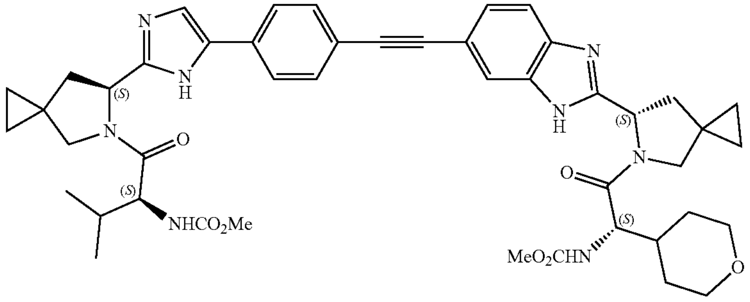

TABLE 9-continued
| Compounds 441-545 |
| --- |
| 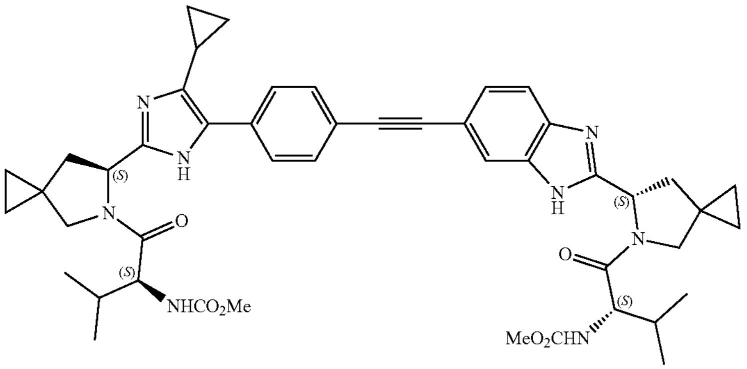 |
| 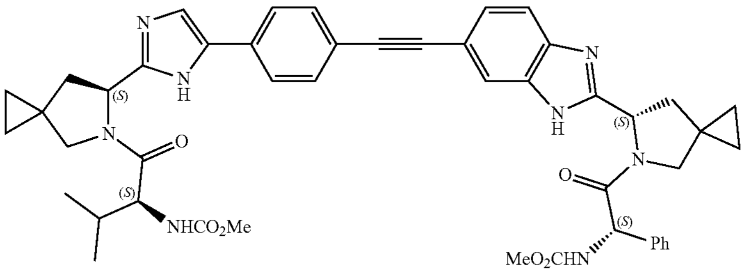 |
| 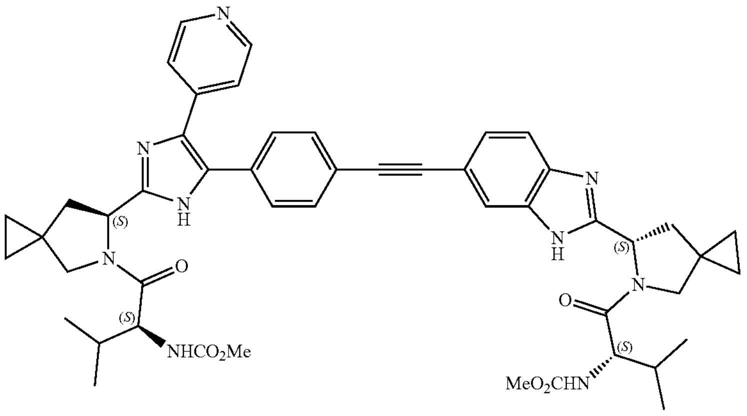 |
| 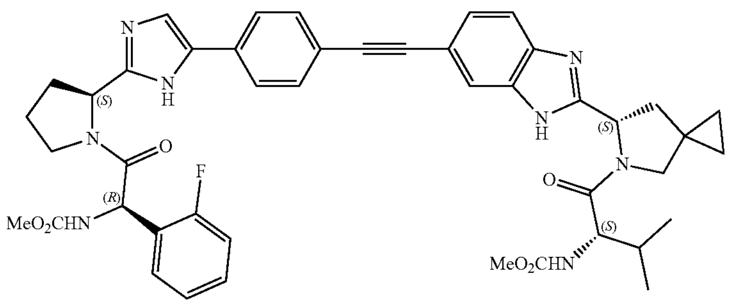 |

TABLE 9-continued
| Compounds 441-545 |
| --- |
| 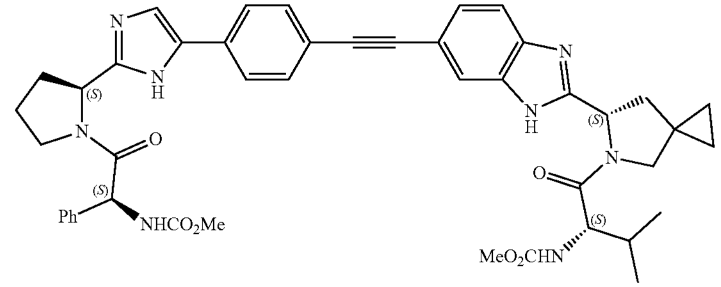 |
| 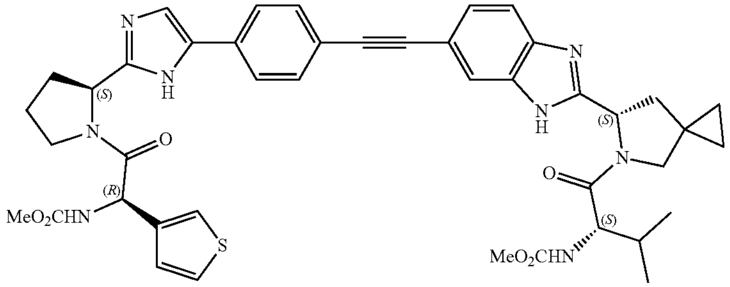 |
| 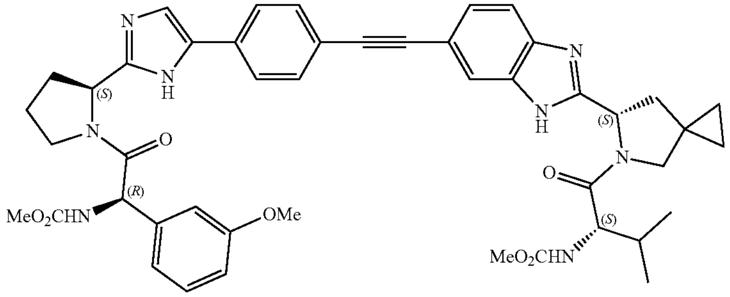 |
| 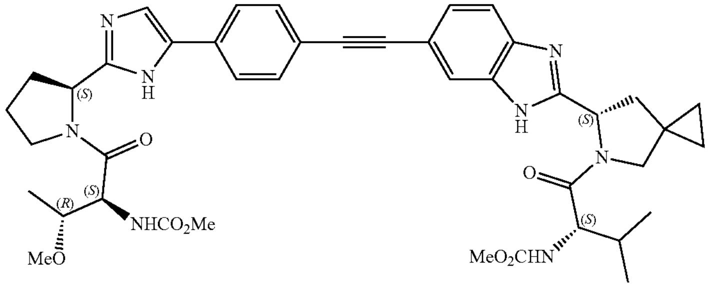 |
| 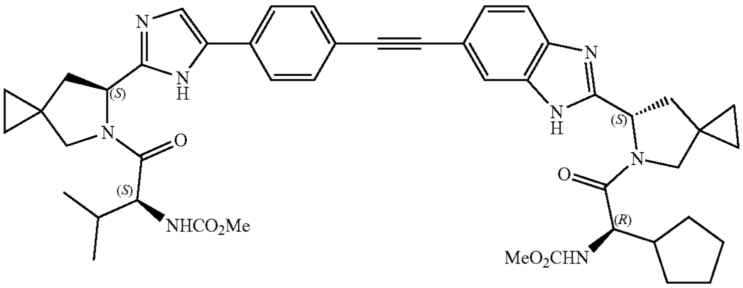 |

TABLE 9-continued
| Compounds 441-545 |
| --- |
| 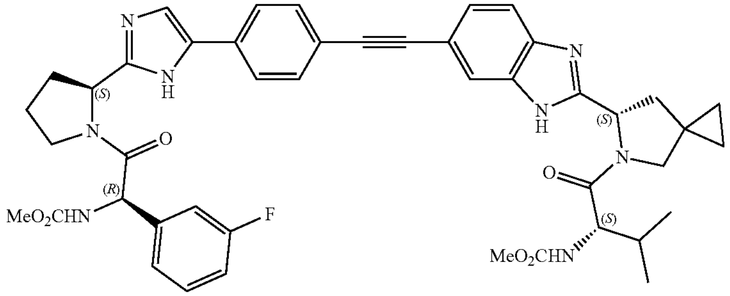 |
| 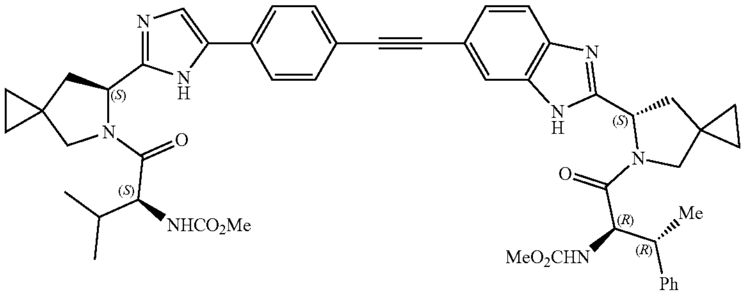 |
| 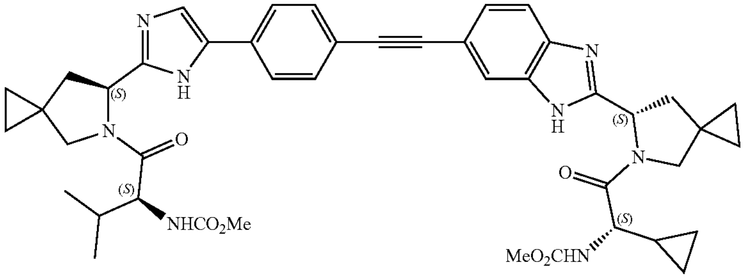 |
| 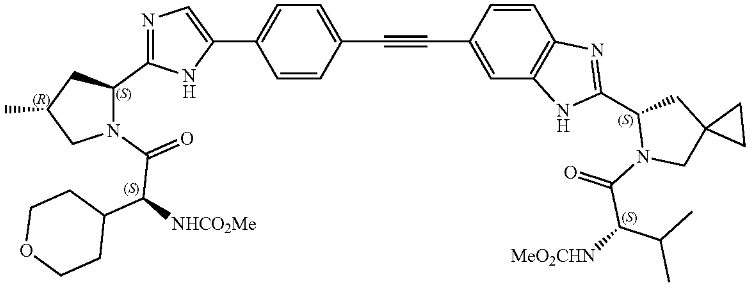 |
| 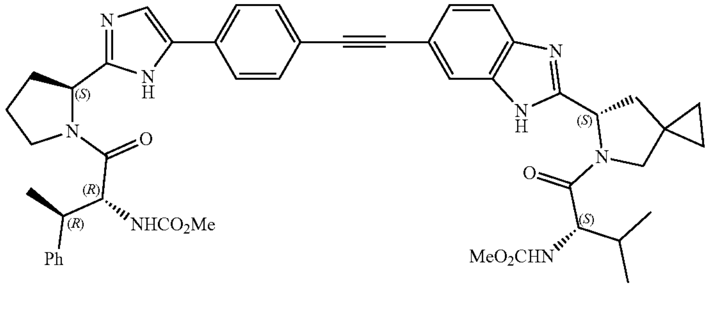 |

TABLE 9-continued
Compounds 441-545
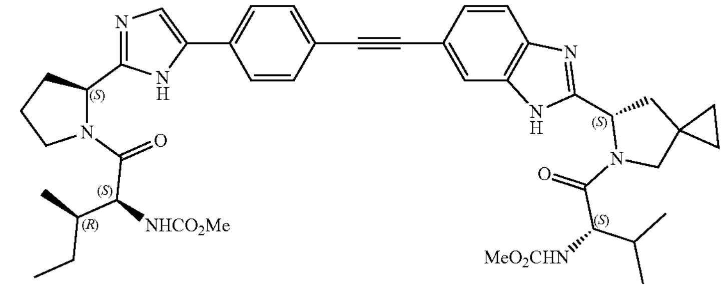
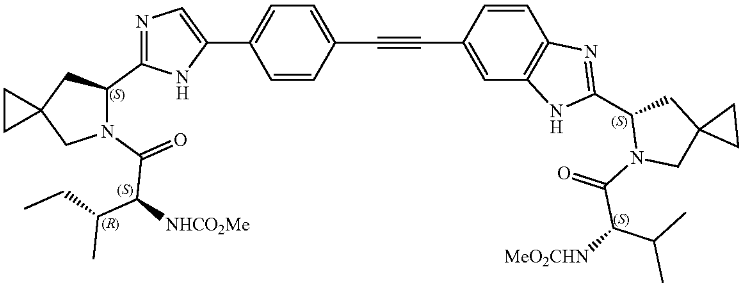
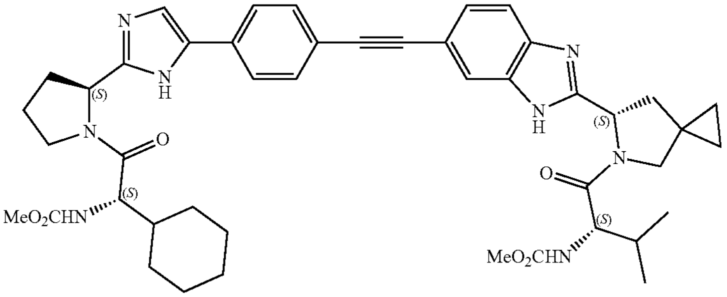
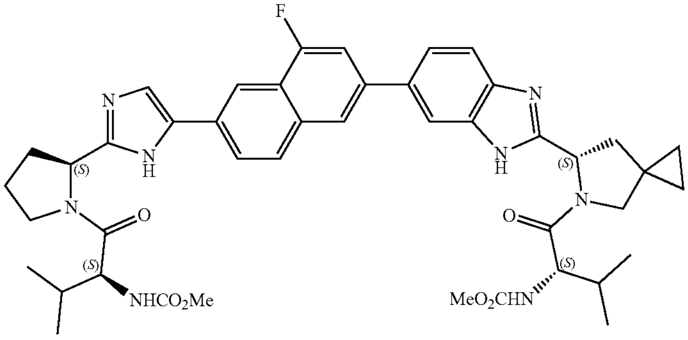
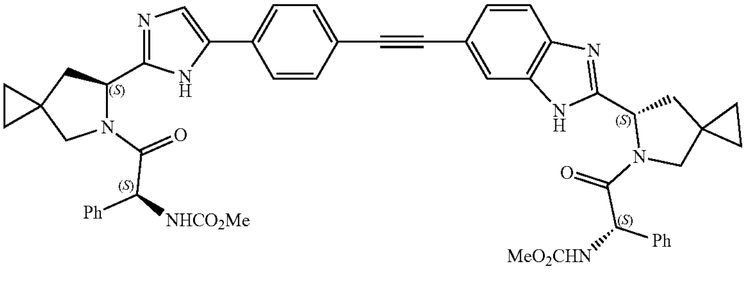

TABLE 9-continued
| Compounds 441-545 |
| --- |
| 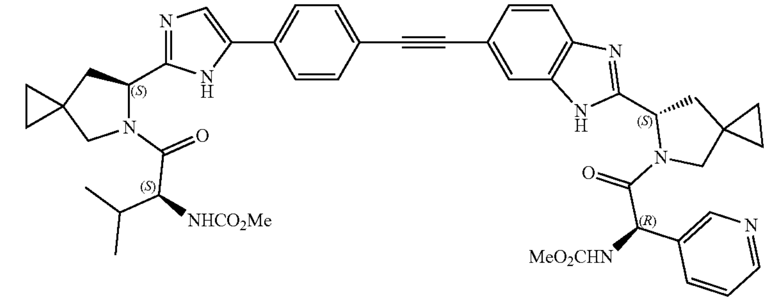 |
| 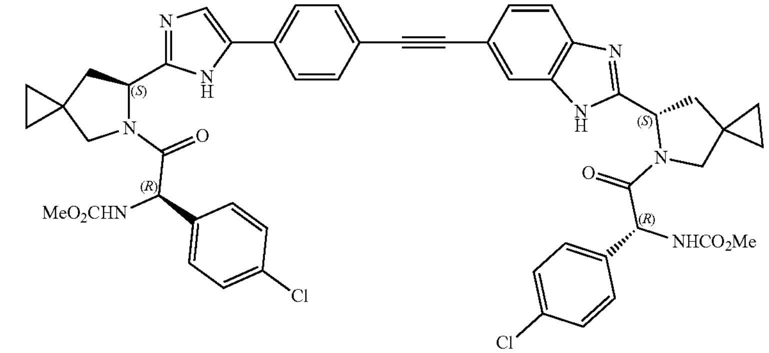 |
| 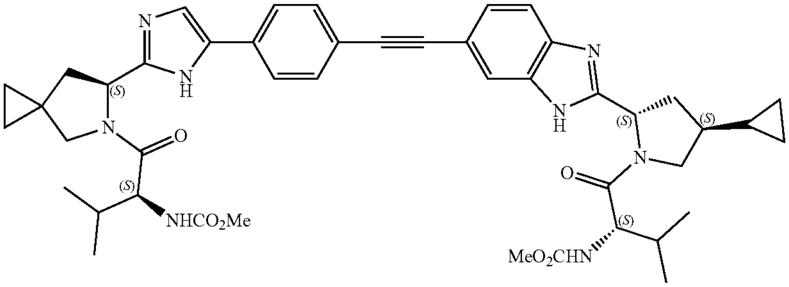 |
| 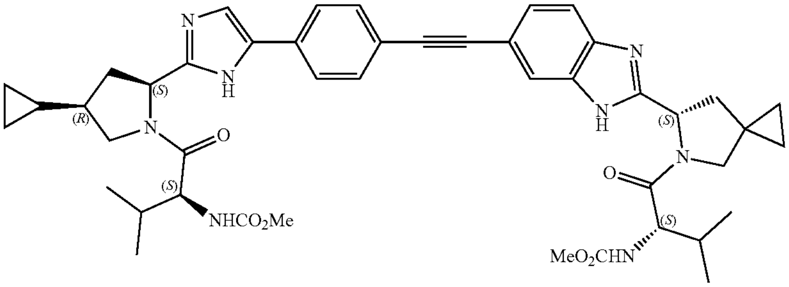 |
| 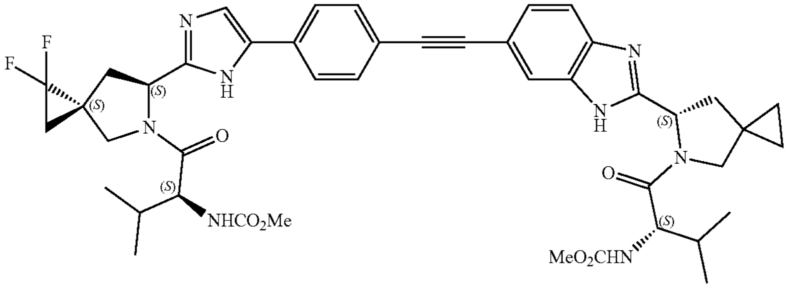 |

TABLE 9-continued
| Compounds 441-545 |
| --- |
| 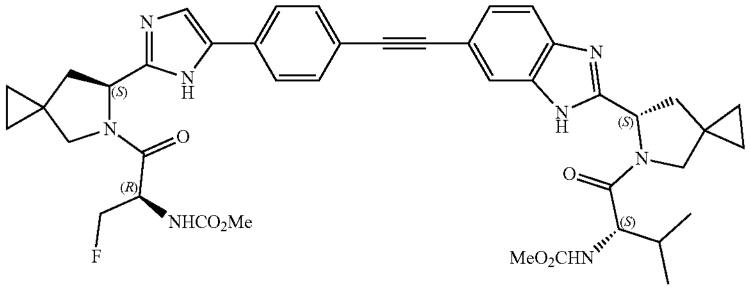 |
| 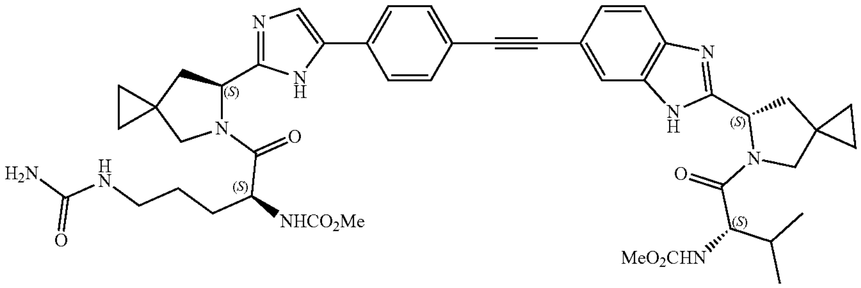 |
| 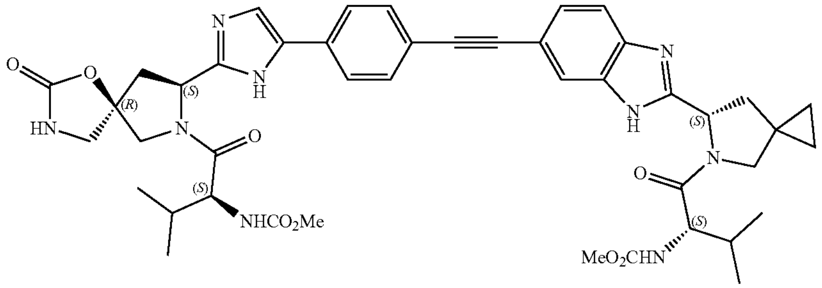 |
| 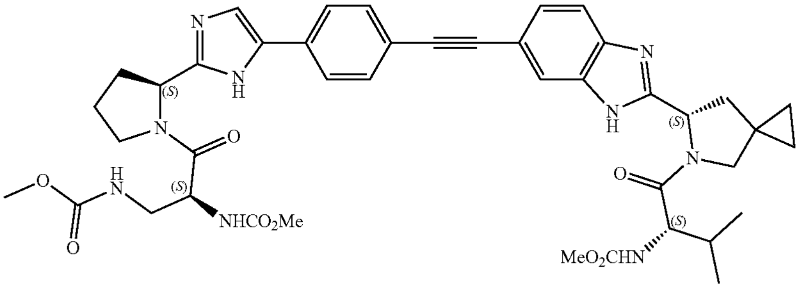 |
| 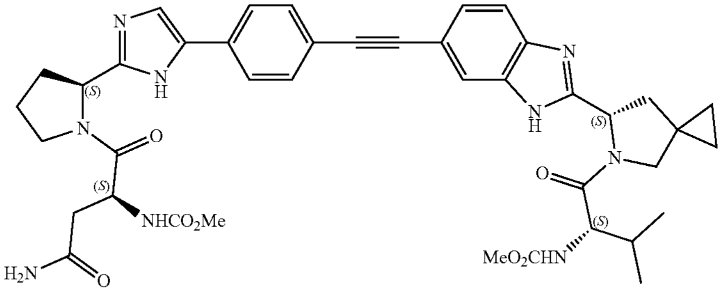 |

TABLE 9-continued
| Compounds 441-545 |
| --- |
| 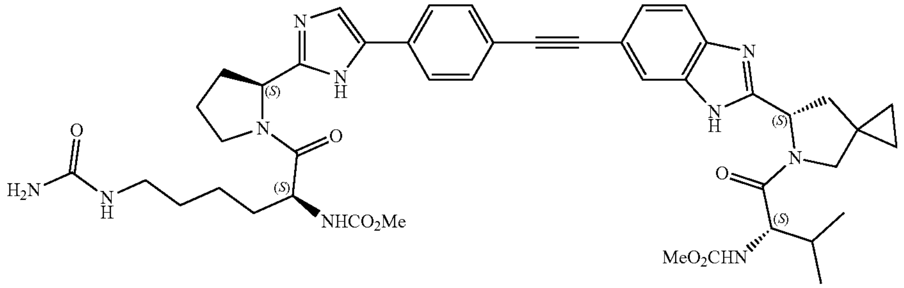 |
| 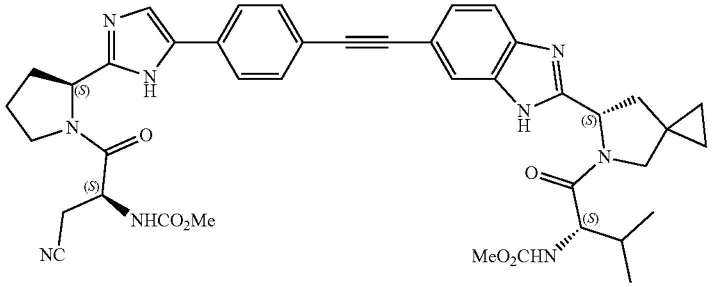 |
| 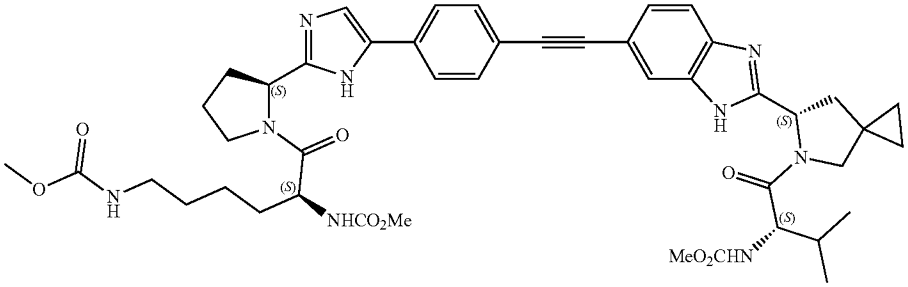 |
| 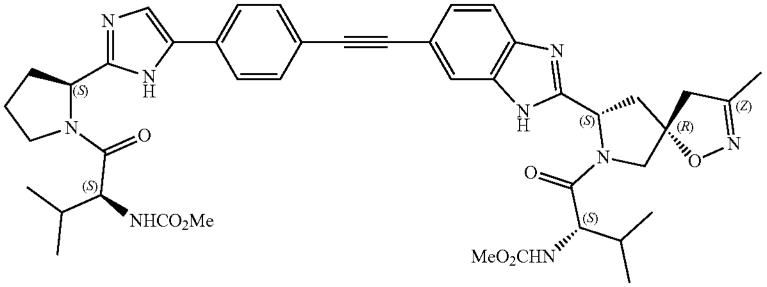 |
| 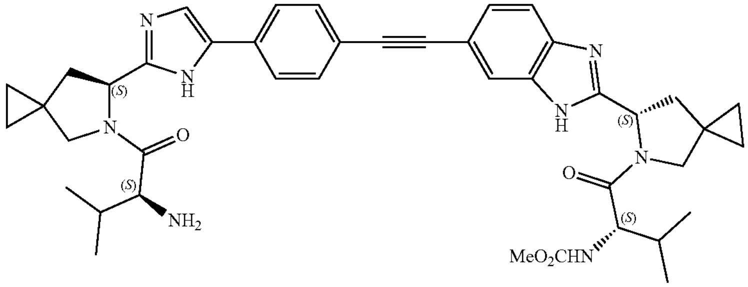 |

TABLE 9-continued
Compounds 441-545
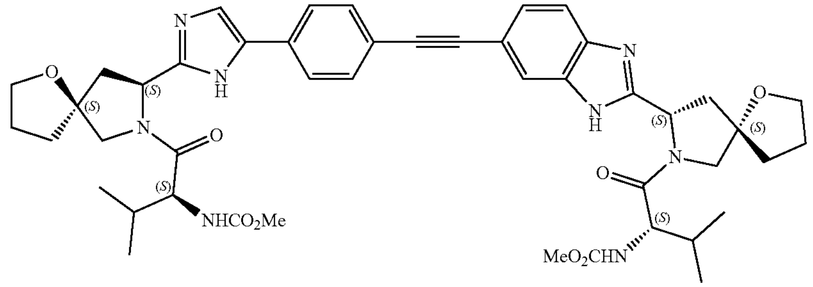
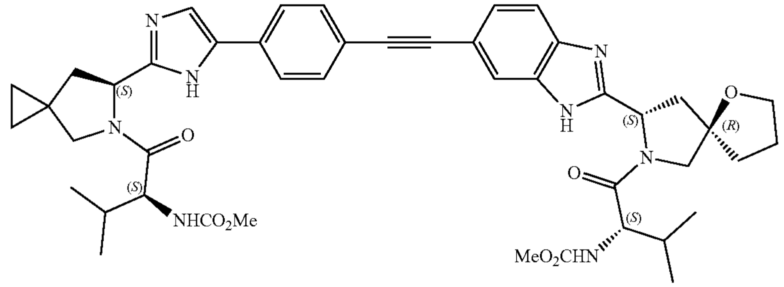
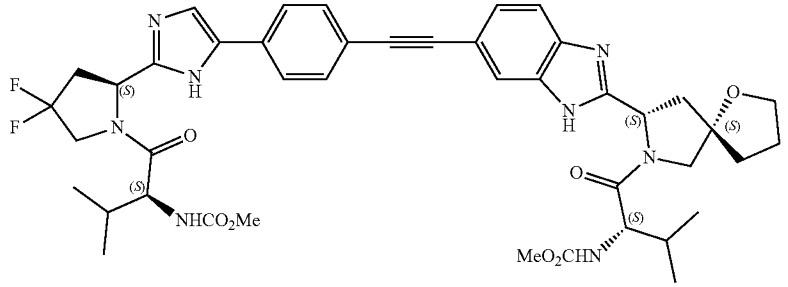
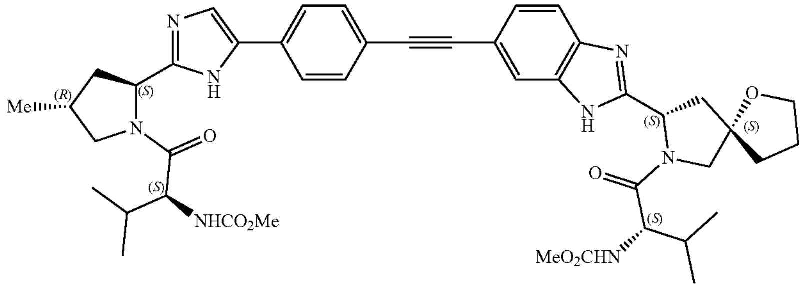
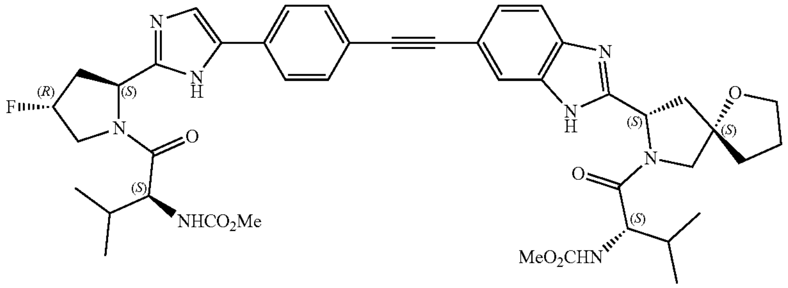

TABLE 9-continued
| Compounds 441-545 |
| --- |
| 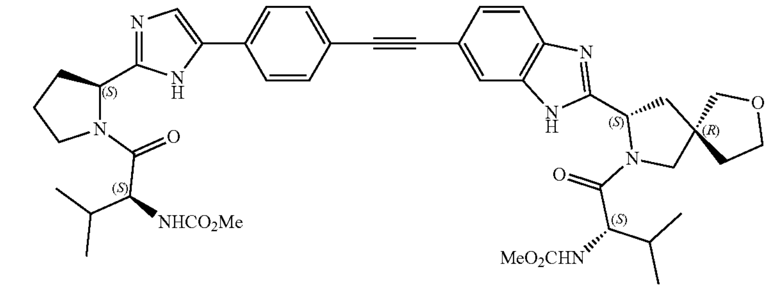 |
| 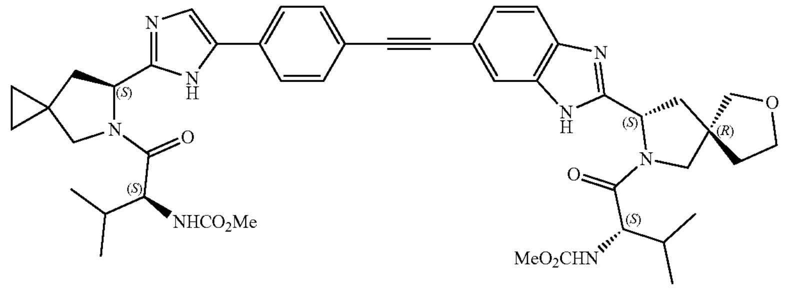 |
| 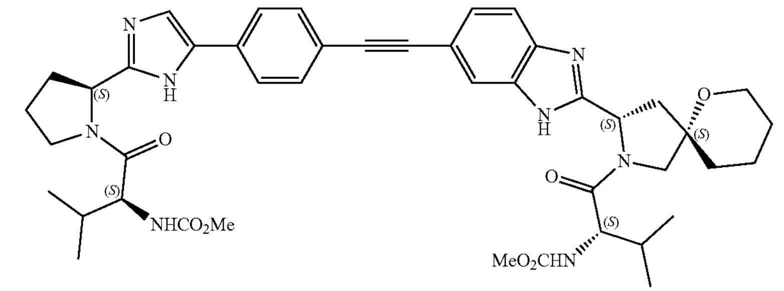 |
| 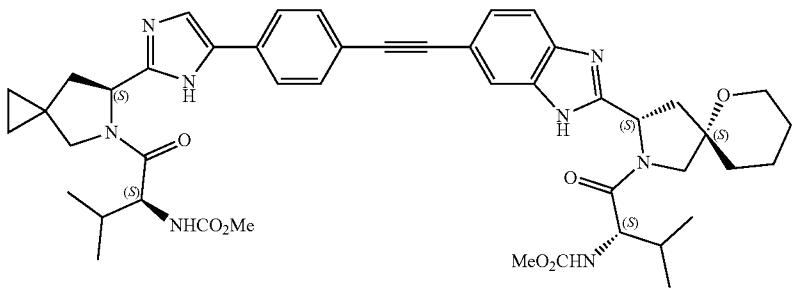 |
| 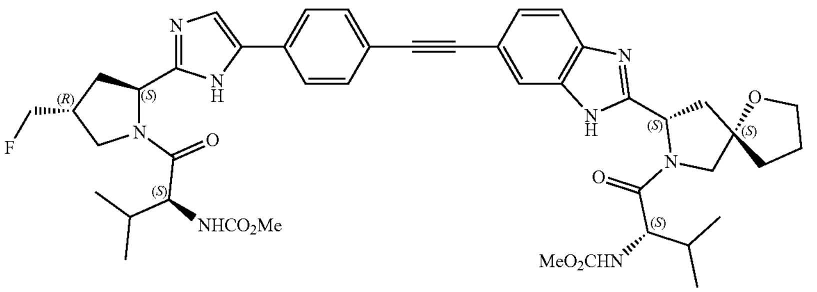 |

TABLE 9-continued
Compounds 441-545
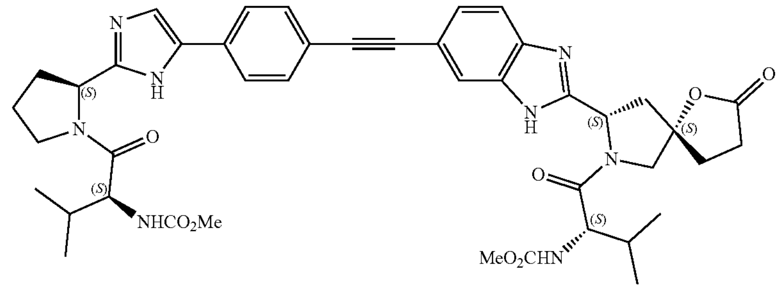
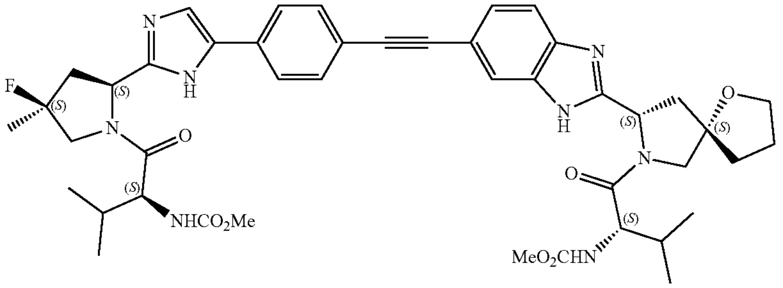
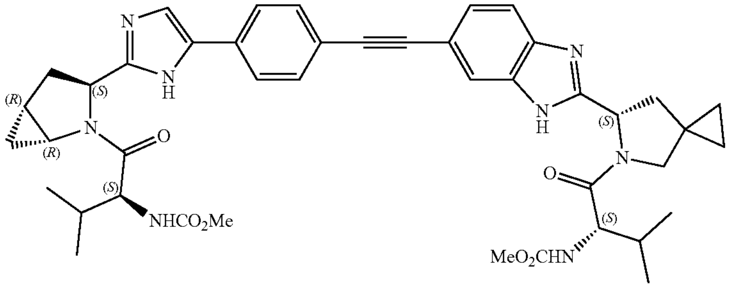
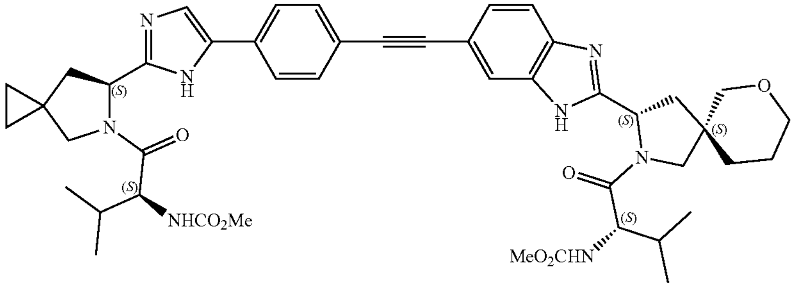
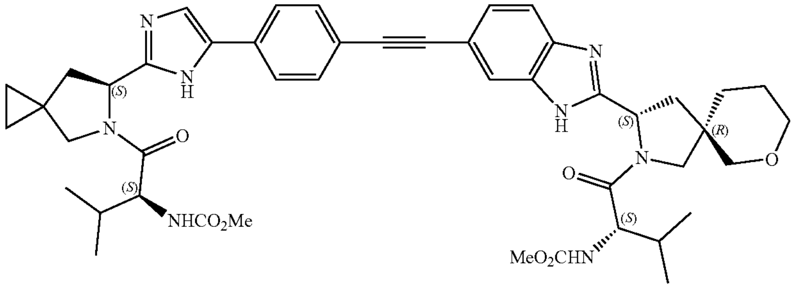

TABLE 9-continued
Compounds 441-545
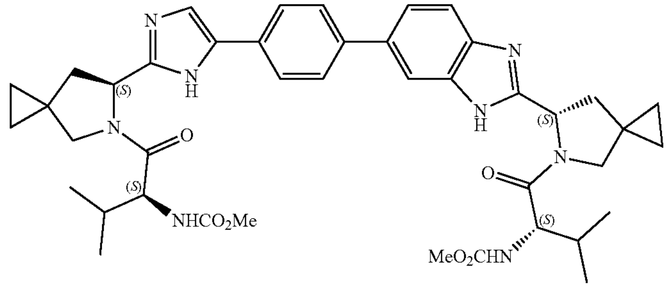
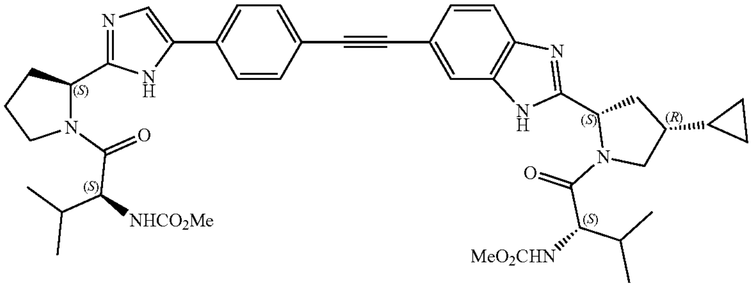
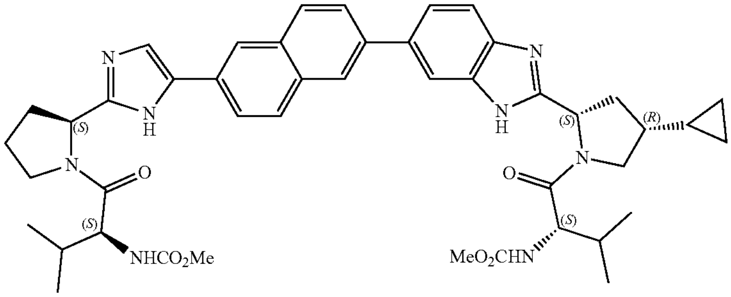
tentative
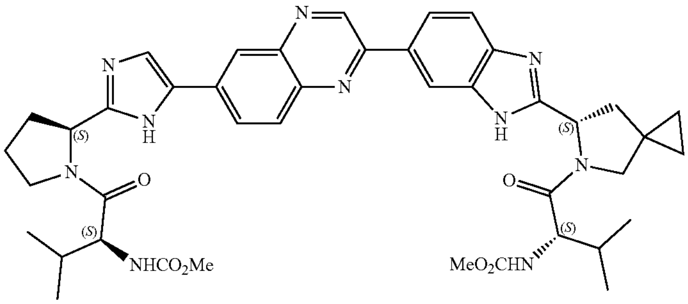
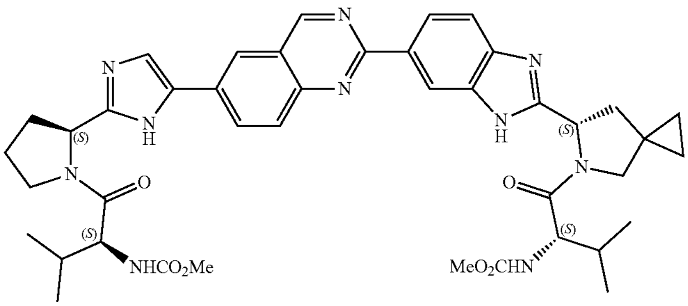

TABLE 9-continued
| Compounds 441-545 |
| --- |
| 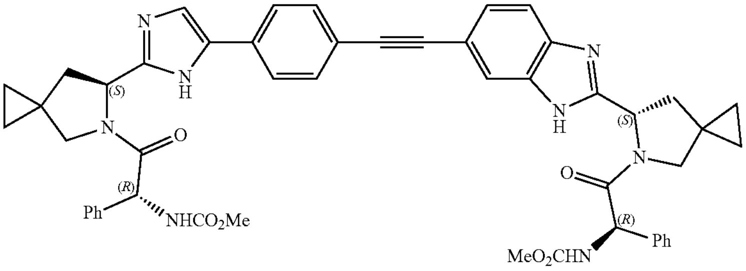 |
| 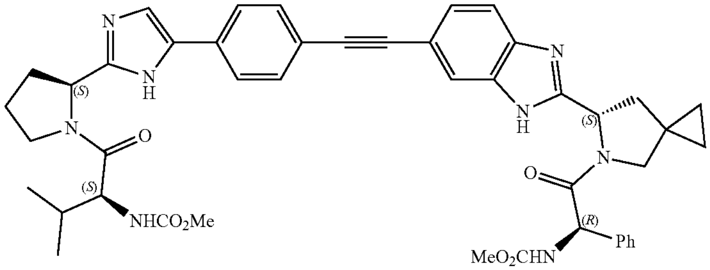 |
| 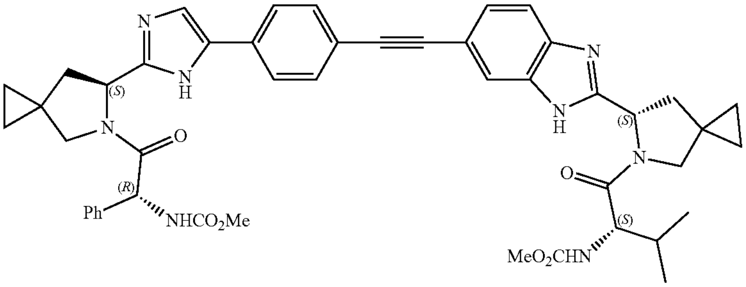 |
| 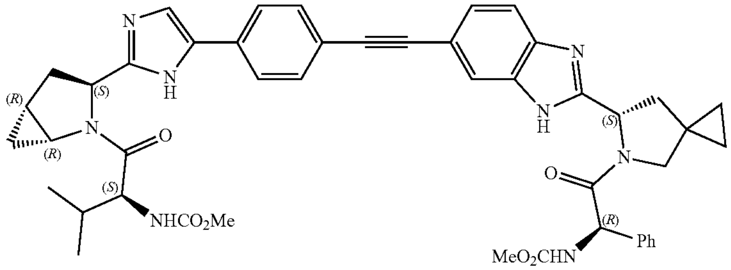 |
| 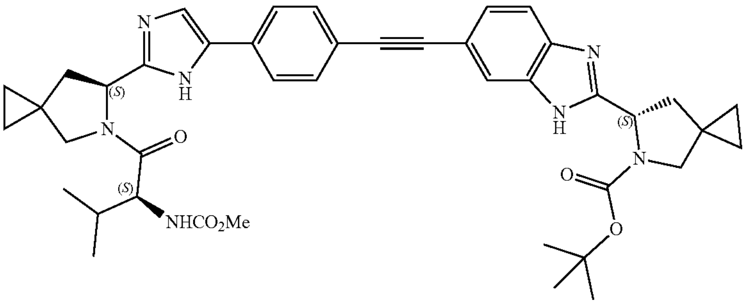 |

TABLE 9-continued
| Compounds 441-545 |
| --- |
| 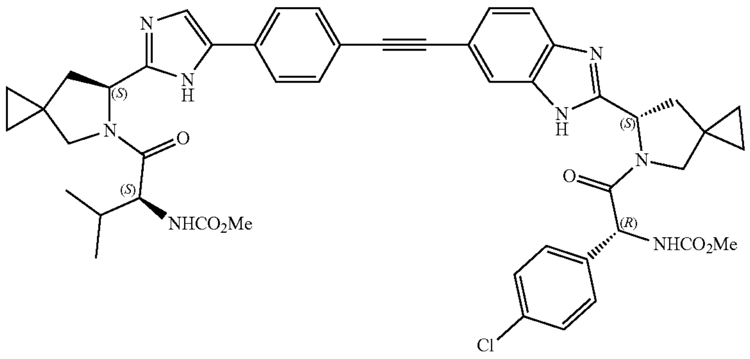 |
| 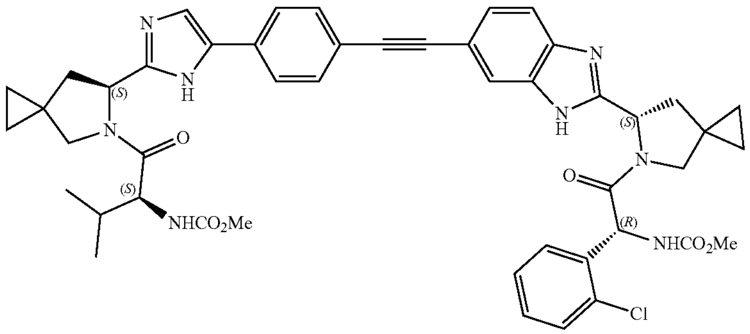 |
| 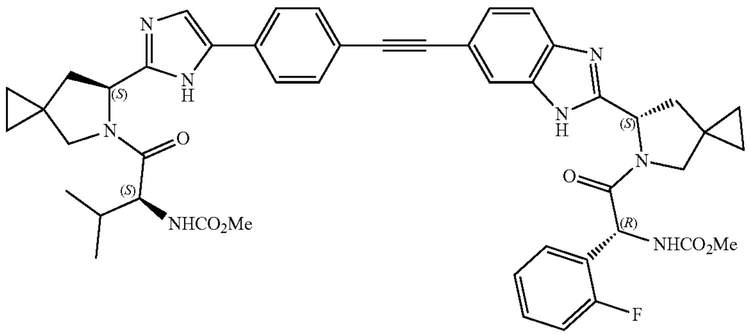 |
| 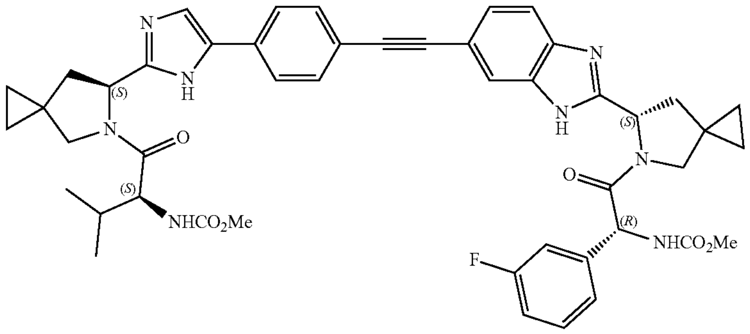 |

TABLE 9-continued
| Compounds 441-545 |
| --- |
| 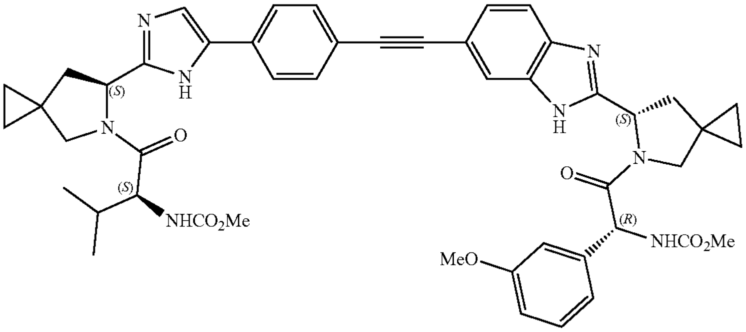 |
| 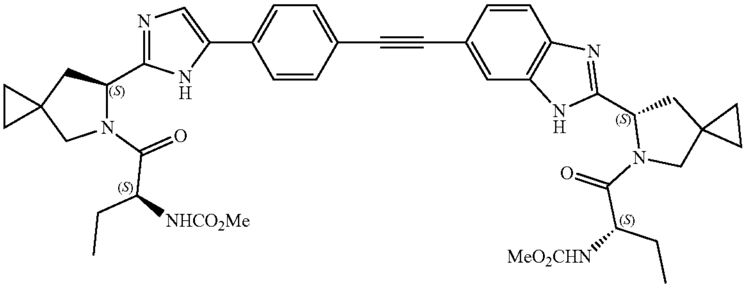 |
| 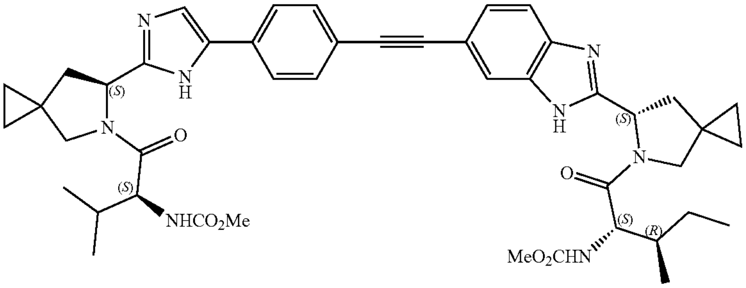 |
| 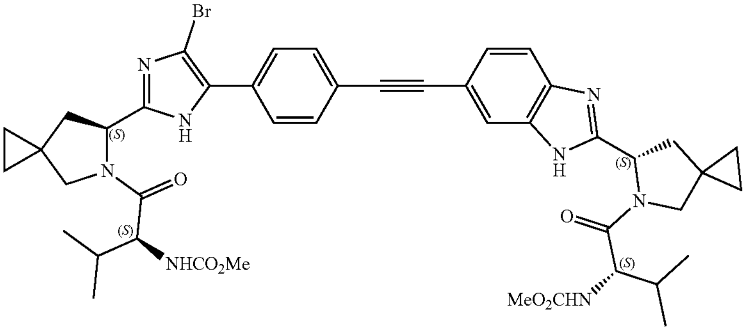 |
| 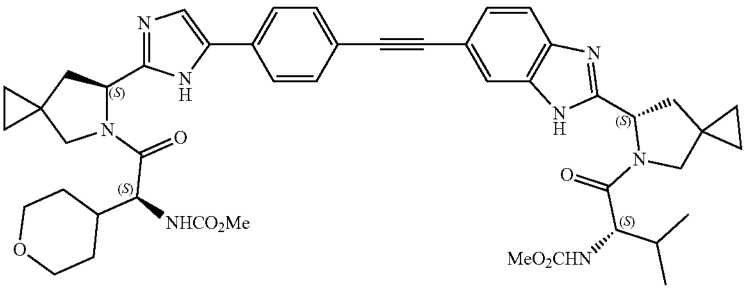 |

TABLE 9-continued
| Compounds 441-545 |
| --- |
| 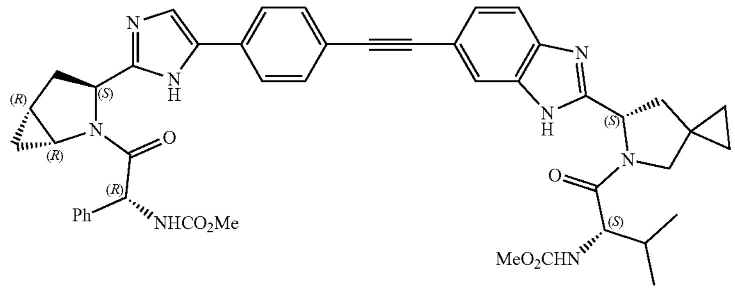 |
| 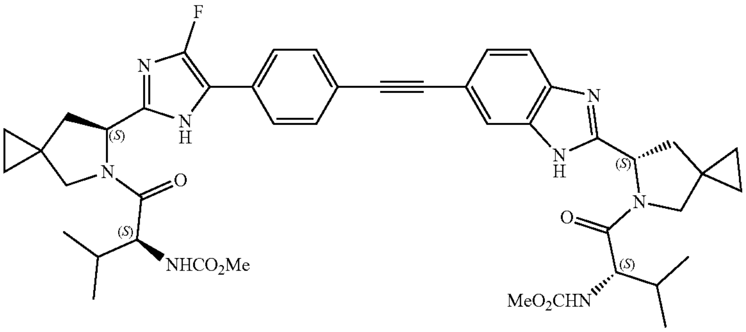 |
| 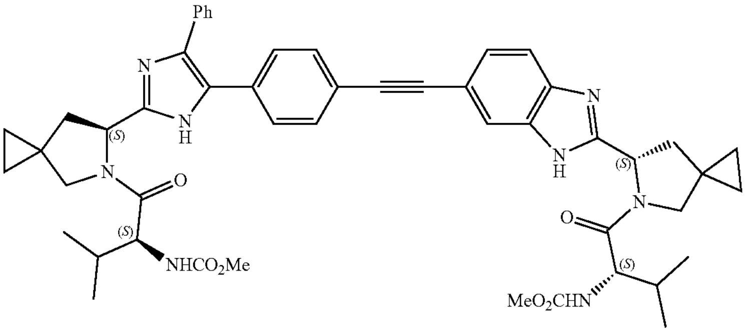 |
| 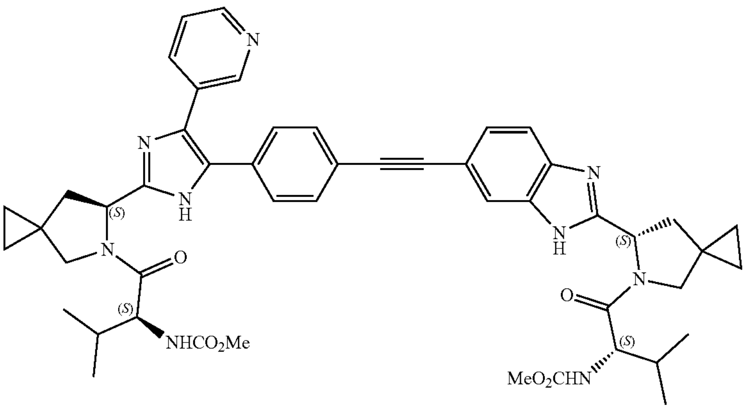 |

TABLE 9-continued
Compounds 441-545
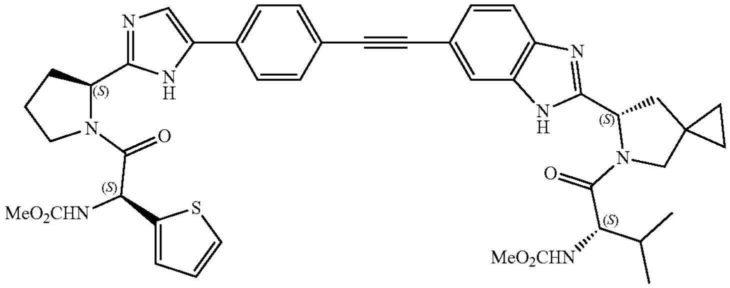
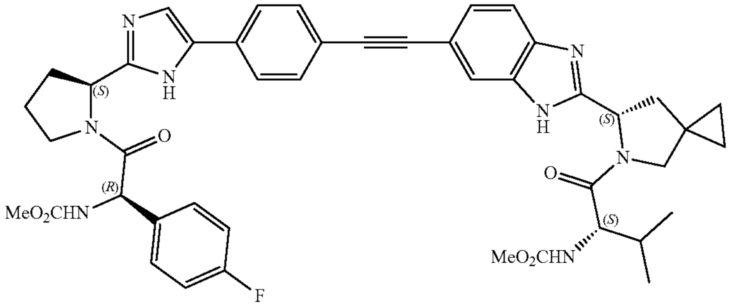
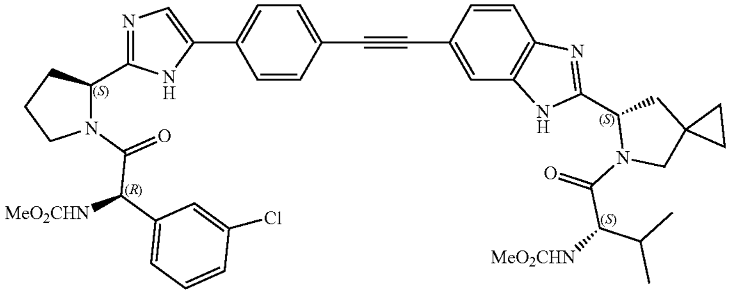
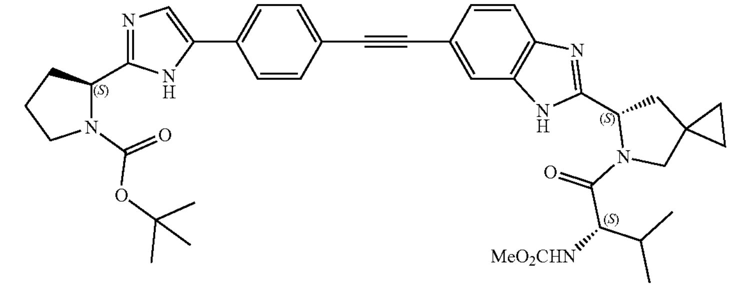
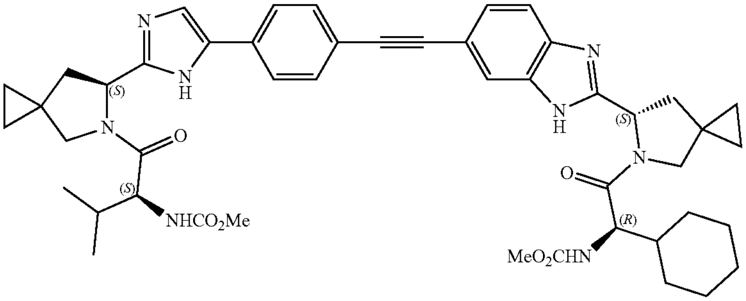

TABLE 9-continued
Compounds 441-545
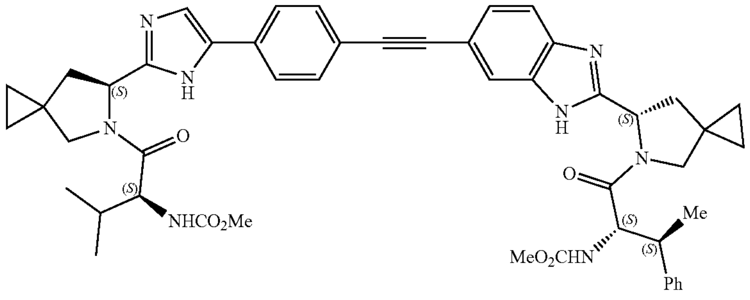
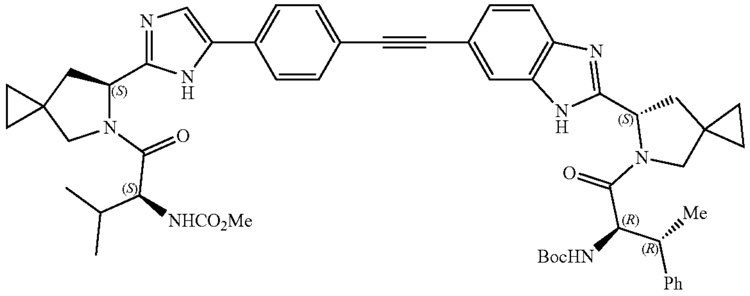
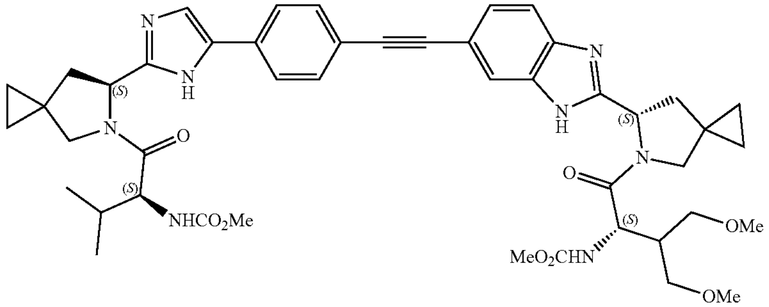
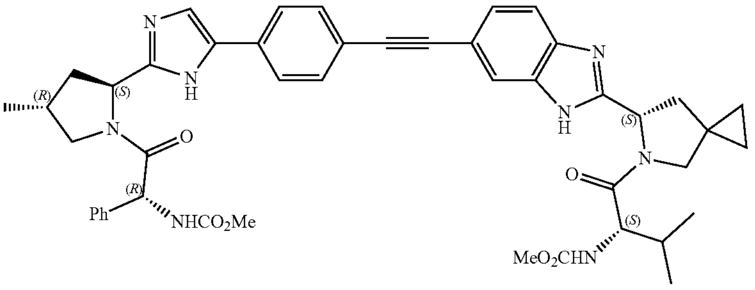
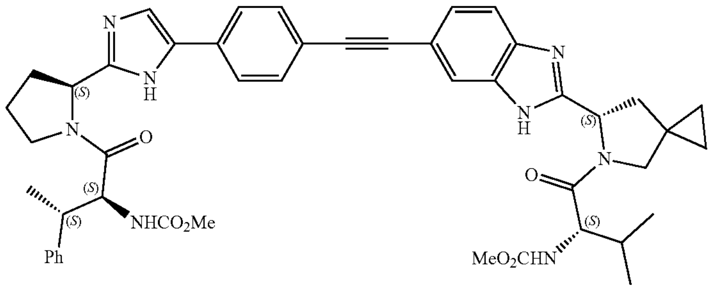

TABLE 9-continued
| Compounds 441-545 |
| --- |
| 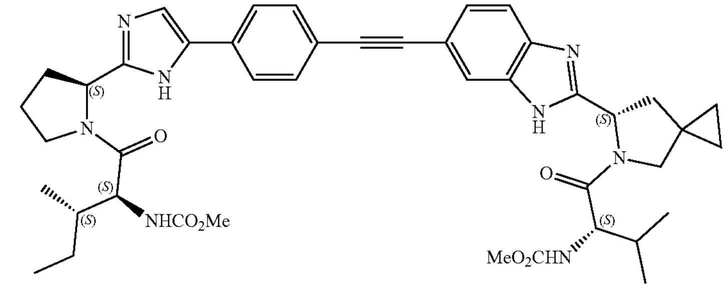 |
| 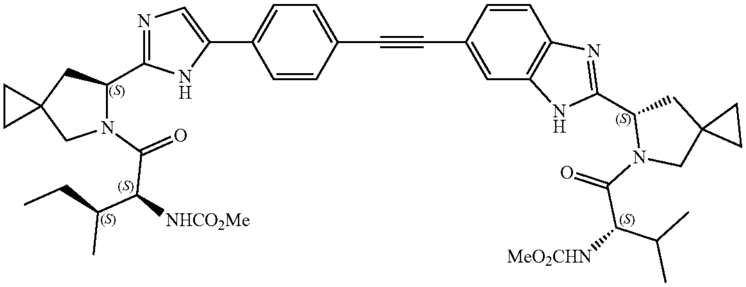 |
| 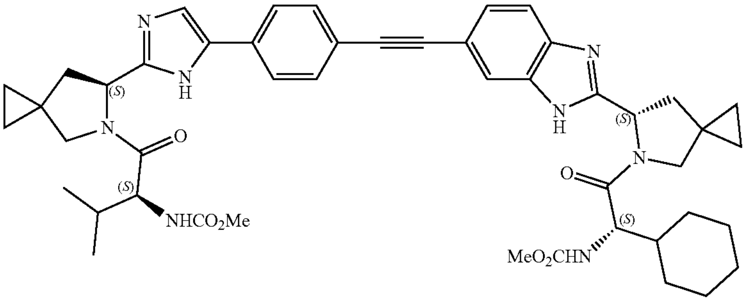 |
| 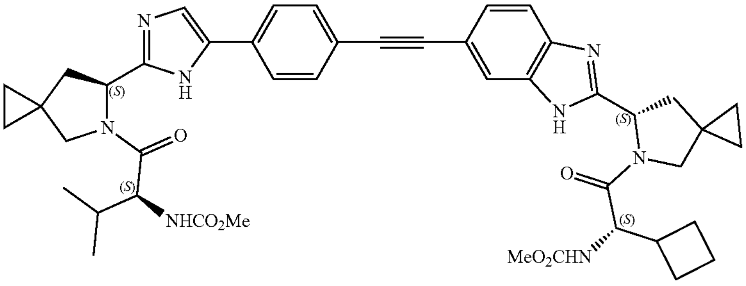 |
| 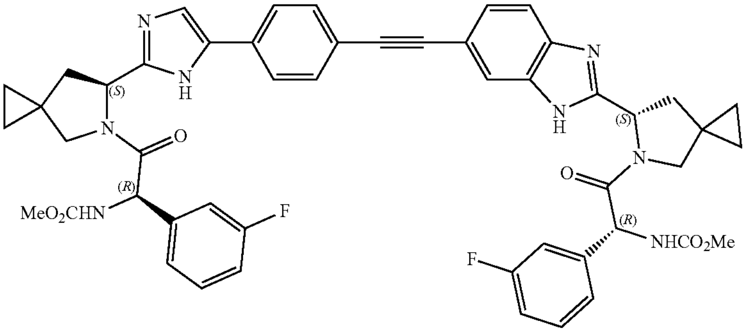 |

TABLE 9-continued
Compounds 441-545
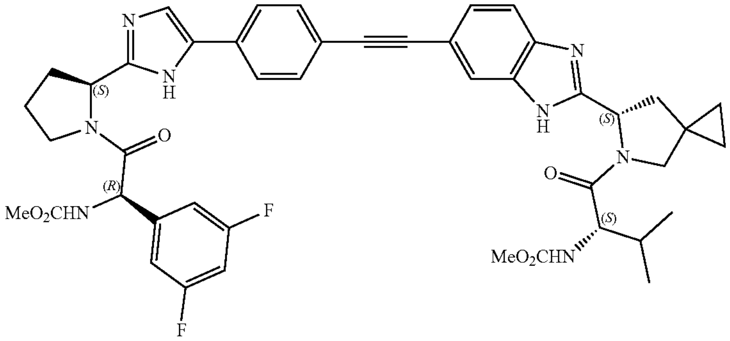
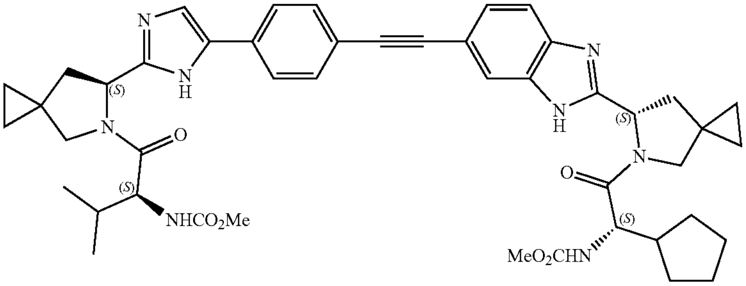
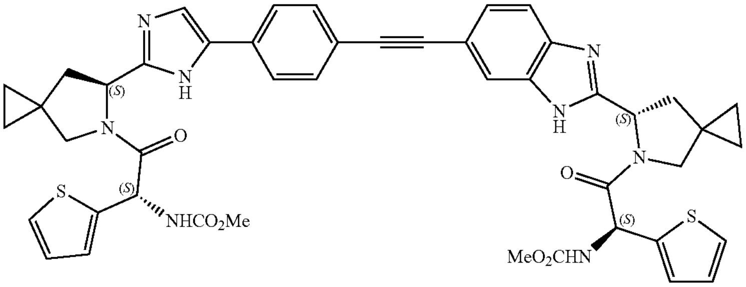
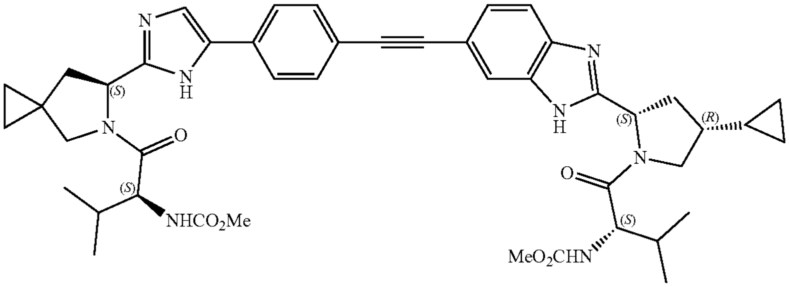
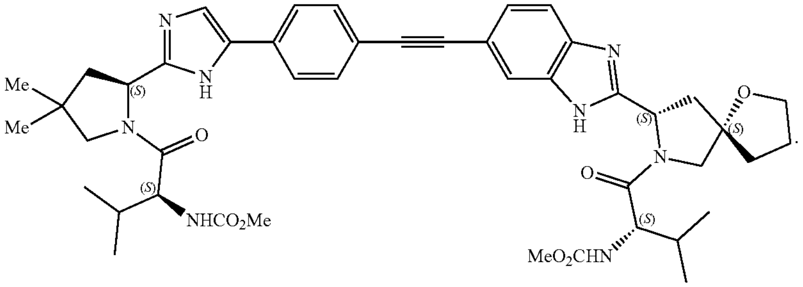

It will be appreciated that the description of the present invention herein should be construed in congruity with the laws and principals of chemical bonding. In some instances it may be necessary to remove a hydrogen atom in order to accommodate a substitutent at any given location.

It is intended that the definition of any substituent or variable (e.g., $R^1$, $R^2$, X, u, m, etc.) at a particular location in a molecule be independent of its definitions elsewhere in that molecule. For example, when u is 2, each of the two $R^1$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It should be understood that the compounds encompassed by the present invention are those that are suitably stable for use as pharmaceutical agent.

It will be further appreciated that reference herein to therapy and/or treatment includes, but is not limited to, prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

A further embodiment of the present invention includes pharmaceutical compositions comprising any single compound or a combination of two or more compounds delineated herein, or a pharmaceutically acceptable salt thereof, with a pharmaceutically acceptable carrier or excipient.

Yet a further embodiment of the present invention is a pharmaceutical composition comprising any single compound or a combination of two or more compounds delineated herein, or a pharmaceutically acceptable salt thereof, in combination with one or more agents known in the art, with a pharmaceutically acceptable carrier or excipient.

It will be further appreciated that compounds of the present invention can be administered as the sole active pharmaceutical agent, or used in combination with one or more agents to treat or prevent hepatitis C infections or the symptoms associated with HCV infection. Other agents to be administered in combination with a compound or combination of compounds of the present invention include therapies for disease caused by HCV infection that suppresses HCV viral replication by direct or indirect mechanisms. These agents include, but are not limited to, host immune modulators (for example, interferon-alpha, pegylated interferon-alpha, consensus interferon, interferon-beta, interferon-gamma, CpG oligonucleo-tides and the like); antiviral compounds that inhibit host cellular functions such as inosine monophosphate dehydrogenase (for example, ribavirin and the like); cytokines that modulate immune function (for example, interleukin 2, interleukin 6, and interleukin 12); a compound that enhances the development of type 1 helper T cell response; interfering RNA; anti-sense RNA; vaccines comprising HCV antigens or antigen adjuvant combinations directed against HCV; agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like; and any agent or combination of agents that inhibit the replication of HCV by targeting other proteins of the viral genome involved in the viral replication and/or interfere with the function of other viral targets, such as inhibitors of NS3/NS4A protease, NS3 helicase, NS5B polymerase, NS4A protein and NS5A protein.

According to yet another embodiment, the pharmaceutical compositions of the present invention may further comprise other inhibitor(s) of targets in the HCV life cycle, including, but not limited to, helicase, polymerase, metalloprotease, NS4A protein, NS5A protein, and internal ribosome entry site (IRES).

Accordingly, one embodiment of the present invention is directed to a method for treating or preventing an infection caused by an RNA-containing virus comprising co-administering to a patient in need of such treatment one or more agents selected from the group consisting of a host immune modulator and a second or more antiviral agents, or a combination thereof, with a therapeutically effective amount of a compound or combination of compounds of the present invention, or a pharmaceutically acceptable salt thereof.

Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome. A non-limiting example of the RNA-containing virus is hepatitis C virus (HCV).

A further embodiment of the present invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the present invention, or a pharmaceutically acceptable salt thereof. A non-limiting example of the RNA-containing virus is hepatitis C virus (HCV).

Yet another embodiment of the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the present invention, or a pharmaceutically acceptable salt thereof. An agent that treats patients for disease caused by hepatitis B (HBV) infection may be for example, but not limited thereto, L-deoxythymidine, adefovir, lamivudine or tenfovir, or any combination thereof. A non-limiting example of the RNA-containing virus is hepatitis C virus (HCV).

Another further embodiment of the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the present invention, or a pharmaceutically acceptable salt thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. A non-limiting example of the RNA-containing virus is hepatitis C virus (HCV).

It can occur that a patient may be co-infected with hepatitis C virus and one or more other viruses, including but not limited to human immunodeficiency virus (HIV), hepatitis A virus (HAV) and hepatitis B virus (HBV). Thus also contemplated herein is combination therapy to treat such co-infections by co-administering a compound according to the present invention with at least one of an HIV inhibitor, an HAV inhibitor and an HBV inhibitor.

In addition, the present invention provides the use of a compound or a combination of compounds of the invention, or a therapeutically acceptable salt thereof, and one or more agents selected from the group consisting of a host immune modulator and one or more additional antiviral agents, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant. Preferably said additional antiviral agent inhibits replication of HCV either by inhibiting host cellular functions associated with viral replication or by targeting proteins of the viral genome.

When used in the above or other treatments, combination of compound or compounds of the present invention, together with one or more agents as defined herein above, can be employed in pure form or, where such forms exist, or as a pharmaceutically acceptable salt thereof. Alternatively, such combination of therapeutic agents can be administered as a pharmaceutical composition containing a therapeutically effective amount of the compound or combination of compounds of interest, or their pharmaceutically acceptable salt thereof, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, a still further embodiment of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt thereof, and one or more agents as defined hereinabove, with a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including, but not limited to, agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other agents that can be administered in combination with a compound of the present invention include a cytochrome P450 monooxygenase inhibitor (also referred to herein as a CYP inhibitor), which is expected to inhibit metabolism of the compounds of the invention. Therefore, the cytochrome P450 monooxygenase inhibitor would be in an amount effective to inhibit metabolism of the compounds of this invention. Accordingly, the CYP inhibitor is administered in an amount sufficient to improve one or more pharmacokinetic (PK) feautures including, but not limited to, plasma concentration, bioavailiablity, area under the plasma concentration time curve (AUC), elimination half-life, and systemic clearance, of a compound of the invention when one or more of its PK feautures of said compound is improved in comparison to that in the absence of the CYP inhibitor.

In one embodiment, the invention provides methods for improving the pharmacokinetics of compounds of the invention. The advantages of improving the pharmacokinetics of drugs are recognized in the art (see, for example, US Patent Publication No.'s. 2004/0091527; US 2004/0152625; and US 2004/0091527). Accordingly, one embodiment of this invention provides a method comprising administering an inhibitor of CYP3A4 and a compound of the invention. Another embodiment of this invention provides a method comprising administering a compound of the invention and an inhibitor of isozyme 3A4 ("CYP3A4"), isozyme $2C_{19}$ ("CYP$2C_{19}$"), isozyme 2D6 ("CYP2D6"), isozyme 1A2 ("CYP1A2"), isozyme $2C_9$ ("CYP$2C_9$"), or isozyme 2E1 ("CYP2E1"). In a preferred embodiment, the CYP inhibitor preferably inhibits CYP3A4. Any CYP inhibitor that improves the pharmacokinetics of the relevant compound of the invention may be used in a method of this invention. These CYP inhibitors include, but are not limited to, ritonavir (see, for example, WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, ditiazem, erythromycin, VX-944, and VX-497. Preferred CYP inhibitors include ritonavir, ketoconazole, troleandomycin, 4-methyl pyrazole, cyclosporin, and clomethiazole.

It will be understood that the administration of the combination of the invention by means of a single patient pack, or patient packs of each formulation, containing within a package insert instructing the patient to the correct use of the invention is a desirable additional feature of this invention.

According to a further aspect of the invention, is a pack comprising at least a compound of the invention and a CYP inhibitor and an information insert containing directions on the use of the combination of the invention. In an alternative embodiment of this invention, the pack further comprises one or more of additional agent as described herein. The additional agent or agents may be provided in the same pack or in separate packs.

Another aspect of this involves a packaged kit for a patient to use in the treatment of HCV infection or in the prevention of HCV infection, comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a compound of the invention and a CYP inhibitor (and optionally an additional agent) or derivatives thereof are prepared in a conventional manner. Typically, such a kit will comprise, e. g. a composition of a compound of the invention and optionally the additional agent (s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i. e., the dosage forms, the container means, and the written instructions for use. Such packaging means may take the form of a cardboard or paper box, a plastic or foil pouch, etc.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The terms "$C_1$-$C_4$ alkyl," "$C_1$-$C_6$ alkyl," "$C_1$-$C_8$ alkyl," "$C_2$-$C_4$ alkyl," or "$C_3$-$C_6$ alkyl," as used herein, refer to saturated, straight- or branched-chain hydrocarbon radicals containing between one and four, one and six, one and eight carbon atoms, or the like, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," "$C_2$-$C_4$ alkenyl," "$C_3$-$C_4$ alkenyl," or "$C_3$-$C_6$ alkenyl," as used herein, refer to straight- or branched-chain hydrocarbon radicals containing from two to eight, or two to four carbon atoms, or the like, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," "$C_2$-$C_4$ alkynyl," "$C_3$-$C_4$ alkynyl," or "$C_3$-$C_6$ alkynyl," as used herein, refer to straight- or branched-chain hydrocarbon radicals containing from two to eight, or two to four carbon atoms, or the like, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$-cycloalkyl", or "$C_5$-$C_7$-cycloalkyl," as used herein, refers to a monocyclic or polycyclic saturated carbocyclic ring compound, and the carbon atoms may be optionally oxo-substituted. Examples of $C_3$-$C_8$-cycloalkyl include, but not limited to, cyclopropyl, cyclobutyl, cyclopentyl, cyclohexyl, cyclopentyl and cyclooctyl; and examples of $C_5$-$C_7$-cycloalkyl include, but not limited to, cyclopentyl, cyclohexyl, bicyclo [2.2.1] heptyl, and the like.

The term "$C_3$-$C_8$ cycloalkenyl", or "$C_5$-$C_7$ cycloalkenyl" as used herein, refers to monocyclic or polycyclic carbocyclic ring compound having at least one carbon-carbon double bond, and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

The term "arylalkyl", as used herein, refers to an aryl-substituted alkyl group. More preferred arylalkyl groups are aryl-$C_1$-$C_6$-alkyl groups. The term "heteroarylalkyl", as used herein, refers to a heteroaryl-substituted alkyl group. More preferred heteroarylalkyl groups are heteroaryl-$C_1$-$C_6$-alkyl groups.

It is understood that any alkyl, alkenyl, alkynyl, cycloalkyl and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched or cyclic and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can, for example, be selected from one or more of the specified functional groups or a combination thereof, or a group wherein one or more carbons of a non-aromatic hydrocarbon (optionally substituted) is replaced by a specified functional group. In some examples, the aliphatic group can be represented by the formula M-Y-M', where M and M' are each independently absent or an alkyl, alkenyl or alkynyl, each optionally substituted, and Y is a functional group. In some examples, Y is selected from the group consisting of C(O), $S(O)_2$, C(O)O, $C(O)N(R^{11})$, OC(O)O, $OC(O)N(R^{11})$, $S(O)_2N(R^{11})$, $N(R^{11})C(O)N(R^{11})$, $N(R^{1})C(O)C(O)N(R^{11})$, $N(R^{11})S(O)_2N(R^{11})$, $C(O)N(R^{11})S(O)_2$ or $C(O)N(R^{11})S(O)_2N(R^{11})$; wherein $R^{11}$ is as previously defined. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated, (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent group when used as a linkage to connect two groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, $—NO_2$, $—N_3$, —CN, $—NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O— heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, $—CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, $—OCO_2$—$C_1$-$C_{12}$-alkyl, $—OCO_2$—$C_2$-$C_8$-alkenyl, $—OCO_2$—$C_2$-$C_8$-alkynyl, $—OCO_2$—$C_3$-$C_{12}$-cycloalkyl, $—OCO_2$-aryl, $—OCO_2$-heteroaryl, $—OCO_2$-heterocycloalkyl, $—CO_2$—$C_1$-$C_{12}$ alkyl, $—CO_2$—$C_2$-$C_8$ alkenyl, $—CO_2$—$C_2$-$C_8$ alkynyl, $CO_2$—$C_3$-$C_{12}$-cycloalkyl, $—CO_2$-aryl, $CO_2$-heteroaryl, $CO_2$-heterocyloalkyl, $—OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, $—NHCO_2$—$C_1$-$C_{12}$-alkyl, $—NHCO_2$—$C_2$-$C_8$-alkenyl, $—NHCO_2$—$C_2$-$C_8$-alkynyl, $—NHCO_2$—$C_3$-$C_{12}$-cycloalkyl, $—NHCO_2$-aryl, $—NHCO_2$-heteroaryl, $—NHCO_2$-heterocycloalkyl, $—NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH— heteroaryl, —NHC(S)NH-heterocycloalkyl, $—NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, $—SO_2NH_2$, $—SO_2NH$—$C_1$-$C_{12}$-alkyl, $—SO_2NH$—$C_2$-$C_8$-alkenyl, $—SO_2NH$—$C_2$-$C_8$-alkynyl, $—SO_2NH$—$C_3$-$C_{12}$-cycloalkyl, $—SO_2NH$-aryl, $—SO_2NH$-heteroaryl, $—SO_2NH$-heterocycloalkyl, $—NHSO_2$—$C_1$-$C_{12}$-alkyl, $—NHSO_2$—$C_2$-$C_8$-alkenyl, $—NHSO_2$—$C_2$-$C_8$-alkynyl, $—NHSO_2$—$C_3$-$C_{12}$-cycloalkyl, $—NHSO_2$-aryl, $—NHSO_2$-heteroaryl, $—NHSO_2$-heterocycloalkyl, $—CH_2NH_2$, $—CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-cycloalkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenylmethoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent' as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.). "Design and Application of Prodrugs, Textbook of Drug Design and Development, Chapter 5, 113-191 (1991); Bundgaard, et al., *Journal of Drug Deliver Reviews,* 8:1-38(1992); Bundgaard, *J. of Pharmaceutical Sciences,* 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically exipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" include, but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or anti-microbial and anti-viral agents (e.g. ribavirin and amantidine). The compositions according to the invention may also be used in combination with gene replacement therapy.

Combination and Alternation Therapy for HCV

It has been recognized that drug-resistant variants of HCV can emerge after prolonged treatment with an antiviral agent. Drug resistance most typically occurs by mutation of a gene that encodes for a protein such as an enzyme used in viral replication, and most typically in the case of HCV, RNA polymerase, protease, or helicase.

Recently, it has been demonstrated that the efficacy of a drug against a viral infection, such as HIV, can be prolonged, augmented, or restored by administering the drug in combination or alternation with a second, and perhaps third, antiviral compound that induces a different mutation from that caused by the principal drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus. A compound of the present invention can also be administered in combination or alternation with antiviral agent. Examplary antiviral agents include ribavarin, interferon, interleukin or a stabilized prodrug of any of them. More broadly described, the compound can be administered in combination or alternation with any of the anti-HCV drugs listed in Table 10 below.

TABLE 10

Table of anti-Hepatitis C Compounds in Current Clinical Development

| Drug name | Drug category | Pharmaceutical Company |
|---|---|---|
| PEGASYS pegylated interferon alfa-2a | Long acting interferon | Roche |
| INFERGEN interferon alfacon-1 | Long acting interferon | InterMune |
| OMNIFERON natural interferon | Long acting interferon | Viragen |
| ALBUFERON | Long acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | InterMune |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody | NABI |
| | Therapeutic vaccine | Innogenetics |
| VIRAMIDINE | Nucleoside Analogue | ICN |
| ZADAXIN (thymosin alfa-1) | Immunomodulator | Sci Clone |
| CEPLENE (histamine) | Immunomodulator | Maxim |
| VX 950/LY 570310 | Protease inhibitor | Vertex/Eli Lilly |

TABLE 10-continued

Table of anti-Hepatitis C Compounds in Current Clinical Development

| Drug name | Drug category | Pharmaceutical Company |
|---|---|---|
| ISIS 14803 | Antisense | Isis Pharmaceutical/Elan |
| IDN-6556 | Caspase inhibitor | Idun Pharmaceuticals |
| JTK 003 | Polymerase Inhibitor | AKROS Pharma |
| Tarvacin | Anti-Phospholipid Therapy | Peregrine |
| HCV-796 | Polymerase Inhibitor | ViroPharma/Wyeth |
| CH-6 | Protease inhibitor | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD2O Monoclonal Antibody | Genetech/IDEC |
| NM283 (Valopicitabine) | Polymerase Inhibitor | Idenix Pharmaceuticals |
| HEPX ™-C | Monoclonal Antibody | XTL |
| IC41 | Therapeutic Vaccine | Intercell |
| Medusa Interferon | Longer acting interferon | Flamel Technology |
| E-1 | Therapeutic Vaccine | Innogenetics |
| Multiferon | Long Acting Interferon | Viragen |
| BILN 2061 | Protease inhibitor | Boehringer-Ingelheim |
| TMC435350 | Protease inhibitor | Tibotec/Medivir |
| Telaprevir (VX-950) | Protease inhibitor | Vertex |
| Boceprevir (SCH 503034) | Protease inhibitor | Schering-Plough |
| ACH-1625 | Protease inhibitor | Achillion |
| ABT-450 | Protease inhibitor | Abbott/Enanta |
| BI-201335 | Protease inhibitor | Boehringer-Ingelheim |
| PHX-1766 | Protease inhibitor | Phenomix |
| VX-500 | Protease inhibitor | Vertex |
| MK-7009 | protease inhibitor | Merck |
| R7227 (ITMN-191) | protease inhibitor | InterMune |
| Narlaprevir (SCH 900518) | Protease inhibitor | Schering/Merck |
| Alinia (nitazoxanide) | To be determined | Romark |
| ABT-072 | Polymemse Inhibitor | Abbott |
| ABT-333 | Polymemse Inhibitor | Abbott |
| Filibuvir (PF-00868554) | Polymerase Inhibitor | Pfizer |
| VCH-916 | Polymemse Inhibitor | Vertex |
| R7128 (PSI6130) | Polymerase Inhibitor | Roche/Pharmasset |
| IDX184 | Polymerase Inhibitor | Idenix |
| R1626 | Polymerase inhibitor | Roche |
| MK-3281 | Polymerase inhibitor | Merck |
| PSI-7851 | Polymerase inhibitor | Pharmasset |
| ANA598 | Polymemse inhibitor | Anadys Pharmaceuticals |
| BI-207127 | Polymerase inhibitor | Boehringer-Ingelheim |
| GS-9190 | Polymerase inhibitor | Gilead |
| VCH-759 | Polymemse Inhibitor | Vertex |
| Clemizole | NS4B inhibitor | Eiger Biopharmaceuticals |
| A-832 | NS5A inhibitor | ArrowTherapeutics |
| BMS-790052 | NS5A inhibitor | Bristol-Myers-Squibb |
| ITX5061 | Entry inhibitor | iTherx |
| GS-9450 | Caspase inhibitor | Gilead |
| ANA773 | TLR agonist | Anadys |
| CYT107 | immunomodulator | Cytheris |
| SPC3649 (LNA-ANTIMIR ™-122) | microRNA | Santaris Pharma |
| Debio 025 | Cyclophilin inhibitor | Debiopharm |
| SCY-635 | Cyclophilin inhibitor | Scynexis |

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $BoC_2O$ for di-tert-butyl-dicarbonate; Boc for t-butoxycarbonyl; Bpoc for 1-methyl-1-(4-biphenylyl)ethyl carbonyl; BtOH for 1-hydroxybenzotriazole; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phos-phonium Hexafluorophosphate; Brine for sodium chloride solution in water; Cbz for carbobenzyloxy; CDI for carbonyldiimidazole; $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphosphino butane; DBU for 1,8-diazabicyclo[5.4.0]undec-7-ene; DCC for N,N'-dicyclohexylcarbodiimide; DEAD for diethylazodicarboxylate; DIAD for diisopropyl azodicarboxylate; DIBAL-H for diisobutylaluminium hydride; DIPEA or $(i\text{-}Pr)_2EtN$ for N,N-diisopropylethyl amine; Dess-Martin periodinane for 1,1,1-tris(acetyloxy)-1,1-dihydro-1,2-benziodoxol-3-(1H)-one; DMAP for 4-dimethylaminopyridine; DME for 1,2-dimethoxy-ethane; DMF for N,N-dimethylformamide; DMSO for dimethyl sulfoxide; DMT for di(p-methoxyphenyl)phenylmethyl or dimethoxytrityl; DPPA for diphenylphosphoryl azide; EDC for N-(3-dimethylaminopropyl)-N'-ethylcarbodiimide; EDC HCl for N-(3-dimethylamino-propyl)-N'-ethylcarbodiimide hydrochloride; EtOAc for ethyl acetate; EtOH for ethanol; $Et_2O$ for diethyl ether; Fmoc for 9-fluorenylmethoxycarbonyl; Grubbs-1 catalyst for benzylidene-bis(tricyclohexylphosphine)dichlororuthenium; HATU for O-(7-azabenzotriazol-1-yl)-N,N,N',N'-tetramethyluronium hexafluorophosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethylpiperidinate; MeOH for methanol; Mg for magnesium; MOM for methoxymethyl; Ms for mesyl or $-SO_2-CH_3$; $Ms_2O$ for methanesulfonic anhydride or mesyl-anhydride; $NaBH_4$ for sodium borohydride; $NaBH_3CN$ for sodium cyanoborohydride; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMMO for N-methylmorpholine N-oxide; $NaIO_4$ for sodium periodate; Ni for nickel; OH for hydroxyl; $OsO_4$ for osmium tetroxide; Pd for palladium; Ph for phenyl; PMB for p-methoxybenzyl; POPd for dihydrogen dichlorobis(di-tert-butylphosphinito-κP)palladate(II); $Pd_2(dba)_3$ for tris(dibenzylidene-acetone) dipalladium (O); $Pd(PPh_3)_4$ for tetrakis (triphenylphosphine)palladium (O); $PdCl_2(PPh_3)_2$ for trans-dichlorobis(triphenyl-phosphine)palladium (II); Pt for platinum; Rh for rhodium; rt for romm temperature; Ru for ruthenium; SEM for (trimethylsilyl)ethoxymethyl; TBAF for tetrabutylammonium fluoride; TBS for tert-butyl dimethylsilyl; TEA or $Et_3N$ for triethylamine; Teoc for 2-trimethylsilyl-ethoxy-carbonyl; TFA for trifluoroacetic acid; THF for tetrahydrofuran; TMEDA for N,N,N',N'-tetramethylethylenediamine; TPP or $PPh_3$ for triphenyl-phosphine; Troc for 2,2,2-trichloroethyl carbonyl; Ts for tosyl or $-SO_2-C_6H_4CH_3$; $Ts_2O$ for tolylsulfonic anhydride or tosyl-anhydride; TsOH for p-tolylsulfonic acid; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

The compounds of the present invention may be prepared via several different synthetic routes from a variety of benzimidazole and imidazole related intermediates. A retrosynthesis of those title compounds include direct formation of a suitably linked benzimidazole and imidazole core structure followed by attachment of a suitable $R^6$ group, plus some functional group manipulations in between and/or after.

A general synthesis and further elaboration of some benzimidazole related intermediates are summarized in Scheme 1.

The synthesis starts from the construction of an optionally substituted benzimidazole 1-2, which may be obtained by condensation of an amino acid or its derivative 1-1.1 or 1-1.2 and an o-phenylenediamine 1-1 under the conditions to those skilled in the art. The benzimidazole ring closure may be realized either in one pot by heat, optionally in the presence of an acid and/or with a dehydration reagent such as polyphosphoric acid; or in two steps: 1) amide formation between diamine 1-1 and amino acid 1-1.1 or 1-1.2 in the presence of a condensation reagent such as EDC HCl, DCC or the like; or through mixed anhydride approach by reacting acid 1-1.1 or 1-1.2 with a chloroformate such as methyl chloroformate, isobutyl chloroformate, or the like, in the presence of a base such as TEA, DIPEA, DMAP, N-methylmorpholine, or the like, followed by treating the mixed anhydride with diamine 1-1; and 2) the heterocyclic ring closure in the presence of an acid such as acetic acid, sulfuric acid or the like or a dehydration reagent such as HATU or the like, optionally with heat.

Optionally, the NH group in the newly formed benzimidazole ring of 1-2 may be protected with an amino protecting group, such as SEM (i.e. SEM-Cl, NaH), Boc, Cbz, Teoc, Troc, or the like. The protected benzimidazole 1-2 may be subjected to lithium-halogen exchange with various (n-, s-, or t-) butyl lithium and the resulting lithiate can be trapped with a nucleophile, i.e. a halide such as various allyl halide to give the allylated 1-6 as a key intermediate. Alternatively, 1-6 may be obtained from the Stille reaction conditions to those skilled in the art (see reviews: A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European* 1 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), using an allylstanne such as allyltributylstanne as the allyl donor. Analogously a key vinyl intermediates 1-3 may be prepared by Stille reaction from bromide 1-2 with tributylvinylstanne. Also, Sonogashira coupling between bromide 1-2 and propargyl alcohol or trimethylsilylacetylene can generate propargyl alcohol 1-4 or alkyne 1-5 after removal of TMS. Further bromination of intermediate 1-4 may form the propargyl bromide 1-9. In addition, benzimidazole bromide 1-2 may be converted to methyl ketone 1-7 by coupling with tributyl(1-ethoxyvinyl)tin under Stille coupling conditions followed by acidic hydrolysis.

Scheme 1
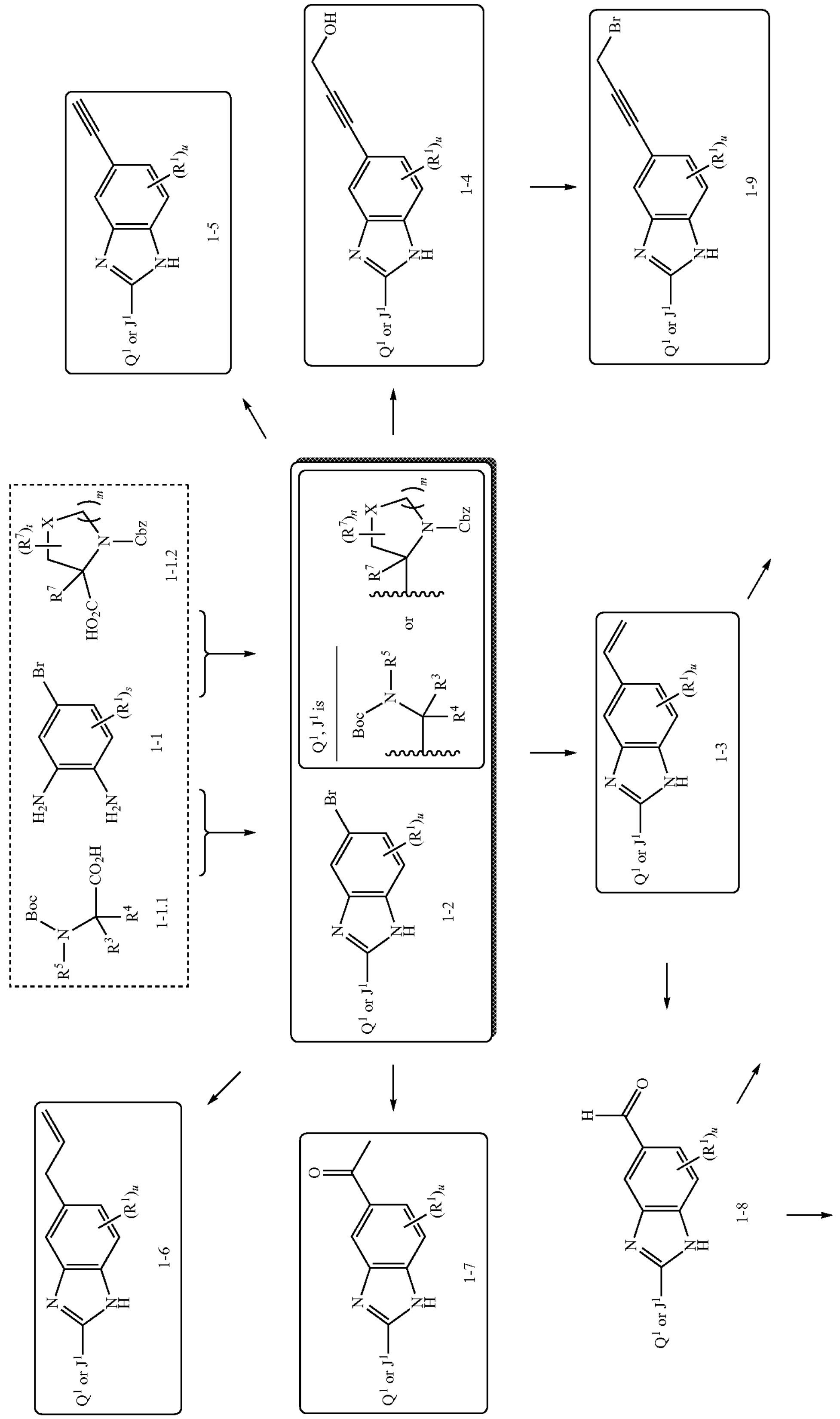
1-1.1 1-1 1-1.2 1-2 1-3 1-4 1-5 1-6 1-7 1-8 1-9

-continued
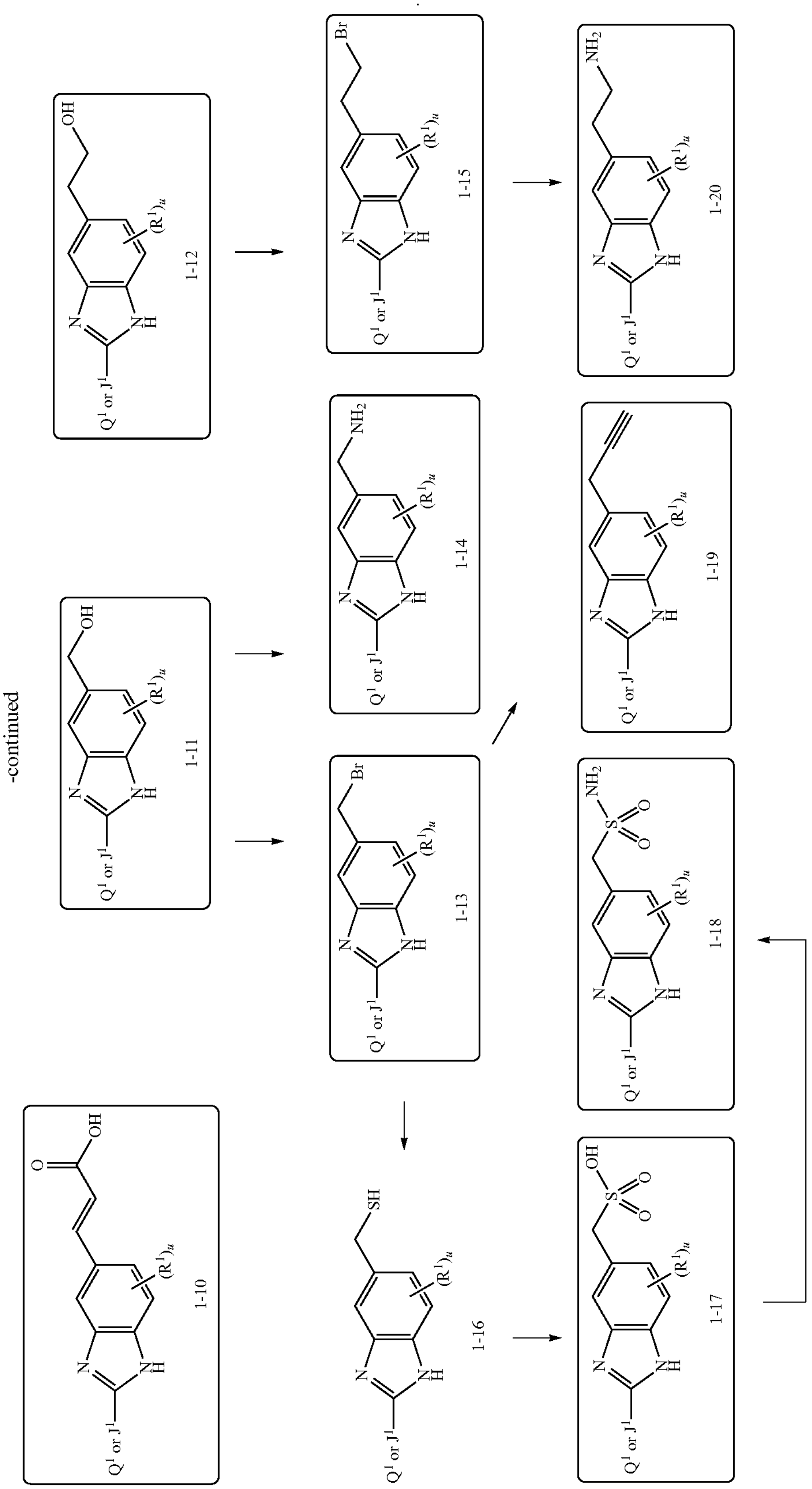
1-10
1-11
1-12
1-13
1-14
1-15
1-16
1-17
1-18
1-19
1-20

-continued
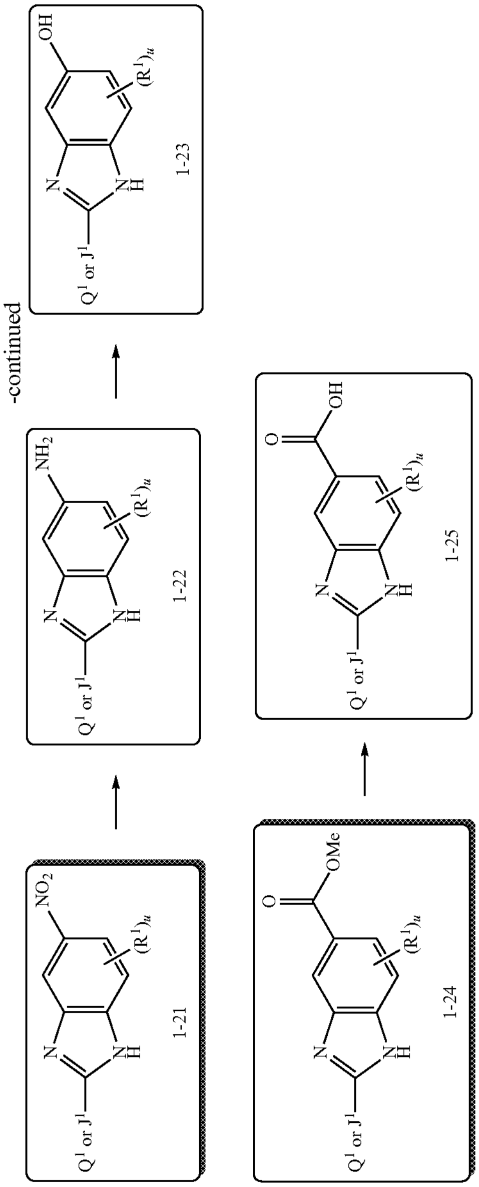
1-21
1-22
1-23
1-24
1-25

Further elaboration of the benzimidazole intermediates starts from the vinyl intermediate 1-3, which may be transformed to aldehyde 1-8 through ozonolysis cleavage or to alcohol 1-12 by hydroboration-oxidation sequence. Alcohol 1-12 may be converted to bromide 1-15 by the well-known bromination procedure, which can be further functionalized to amine 1-20 through azide substitution followed by reduction. Aldehyde 1-8 can then either be reduced to alcohol 1-11, or be converted to α, β-unsaturated acid 1-10 through Horner-Wadsworth-Emmons aldehyde homologation reaction followed by saponification. Alcohol 1-11 may be similarly converted to the corresponding amine intermediate 1-14 and bromide intermediate 1-13 as described previously. Bromide 1-13 can be homologated to alkyne intermediate 1-19 with a metal acetylide. In addition, bromide 1-13 may be also transformed to thiol 1-16 through nucleophilic substitution, which can be further oxidized to sulfonic acid 1-17. Sulfonamide 1-18 may then be derived from 1-17 through the sulfonyl chloride activation process.

The compounds of the present invention may also be derived from nitrobenzimidazole 1-21, which can be prepared from the corresponding 4-nitro-1,2-diaminobenzene using the similar procedures described above. Intermediate 1-21 can be converted to amine 1-22 through $NO_2$-reduction (i.e. $H_2$, catalytical Pd). Diazotization of amine 1-22 with a nitrite such as sodium nitrite, isobutyl nitrite, or the like, in an aqueous acid such as acetic acid, hydrochloric acid, sulfuric acid, or the like, optionally in the presence of a copper or copper salt, may afford hydroxy 1-23.

Analogously, benzimidazolecarboxylate 1-24, which can be prepared from the corresponding 4-methyl-1,2-diaminobenzoate using the procedures described above, may be hydrolyzed to the corresponding carboxylic acid 1-25.

It should be noted that optionally the NH group of all the benzimidazole related intermediates listed above may be protected with an amino protecting group, such as SEM (i.e. SEM-Cl, NaH), Boc, Cbz, Teoc, Troc, or the like.

Scheme 2
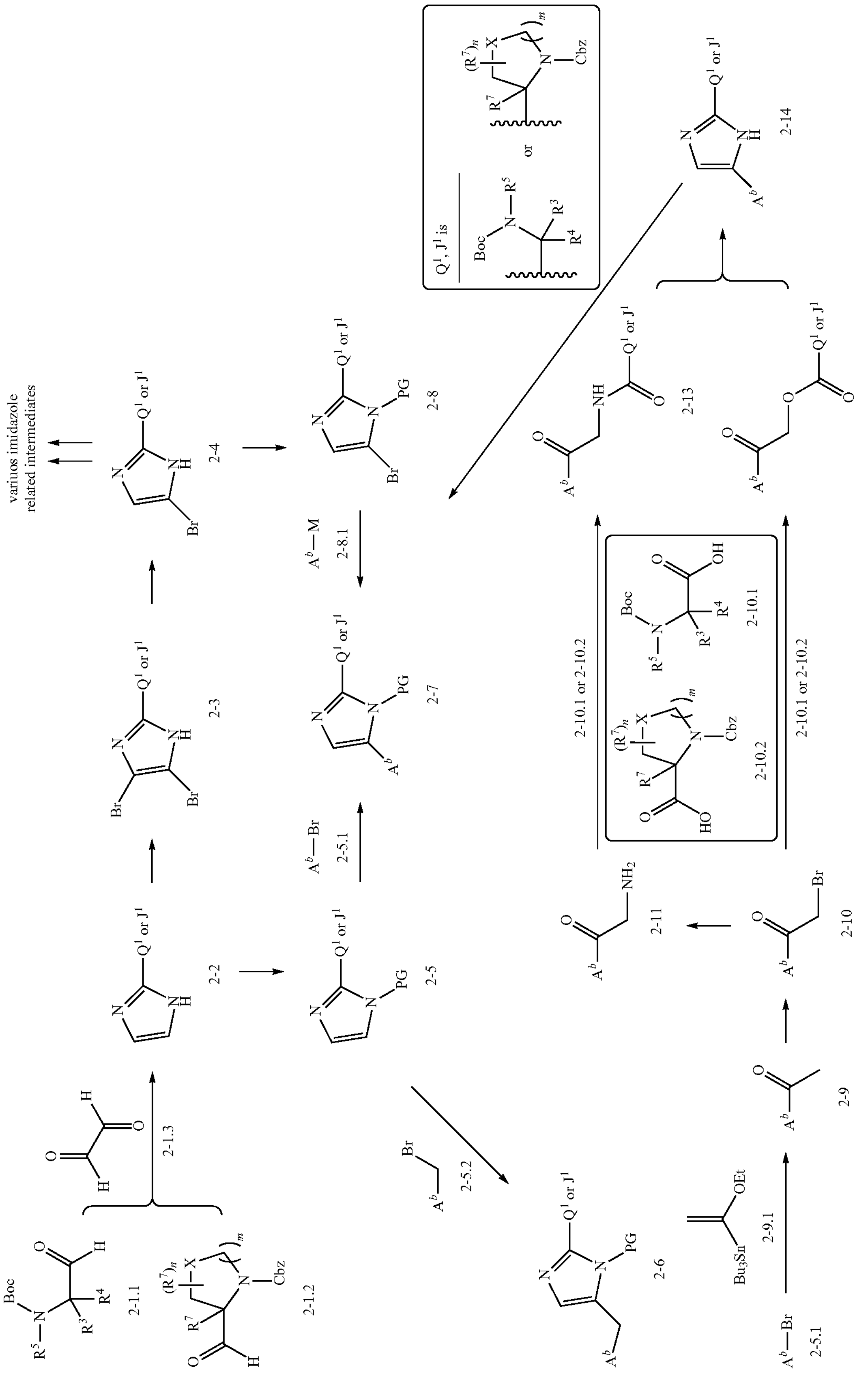
$A^b$ = aryl, heteroaryl

A typical synthesis of imidazole related intermediates are analogous to that of the benzimidazole intermediates. As shown in Scheme 2, bromo-imidazole 2-4 can be synthesized in a three-step sequence: 1) condensation between amino acid derived aldehyde 2-1.1 or 2-1.2 and glyoxal 2-1.3 in the presence of methanolic ammonia to generate imidazole 2-2; 2) bromination of 2-2 with excess amount of bromination reagent such as 2,4,4,6-tetrabromo-2,5-cyclohexadienone, NBS, etc. to afford dibromide 2-3; and 3) selective reduction of the dibromide 2-3 by heating in aq. $Na_2SO_3$ or aq. $NaHSO_3$. 2-4 then may be served as a universal intermediate further elaborable to many other imidazole derivatives using the chemistry discussed in Scheme 1, some of which are listed in the table below.

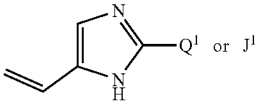

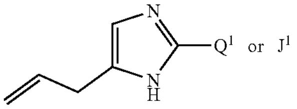

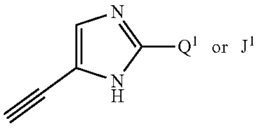

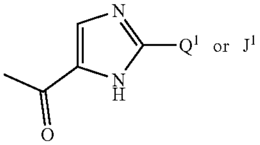

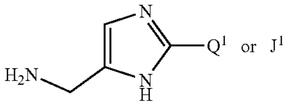

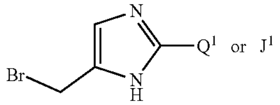

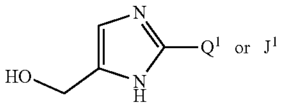

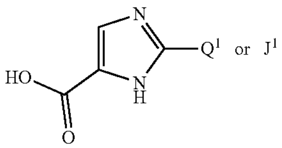

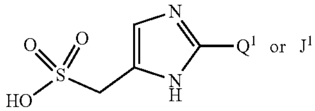

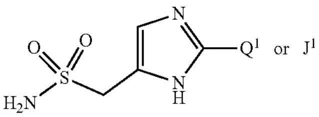

-continued

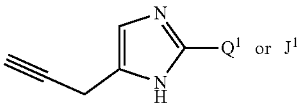

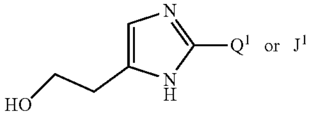

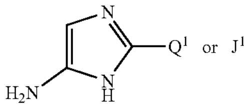

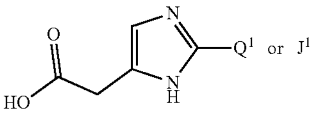

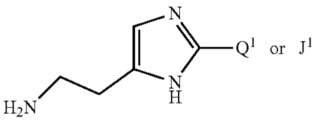

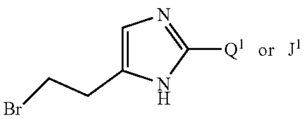

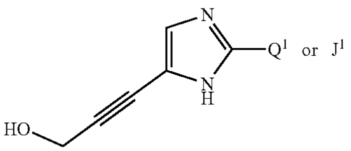

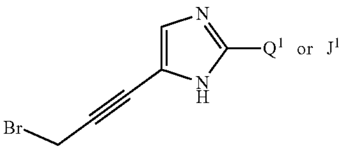

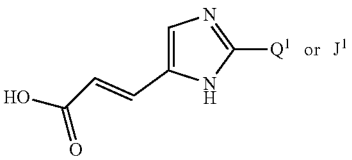

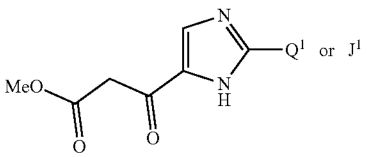

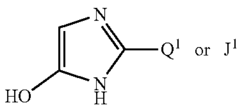

-continued

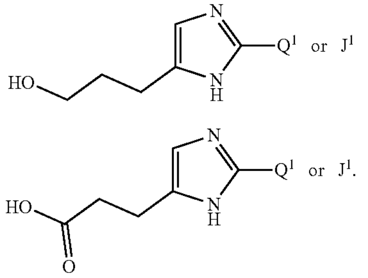

Optionally, the NH group of imidazole related intermediates listed above may be protected with an amino protecting group (shown in Scheme 2 as PG), such as SEM (i.e. SEM-Cl, NaH), Boc, Cbz, Teoc, Troc, or the like. The protected imidazole 2-5 may be deprotonated with a strong base such as LDA, BuLi, etc to generate a carbon anion, which may either undergo a nucleophilic substitution with an activated halide such as 2-5.2 to afford aryl or heteroaryl substituted imidazole 2-6 or couple with an aryl or heteroaryl halide 2-5.1 in the presence appropriate transition metal salt to generate bicyclic heteroaryl 2-7. Similarly, the protected bromo imidazole 2-8 may be subjected to lithium-halogen exchange with various (n-, s-, or t-) butyl lithium, the resulting lithiate may undergo similar reactions to afford 2-6 and 2-7. Also, when 2-8 is treated with metalated aryl or heteroaryl 2-8.1, in which M at each occurrence is independently a boron, tin, silicon, zinc, zirconium, or copper species, under Suzuki or Stille conditions to those skilled in the art (see reviews: A. Suzuki, *Pure Applied Chem.* 1991, 63, 419; A. Suzuki, *Handbook of Organopalladium Chemistry for Organic Synthesis* 2002, 1, 249; A. Anastasia, et al, *Handbook of Organopalladium Chemistry for Organic Synthesis* 2002, 1, 311; F. Bellina, et al, *Synthesis* 2004, 2419; M. G. Organ, et al, *Synthesis* 2008, 2776; A. T. Lindhardt, et al, *Chem.—A European* 1 2008, 14, 8756; E. A. B. Kantchev, et al, *Angew. Chem. Int. Ed.* 2007, 46, 2768; V. Farina, et al, *Advances in Metal-Organic Chem.* 1996, 5, 1), to provide coupling product 2-7. In addition to these direct coupling strategy, aryl or heteroaryl bromide 2-5.1 may be converted to methyl ketone 2-9 under Stille coupling conditions with tributyl(1-ethoxyvinyl)tin 2-9.1. 2-9 may be brominated under conditions to those skilled in the art to afford bromide 2-10, which may be either converted to the corresponding amine 2-11, or coupled with protected amino acid 2-10.1 or 2-10.2 in the presence of a base such as $Et_3N$ and DIPEA to afford keto-ester 2-12. Similarly, amine 2-11 may be converted to the corresponding keto-amide 2-13 via condensation with appropriate amino acid under standard amide formation conditions. 2-12 and 2-13 may be transformed to key intermediate 2-14 via heating with $(NH_4)OAc$ under thermal or microwave conditions.

With a variety of suitably substituted benzimidazoles and imidazoles in hand, such as those listed in Scheme 1, Scheme 2 and the table above, the compounds of the present invention may be prepared through various coupling strategy or a combination of strategies to connect two fragments, optionally with a suitable cyclic or acyclic linker or formation of a cyclic or acyclic linker. The said strategy includes, but not limited to, Stille coupling, Suzuki coupling, Sonogashira coupling, Heck coupling, Buchwald amidation, Buchwald amination, amide coupling, ester bond formation, William etherification, Buchwald etherification, alkylation, pericyclic reaction with different variations, or the like.

An example of the strategies that may be used to prepare the compounds of the present invention is shown in Scheme 3, wherein $R^2$ is independently Both bromides 3-1 and 3-2 can be prepared using the procedures described in Scheme 1 and Scheme 2. Bromide 3-2 can be converted to the corresponding metalated aryl 3-3 under Suzuki or Stille conditions, which may be further coupled with benzimidazole bromide 2-1 under similar conditions to generate a structural core 3-4.

Scheme 3

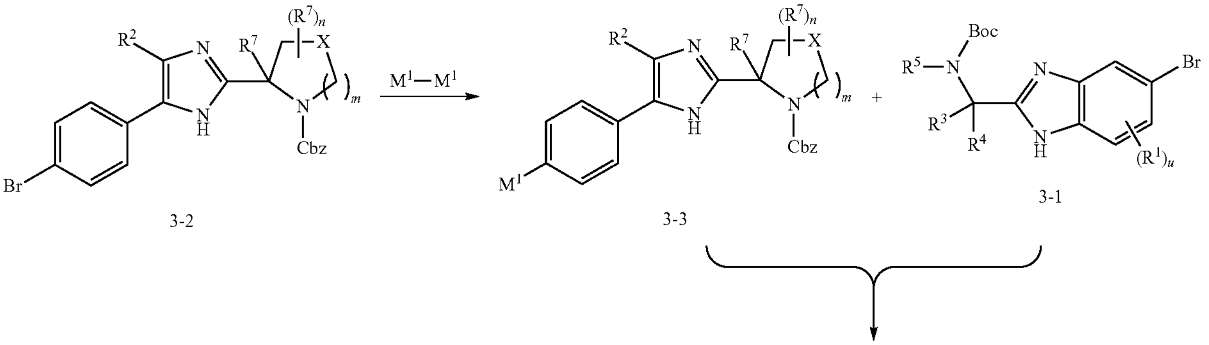

3-2 3-3 3-1

-continued

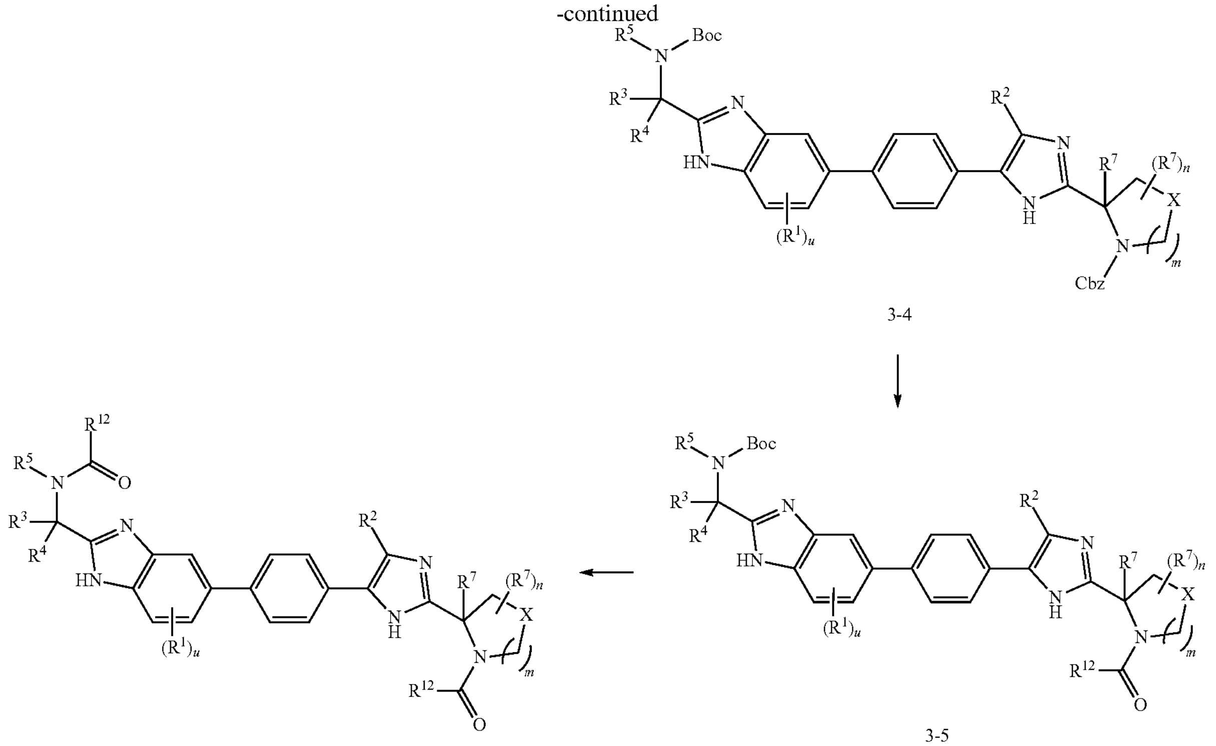

3-4

3-5

I-1

$M^1$ = boron or tin species

Compound 3-4 may then serve as a common intermediate for further derivatizations to 3-5 in two steps: 1) mono-deprotection of the linear or cyclic amine moiety may be accomplished, for example, treatment to hydrogenolytic conditions under Pd catalyst in the presence of a base such as potassium carbonate to remove the Cbz protection group; and 2) the released amine functionality may be acylated with an carboxylic acid under standard acylation conditions, for example a coupling reagent such as HATU in combination with an organic base such as DIPEA can be used in this regard; alternatively, the released amine may be reacted with an isocyanate, carbamoyl chloride or chloroformate to provide an urea or carbamate. Various carboxylic acids including amino acids in racemic or optical form are commercially available, and/or can be synthesized in racemic or optical form, see references cited in reviews by D. Seebach, et al, *Synthesis* 2009, 1; C. Cativiela and M. D. Diaz-de-Villegas, *Tetrahedron: Asymmetry* 2007, 18, 569; 2000, 11, 645; and 1998, 9, 3517; and experimental examples compiled in patent application WO 2008/021927A2 by C. Bachand, et al, from BMS, which is incorporated herein by reference. 3-5 may be further deprotected under hydrolytic conditions in the presence of an acid such as TFA or hydrogen chloride to remove the Boc protection group and the released amine functionality can be further derivatized to the title compounds I-1 using the conditions described above. Other examples of some of the linkers that can be used to construct the title compounds of the present invention are compiled in the table below, in which PG and PG' at each occurrence are each independently amino or alcohol protecting group, such as Boc, Cbz, Troc, Teoc, PMB, TMS etc. These linkers are either commercially available or may be synthesized in several steps through strategies which are known to those skilled in the art.

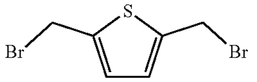

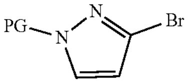

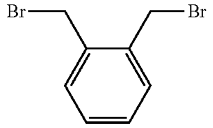

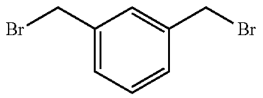

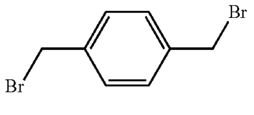

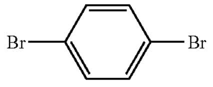

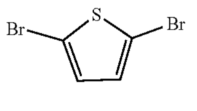

-continued
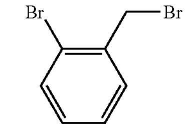
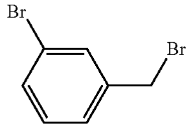
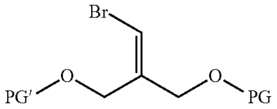
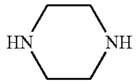
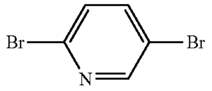
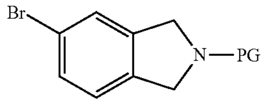
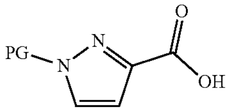
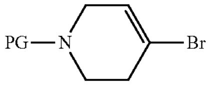
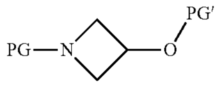
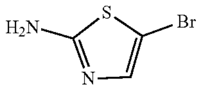
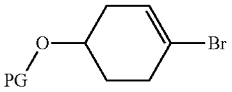
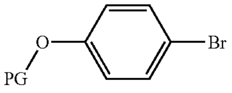
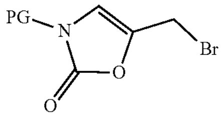
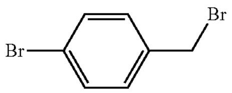
-continued
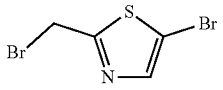
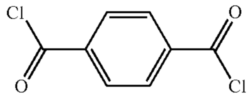 [SMILES: O=C(Cl)c1ccc(C(=O)Cl)cc1]
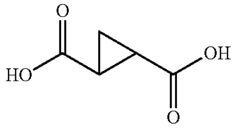
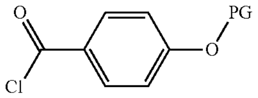
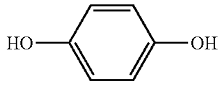
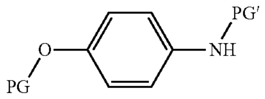
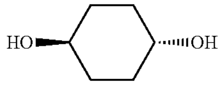
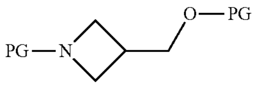
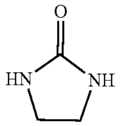
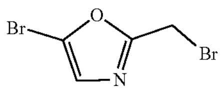
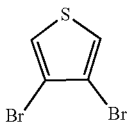
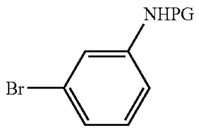
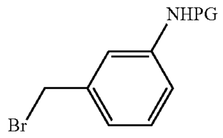

-continued

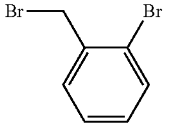

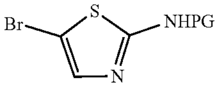

Alternatively, as shown in Scheme 4, the compounds of the present invention (for example I-1) may also be derived from bromobenzimidazoles 4-1 and imidazole 4-2 using the procedures described previously. The intermediates 4-1 and 4-2 have the desired acyl groups already installed as seen in amino acid derivatives 2-10.1b and 2-10.2b, which can be prepared from protected amino acids 2-10.1a and 2-10.2a through the sequences shown in Scheme 1 and 2.

Scheme 4

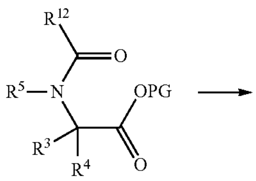

2-10.1a

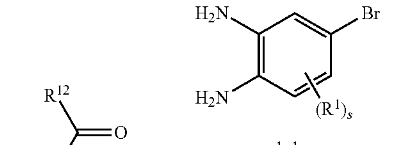

1-1

2-10.1b

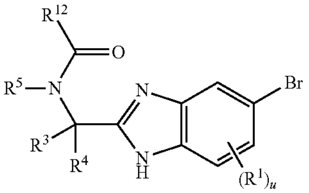

4-1

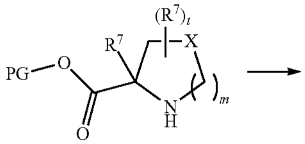

2-10.2a

-continued

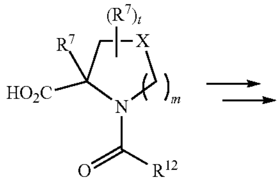

2-10.2b

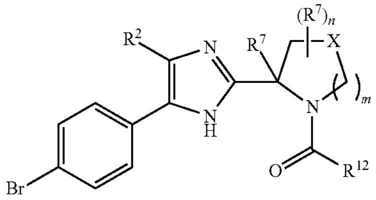

4-2

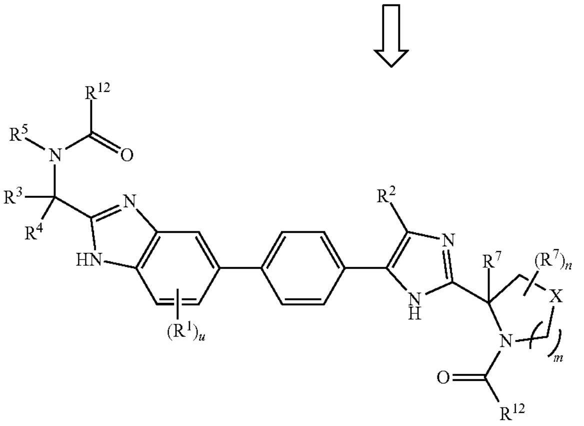

I-1

PG is carboxylic acid protecting group $R^2$ is independently R1

The compounds of the present invention containing benzimidazole linked with other five-membered heteroaryl other than imidazole may be prepared using similar procedures described above in Schemes 1-4. For example, some intermediates containing a desired, suitably substituted five-membered heteroaryl have been published in US 2008/0311075A1 by C. Bachand, et al from BMS, which is incorporated by reference. Theses intermediates are compiled in the following table.

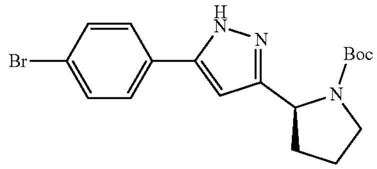 [SMILES: CC(C)(C)OC(=O)N1CCC[C@H]1c1cc(-c2ccc(Br)cc2)[nH]n1]

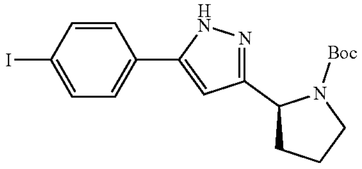 [SMILES: CC(C)(C)OC(=O)N1CCC[C@H]1c1cc(-c2ccc(I)cc2)[nH]n1]

-continued

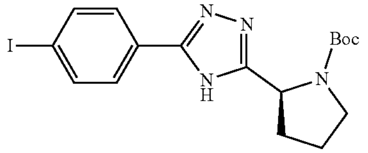 [SMILES: CC(C)(C)OC(=O)N1CCC[C@H]1c1nnc(-c2ccc(I)cc2)[nH]1]

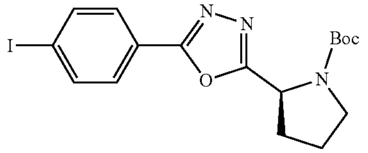 [SMILES: CC(C)(C)OC(=O)N1CCC[C@H]1c1nnc(-c2ccc(I)cc2)o1]

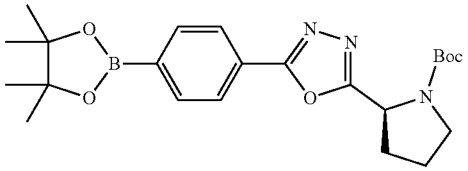

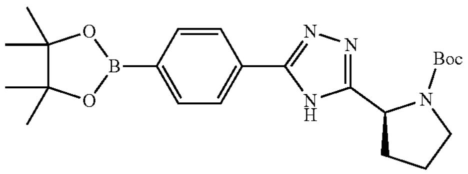

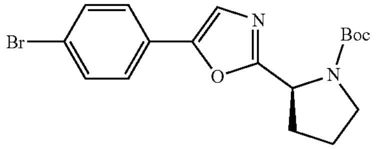 [SMILES: CC(C)(C)OC(=O)N1CCC[C@H]1c1ncc(-c2ccc(Br)cc2)o1]

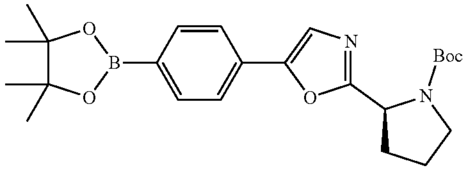 [SMILES: CC(C)(C)OC(=O)N1CCC[C@H]1c1ncc(-c2ccc(B3OC(C)(C)C(C)(C)O3)cc2)o1]

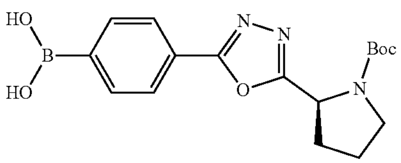 [SMILES: CC(C)(C)OC(=O)N1CCC[C@H]1c1nnc(-c2ccc(B(O)O)cc2)o1]

It will be appreciated that, with appropriate manipulation and protection of any chemical functionality, synthesis of compounds of Formula (I) is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

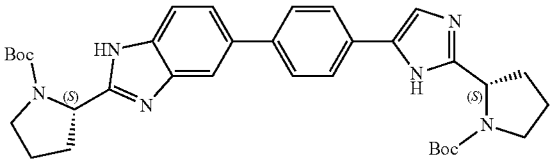

Step 1a. A mixture of N-Boc-L-proline (5.754 g, 26.7 mmol) and TEA (3.73 mL, 26.7 mmol) in THF (60 mL) at −20° C. was treated with ethyl chloroformate (2.55 mL, 26.7 mmol) for 30 minutes before a slow addition of 4-bromo-1,2-diaminobenzene (5.00 g, 26.7 mmol) in THF (20 mL). It was then kept at −20° C. for 1 hour and then slowly warmed up to rt and stirred at rt overnight. The volatiles were evaporated and the residue was partitioned (EtOAc—water). The organics were washed with brine, dried ($Na_2SO_4$), filtered and evaporated to give the crude desired compound as a dark brown foam (10.7 g). ESIMS m/z=384.18, 386.18 $[M+H]^+$.

Step 1b. A solution of the crude compound from step 1a (10.7 g, 26.7 mmol at most) in glacial acetic acid (100 mL) was heated at 50° C. for 2 hours. The volatiles were evaporated off and the residue was partitioned (EtOAc—aqueous $NaHCO_3$). The organics were washed with brine, dried ($Na_2SO_4$), filtered and evaporated. The residue was purified by chromatography (silica, hexanes-ethyl acetate) to give the desired compound as a brown foam (5.78 g, 59%). ESIMS m/z=366.17, 368.17 $[M+H]^-$. $^1H$ NMR ($CDCl_3$) 10.96, 10.93 (2 s, 1H), 7.81, 7.30 (2 s, 1H), 7.53, 7.17 (2d, J=8.5 Hz, 1H), 7.23, 7.03 (2d, J=8.5 Hz, 1H), 5.09, 5.07 (2s, 1H), 3.42-3.49 (m, 2H), 2.75-2.85 (m, 1H), 2.13-2.23 (m, 2H), 1.97-2.00 (m, 1H), 1.48 (s, 9H).

Step 1c. A mixture of 2,4'-dibromoacetophenone (5.00 g, 18.0 mmol), N-Boc-L-proline (3.87 g, 18.0 mmol) and in $CH_3CN$ (60 mL) was treated with TEA (5.40 mL, 37.8 mmol) at room temperature until the disappearance of the starting material. The volatiles were evaporated and the residue was partitioned (EtOAc—water). The organics were washed with brine, dried ($Na_2SO_4$), filtered and evaporated. The residue was purified by chromatography (silica, hexanes-ethyl acetate) to give the desired compound as a light yellow foam (6.73 g, 91%). $^1H$ NMR ($CDCl_3$) 7.76 (t, J=8.0 Hz, 2H), 7.63 (dd, J=5.0, 8.5 Hz, 2H), 5.51, 5.16 (2d, J=16.0 Hz, 1H), 5.32, 5.28 (2d, J=16.5 Hz, 1H), 4.48, 4.40 (dd, J=5.0, 8.5 Hz, 1H), 3.56 (m, 1H), 3.43 (m, 1H), 2.30 (m, 2H), 2.06 (m, 1H), 1.92 (m, 1H), 1.46, 1.43 (2s, 9H).

Step 1d. A solution of the compound from step 1c (6.73 g, 16.3 mmol) in toluene (100 mL) was treated with ammonium acetate (25.1 g, 0.327 mol) at 100° C. for 14 hours. The volatiles were evaporated and the residue was partitioned (EtOAc—aqueous $NaHCO_3$). The organics were washed with brine, dried ($Na_2SO_4$), filtered and evaporated. The residue was purified by chromatography (silica, hexanes-ethyl acetate) to give the desired compound as a yellow foam (6.10 g, 95%). ESIMS m/z=392.24, 394.24 $[M+H]^+$. $^1H$ NMR ($CDCl_3$) 7.57 (bs, 1H), 7.48 (m, 3H), 7.23 (s, 1H), 4.97 (m, 1H), 3.42 (m, 2H), 2.99 (m, 1H), 2.16 (m, 2H), 1.97 (m, 1H), 1.46 (s, 9H).

Step 1e. A mixture of the compound from step 1d (1.00 g, 2.55 mmol), bis(pinacolato) diboron (1.35 g, 5.33 mmol), $Pd(PPh_3)_4$ (0.147 g, 0.128 mmol) and potassium acetate (0.640 g, 6.53 mmol) in 1,4-dioxane (20 mL) was degassed and heated at 80° C. under Na for 14 hours. The volatiles were evaporated and the residue was partitioned (EtOAc—water). The organics were washed with brine, dried ($Na_2SO_4$), filtered and evaporated. The residue was purified by chromatography (silica, hexanes-ethyl acetate) to give the desired compound as a light yellow solid (0.978 g, 87%). ESIMS m/z=440.39 $[M+H]^+$. $^1H$ NMR ($CDCl_3$) 11.03, 10.55 (2s, 1H), 7.79 (m, 3H), 7.45 (m, 1H), 7.26 (m, 1H), 4.97 (m, 1H), 3.41 (m, 2H), 3.06, 2.91 (2m, 1H), 2.17 (m, 2H), 1.97 (m, 1H), 1.49 (s, 9H), 1.35 (s, 12H).

Step 1f. A mixture of compound from step 1b (0.188 g, 0.512 mmol), the compound from step 1e (0.150 g, 0.342 mmol) $Pd(PPh_3)_4$, (39.4 mg, 34.1 μmol) and $NaHCO_3$ (0.115 g, 1.37 mmol) in DME (6 mL) and $H_2O$ (2 mL) was degassed and heated at 80° C. under Na for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a white needle crystal (0.106 g, 52%). ESIMS m/z=599.59 $[M+H]^+$.

Step 2a. A solution of the compound of example 1 (20.0 mg, 33.4 μmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=399.35 $[M+H]^+$.

Step 2b. A mixture of the crude compound from step 2a (33.4 μmol at most) and (R)-(methoxycarbonyl)amino phenyl acetic acid (prepared according to WO 2008/021927, 20.9 mg, 0.100 mmol) in DMF (3 mL) was treated with HATU (31.7 mg, 83.5 μmol) in the presence of DIPEA (83.0 μL, 0.668 mmol) for 2 hours at rt and the volatiles were evaporated off to provide a brown syrup. It was purified by chromatography (silica, $CH_2Cl_2$-MeOH) to give the title compound as a yellow solid (23.8 mg, 2 steps 91%). ESIMS m/z=781.67 $[M+H]^+$.

Example 1-1

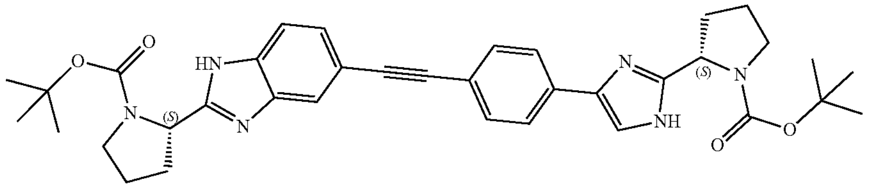

Step 1-1a. A mixture of the compound from step 1d (0.559 g, 1.425 mmol), trimethylsilylacetylene (0.60 ml, 4.275 mmol), CuI (28.5 mg, 0.150 mmol) and $Pd(PPh_3)_2Cl_2$ (80.0 mg, 0.114 mmol) in $Et_3N$ (15 mL) was heated at 80° C. under $N_2$ for 6 hours before being evaporated. The residue was purified by chromatography (silica, hexanes-ethyl acetate with 1% $Et_3N$ in ethyl acetate) to give the desired compound as a yellow foam (0.484 g, 83%). ESIMS m/z=410.24 $[M+H]^+$.

Step 1-1b. A suspension of the compound from step 1-1a (0.484 g, 1.182 mmol) and $K_2CO_3$ (0.408 g, 2.954 mmol) in methanol (12 ml) was stirred at rt for 3 hour. The volatiles were evaporated off. The residue was purified by chromatography (silica, dichloromethane-ethyl acetate) to give the desired compound as a yellow foam (0.370 g, 93%). ESIMS m/z=338.24 $[M+H]^+$.

Step 1-1c. A mixture of the compound from step 1-1b (80.0 mg, 0.2371 mmol), the compound from step 1b (86.8 mg, 0.2371 mmol), CuI (2.2 mg, 0.01185 mmol) and $Pd(PPh_3)_2Cl_2$ (16.6 mg, 0.02371 mmol) in $Et_3N$ (0.3 mL) and $CH_3CN$ (2 mL) was heated at 85° C. under $H_2/N_2$ mixed gas for 2 hours before being evaporated. The residue was purified by chromatography (silica, hexanes-ethyl acetate with 1% $Et_3N$ in ethyl acetate) to give the title compound as a yellow solid (48.3 mg, 33%). ESIMS m/z=623.32 $[M+H]^+$.

Example 2

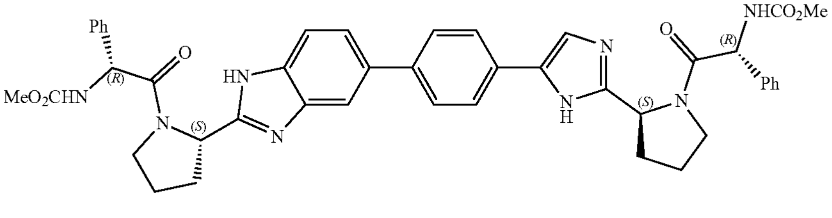

Example 2-1

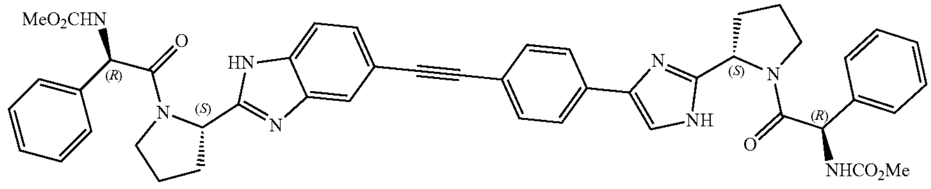

Step 2-1a. A solution of the compound of example 1-1 (48.3 mg, 0.0776 mmol) in 1,4-dioxane (1.5 mL) was treated with HCl in 1,4-dioxane (4 M, 6 mL) at rt for 30 minutes. The volatiles were evaporated off to give the crude desired compound as a yellow solid which was used directly in the next step.

Step 2-1b. A mixture of the crude compound from step 2-1a (0.127 mmol at most) and (R)-(methoxycarbonyl) amino phenyl acetic acid (prepared according to WO 2008/021927, 40.6 mg, 0.194 mmol) in DMF (1.5 mL) was treated with HATU (67.8 mg, 0.178 mmol) in the presence of DIPEA (0.27 mL, 1.551 mmol) for 2 hours at rt and the volatiles were evaporated off to provide a brown syrup. It was purified by chromatography (silica, $CH_2Cl_2$-MeOH) to give the title compound as a yellow solid (36.2 mg, 2 steps 58%). ESIMS m/z=805.29 $[M+H]^+$.

Example 2-2

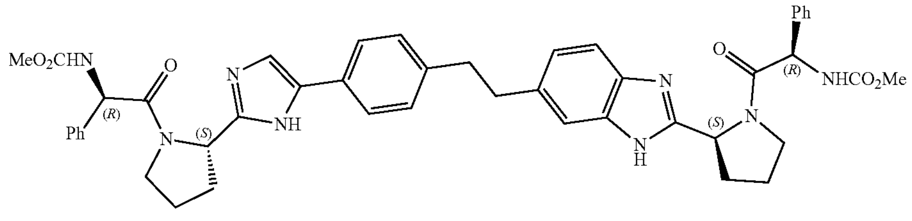

A solution of the compound of example 2-1 (23.0 mg, 0.0286 mmol) in ethanol (2 mL) was treated with $Pd(OH)_2$ (20 wt % on carbon, 23 mg) at rt with a hydrogen balloon for 7 hour. The mixture was filtered through a short pad of Celite. The volatiles were evaporated off. The residue was purified by chromatography (silica, $CH_2Cl_2$-MeOH) to give the title compound as a white solid (16.0 mg, 70%). ESIMS m/z=809.40 $[M+H]^+$.

The compounds of examples 3-356 and 358-440 may be prepared using procedures similar to those described in examples 1, 2, 1-1, 2-1, 2-2, 357 (described below), and 441-545 (described below), and/or as described in the Synthetic Methods.

TABLE 1a
Examples 3-219.
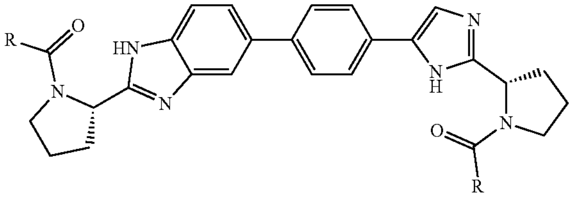
| Entry | 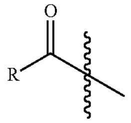 |
|---|---|
| 3 | 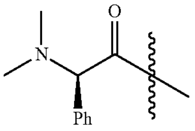 [SMILES: *C(=O)[C@@H](c1ccccc1)N(C)C] |
| 4 | 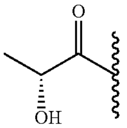 [SMILES: *C(=O)[C@@H](C)O] |
| 5 | 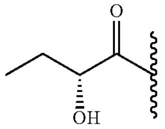 [SMILES: *C(=O)[C@H](O)CC] |
| 6 | 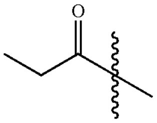 [SMILES: *C(=O)CC] |
| 7 | 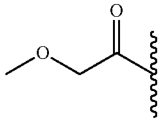 [SMILES: *C(=O)COC] |
| 8 | 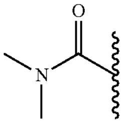 [SMILES: *C(=O)N(C)C] |
| 9 | 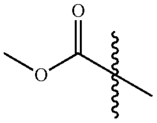 [SMILES: *C(=O)OC] |
| 10 | 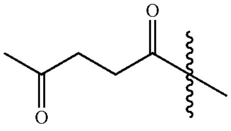 [SMILES: *C(=O)CCC(C)=O] |
| 11 | 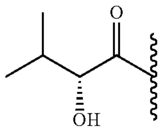 [SMILES: *C(=O)[C@H](O)C(C)C] |
TABLE 1a-continued
Examples 3-219.
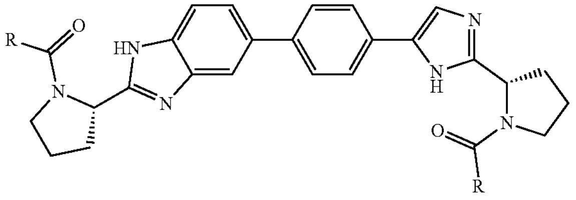
| Entry | 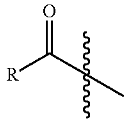 |
|---|---|
| 12 | 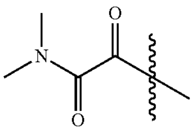 [SMILES: *C(=O)C(=O)N(C)C] |
| 13 | 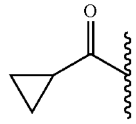 [SMILES: *C(=O)C1CC1] |
| 14 | 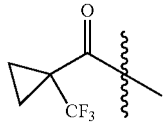 |
| 15 | 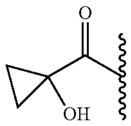 [SMILES: *C(=O)C1(O)CC1] |
| 16 | 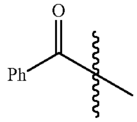 [SMILES: *C(=O)c1ccccc1] |
| 17 | 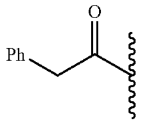 [SMILES: *C(=O)Cc1ccccc1] |
| 18 | 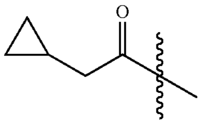 [SMILES: *C(=O)CC1CC1] |
| 19 | 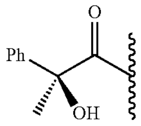 [SMILES: *C(=O)[C@@](C)(O)c1ccccc1] |
| 20 | 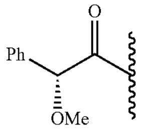 |

TABLE 1a-continued
Examples 3-219.
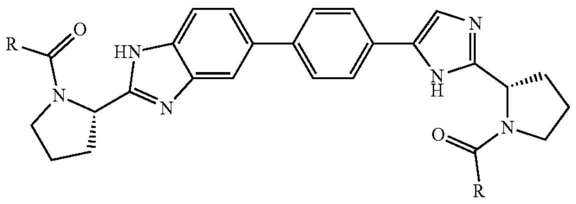
| Entry | 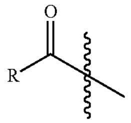 |
|---|---|
| 21 | 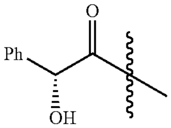 [SMILES: *C(=O)[C@H](O)c1ccccc1] |
| 22 | 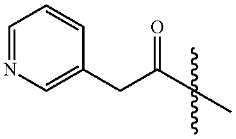 [SMILES: *C(=O)Cc1cccnc1] |
| 23 | 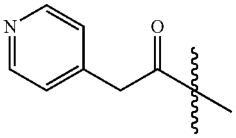 [SMILES: *C(=O)Cc1ccncc1] |
| 24 | 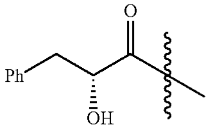 [SMILES: *C(=O)[C@H](O)Cc1ccccc1] |
| 25 | 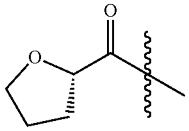 [SMILES: *C(=O)[C@@H]1CCCO1] |
| 26 | 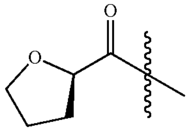 [SMILES: *C(=O)[C@H]1CCCO1] |
| 27 | 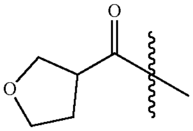 [SMILES: *C(=O)C1CCOC1] |
| 28 | 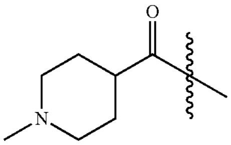 [SMILES: *C(=O)C1CCN(C)CC1] |
TABLE 1a-continued
Examples 3-219.
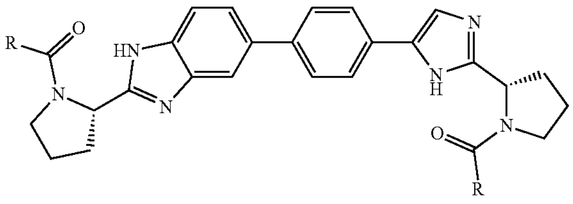
| Entry | 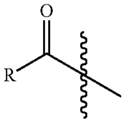 |
|---|---|
| 29 | 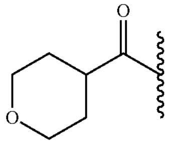 [SMILES: *C(=O)C1CCOCC1] |
| 30 | 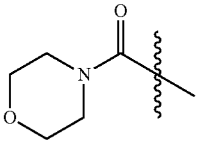 [SMILES: *C(=O)N1CCOCC1] |
| 31 | 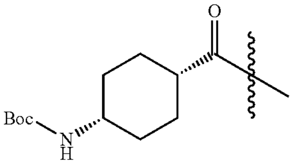 [SMILES: *C(=O)[C@H]1CC[C@@H](NC(=O)OC(C)(C)C)CC1] |
| 32 | 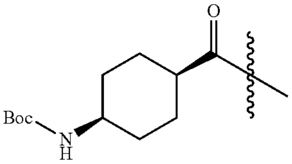 [SMILES: *C(=O)[C@H]1CC[C@@H](NC(=O)OC(C)(C)C)CC1] |
| 33 | 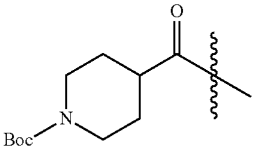 [SMILES: *C(=O)C1CCN(C(=O)OC(C)(C)C)CC1] |
| 34 | 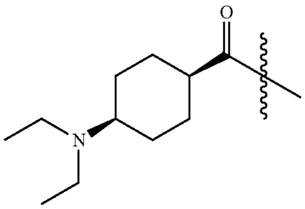 [SMILES: *C(=O)[C@H]1CC[C@@H](N(CC)CC)CC1] |
| 35 | 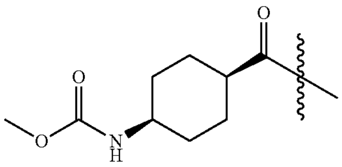 [SMILES: *C(=O)[C@H]1CC[C@@H](NC(=O)OC)CC1] |

TABLE 1a-continued
Examples 3-219.
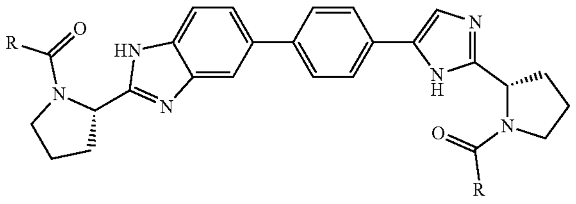
| Entry | 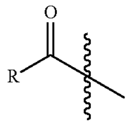 |
|---|---|
| 36 | 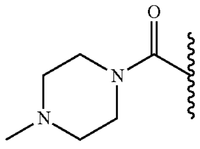 [SMILES: *C(=O)N1CCN(C)CC1] |
| 37 | 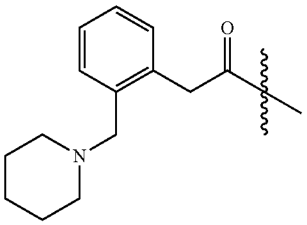 [SMILES: *C(=O)Cc1ccccc1CN1CCCCC1] |
| 38 | 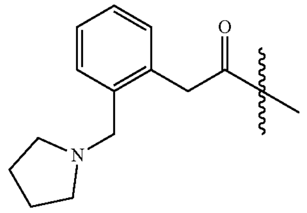 [SMILES: *C(=O)Cc1ccccc1CN1CCCC1] |
| 39 | 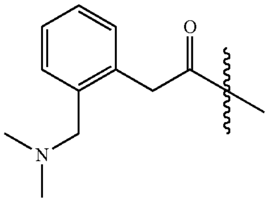 [SMILES: *C(=O)Cc1ccccc1CN(C)C] |
| 40 | 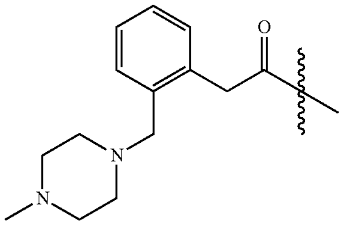 [SMILES: *C(=O)Cc1ccccc1CN1CCN(C)CC1] |
TABLE 1a-continued
Examples 3-219.
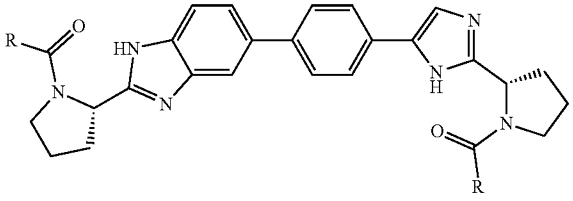
| Entry | 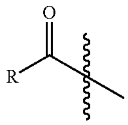 |
|---|---|
| 41 | 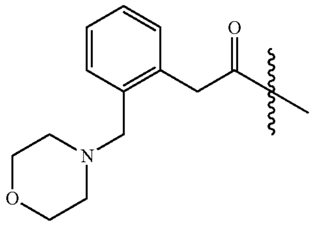 [SMILES: *C(=O)Cc1ccccc1CN1CCOCC1] |
| 42 | 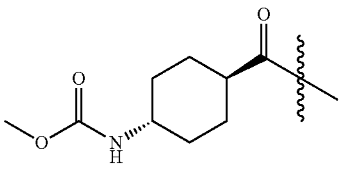 [SMILES: *C(=O)[C@H]1CC[C@H](NC(=O)OC)CC1] |
| 43 | 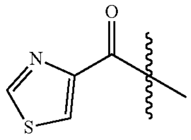 [SMILES: *C(=O)c1cscn1] |
| 44 | 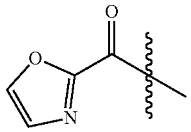 [SMILES: *C(=O)c1ncco1] |
| 45 | 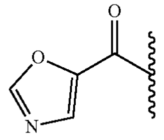 [SMILES: *C(=O)c1cnco1] |
| 46 | 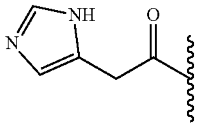 [SMILES: *C(=O)Cc1cnc[nH]1] |
| 47 | 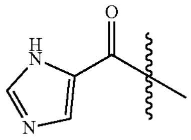 [SMILES: *C(=O)c1cnc[nH]1] |

TABLE 1a-continued
Examples 3-219.
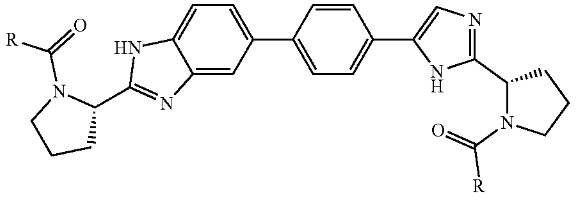
| Entry | 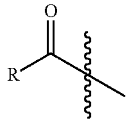 |
|---|---|
| 48 | 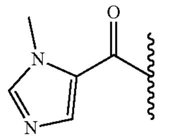 [SMILES: *C(=O)c1cncn1C] |
| 49 | 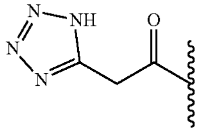 [SMILES: *C(=O)Cc1nnn[nH]1] |
| 50 | 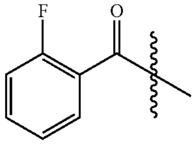 [SMILES: *C(=O)c1ccccc1F] |
| 51 | 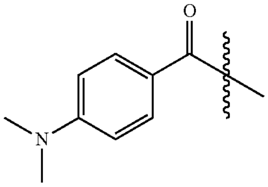 [SMILES: *C(=O)c1ccc(N(C)C)cc1] |
| 52 | 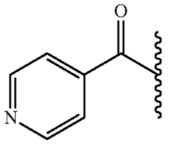 [SMILES: *C(=O)c1ccncc1] |
| 53 | 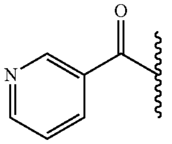 [SMILES: *C(=O)c1cccnc1] |
| 54 | 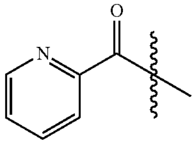 [SMILES: *C(=O)c1ccccn1] |
| 55 | 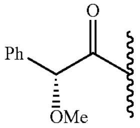 [SMILES: *C(=O)[C@H](OC)c1ccccc1] |
TABLE 1a-continued
Examples 3-219.
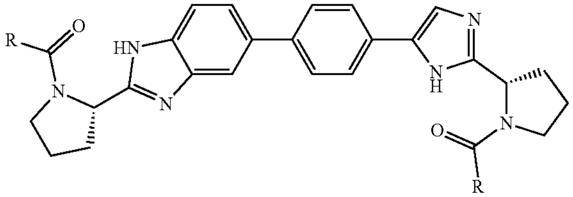
| Entry | 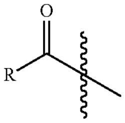 |
|---|---|
| 56 | 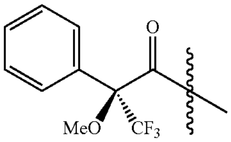 [SMILES: *C(=O)[C@@](OC)(c1ccccc1)C(F)(F)F] |
| 57 | 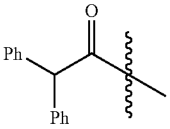 |
| 58 | 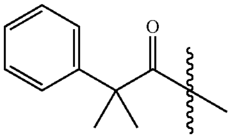 [SMILES: *C(=O)C(C)(C)c1ccccc1] |
| 59 | 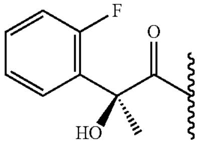 [SMILES: *C(=O)[C@@](C)(O)c1ccccc1F] |
| 60 | 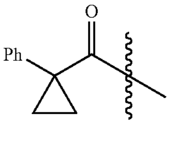 |
| 61 | 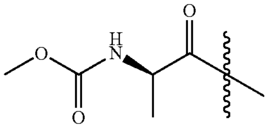 [SMILES: *C(=O)[C@@H](C)NC(=O)OC] |
| 62 | 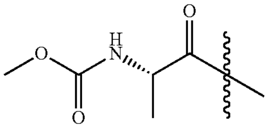 [SMILES: *C(=O)[C@H](C)NC(=O)OC] |
| 63 | 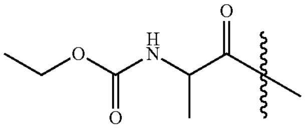 [SMILES: *C(=O)C(C)NC(=O)OCC] |

TABLE 1a-continued
Examples 3-219.
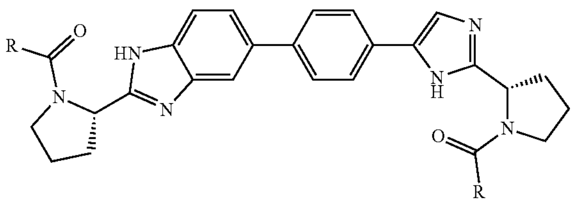
| Entry | 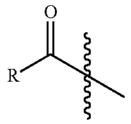 |
| --- | --- |
| 64 | 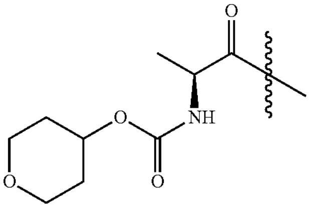 [SMILES: *C(=O)[C@H](C)NC(=O)OC1CCOCC1] |
| 65 | 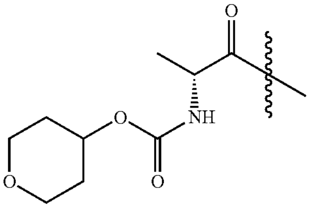 [SMILES: *C(=O)[C@@H](C)NC(=O)OC1CCOCC1] |
| 66 | 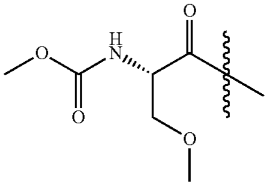 [SMILES: *C(=O)[C@H](COC)NC(=O)OC] |
| 67 | 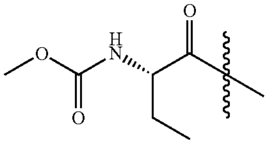 [SMILES: *C(=O)[C@H](CC)NC(=O)OC] |
| 68 | 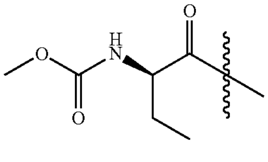 [SMILES: *C(=O)[C@@H](CC)NC(=O)OC] |
| 69 | 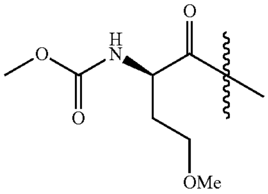 [SMILES: *C(=O)[C@@H](CCOC)NC(=O)OC] |
TABLE 1a-continued
Examples 3-219.
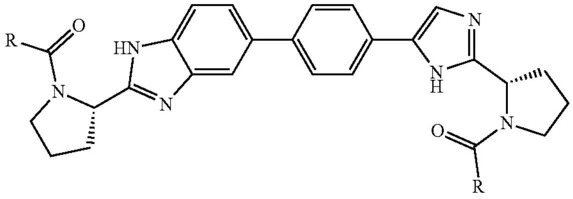
| Entry | 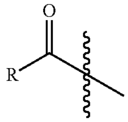 |
| --- | --- |
| 70 | 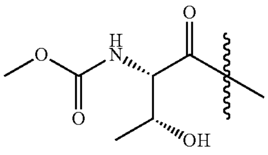 [SMILES: *C(=O)[C@@H](NC(=O)OC)[C@@H](C)O] |
| 71 | 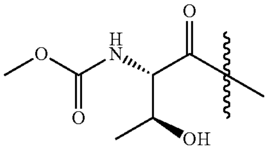 [SMILES: *C(=O)[C@@H](NC(=O)OC)[C@H](C)O] |
| 72 | 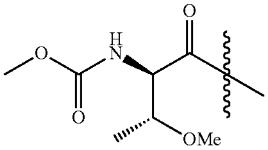 [SMILES: *C(=O)[C@H](NC(=O)OC)[C@@H](C)OC] |
| 73 | 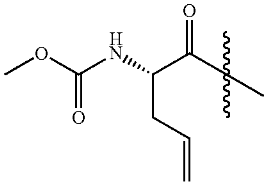 [SMILES: *C(=O)[C@H](CC=C)NC(=O)OC] |
| 74 | 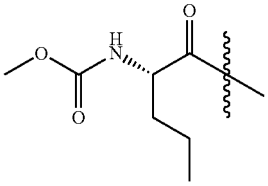 [SMILES: *C(=O)[C@H](CCC)NC(=O)OC] |
| 75 | 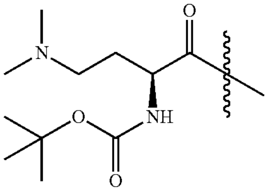 [SMILES: *C(=O)[C@H](CCN(C)C)NC(=O)OC(C)(C)C] |
| 76 | 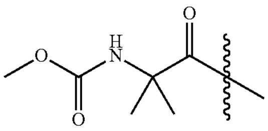 [SMILES: *C(=O)C(C)(C)NC(=O)OC] |

TABLE 1a-continued
Examples 3-219.
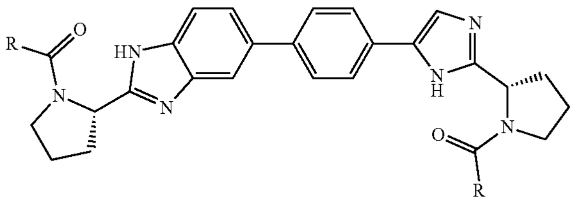
| Entry | 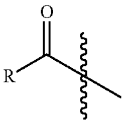 |
|---|---|
| 77 | 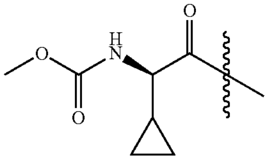 [SMILES: *C(=O)[C@H](NC(=O)OC)C1CC1] |
| 78 | 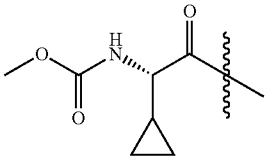 [SMILES: *C(=O)[C@@H](NC(=O)OC)C1CC1] |
| 79 | 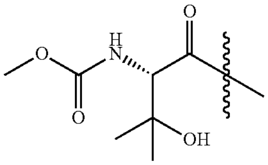 [SMILES: *C(=O)[C@@H](NC(=O)OC)C(C)(C)O] |
| 80 | 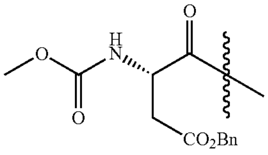 [SMILES: *C(=O)[C@H](CC(=O)OCc1ccccc1)NC(=O)OC] |
| 81 | 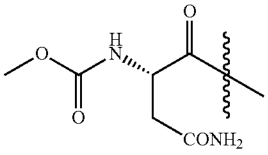 |
| 82 | 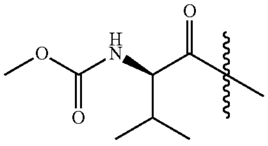 [SMILES: *C(=O)[C@H](NC(=O)OC)C(C)C] |
| 83 | 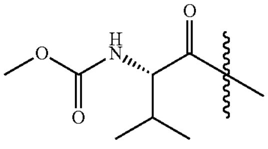 [SMILES: *C(=O)[C@@H](NC(=O)OC)C(C)C] |
TABLE 1a-continued
Examples 3-219.
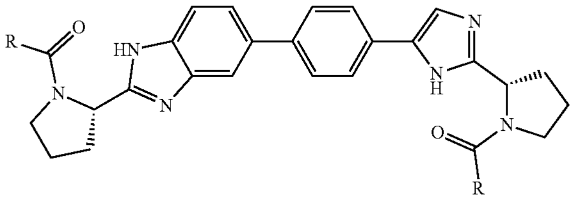
| Entry | 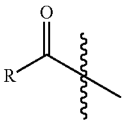 |
|---|---|
| 84 | 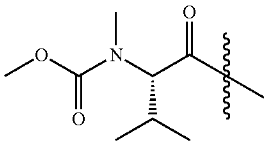 [SMILES: *C(=O)[C@H](C(C)C)N(C)C(=O)OC] |
| 85 | 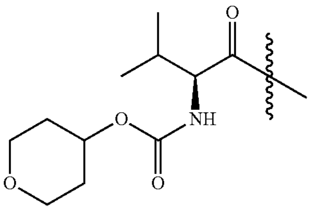 [SMILES: *C(=O)[C@@H](NC(=O)OC1CCOCC1)C(C)C] |
| 86 | 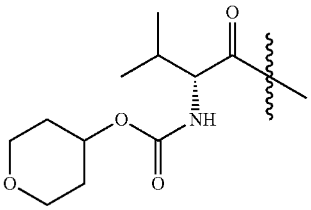 [SMILES: *C(=O)[C@H](NC(=O)OC1CCOCC1)C(C)C] |
| 87 | 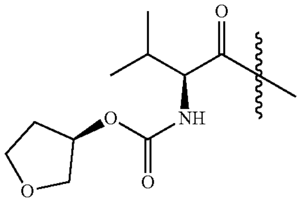 [SMILES: *C(=O)[C@@H](NC(=O)O[C@@H]1CCOC1)C(C)C] |
| 88 | 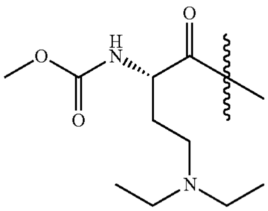 [SMILES: *C(=O)[C@H](CCN(CC)CC)NC(=O)OC] |
| 89 | 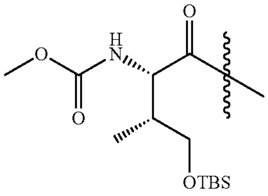 [SMILES: *C(=O)[C@@H](NC(=O)OC)[C@@H](C)CO[Si](C)(C)C(C)(C)C] |

TABLE 1a-continued
Examples 3-219.
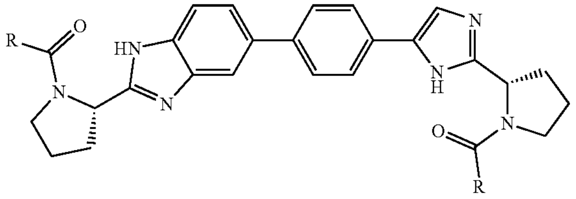
| Entry | 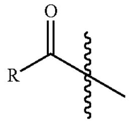 |
|---|---|
| 90 | 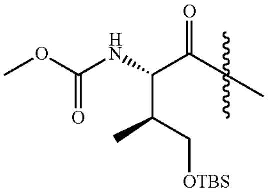 [SMILES: *C(=O)[C@@H](NC(=O)OC)[C@H](C)CO[Si](C)(C)C(C)(C)C] |
| 91 | 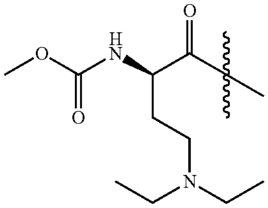 [SMILES: *C(=O)[C@@H](CCN(CC)CC)NC(=O)OC] |
| 92 | 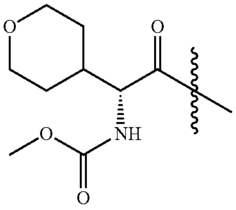 [SMILES: *C(=O)[C@H](NC(=O)OC)C1CCOCC1] |
| 93 | 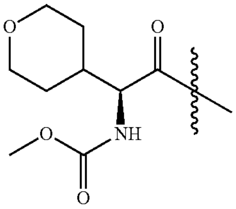 [SMILES: *C(=O)[C@@H](NC(=O)OC)C1CCOCC1] |
| 94 | 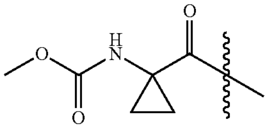 [SMILES: *C(=O)C1(NC(=O)OC)CC1] |
| 95 | 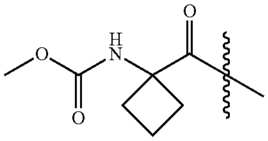 [SMILES: *C(=O)C1(NC(=O)OC)CCC1] |
TABLE 1a-continued
Examples 3-219.
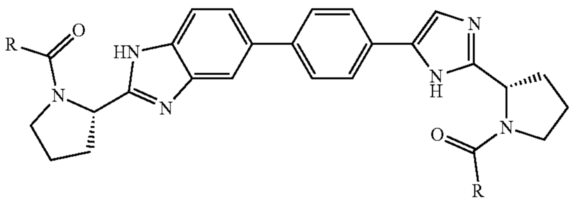
| Entry | 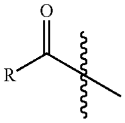 |
|---|---|
| 96 | 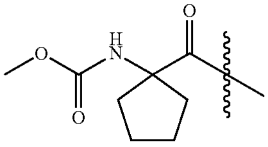 [SMILES: *C(=O)C1(NC(=O)OC)CCCC1] |
| 97 | 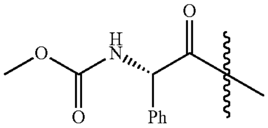 [SMILES: *C(=O)[C@@H](NC(=O)OC)c1ccccc1] |
| 98 | 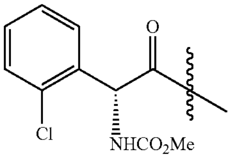 |
| 99 | 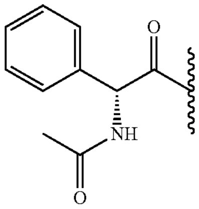 [SMILES: *C(=O)[C@H](NC(C)=O)c1ccccc1] |
| 100 | 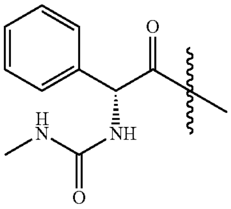 [SMILES: *C(=O)[C@H](NC(=O)NC)c1ccccc1] |
| 101 | 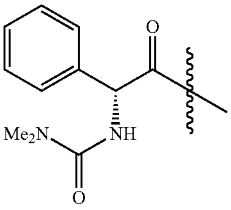 [SMILES: *C(=O)[C@H](NC(=O)N(C)C)c1ccccc1] |

TABLE 1a-continued
Examples 3-219.
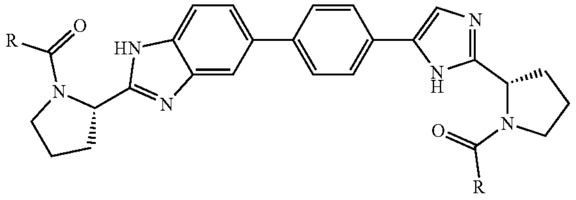
| Entry | 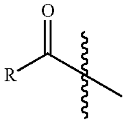 |
|---|---|
| 102 | 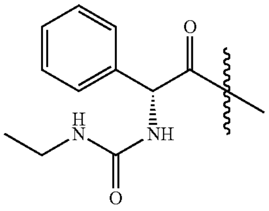 [SMILES: *C(=O)[C@H](NC(=O)NCC)c1ccccc1] |
| 103 | 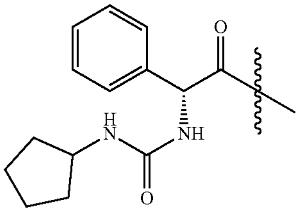 [SMILES: *C(=O)[C@H](NC(=O)NC1CCCC1)c1ccccc1] |
| 104 | 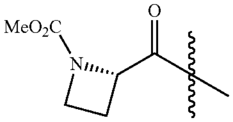 [SMILES: *C(=O)[C@@H]1CCN1C(=O)OC] |
| 105 | 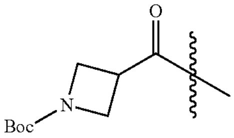 [SMILES: *C(=O)C1CN(C(=O)OC(C)(C)C)C1] |
| 106 | 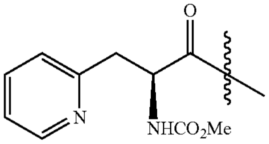 |
| 107 | 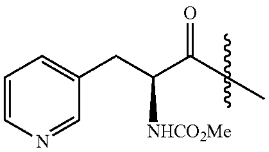 |
| 108 | 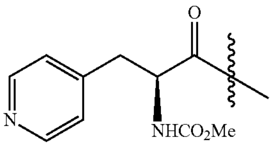 |
TABLE 1a-continued
Examples 3-219.
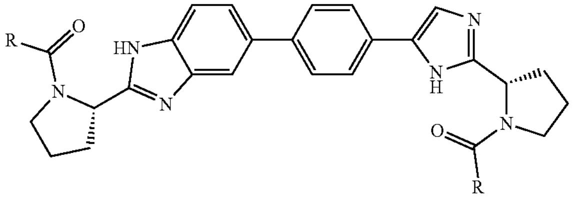
| Entry | 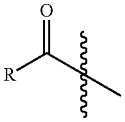 |
|---|---|
| 109 | 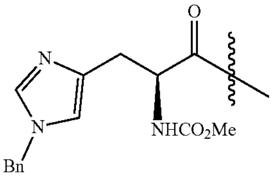 |
| 110 | 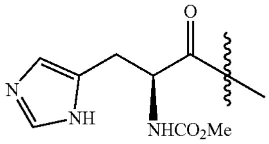 |
| 111 | 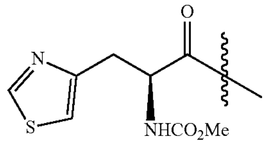 |
| 112 | 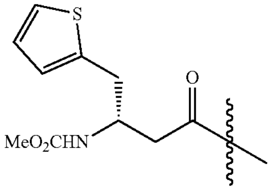 |
| 113 | 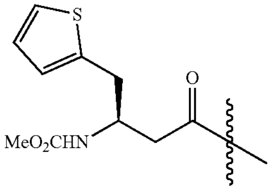 |
| 114 | 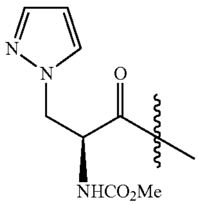 |

TABLE 1a-continued
Examples 3-219.
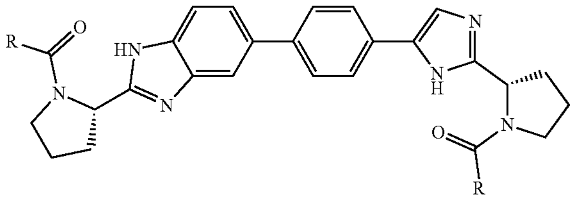
| Entry | 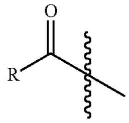 |
|---|---|
| 115 | 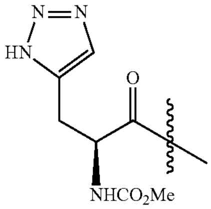 |
| 116 | 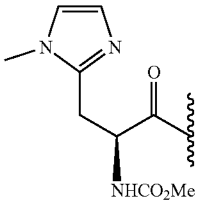 |
| 117 | 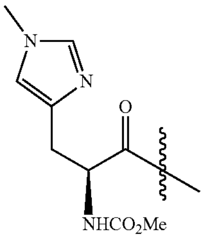 |
| 118 | 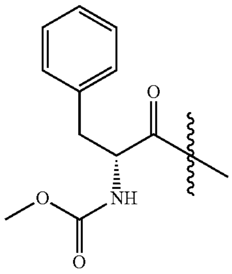 [SMILES: *C(=O)[C@@H](Cc1ccccc1)NC(=O)OC] |
| 119 | 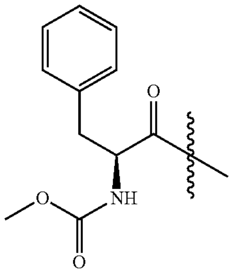 [SMILES: *C(=O)[C@H](Cc1ccccc1)NC(=O)OC] |
TABLE 1a-continued
Examples 3-219.
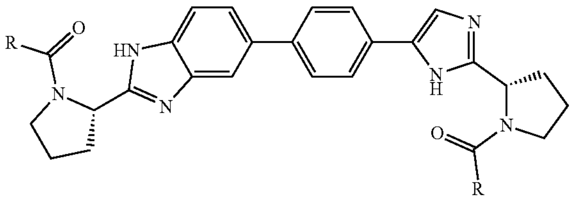
| Entry | 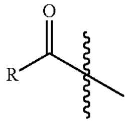 |
|---|---|
| 120 | 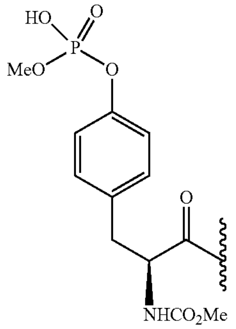 |
| 121 | 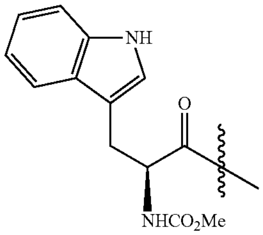 |
| 122 | 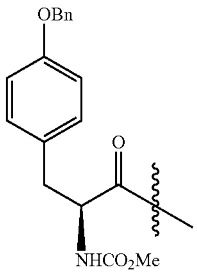 |
| 123 | 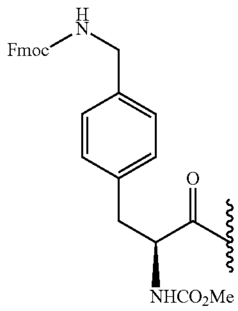 |

TABLE 1a-continued
Examples 3-219.
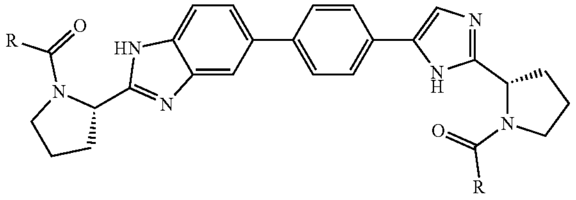
| Entry | 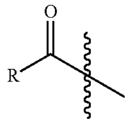 |
|---|---|
| 124 | 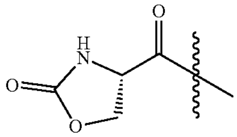 [SMILES: *C(=O)[C@@H]1COC(=O)N1] |
| 125 | 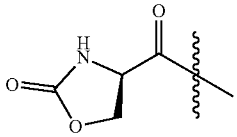 [SMILES: *C(=O)[C@H]1COC(=O)N1] |
| 126 | 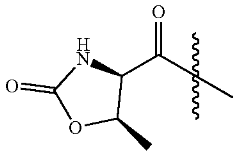 [SMILES: *C(=O)[C@@H]1NC(=O)O[C@@H]1C] |
| 127 | 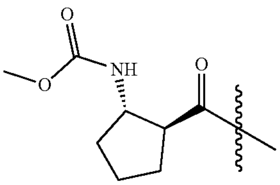 [SMILES: *C(=O)[C@H]1CCC[C@@H]1NC(=O)OC] |
| 128 | 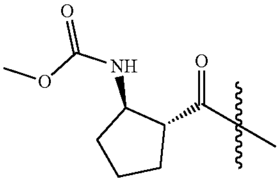 [SMILES: *C(=O)[C@@H]1CCC[C@H]1NC(=O)OC] |
| 129 | 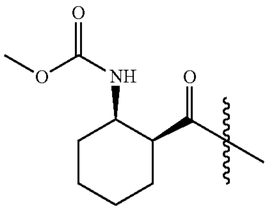 [SMILES: *C(=O)[C@H]1CCCC[C@H]1NC(=O)OC] |
| 130 | 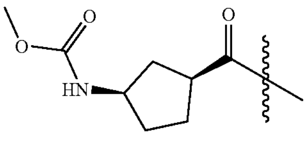 [SMILES: *C(=O)[C@H]1CC[C@@H](NC(=O)OC)C1] |
TABLE 1a-continued
Examples 3-219.
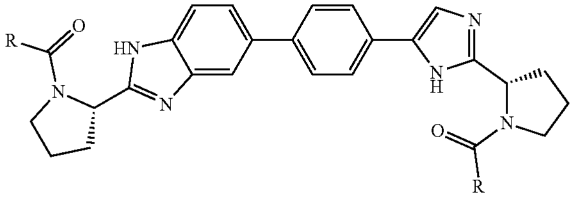
| Entry | 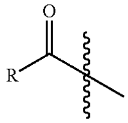 |
|---|---|
| 131 | 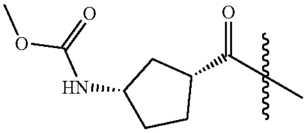 [SMILES: *C(=O)[C@@H]1CC[C@H](NC(=O)OC)C1] |
| 132 | 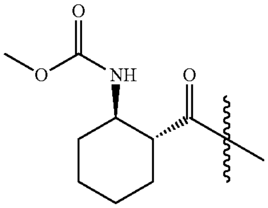 [SMILES: *C(=O)[C@@H]1CCCC[C@H]1NC(=O)OC] |
| 133 | 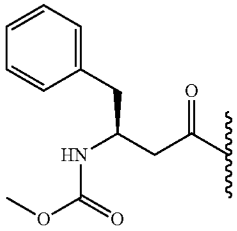 [SMILES: *C(=O)C[C@H](Cc1ccccc1)NC(=O)OC] |
| 134 | 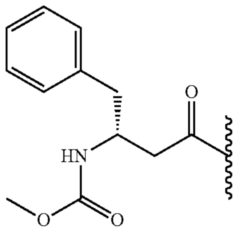 [SMILES: *C(=O)C[C@@H](Cc1ccccc1)NC(=O)OC] |
| 135 | 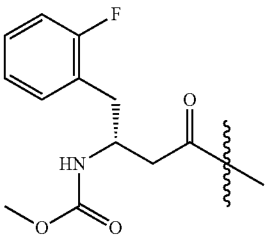 [SMILES: *C(=O)C[C@@H](Cc1ccccc1F)NC(=O)OC] |

TABLE 1a-continued
| Examples 3-219. | |
|---|---|
| 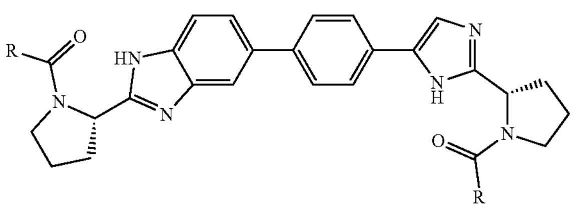 | |
| Entry | 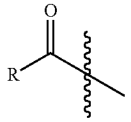 |
| 136 | 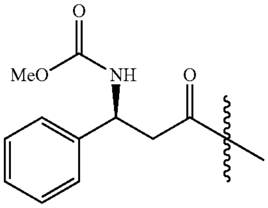 [SMILES: *C(=O)C[C@H](NC(=O)OC)c1ccccc1] |
| 137 | 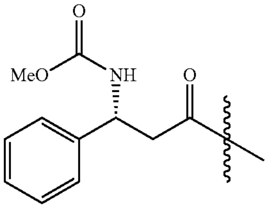 [SMILES: *C(=O)C[C@@H](NC(=O)OC)c1ccccc1] |
| 138 | 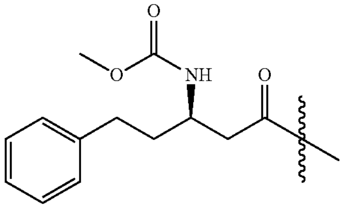 [SMILES: *C(=O)C[C@@H](CCc1ccccc1)NC(=O)OC] |
| 139 | 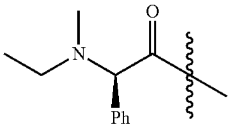 [SMILES: *C(=O)[C@@H](c1ccccc1)N(C)CC] |
| 140 | 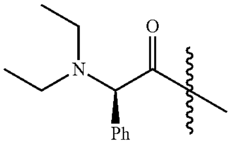 [SMILES: *C(=O)[C@@H](c1ccccc1)N(CC)CC] |
| 141 | 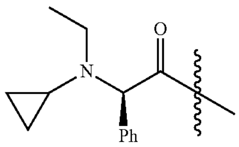 [SMILES: *C(=O)[C@@H](c1ccccc1)N(CC)C1CC1] |
TABLE 1a-continued
| Examples 3-219. | |
|---|---|
| 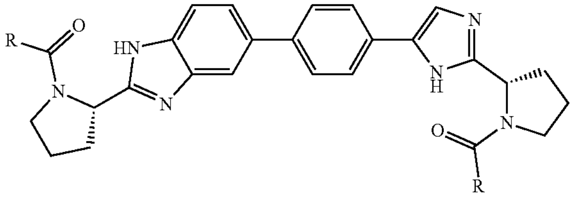 | |
| Entry | 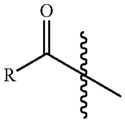 |
| 142 | 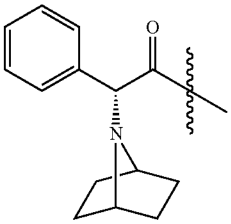 [SMILES: *C(=O)[C@@H](c1ccccc1)N1C2CCC1CC2] |
| 143 | 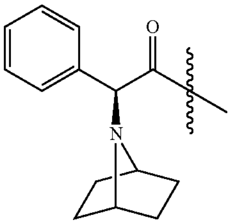 [SMILES: *C(=O)[C@H](c1ccccc1)N1C2CCC1CC2] |
| 144 | 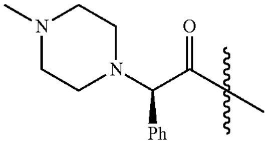 [SMILES: *C(=O)[C@@H](c1ccccc1)N1CCN(C)CC1] |
| 145 | 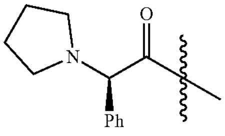 [SMILES: *C(=O)[C@@H](c1ccccc1)N1CCCC1] |
| 146 | 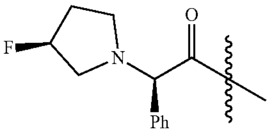 [SMILES: *C(=O)[C@@H](c1ccccc1)N1CC[C@H](F)C1] |
| 147 | 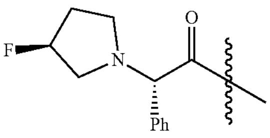 [SMILES: *C(=O)[C@H](c1ccccc1)N1CC[C@H](F)C1] |
| 148 | 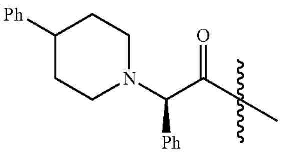 [SMILES: *C(=O)[C@@H](c1ccccc1)N1CCC(c2ccccc2)CC1] |

TABLE 1a-continued
Examples 3-219.
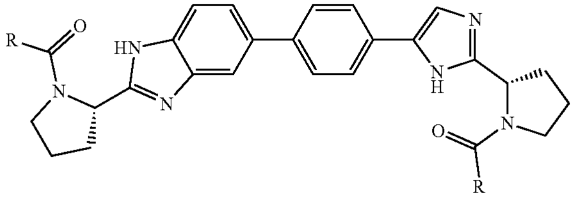
| Entry | 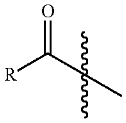 |
|---|---|
| 149 | 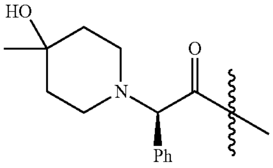 [SMILES: *C(=O)[C@@H](c1ccccc1)N1CCC(C)(O)CC1] |
| 150 | 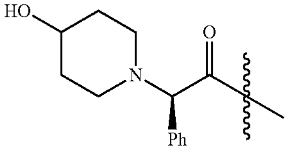 [SMILES: *C(=O)[C@@H](c1ccccc1)N1CCC(O)CC1] |
| 151 | 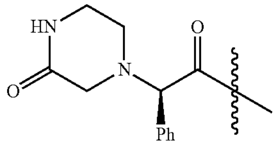 [SMILES: *C(=O)[C@@H](c1ccccc1)N1CCNC(=O)C1] |
| 152 | 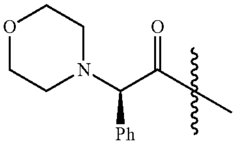 [SMILES: *C(=O)[C@@H](c1ccccc1)N1CCOCC1] |
| 153 | 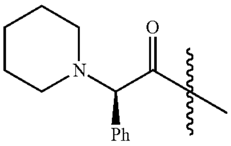 [SMILES: *C(=O)[C@@H](c1ccccc1)N1CCCCC1] |
| 154 | 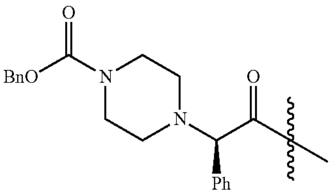 [SMILES: *C(=O)[C@@H](c1ccccc1)N1CCN(C(=O)OCc2ccccc2)CC1] |
| 155 | 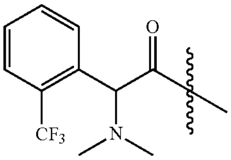 |
TABLE 1a-continued
Examples 3-219.
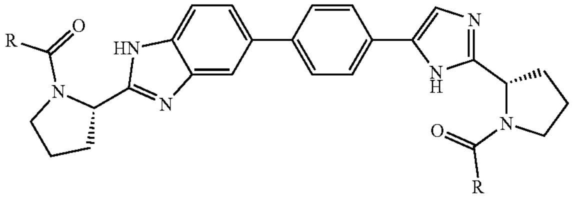
| Entry | 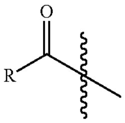 |
|---|---|
| 156 | 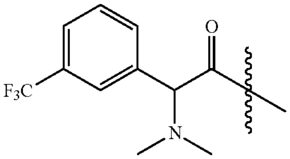 [SMILES: *C(=O)C(c1cccc(C(F)(F)F)c1)N(C)C] |
| 157 | 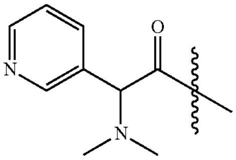 [SMILES: *C(=O)C(c1cccnc1)N(C)C] |
| 158 | 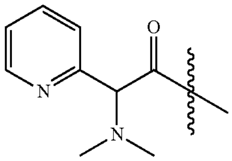 [SMILES: *C(=O)C(c1ccccn1)N(C)C] |
| 159 | 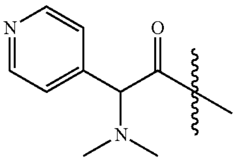 [SMILES: *C(=O)C(c1ccncc1)N(C)C] |
| 160 | 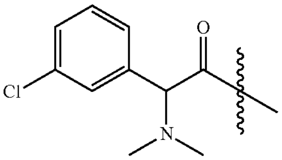 [SMILES: *C(=O)C(c1cccc(Cl)c1)N(C)C] |
| 161 | 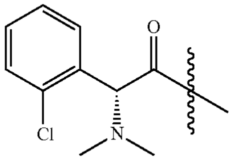 |
| 162 | 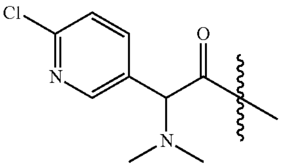 [SMILES: *C(=O)C(c1ccc(Cl)nc1)N(C)C] |

TABLE 1a-continued
| Examples 3-219. | |
|---|---|
| | 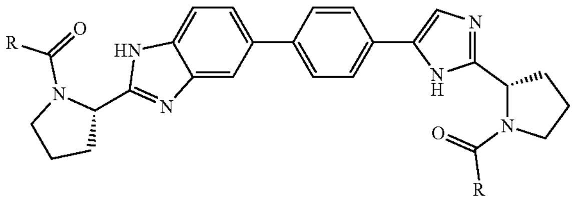 |
| Entry | 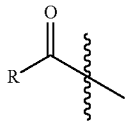 |
| 163 | 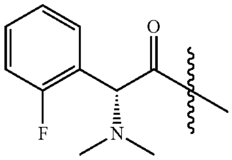 |
| 164 | 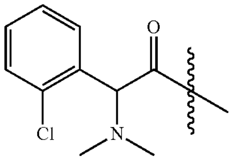 |
| 165 | 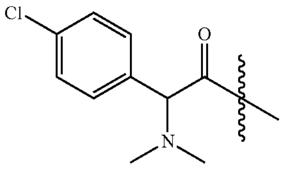 [SMILES: *C(=O)C(c1ccc(Cl)cc1)N(C)C] |
| 166 | 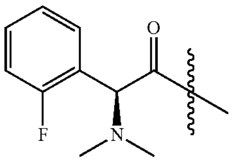 [SMILES: *C(=O)[C@H](c1ccccc1F)N(C)C] |
| 167 | 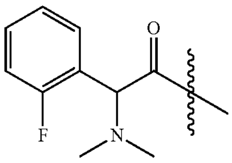 |
| 168 | 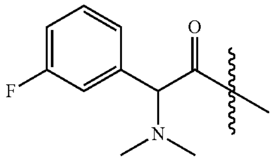 [SMILES: *C(=O)C(c1cccc(F)c1)N(C)C] |
TABLE 1a-continued
| Examples 3-219. | |
|---|---|
| | 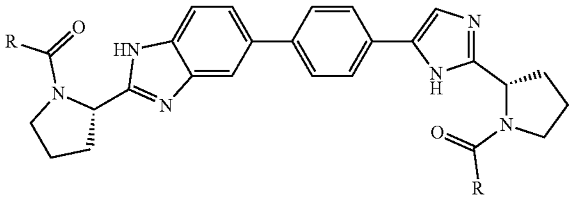 |
| Entry | 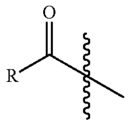 |
| 169 | 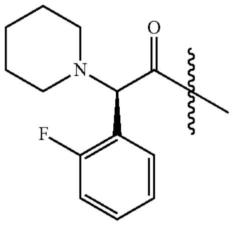 [SMILES: *C(=O)[C@@H](c1ccccc1F)N1CCCCC1] |
| 170 | 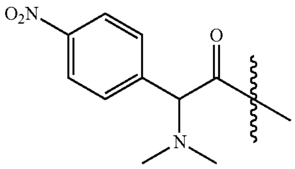 [SMILES: *C(=O)C(c1ccc([N+](=O)[O-])cc1)N(C)C] |
| 171 | 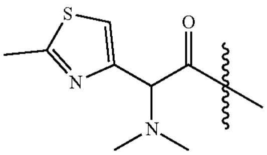 [SMILES: *C(=O)C(c1csc(C)n1)N(C)C] |
| 172 | 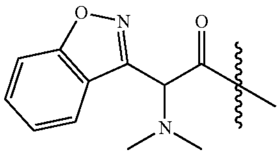 [SMILES: *C(=O)C(c1noc2ccccc12)N(C)C] |
| 173 | 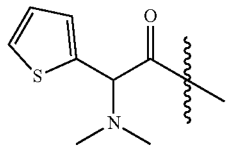 [SMILES: *C(=O)C(c1cccs1)N(C)C] |
| 174 | 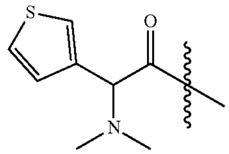 [SMILES: *C(=O)C(c1ccsc1)N(C)C] |
| 175 | 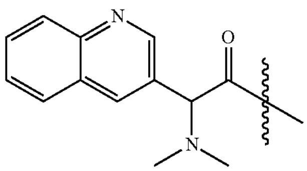 [SMILES: *C(=O)C(c1cnc2ccccc2c1)N(C)C] |

TABLE 1a-continued
Examples 3-219.
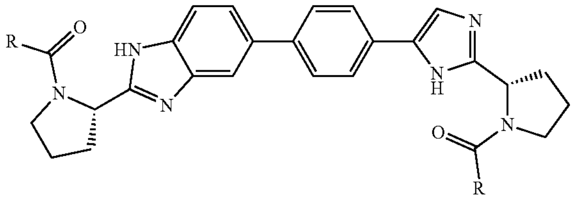
| Entry | 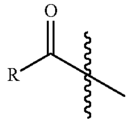 |
| --- | --- |
| 176 | 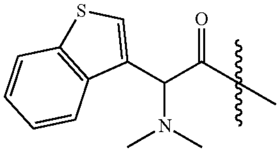 [SMILES: *C(=O)C(c1csc2ccccc12)N(C)C] |
| 177 | 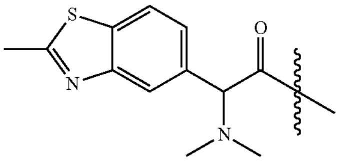 [SMILES: *C(=O)C(c1ccc2sc(C)nc2c1)N(C)C] |
| 178 | 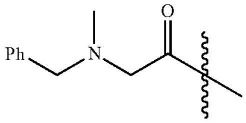 [SMILES: *C(=O)CN(C)Cc1ccccc1] |
| 179 | 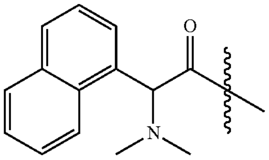 [SMILES: *C(=O)C(c1cccc2ccccc12)N(C)C] |
| 180 | 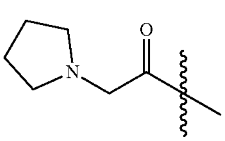 [SMILES: *C(=O)CN1CCCC1] |
| 181 | 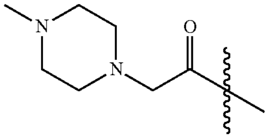 [SMILES: *C(=O)CN1CCN(C)CC1] |
| 182 | 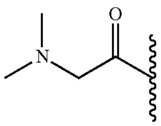 [SMILES: *C(=O)CN(C)C] |
TABLE 1a-continued
Examples 3-219.
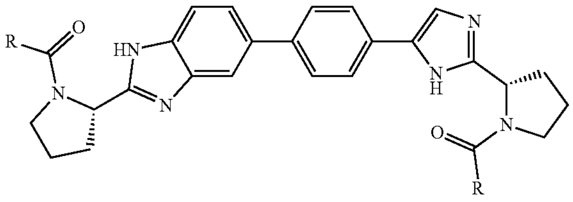
| Entry | 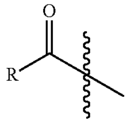 |
| --- | --- |
| 183 | 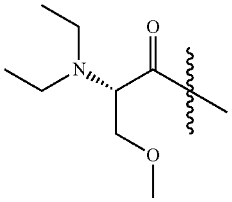 [SMILES: *C(=O)[C@H](COC)N(CC)CC] |
| 184 | 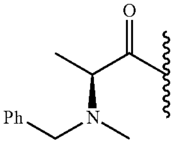 [SMILES: *C(=O)[C@H](C)N(C)Cc1ccccc1] |
| 185 | 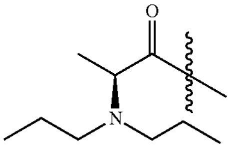 [SMILES: *C(=O)[C@H](C)N(CCC)CCC] |
| 186 | 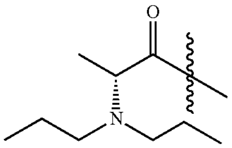 [SMILES: *C(=O)[C@@H](C)N(CCC)CCC] |
| 187 | 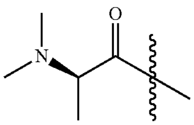 [SMILES: *C(=O)[C@@H](C)N(C)C] |
| 188 | 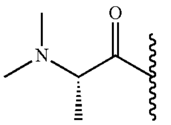 [SMILES: *C(=O)[C@H](C)N(C)C] |
| 189 | 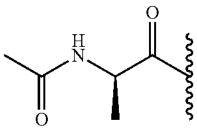 [SMILES: *C(=O)[C@@H](C)NC(C)=O] |
| 190 | 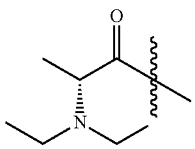 [SMILES: *C(=O)[C@@H](C)N(CC)CC] |

TABLE 1a-continued
| Examples 3-219. | |
|---|---|
| 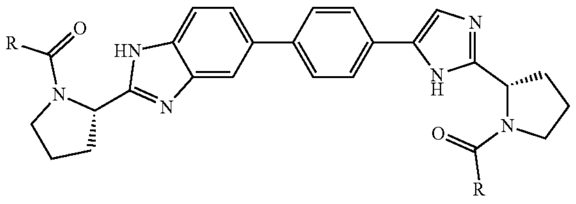 | |
| Entry | 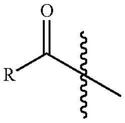 |
| 191 | 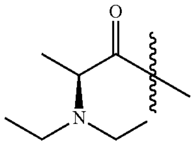 [SMILES: *C(=O)[C@H](C)N(CC)CC] |
| 192 | 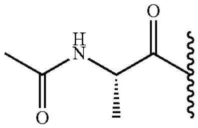 [SMILES: *C(=O)[C@H](C)NC(C)=O] |
| 193 | 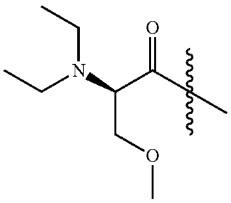 [SMILES: *C(=O)[C@@H](COC)N(CC)CC] |
| 194 | 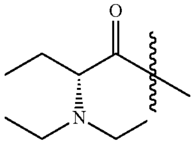 [SMILES: *C(=O)[C@@H](CC)N(CC)CC] |
| 195 | 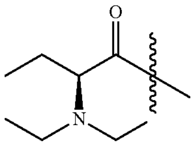 [SMILES: *C(=O)[C@H](CC)N(CC)CC] |
| 196 | 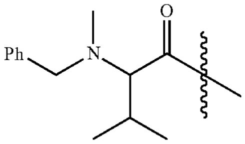 [SMILES: *C(=O)C(C(C)C)N(C)Cc1ccccc1] |
| 197 | 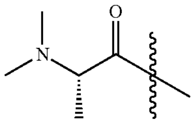 [SMILES: *C(=O)[C@H](C)N(C)C] |
TABLE 1a-continued
| Examples 3-219. | |
|---|---|
| 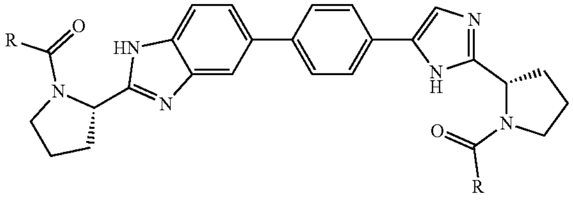 | |
| Entry | 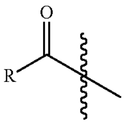 |
| 198 | 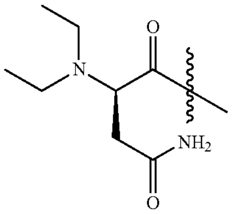 [SMILES: *C(=O)[C@@H](CC(N)=O)N(CC)CC] |
| 199 | 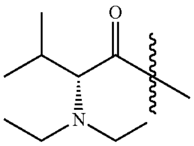 [SMILES: *C(=O)[C@@H](C(C)C)N(CC)CC] |
| 200 | 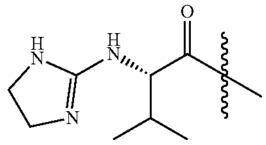 |
| 201 | 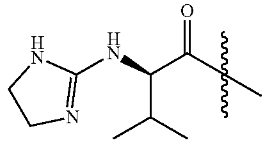 [SMILES: *C(=O)[C@H](NC1=NCCN1)C(C)C] |
| 202 | 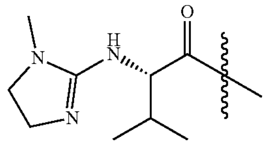 [SMILES: *C(=O)[C@@H](NC1=NCCN1C)C(C)C] |
| 203 | 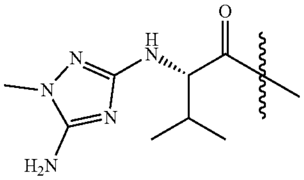 [SMILES: *C(=O)[C@@H](Nc1nc(N)n(C)n1)C(C)C] |
| 204 | 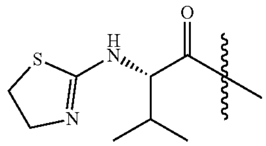 [SMILES: *C(=O)[C@@H](NC1=NCCS1)C(C)C] |

TABLE 1a-continued
Examples 3-219.
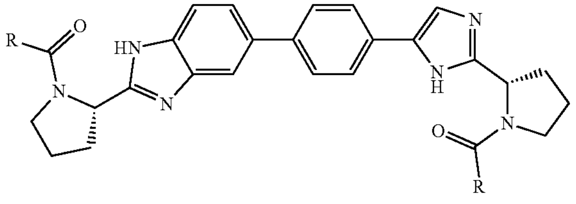
| Entry | 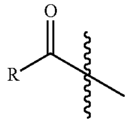 |
|---|---|
| 205 | 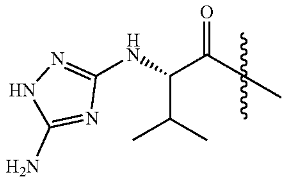 |
| 206 | 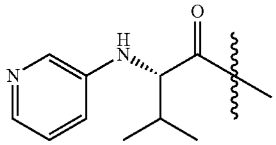 [SMILES: *C(=O)[C@@H](Nc1cccnc1)C(C)C] |
| 207 | 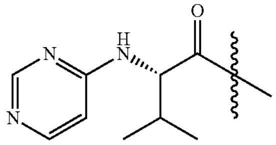 [SMILES: *C(=O)[C@@H](Nc1ccncn1)C(C)C] |
| 208 | 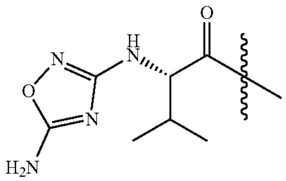 [SMILES: *C(=O)[C@@H](Nc1noc(N)n1)C(C)C] |
| 209 | 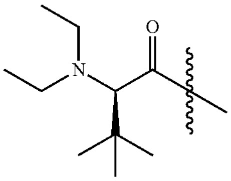 [SMILES: *C(=O)[C@H](N(CC)CC)C(C)(C)C] |
| 210 | 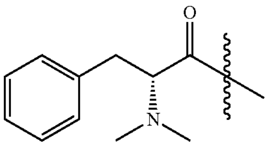 [SMILES: *C(=O)[C@@H](Cc1ccccc1)N(C)C] |
| 211 | 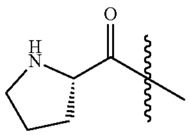 [SMILES: *C(=O)[C@@H]1CCCN1] |
TABLE 1a-continued
Examples 3-219.
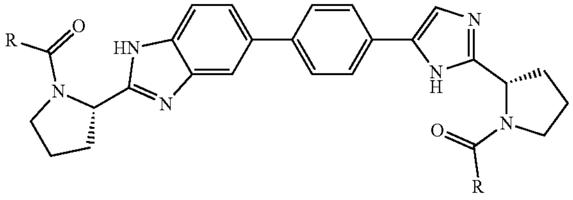
| Entry | 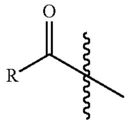 |
|---|---|
| 212 | 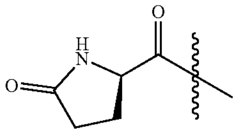 [SMILES: *C(=O)[C@H]1CCC(=O)N1] |
| 213 | 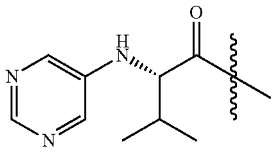 [SMILES: *C(=O)[C@@H](Nc1cncnc1)C(C)C] |
| 214 | 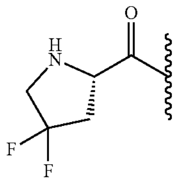 [SMILES: *C(=O)[C@@H]1CC(F)(F)CN1] |
| 215 | 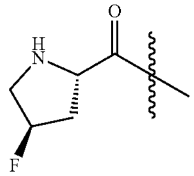 [SMILES: *C(=O)[C@@H]1C[C@@H](F)CN1] |
| 216 | 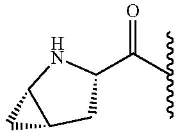 [SMILES: *C(=O)[C@@H]1C[C@@H]2C[C@@H]2N1] |
| 217 | 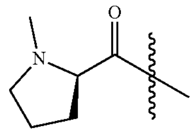 [SMILES: *C(=O)[C@H]1CCCN1C] |

TABLE 1a-continued
Examples 3-219.
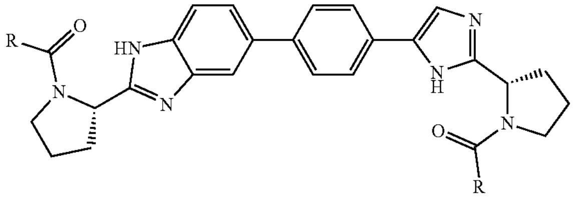
| Entry | 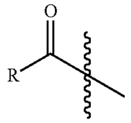 |
|---|---|
| 218 | 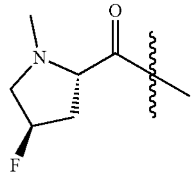 [SMILES: *C(=O)[C@@H]1C[C@@H](F)CN1C] |
TABLE 1a-continued
Examples 3-219.
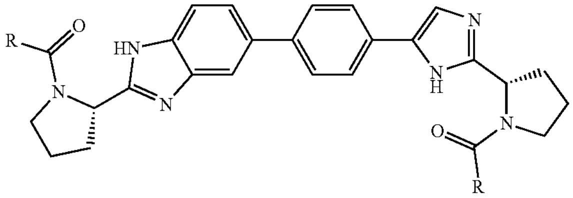
| Entry | 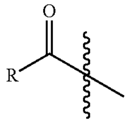 |
|---|---|
| 219 | 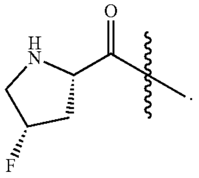 [SMILES: *C(=O)[C@@H]1C[C@H](F)CN1] |
TABLE 2
Examples 220-229.
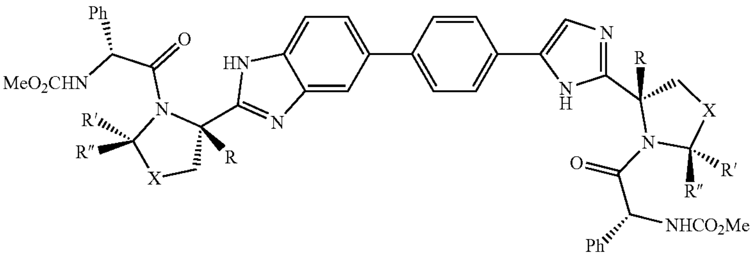
| Entry | R | R' | R'' | X | Entry | R | R' | R'' | X |
|---|---|---|---|---|---|---|---|---|---|
| 220 | Me | H | H | $CH_2$ | 221 | H | H | H | $CF_2$ |
| 222 | Me | H | H | S | 223 | H | H | H | 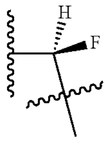 |
| 224 | Me | H | H | O | 225 | H | H | H | 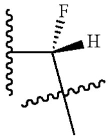 |
| 226 | H | Ph | H | $CH_2$ | 227 | H | H | H | 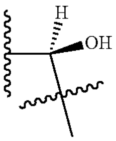 |

TABLE 2-continued
Examples 220-229.
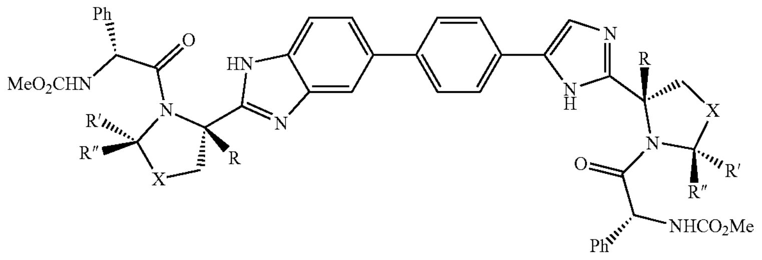
| Entry | R | R' | R" | X | Entry | R | R' | R" | X |
|---|---|---|---|---|---|---|---|---|---|
| 228 | H | H | Ph | $CH_2$ | 229 | H | H | H | 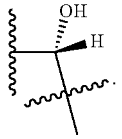 |
Example 230
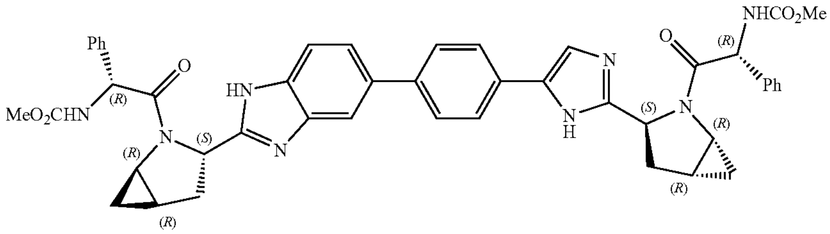
Example 231
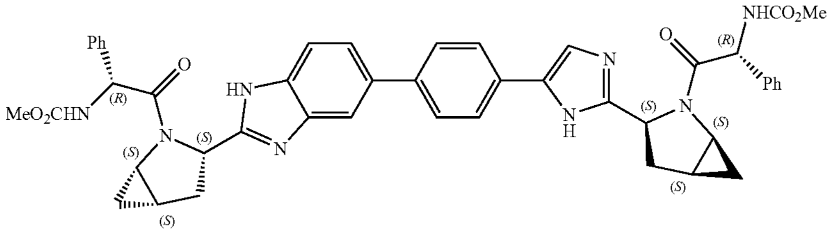
Example 232
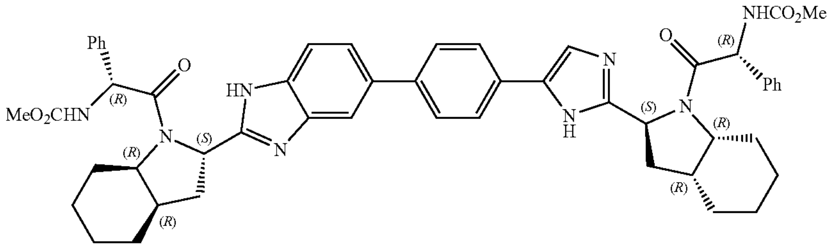
Example 233
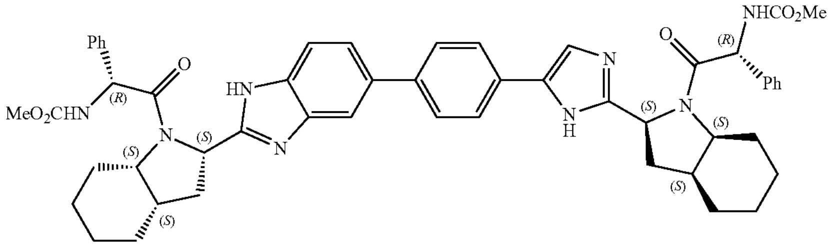

TABLE 3
Examples 234-243.
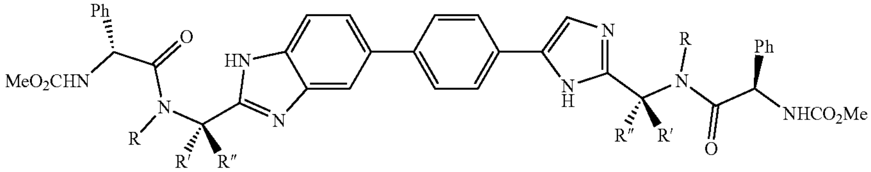
| Entry | R | R' | R" | Entry | R | R' | R" |
|---|---|---|---|---|---|---|---|
| 234 | Me | Me | H | 235 | H | Me | H |
| 236 | Me | H | Me | 237 | cyclopropyl | Me | H |
| 238 | Me | Me | Me | 239 | Me | cyclopropyl | H |
| 240 | Me | Allyl | H | 241 | Et | Me | H |
| 242 | Me | $CHMe_2$ | H | 243 | Me | Et | H. |
TABLE 4
Examples 244-263.
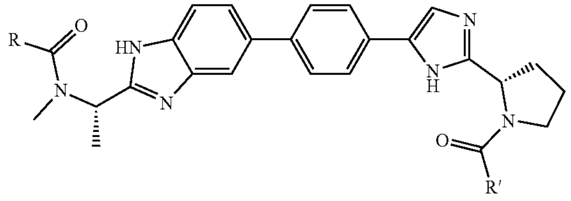
| Entry | R | R' |
|---|---|---|
| 244 | 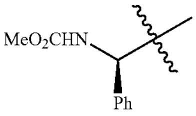 | 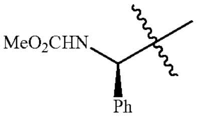 |
| 245 | 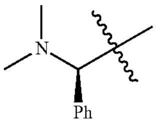 [SMILES: *[C@@H](c1ccccc1)N(C)C] | 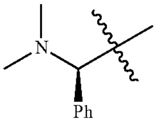 [SMILES: *[C@@H](c1ccccc1)N(C)C] |
| 246 | 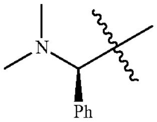 [SMILES: *[C@@H](c1ccccc1)N(C)C] | 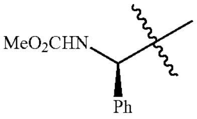 |
| 247 | 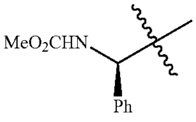 | 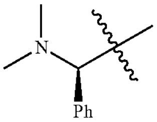 [SMILES: *[C@@H](c1ccccc1)N(C)C] |
| 248 | 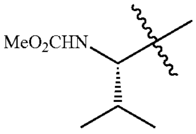 | 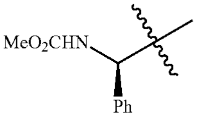 |
| 249 | 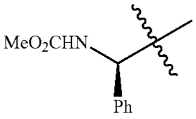 | 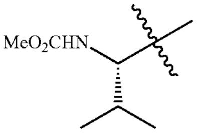 |
TABLE 4-continued
Examples 244-263.
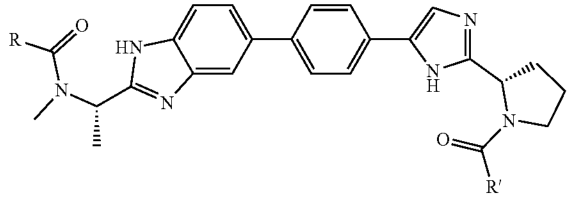
| Entry | R | R' |
|---|---|---|
| 250 | 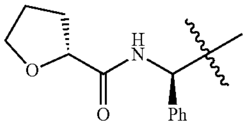 [SMILES: *[C@H](NC(=O)[C@H]1CCCO1)c1ccccc1] | 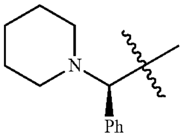 |
| 251 | 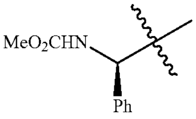 | 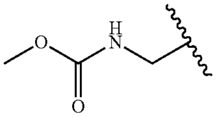 [SMILES: *CNC(=O)OC] |
| 252 | 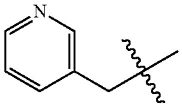 [SMILES: *Cc1cccnc1] | 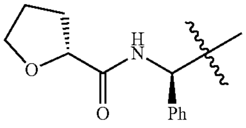 [SMILES: *[C@H](NC(=O)[C@H]1CCCO1)c1ccccc1] |
| 253 | 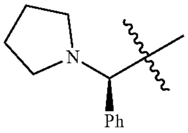 [SMILES: *[C@@H](c1ccccc1)N1CCCC1] | 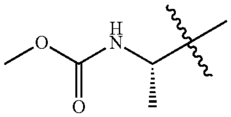 [SMILES: *[C@H](C)NC(=O)OC] |
| 254 | 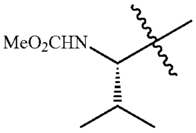 | 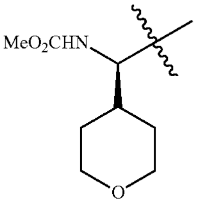 |

TABLE 4-continued
Examples 244-263.
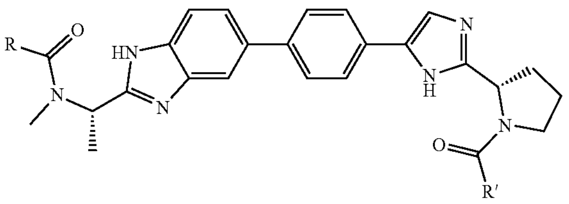
| Entry | R | R' |
|---|---|---|
| 255 | 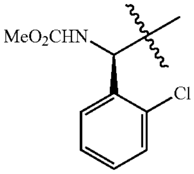 | 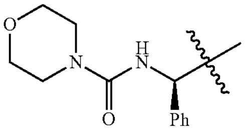 [SMILES: *[C@H](NC(=O)N1CCOCC1)c1ccccc1] |
| 256 | 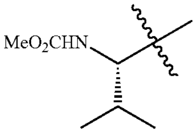 | 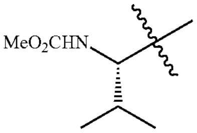 |
| 257 | 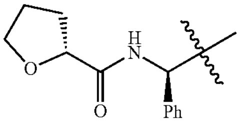 [SMILES: *[C@H](NC(=O)[C@H]1CCCO1)c1ccccc1] | 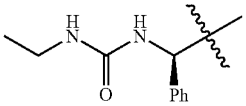 [SMILES: *[C@H](NC(=O)NCC)c1ccccc1] |
| 258 | 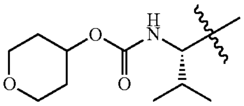 [SMILES: *[C@@H](NC(=O)OC1CCOCC1)C(C)C] | 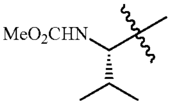 |
| 259 | 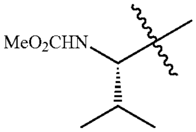 | 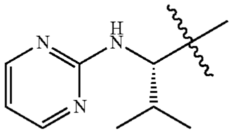 [SMILES: *[C@@H](Nc1ncccn1)C(C)C] |
| 260 | 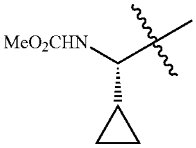 | 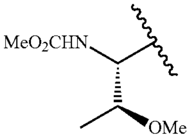 |
| 261 | 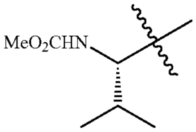 | 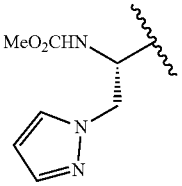 |
| 262 | 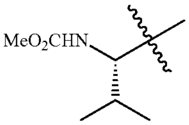 | 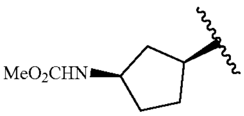 |
TABLE 4-continued
Examples 244-263.
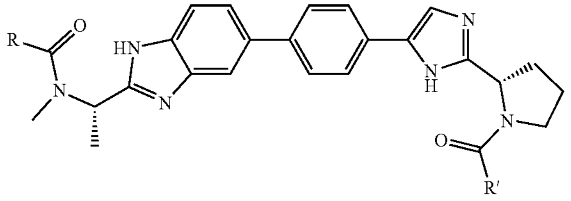
| Entry | R | R' |
|---|---|---|
| 263 | 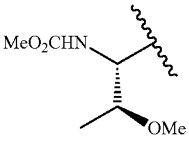 | 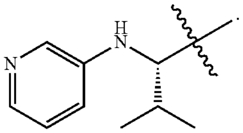 [SMILES: *[C@@H](Nc1cccnc1)C(C)C] |
TABLE 5
Examples 264-273.
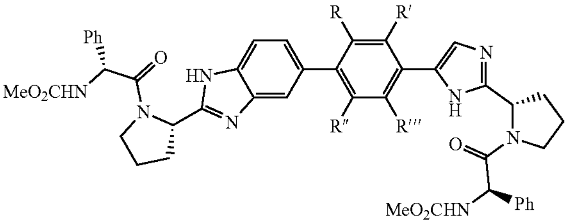
| Entry | R | R' | R'' | R''' |
|---|---|---|---|---|
| 264 | F | H | H | H |
| 265 | F | F | H | H |
| 266 | Me | H | H | H |
| 267 | Me | Me | H | H |
| 268 | H | H | Me | Me |
| 269 | H | H | Et | Et |
| 270 | $CF_3$ | H | H | H |
| 271 | $CF_3$ | H | $CF_3$ | H |
| 272 | Cl | H | H | H |
| 273 | Cl | H | Cl | H. |
TABLE 6
Examples 274-299.
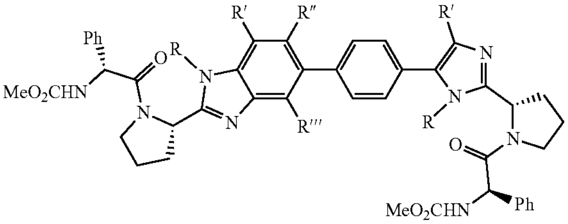
| Entry | R | R' | R'' | R''' |
|---|---|---|---|---|
| 274 | Me | H | H | H |
| 275 | H | $CO_2H$ | H | H |
| 276 | H | F | H | H |
| 277 | H | H | $CO_2H$ | H |
| 278 | H | H | F | H |
| 279 | H | H | H | $CO_2H$ |
| 280 | H | H | H | F |
| 281 | H | $CO_2Me$ | H | H |

TABLE 6-continued
Examples 274-299.
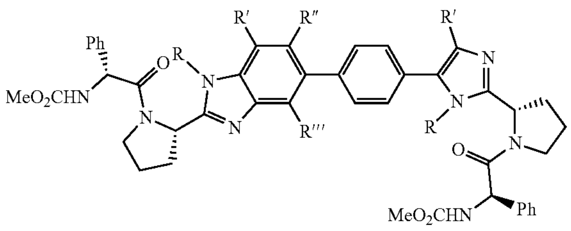
| Entry | R | R' | R'' | R''' |
|---|---|---|---|---|
| 282 | H | Cl | H | H |
| 283 | H | H | $CO_2Me$ | H |
| 284 | H | H | Cl | H |
| 285 | H | H | H | $CO_2Me$ |
| 286 | H | H | H | Cl |
| 287 | H | $CONH_2$ | H | H |
| 288 | H | Me | H | H |
| 289 | H | H | $CONH_2$ | H |
| 290 | H | H | Me | H |
| 291 | H | H | H | $CONH_2$ |
| 292 | H | H | H | Me |
| 293 | H | OMe | H | H |
| 294 | H | $CF_3$ | H | H |
| 295 | H | H | OMe | H |
| 296 | H | H | $CF_3$ | H |
| 297 | H | H | H | OMe |
| 298 | H | H | H | $CF_3$ |
| 299 | $CO_2Me$ | H | H | H. |
TABLE 7
Examples 300-434.
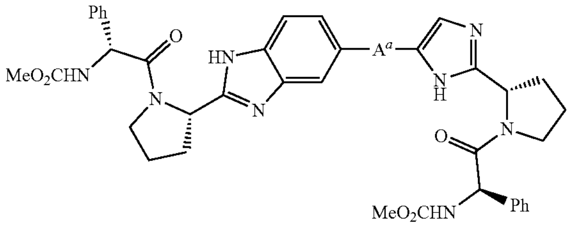
| Entry | $A^a$ |
|---|---|
| 300 | 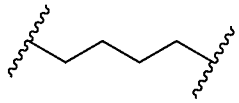 [SMILES: *CCCC*] |
| 301 | 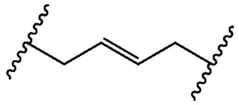 [SMILES: *C/C=C/C*] |
| 302 | 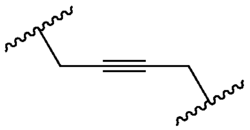 [SMILES: *CC#CC*] |
TABLE 7-continued
Examples 300-434.
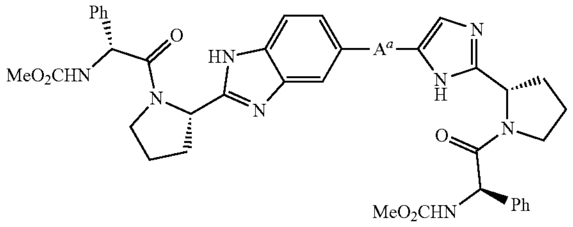
| Entry | $A^a$ |
|---|---|
| 303 | 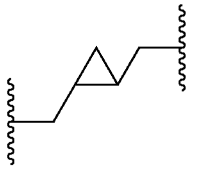 [SMILES: *CC1CC1C*] |
| 304 | 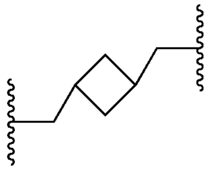 [SMILES: *CC1CC(C*)C1] |
| 305 | 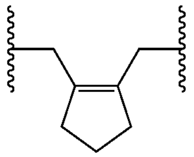 [SMILES: *CC1=C(C*)CCC1] |
| 306 | 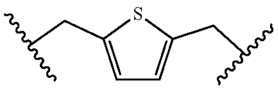 [SMILES: *Cc1ccc(C*)s1] |
| 307 | 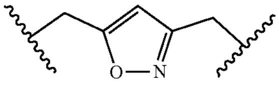 [SMILES: *Cc1cc(C*)on1] |
| 308 | 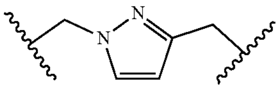 |
| 309 | 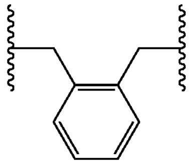 [SMILES: *Cc1ccccc1C*] |
| 310 | 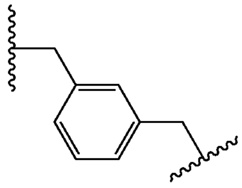 [SMILES: *Cc1cccc(C*)c1] |

TABLE 7-continued
Examples 300-434.
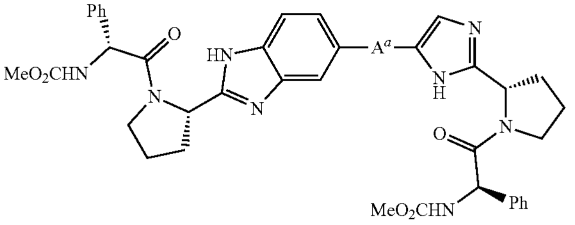
| Entry | $A^a$ |
| --- | --- |
| 311 | 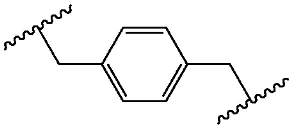 [SMILES: *Cc1ccc(C*)cc1] |
| 312 | 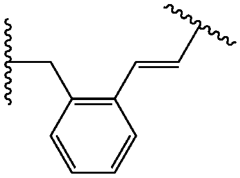 [SMILES: */C=C/c1ccccc1C*] |
| 313 | 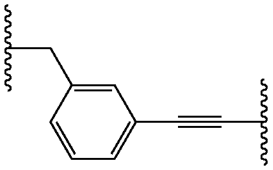 [SMILES: *C#Cc1cccc(C*)c1] |
| 314 | 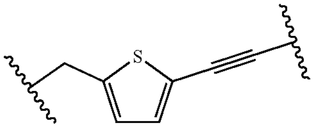 [SMILES: *C#Cc1ccc(C*)s1] |
| 315 | 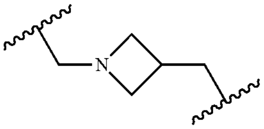 [SMILES: *CC1CN(C*)C1] |
| 316 | 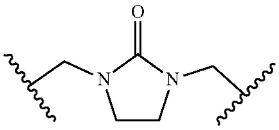 [SMILES: *CN1CCN(C*)C1=O] |
| 317 | 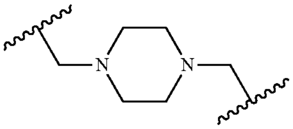 [SMILES: *CN1CCN(C*)CC1] |
| 318 | 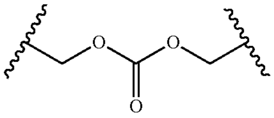 [SMILES: *COC(=O)OC*] |
TABLE 7-continued
Examples 300-434.
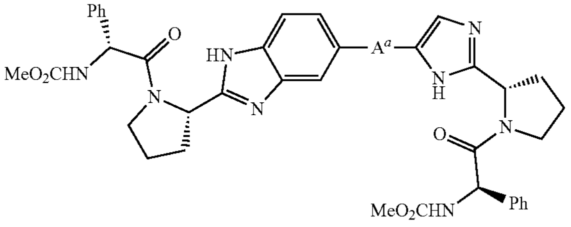
| Entry | $A^a$ |
| --- | --- |
| 319 | 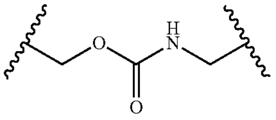 [SMILES: *CNC(=O)OC*] |
| 320 | 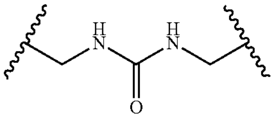 |
| 321 | 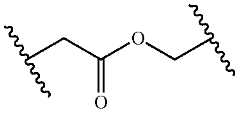 [SMILES: *COC(=O)C*] |
| 322 | 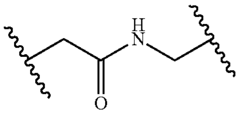 |
| 323 | 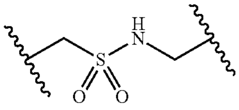 [SMILES: *CNS(=O)(=O)C*] |
| 324 | 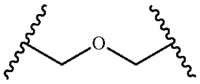 [SMILES: *COC*] |
| 325 | 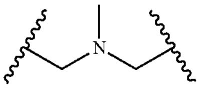 [SMILES: *CN(C)C*] |
| 326 | 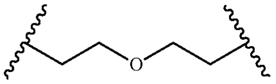 [SMILES: *CCOCC*] |
| 327 | 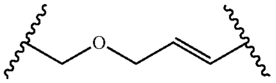 [SMILES: */C=C/COC*] |
| 328 | 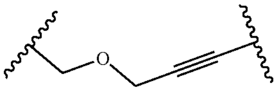 [SMILES: *C#CCOC*] |
| 329 | 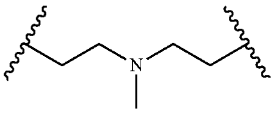 [SMILES: *CCN(C)CC*] |

TABLE 7-continued
Examples 300-434.
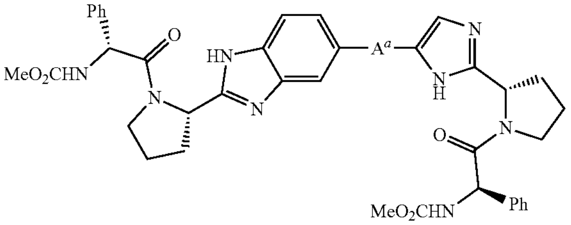
| Entry | $A^a$ |
| --- | --- |
| 330 | 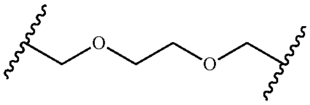 [SMILES: *COCCOC*] |
| 331 | 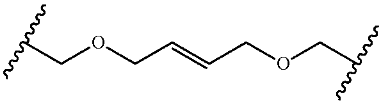 [SMILES: *COC/C=C/COC*] |
| 332 | 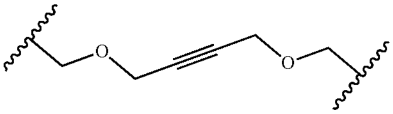 [SMILES: *COCC#CCOC*] |
| 333 | 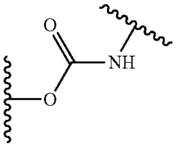 [SMILES: *NC(=O)O*] |
| 334 | 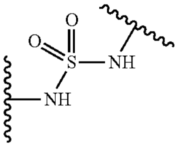 [SMILES: *NS(=O)(=O)N*] |
| 335 | 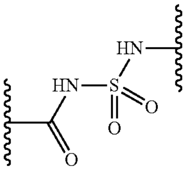 [SMILES: *NS(=O)(=O)NC(*)=O] |
| 336 | 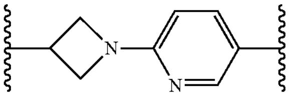 [SMILES: *c1ccc(N2CC(*)C2)nc1] |
| 337 | 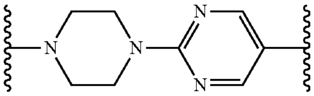 [SMILES: *c1cnc(N2CCN(*)CC2)nc1] |
| 338 | 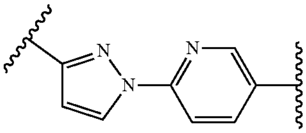 [SMILES: *c1ccc(-n2ccc(*)n2)nc1] |
TABLE 7-continued
Examples 300-434.
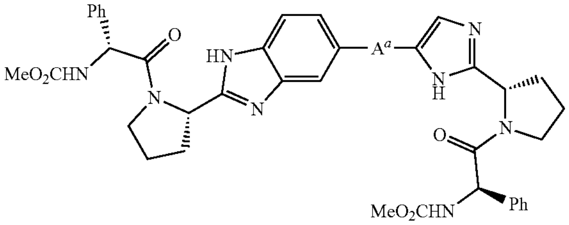
| Entry | $A^a$ |
| --- | --- |
| 339 | 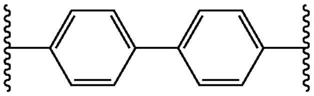 [SMILES: *c1ccc(-c2ccc(*)cc2)cc1] |
| 340 | 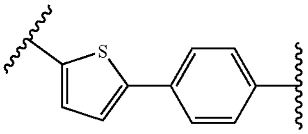 [SMILES: *c1ccc(-c2ccc(*)s2)cc1] |
| 341 | 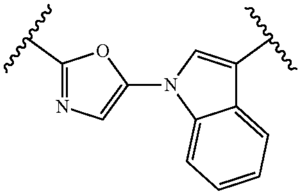 [SMILES: *c1ncc(-n2cc(*)c3ccccc32)o1] |
| 342 | 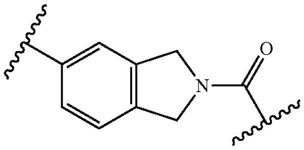 [SMILES: *C(=O)N1Cc2ccc(*)cc2C1] |
| 343 | 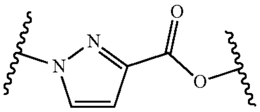 [SMILES: *OC(=O)c1ccn(*)n1] |
| 344 | 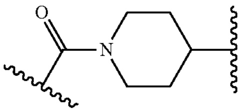 [SMILES: *C(=O)N1CCC(*)CC1] |
| 345 | 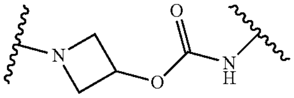 [SMILES: *NC(=O)OC1CN(*)C1] |
| 346 | 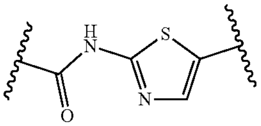 [SMILES: *C(=O)Nc1ncc(*)s1] |
| 347 | 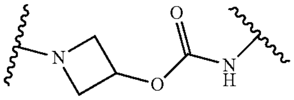 [SMILES: *NC(=O)OC1CN(*)C1] |

TABLE 7-continued
Examples 300-434.
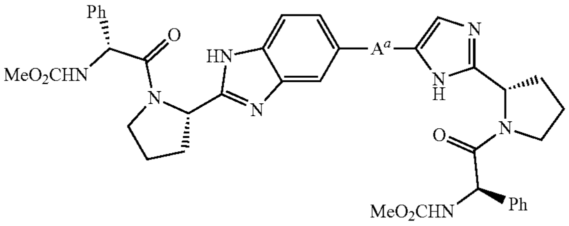
| Entry | $A^a$ |
| --- | --- |
| 348 | 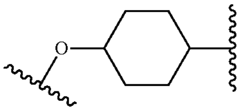 [SMILES: *OC1CCC(*)CC1] |
| 349 | 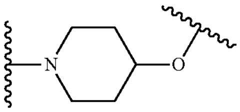 [SMILES: *OC1CCN(*)CC1] |
| 350 | 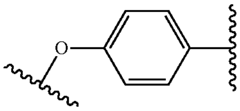 [SMILES: *Oc1ccc(*)cc1] |
| 351 | 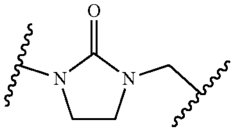 [SMILES: *CN1CCN(*)C1=O] |
| 352 | 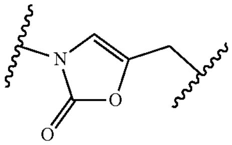 [SMILES: *Cc1cn(*)c(=O)o1] |
| 353 | 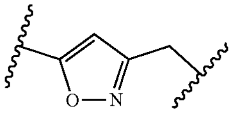 [SMILES: *Cc1cc(*)on1] |
| 354 | 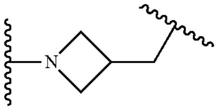 [SMILES: *CC1CN(*)C1] |
| 355 | 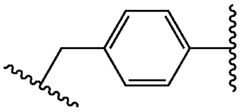 |
| 356 | 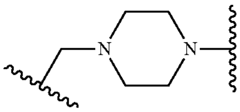 [SMILES: *CN1CCN(*)CC1] |
| 357 | 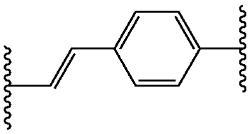 [SMILES: */C=C/c1ccc(*)cc1] |
TABLE 7-continued
Examples 300-434.
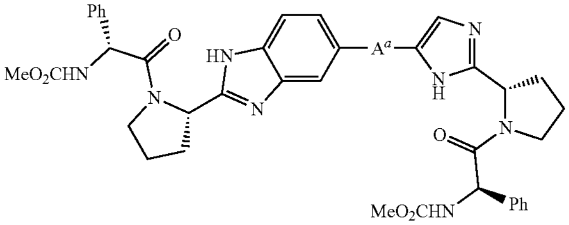
| Entry | $A^a$ |
| --- | --- |
| 358 | 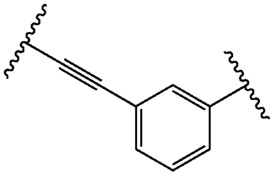 [SMILES: *C#Cc1cccc(*)c1] |
| 359 | 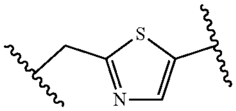 [SMILES: *Cc1ncc(*)s1] |
| 360 | 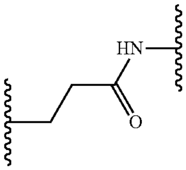 |
| 361 | 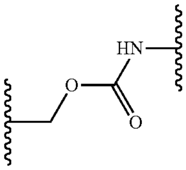 |
| 362 | 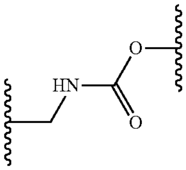 [SMILES: *CNC(=O)O*] |
| 363 | 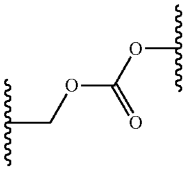 [SMILES: *COC(=O)O*] |
| 364 | 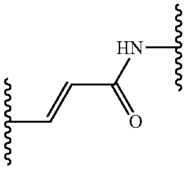 [SMILES: */C=C/C(=O)N*] |

TABLE 7-continued
Examples 300-434.
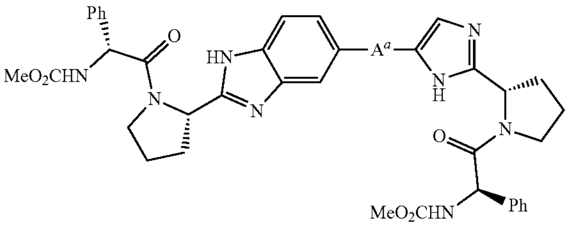
| Entry | $A^a$ |
|---|---|
| 365 | 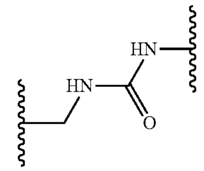 |
| 366 | 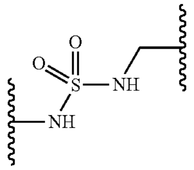 |
| 367 | 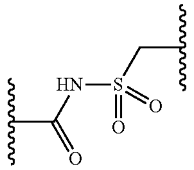 [SMILES: *CS(=O)(=O)NC(*)=O] |
| 368 | 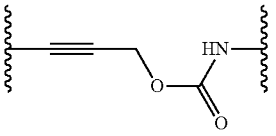 [SMILES: *C#CCOC(=O)N*] |
| 369 | 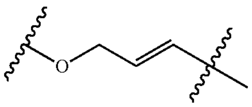 [SMILES: */C=C/CO*] |
| 370 | 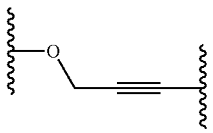 |
| 371 | 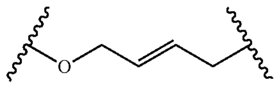 [SMILES: *C/C=C/CO*] |
| 372 | 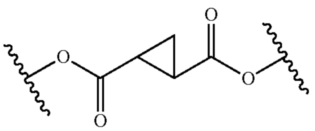 [SMILES: *OC(=O)C1CC1C(=O)O*] |
TABLE 7-continued
Examples 300-434.
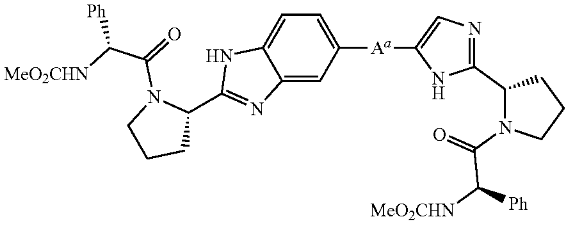
| Entry | $A^a$ |
|---|---|
| 373 | 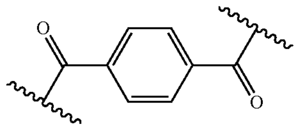 [SMILES: *C(=O)c1ccc(C(*)=O)cc1] |
| 374 | 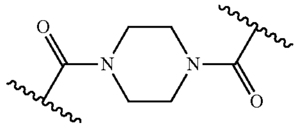 [SMILES: *C(=O)N1CCN(C(*)=O)CC1] |
| 375 | 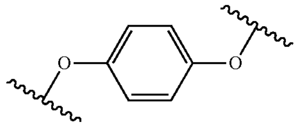 [SMILES: *Oc1ccc(O*)cc1] |
| 376 | 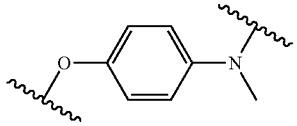 [SMILES: *Oc1ccc(N(*)C)cc1] |
| 377 | 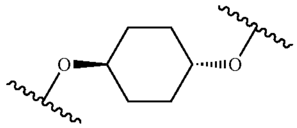 [SMILES: *O[C@H]1CC[C@H](O*)CC1] |
| 378 | 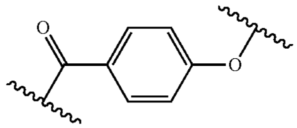 [SMILES: *Oc1ccc(C(*)=O)cc1] |
| 379 | 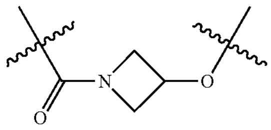 [SMILES: *OC1CN(C(*)=O)C1] |
| 380 | 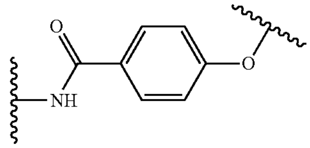 [SMILES: *NC(=O)c1ccc(O*)cc1] |
| 381 | 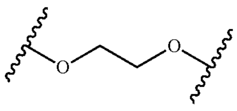 [SMILES: *OCCO*] |

TABLE 7-continued
Examples 300-434.
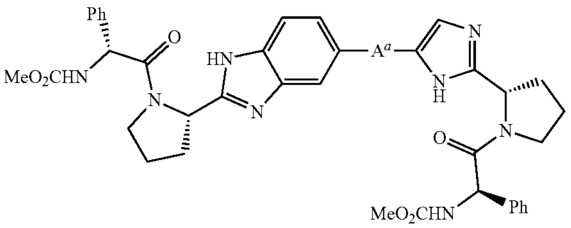
| Entry | $A^a$ |
|---|---|
| 382 | 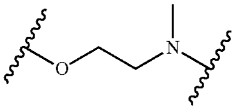 [SMILES: *OCCN(*)C] |
| 383 | 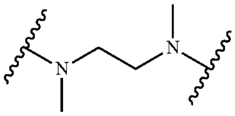 [SMILES: *N(C)CCN(*)C] |
| 384 | 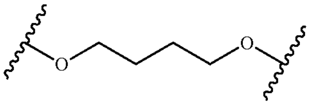 [SMILES: *OCCCCO*] |
| 385 | 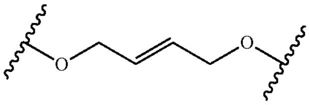 [SMILES: *OC/C=C/CO*] |
| 386 | 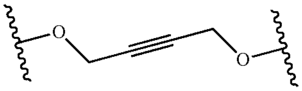 [SMILES: *OCC#CCO*] |
| 387 | 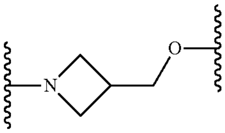 [SMILES: *OCC1CN(*)C1] |
| 388 | 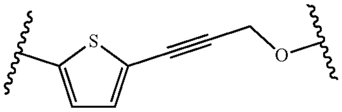 [SMILES: *OCC#Cc1ccc(*)s1] |
| 389 | 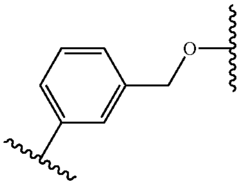 [SMILES: *OCc1cccc(*)c1] |
| 390 | 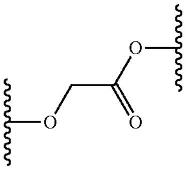 [SMILES: *OCC(=O)O*] |
TABLE 7-continued
Examples 300-434.
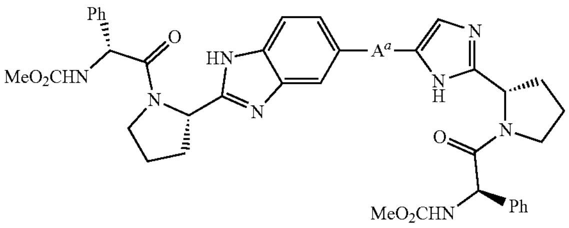
| Entry | $A^a$ |
|---|---|
| 391 | 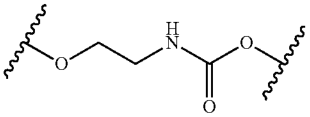 [SMILES: *OCCNC(=O)O*] |
| 392 | 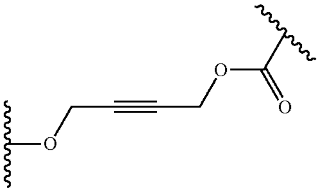 [SMILES: *OCC#CCOC(*)=O] |
| 393 | 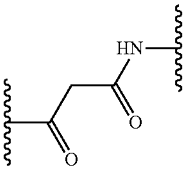 [SMILES: *NC(=O)CC(*)=O] |
| 394 | 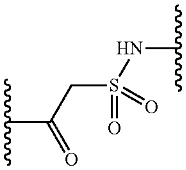 [SMILES: *NS(=O)(=O)CC(*)=O] |
| 395 | 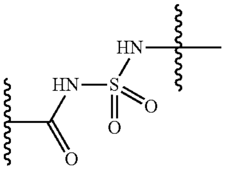 [SMILES: *NS(=O)(=O)NC(*)=O] |
| 396 | 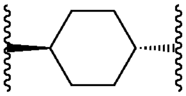 |
| 397 | 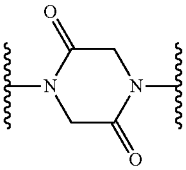 [SMILES: *N1CC(=O)N(*)CC1=O] |
| 398 | 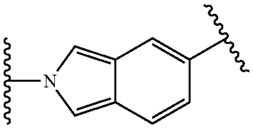 [SMILES: *c1ccc2cn(*)cc2c1] |

TABLE 7-continued
Examples 300-434.
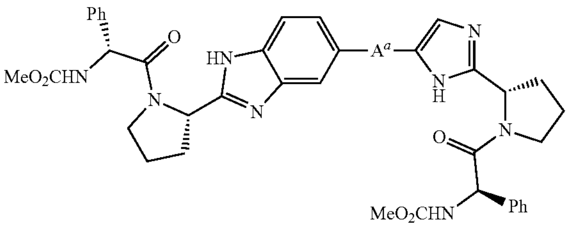
| Entry | $A^a$ |
|---|---|
| 399 | 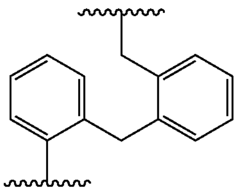 [SMILES: *Cc1ccccc1Cc1ccccc1*] |
| 400 | 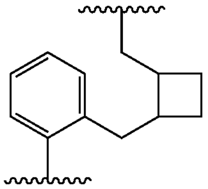 [SMILES: *CC1CCC1Cc1ccccc1*] |
| 401 | 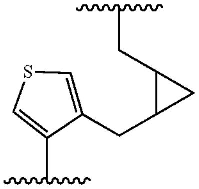 [SMILES: *CC1CC1Cc1cscc1*] |
| 402 | 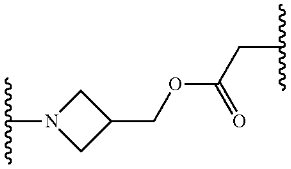 [SMILES: *CC(=O)OCC1CN(*)C1] |
| 403 | 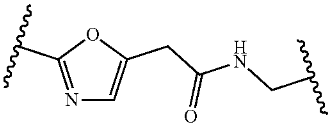 [SMILES: *CNC(=O)Cc1cnc(*)o1] |
| 404 | 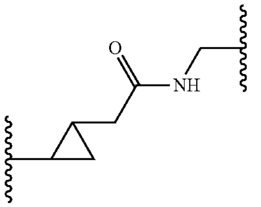 [SMILES: *CNC(=O)CC1CC1*] |
| 405 | 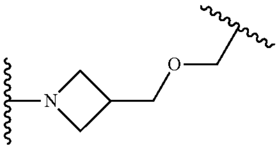 [SMILES: *COCC1CN(*)C1] |
TABLE 7-continued
Examples 300-434.
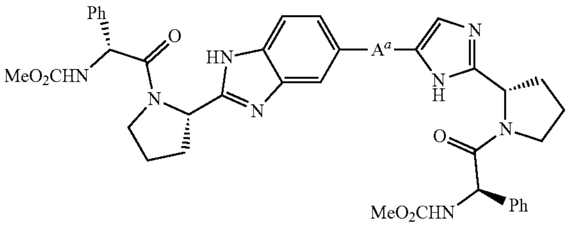
| Entry | $A^a$ |
|---|---|
| 406 | 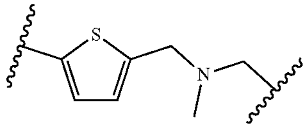 [SMILES: *CN(C)Cc1ccc(*)s1] |
| 407 | 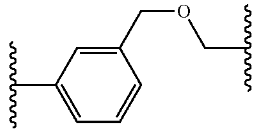 [SMILES: *COCc1cccc(*)c1] |
| 408 | 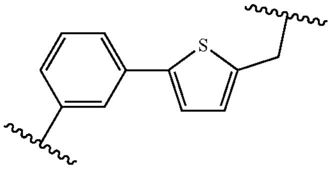 [SMILES: *Cc1ccc(-c2cccc(*)c2)s1] |
| 409 | 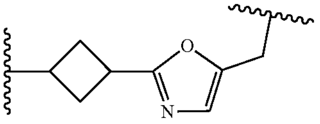 [SMILES: *Cc1cnc(C2CC(*)C2)o1] |
| 410 | 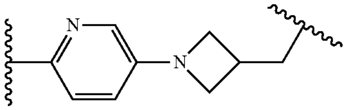 [SMILES: *CC1CN(c2ccc(*)nc2)C1] |
| 411 | 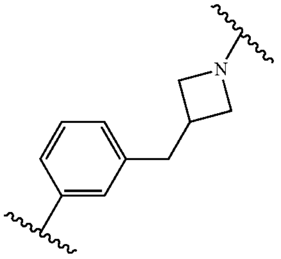 [SMILES: *c1cccc(CC2CN(*)C2)c1] |
| 412 | 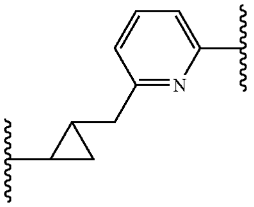 [SMILES: *c1cccc(CC2CC2*)n1] |

TABLE 7-continued
Examples 300-434.
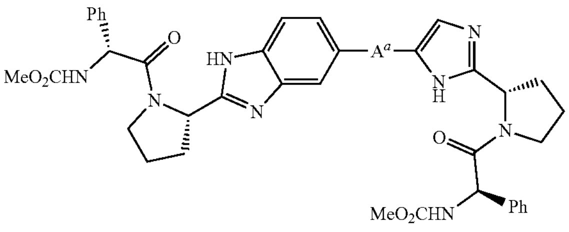
| Entry | $A^a$ |
|---|---|
| 413 | 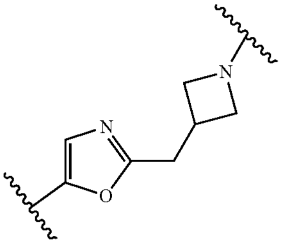 [SMILES: *c1cnc(CC2CN(*)C2)o1] |
| 414 | 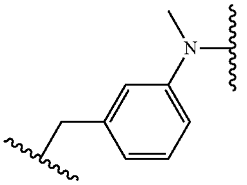 [SMILES: *Cc1cccc(N(*)C)c1] |
| 415 | 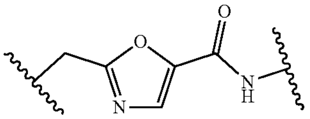 [SMILES: *Cc1ncc(C(=O)N*)o1] |
| 416 | 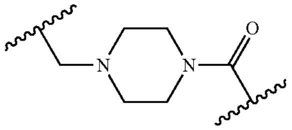 [SMILES: *CN1CCN(C(*)=O)CC1] |
| 417 | 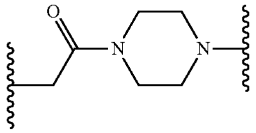 [SMILES: *CC(=O)N1CCN(*)CC1] |
| 418 | 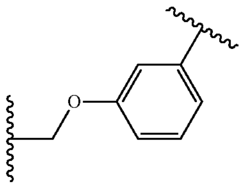 [SMILES: *COc1cccc(*)c1] |
| 419 | 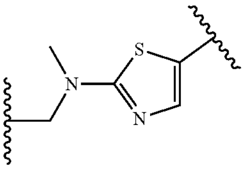 [SMILES: *CN(C)c1ncc(*)s1] |
TABLE 7-continued
Examples 300-434.
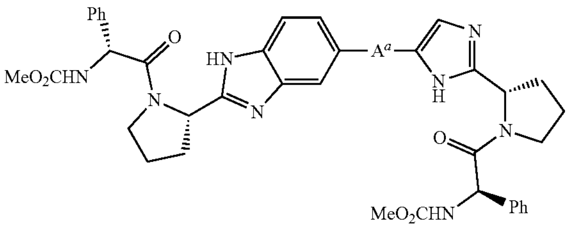
| Entry | $A^a$ |
|---|---|
| 420 | 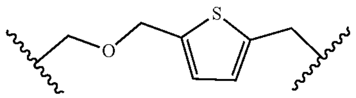 [SMILES: *COCc1ccc(C*)s1] |
| 421 | 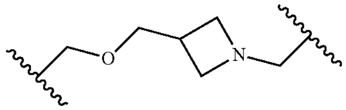 [SMILES: *COCC1CN(C*)C1] |
| 422 | 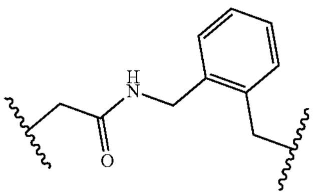 [SMILES: *CC(=O)NCc1ccccc1C*] |
| 423 | 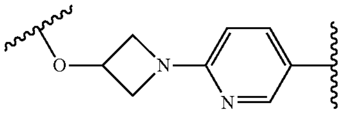 [SMILES: *OC1CN(c2ccc(*)cn2)C1] |
| 424 | 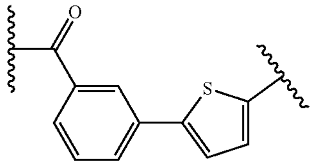 [SMILES: *C(=O)c1cccc(-c2ccc(*)s2)c1] |
| 425 | 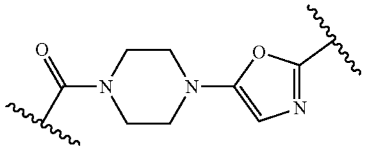 [SMILES: *C(=O)N1CCN(c2cnc(*)o2)CC1] |
| 426 | 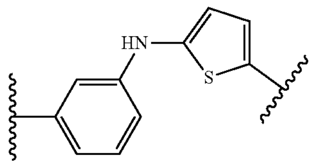 [SMILES: *c1cccc(Nc2ccc(*)s2)c1] |
| 427 | 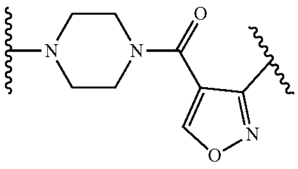 [SMILES: *c1nocc1C(=O)N1CCN(*)CC1] |

TABLE 7-continued
Examples 300-434.
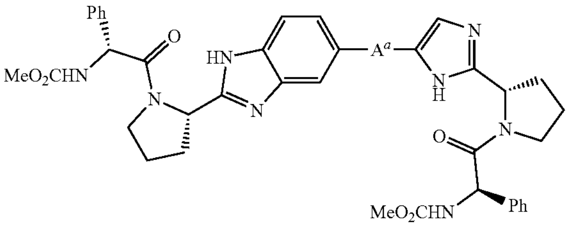
| Entry | $A^a$ |
|---|---|
| 428 | 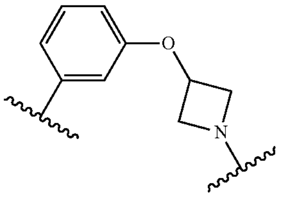 [SMILES: *c1cccc(OC2CN(*)C2)c1] |
| 429 | 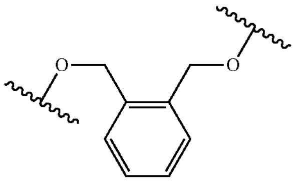 |
| 430 | 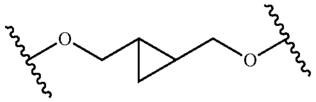 [SMILES: *OCC1CC1CO*] |
| 431 | 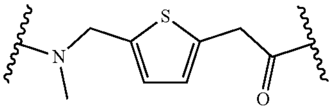 [SMILES: *C(=O)Cc1ccc(CN(*)C)s1] |
| 432 | 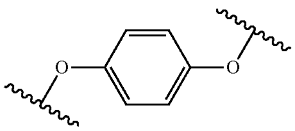 |
| 433 | 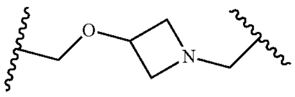 [SMILES: *COC1CN(C*)C1] |
TABLE 7-continued
Examples 300-434.
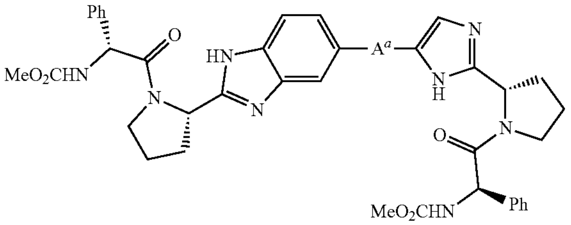
| Entry | $A^a$ |
|---|---|
| 434 | 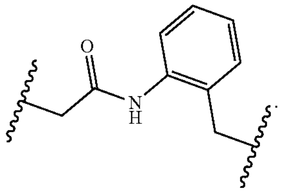 [SMILES: *CC(=O)Nc1ccccc1C*] |
TABLE 8
Examples 435-440.
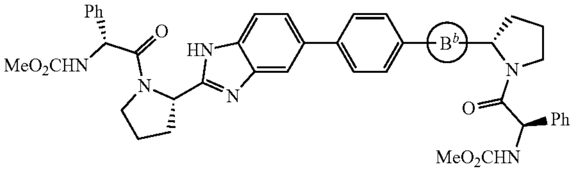
| Entry | $B^b$ |
|---|---|
| 435 | 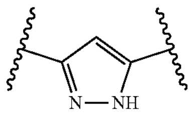 [SMILES: *c1cc(*)[nH]n1] |
| 436 | 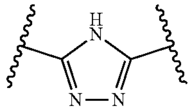 [SMILES: *c1nnc(*)[nH]1] |
| 437 | 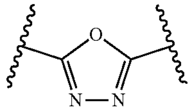 [SMILES: *c1nnc(*)o1] |
| 438 | 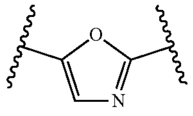 [SMILES: *c1cnc(*)o1] |
| 439 | 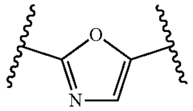 [SMILES: *c1cnc(*)o1] |
| 440 | 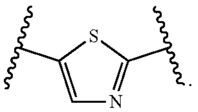 [SMILES: *c1cnc(*)s1] |

Example 357

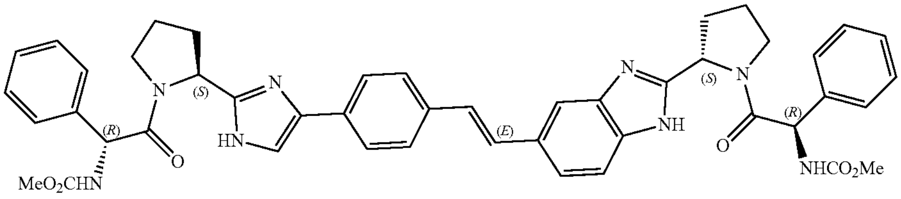

Step 357a. A solution of the compound of example 491 (0.122 g, 0.196 mmol) in 1,4-dioxane (2 mL) was treated with HCl in 1,4-dioxane (4 M, 8 mL) at rt for 1 hour. The volatiles were evaporated off to give the crude desired compound as a yellow solid which was used directly in the next step.

Step 357b. A mixture of the crude compound from step 357a (0.196 mmol at most) and (R)-(methoxycarbonyl) amino phenyl acetic acid (prepared according to WO 2008/021927, 0.102 g, 0.490 mmol) in DMF (3 mL) was treated with HATU (0.171 g, 0.451 mmol) in the presence of DIPEA (0.68 mL, 3.920 mmol) for 2 hours at rt and the volatiles were evaporated off to provide a brown syrup. It was partitioned (EtOAc—$H_2O$). The organic layer was washed with brine, dried ($Na_2SO_4$), filtered and concentrated. The crude was purified by flash column chromatography (silica, $CH_2Cl_2$-MeOH) to give the title compound as a yellow solid (0.144 g, 91% over 2 steps). ESIMS m/z=806.96 $[M+H]^+$.

Example 441

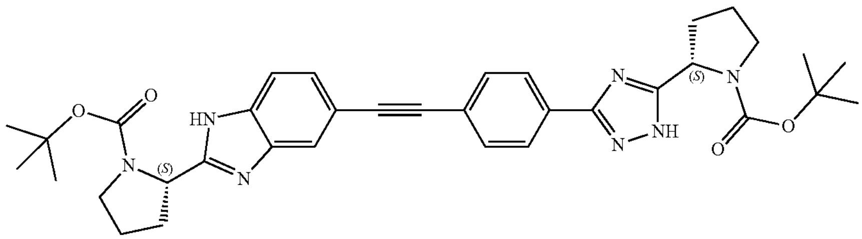

A mixture of (S)-tert-butyl 2-(3-(4-iodophenyl)-1H-1,2,4-triazol-5-yl)pyrrolidine-1-carboxylate (prepared according to US 2008/0311075, 84.9 mg, 0.193 mmol), the compound from step 515d (66.0 mg, 0.212 mmol), CuI (1.1 mg, 5.7 μmol) and $Pd(PPh_3)_2Cl_2$ (6.7 mg, 9.6 μmol) in $CH_3CN$ (5 mL) and triethylamine (5 mL) was degassed and heated to 50° C. under $N_2$ for 3 hours. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the title compound as a light yellow oil (94.0 mg, 78%). ESIMS m/z=624.34 $[M+H]^+$.

Example 442

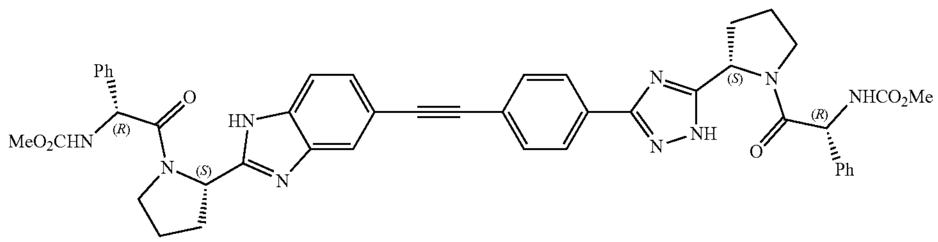

Step 442a. A solution of the compound of Example 441 (90.0 mg, 0.144 mmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=424.11 $[M+H]^+$.

Step 442b. A mixture of the crude compound from step 442a (0.144 mmol at most) and (R)-(methoxycarbonyl) amino phenyl acetic acid (prepared according to WO 2008/021927, 75.4 mg, 0.361 mmol) in DMF (3 mL) was treated with HATU (0.126 g, 0.332 mmol) in the presence of DIPEA (0.36 mL, 2.89 mmol) for 2 hours at rt and the volatiles were evaporated off to provide a brown syrup. It was purified by flash column chromatography (silica, $CH_2Cl_2$-MeOH) to give the title compound as a very light yellow solid (98.1 mg, 2 steps 80%). ESIMS m/z=806.16 $[M+H]^+$.

Example 443

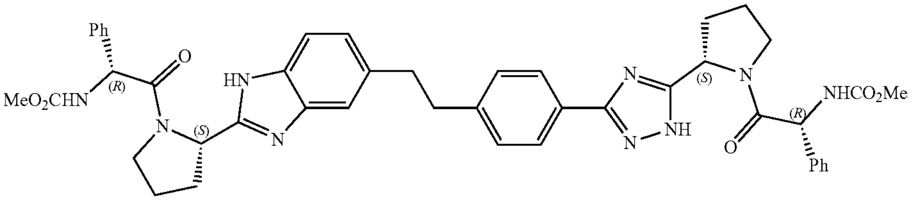

A mixture of the title compound of example 442 (51.6 mg, 63.3 μmol) and $Pd(OH)_2$ on carbon (20%, 50.0 mg) in ethanol (3 mL) was treated with $H_2$ balloon overnight. The mixture was filtered through celite and the filtrate was concentrated. The residue was purified by flash column chromatography (silica, $CH_2Cl_2$-MeOH) to give the title compound as a white solid (42.5 mg, 82%). ESIMS m/z=810.23 $[M+H]^+$.

Example 444

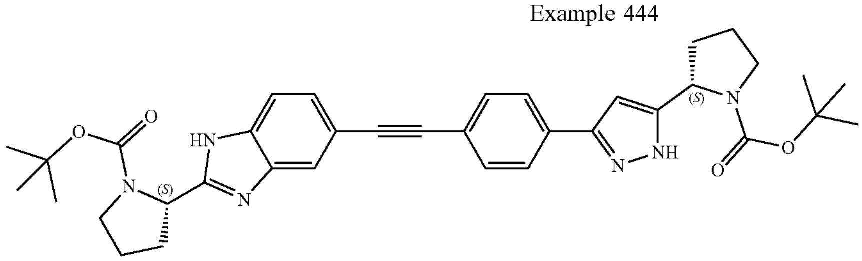

A mixture of (S)-tert-butyl 2-(3-(4-iodophenyl)-1H-pyrazol-5-yl)pyrrolidine-1-carboxylate (prepared according to US 2008/0311075, 85.0 mg, 0.213 mmol), the compound from step 515d (66.2 mg, 0.213 mmol), CuI (1.1 mg, 5.8 μmol) and $Pd(PPh_3)_2Cl_2$ (6.7 mg, 9.6 μmol) in $CH_3CN$ (5 mL) and triethylamine (5 mL) was degassed and heated at 60° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the title compound as a light yellow oil (91.1 mg, 76%). ESIMS m/z=623.20 $[M+H]^+$.

Example 445

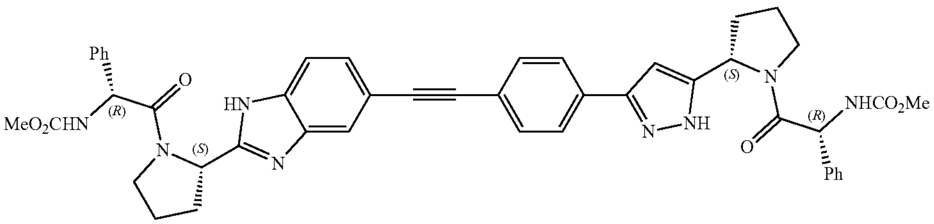

The title compound was synthesized from the compound of Example 444 using procedures similar to that described in Example 442. ESIMS m/z=805.36 [M+H]$^+$.

Example 446 were washed with brine, dried ($Na_2SO_4$), filtered and evaporated. The residue was purified by flash column chromatography (silica, hexanes-ethyl acetate) to give the desired compound as a colorless oil (0.127 g, 60%). ESIMS m/z=328.23 [M+H]$^+$.

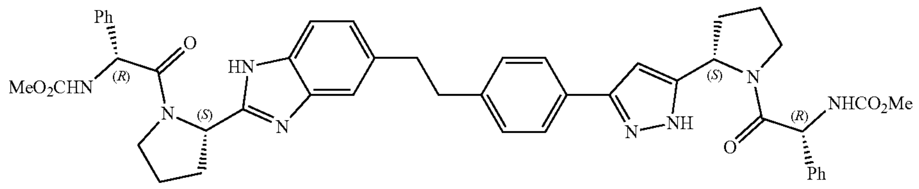

The title compound was synthesized from the compound of Example 445 using procedures similar to that described in Example 443. ESIMS m/z=809.42 [M+H]$^+$.

Example 447

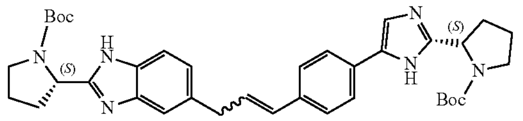

and/or

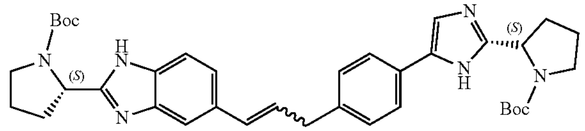

Step 447a. A mixture of the compound of step 1b (0.250 g, 0.683 mmol), allyltributyl-stannane (0.26 mL, 0.820

Step 447b. A mixture of the compound of step 1d (0.180 g, 0.459 mmol), the compound of step 447a (0.150 g, 0.459 mmol), triethylamine (0.64 mL, 4.59 mmol), tri-o-tolylphosphine (18.0 mg, 57.3 μmol) and $Pd(OAc)_2$ (5.1 mg, 22.9 μmol) in $CH_3CN$ (8 mL) was degassed and heated to 90° C. under $N_2$ overnight. The volatiles were evaporated and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the title compounds as a light yellow solid (0.165 g, 70%). The regio- and stereochemistry of the olefinic double bond was not determined. ESIMS m/z=639.36 [M+H]$^+$.

Example 448

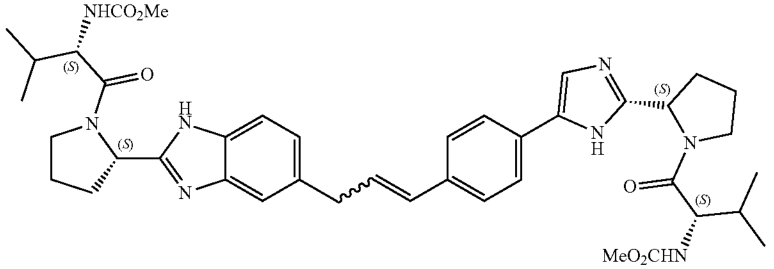

and/or

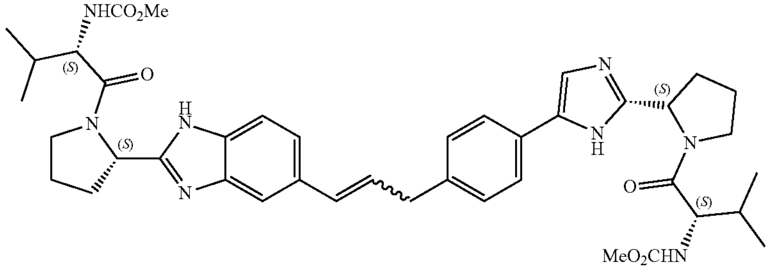

mmol) and $Pd(PPh_3)_4$ (39.4 mg, 34.1 μmol) in toluene (6 mL) was degassed and heated at 110° C. under $N_2$ overnight. The volatiles were evaporated and the residue was partitioned (EtOAc—saturated aqueous $NaHCO_3$). The organics Step 448a. A solution of the compound of Example 447 (0.104 g, 0.163 mmol) in 1,4-dioxane (1 mL) was treated with HCl in 1,4-dioxane (4 M, 4 mL) at rt for 30 minutes. The volatiles were evaporated off to give the crude desired compound as a yellow solid which was directly used in the next step. ESIMS m/z=439.24 $[M+H]^+$.

Step 448b. A mixture of the crude compound of step 448a (0.163 mmol at most) and (S)-2-(methoxycarbonylamino)-3-methylbutanoic acid (prepared according to WO 2008/021927, 71.3 mg, 0.408 mmol) in DMF (3 mL) was treated with HATU (0.142 g, 0.375 mmol) in the presence of DIPEA (0.41 mL, 3.26 mmol) for 2 hours at rt and the volatiles were evaporated off to provide a brown syrup. It was purified by flash column chromatography (silica, $CH_2Cl_2$-MeOH) to give the title compounds as a white solid (89.5 mg, 2 steps 73%). The regio- and stereochemistry of the olefinic double bond was not determined. ESIMS m/z=753.39 $[M+H]^+$.

Example 449

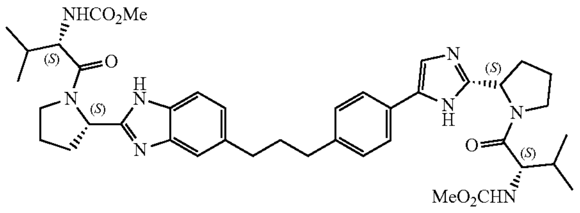

The title compound was synthesized from the compound of Example 448 using procedures similar to that described in Example 443. ESIMS m/z=755.47 $[M+H]^+$.

Example 450

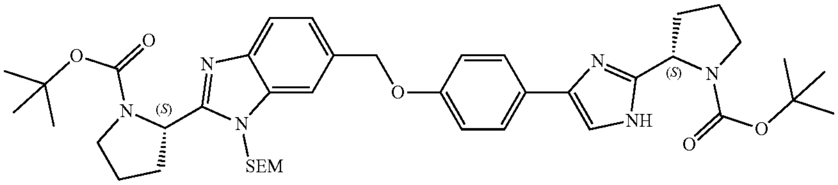

Step 450a. The compound of step 1e (0.200 g, 0.455 mmol) in THF (5 mL) was treated with a mixture of 30% aqueous $H_2O_2$ (0.5 mL) and 1N aqueous NaOH (1 mL) for 30 minutes. The volatiles were removed and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow oil (0.144 g, 96%). ESIMS m/z=330.15 $[M+H]^+$.

Step 450b. The mixture of (S)-1-(tert-butoxycarbonyl) pyrrolidine-2-carboxylic acid (5 g, 23.2 mmol) in acetonitrile (40 mL) was added 1,1'-carbonyldiimidazole (3.95 g, 24.5 mmol). The resulting mixture was stirred at room temperature for 20 min before being added methyl 3,4-diaminobenzoate (3.86 g, 23.2 mmol). The solution was stirred at room temperature for another 3 hours before being partitioned between water and EtOAc. The organic phase was separated, dried ($Na_2SO_4$) and concentrated to afford a brown slurry, which was purified by flash column chromatography (silica, hexane-EtOAc) to give the desired product as a light yellow oil (8.14 g, 98%). ESIMS m/z=364.17 $[M+H]^+$.

Step 450c. The solution of compound from step 450b in acetic acid (150 mL) was stirred at 60° C. for three days before all volatiles were removed. The resulting residue was partitioned between aqueous $NaHCO_3$ and EtOAc. The organic phase was separated, dried ($Na_2SO_4$) and concentrated to afford a brown oil, which was purified by flash column chromatography (silica, hexane-EtOAc) to give the desired product as a light yellow solid (2.02 g, 28%). ESIMS m/z=346.15 $[M+H]^+$.

Step 450d. The solution of compound from step 450c (2.02 g, 5.8 mmol) in DMF (50 mL) was added sodium hydride (55% in mineral oil, 269 mg, 6.4 mmol). The reaction was stirred at room temperature for 1.5 hours before being added 2-(Trimethylsilyl)ethoxymethyl chloride (1.02 mL, 5.8 mmol). The mixture was stirred at room temperature for another 3 hours before being partitioned between water and EtOAc. The organic phase was separated, dried ($Na_2SO_4$) and concentrated to afford a brown oil, which was purified by flash column chromatography (silica, hexane-EtOAc) to give the desired product as a light yellow solid (2.6 g, 94%). ESIMS m/z=475.97 $[M+H]^+$.

Step 450e. The solution of compound from step 450d (2.6 g, 5.47 mmol) in THF (50 mL) and water (25 mL) was added lithium hydroxide monohydrate (690 mg, 16.4 mmol). The resulting mixture was stirred at room temperature for 3 hours before being partitioned between water, AcOH (10 mL) and EtOAc. The organic phase was separated, dried ($Na_2SO_4$) and concentrated to afford a brown oil, which was directly used for the next step without further purification (2.6 g, crude, 100%). ESIMS m/z=462.02 $[M+H]^+$. Step 450f. The solution of compound from step 450e (2.0 g, 4.3 mmol) in THF (45 mL) was added triethylamine (1.85 mL, 12.9 mmol) and ethyl chloroformate (1.05 mL, 10.8 mmol) at 0° C. The resulting mixture stirred at 0° C. for 20 minutes before all volatiles were removed by rotavap. The residue was dissolved in THF (70 mL) before being added sodium borohydride (1 g, 26.4 mmol). The mixture was stirred at 0° C. for another 2 hours before being partitioned between water and EtOAc. The organic phase was separated, dried ($Na_2SO_4$) and concentrated to afford a brown oil, which was purified by flash column chromatography (silica, EtOAc-methanol) to give the desired product as a light yellow solid (1.57 g, 81%). ESIMS m/z=448.13 $[M+H]^+$.

Step 450g. The compound from step 450a (70.0 mg, 0.213 mmol) in THF (5 mL) was treated with the compound from step 450f (95.1 mg, 0.213 mmol), $PPh_3$ (83.6 mg, 0.319 mmol) and DEAD (50.2 μL, 0.319 mmol) overnight before being evaporated to dryness. The residue was partitioned (EtOAc—water) and the organics were washed with brine, dried ($Na_2SO_4$), filtered and evaporated. The residue was purified by flash column chromatography (silica, hexanes-ethyl acetate) to give the title compound as a colorless oil (22.6 mg, 14%). The regiochemistry of the SEM group was not determined. ESIMS m/z=759.39 $[M+H]^+$.

Example 451

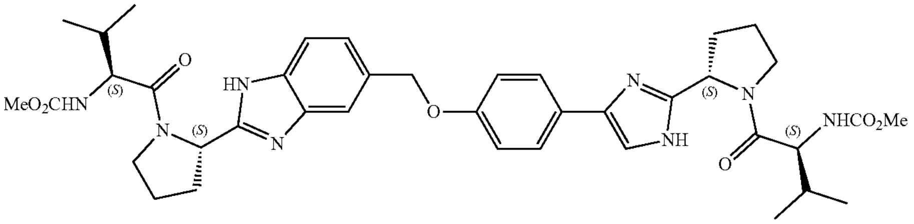

The title compound was synthesized from the compound of Example 450 using procedures similar to that described in steps 497a and 448b. ESIMS m/z=743.32 $[M+H]^+$.

Example 452

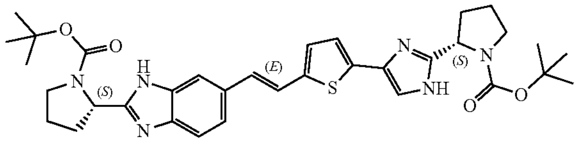

Step 452a. A mixture of 2-bromo-1-(5-bromothiophen-2-yl)ethanone (1.00 g, 3.52 mmol) and N-Boc-L-proline (0.758 g, 3.52 mmol) in $CH_3CN$ (12 mL) was added TEA (1.06 mL, 7.40 mmol) slowly. The mixture was stirred at rt until the disappearance of the starting material. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a yellow sticky oil (1.47 g, 100%). $^1H$ NMR ($CDCl_3$) 7.49 (t, J=4.0 Hz, 1H), 7.13 (dd, J=4.5, 6.0 Hz, 1H), 5.36, 5.04 (2d, J=16.0 Hz, 1H), 5.22, 5.15 (2d, J=16.5 Hz, 1H), 4.45, 4.38 (dd, J=5.5, 7.5 Hz, 1H), 3.56 (m, 1H), 3.41 (m, 1H), 2.25 (m, 2H), 2.05 (m, 1H), 1.90 (m, 1H), 1.46, 1.42 (2s, 9H).

Step 452b. A solution of the compound of step 452a (1.47 g, 3.52 mmol) in toluene (22 mL) was added ammonium acetate (5.42 g, 70.3 mmol) and the resultant mixture was heated at 100° C. for 16 hours. The volatiles were evaporated and the residue was partitioned (EtOAc—aq. $NaHCO_3$). The organics were washed with brine, dried ($Na_2SO_4$), filtered and evaporated.

The residue was purified by flash column chromatography (silica, hexanes-ethyl acetate) to give the desired compound as a brown yellow foam (0.586 g, 42%) with a recovery of the compound from step 452a (0.616 g, 42%). ESIMS m/z=398.16, 400.16 $[M+H]^+$. $^1H$ NMR ($CDCl_3$) 10.55 (bs, 1H), 7.07 (s, 1H), 6.94 (m, 2H), 4.92 (m, 1H), 3.40 (m, 2H), 2.96 (m, 1H), 2.12 (m, 2H), 1.92 (m, 1H), 1.49 (s, 9H).

Step 452c. A mixture of the compound of step 452b (0.150 g, 0.377 mmol), the compound from step 491a (0.118 g, 0.377 mmol), triethylamine (0.52 mL, 3.77 mmol), tri-o-tolylphosphine (14.8 mg, 47.1 μmol) and $Pd(OAc)_2$ (4.2 mg, 18.8 μmol) in $CH_3CN$ (6 mL) was degassed and heated to 110° C. in sealed tube for 36 hours. The volatiles were evaporated and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the title compound as a yellow oil (64.1 mg, 27%). ESIMS m/z=631.26 $[M+H]^+$.

Example 453

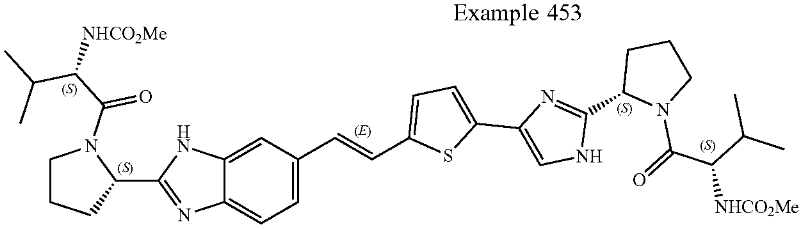

The title compound was synthesized from the compound from Example 452 using procedures similar to that described in Example 448. ESIMS m/z=745.43 $[M+H]^+$.

Example 454

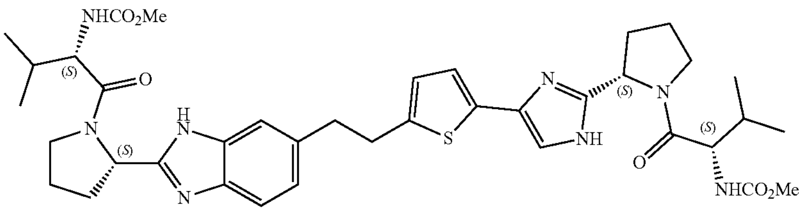

The title compound was synthesized from the compound from Example 453 using procedures similar to that described in Example 443. ESIMS m/z=747.40 $[M+H]^+$.

Example 455

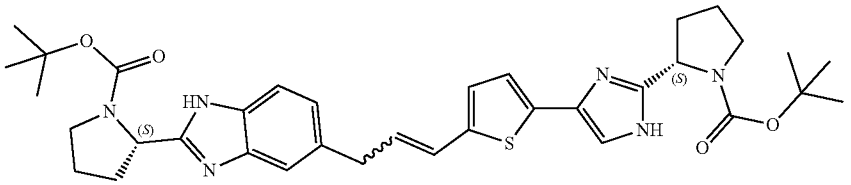

and/or

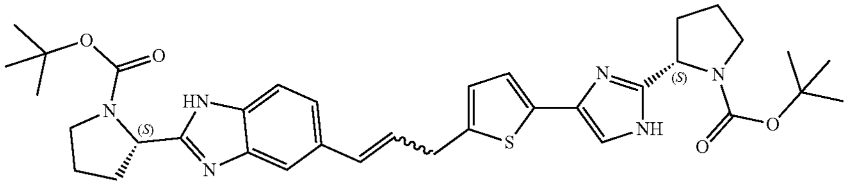

A mixture of the compound from step 452b (0.150 g, 0.377 mmol), the compound from step 447a (0.123 g, 0.377 mmol), triethylamine (0.52 mL, 3.77 mmol), tri-o-tolylphosphine (14.8 mg, 47.1 μmol) and $Pd(OAc)_2$ (4.2 mg, 18.8 μmol) in $CH_3CN$ (6 mL) was degassed and heated to 110° C. in sealed tube for 36 hours. The volatiles were evaporated and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the title compounds as a yellow oil (52.7 mg, 22%). The regio- and stereochemistry of the olefinic double bond was not determined. ESIMS m/z=645.27 $[M+H]^+$.

Example 456

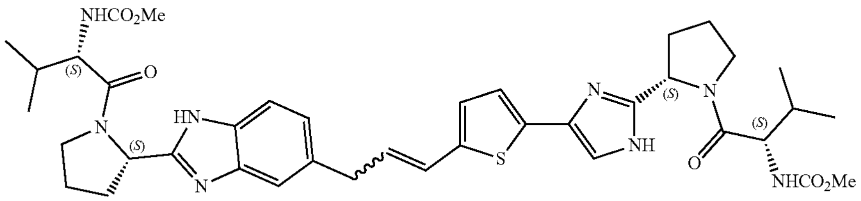

and/or

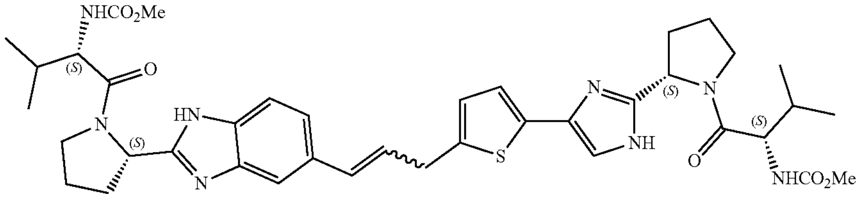

The title compound was synthesized from the compound from Example 455 using procedures similar to that described in Example 448. The regio- and stereochemistry of the olefinic double bond was not determined. ESIMS m/z=759.51 $[M+H]^+$.

Example 457

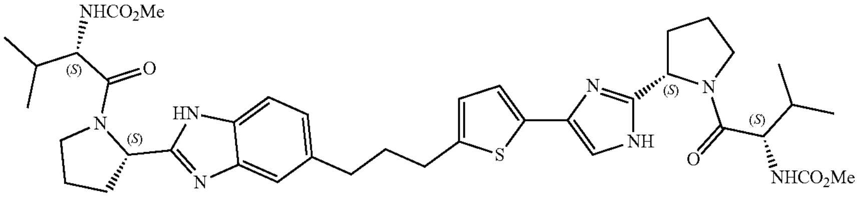

The title compound was synthesized from the compound from Example 456 using procedures similar to that described in Example 443. ESIMS m/z=761.41 [M+H]$^+$.

Example 458

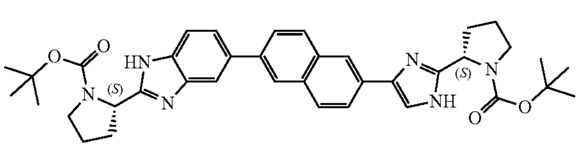

Step 458a. 6-bromo-N-methoxy-N-methyl-2-naphthamide (prepared according to J. Med. Chem., 2006, 49, 4721-4736, 3.57 g, 12.1 mmol) in THF (60 mL) was treated with methyl magnesium bromide (3M in $Et_2O$, 8.09 mL, 24.3 mmol) slowly at 0° C. for 1 hour. The solution was warmed up to rt for 2 hours before being quenched with aqueous $NH_4Cl$. The volatiles were removed and the residue was partitioned (EtOAc—water). The organics were washed with brine, dried ($Na_2SO_4$), filtered and evaporated to give the crude desired compound as a white solid (2.89 g, 96%).

Step 458b. The compound from step 458a (2.89 g, 11.6 mmol) in acetic acid (60 mL) was treated with bromine (0.59 mL, 11.6 mmol) dropwise for 1 hour. The volatiles were evaporated and the residue was partitioned (EtOAc—saturated aqueous $NaHCO_3$). The organics were washed with brine, dried ($Na_2SO_4$), filtered and evaporated to give the crude desired compound as a light yellow solid (3.898 g).

Step 458c. A mixture of the compound from step 458b (at most 11.6 mmol) and N-Boc-L-proline (3.75 g, 17.4 mmol) in $CH_3CN$ (60 mL) was added DIPEA (2.89 mL, 23.2 mmol) slowly. The mixture was stirred at rt until the disappearance of the starting material. The volatiles were evaporated and the residue was partitioned (EtOAc—water). The organics were washed with brine, dried ($Na_2SO_4$), filtered and evaporated to give the crude desired compound as a yellow-white foam (4.762 g). ESIMS m/z=462.03, 464.02 [M+H]$^+$.

Step 458d. A solution of the compound from step 458c (at most 11.6 mmol) in toluene (60 mL) was added ammonium acetate (13.4 g, 0.174 mol) and the resultant mixture was heated up at 100° C. for 14 hours. The volatiles were evaporated and the residue was partitioned (EtOAc—aq. $NaHCO_3$). The organics were washed with brine, dried ($Na_2SO_4$), filtered and evaporated. The residue was purified by flash column chromatography (silica, hexanes-ethyl acetate) to give the desired compound as a yellow brown powder (3.14 g, 4 steps, 61%). ESIMS m/z=442.02, 444.02 [M+H]$^+$.

Step 458e. A mixture of the compound from step 1b (1 g, 2.73 mmol), bis-(pinacolato)-diboron (763 mg, 3.0 mmol), potassium acetate (402 mg, 4.0 mmol) in 1,4-dioxane (9.1 mL) was added tetrakis(triphenylphosphine)palladium(0) (158 mg, 0.14 mmol). The resulting solution was degased and then heated at 80° C. under Na overnight before being evaporated. The residue was purified by chromatography (silica, hexanes-ethyl acetate with 1% $Et_3N$ in ethyl acetate) to give the desired compound as a yellow solid (680 mg, 60%). ESIMS m/z=414.24 [M+H]$^+$.

Step 458f. A mixture of the compound from step 458d (0.100 g, 0.226 mmol), the compound from step 458e (93.4 mg, 0.226 mmol), $Pd(PPh_3)_4$, (13.1 mg, 11.3 µmol) and $NaHCO_3$ (76.0 mg, 0.905 mmol) in DME (6 mL) and $H_2O$ (2 mL) was degassed and heated at 85° C. under Na for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (92.0 mg, 59%). ESIMS m/z=649.54 [M+H]$^+$.

Example 459

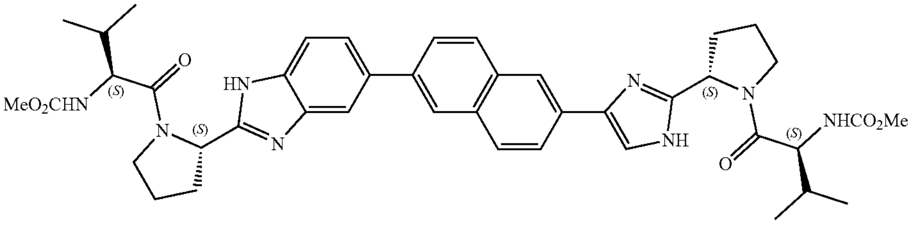

The title compound was synthesized from the compound from Example 458 using procedures similar to that described in Example 448. ESIMS m/z=763.21 [M+H]$^+$.

Example 460

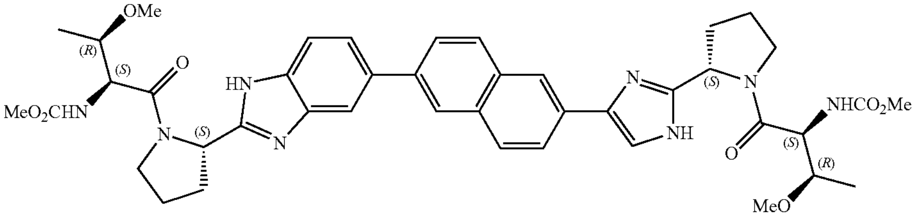

Step 460a. A solution of the compound of example 458 (92.0 mg, 0.142 mmol) in 1,4-dioxane (1 mL) was treated with HCl in 1,4-dioxane (4 M, 4 mL) rt for 30 minutes. The volatiles were evaporated off to give the crude desired compound as a yellow solid which was directly used in the next step. ESIMS m/z=449.39 $[M+H]^+$.

Step 460b. A mixture of the crude compound from step 460a (0.142 mmol at most) and (2S,3R)-3-methoxy-2-(methoxycarbonylamino)butanoic acid (prepared according to WO 2008/021927, 56.9 mg, 0.298 mmol) in DMF (3 mL) was treated with HATU (0.108 g, 0.284 mmol) in the presence of DIPEA (0.35 mL, 2.84 mmol) for 2 hours at rt and the volatiles were evaporated off to provide a brown syrup. It was purified by flash column chromatography (silica, $CH_2Cl_2$-MeOH) to give the title compound as a yellow solid (60.3 mg, 2 steps 54%). ESIMS m/z=795.68 $[M+H]^+$.

Example 461

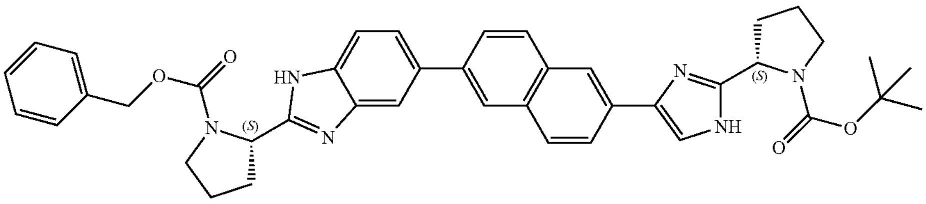

Step 461a. The desired compound was prepared from 4-bromo-1,2-diaminobenzene and N-Cbz-L-proline using procedures similar to that described in steps 1a and 1b. ESIMS m/z=400.11, 402.11 $[M+H]^+$.

Step 461b. A mixture of the compound from step 461a (1.00 g, 2.50 mmol), bis(pinacolato)-diboron (1.27 g, 5.00 mmol) and potassium acetate (0.613 g, 6.25 mmol) in 1,4-dioxane (25 mL) was added $Pd(PPh_3)_4$ (0.144 g, 0.125 mmol). The resultant mixture were degassed and heated up at 85° C. under $N_2$ for 14 hours. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow solid (0.801 g, 72%). ESIMS m/z=448.18 $[M+H]^+$.

Step 461c. A mixture of the compound from step 458d (0.790 g, 1.79 mmol), the compound from step 461b (0.800 g, 1.79 mmol), $Pd(PPh_3)_4$, (0.103 g, 89.4 µmol) and $NaHCO_3$ (0.601 g, 7.16 mmol) in DME (24 mL) and $H_2O$ (8 mL) was degassed and heated at 85° C. under Na for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (0.854 g, 70%). ESIMS m/z=683.14 $[M+H]^+$.

Example 462

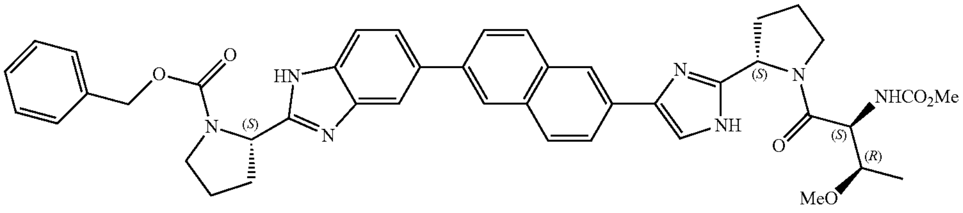

The title compound was synthesized from the compound of Example 461 using procedures similar to that described in Example 460. ESIMS m/z=756.26 $[M+H]^+$.

Example 463

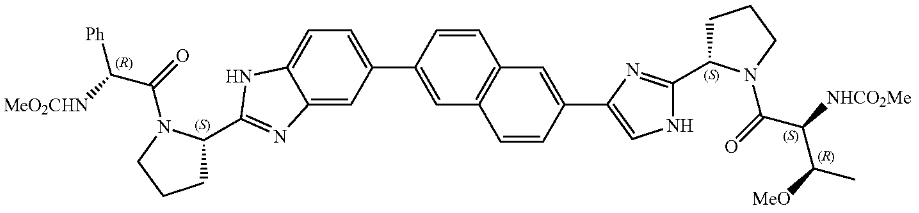

Step 463a. A mixture of the compound from example 462 (0.314 g, 0.416 mmol) and $Pd(OH)_2$ (20 wt % on carbon, 150 mg) in methanol (6 mL) was adjusted pH to 3 with aqueous 6N HCl and then treated with hydrogen (60 psi) for 24 hours. The mixture was filtered through Celite and the filtrate was concentrated to give the crude desired compound as a light yellow solid (0.401 g). ESIMS m/z=622.13 $[M+H]^+$.

Step 463b. The title compound was synthesized from the compound from step 463a using procedures similar to that described in Example 442. ESIMS m/z=813.32 $[M+H]^+$.

Example 464

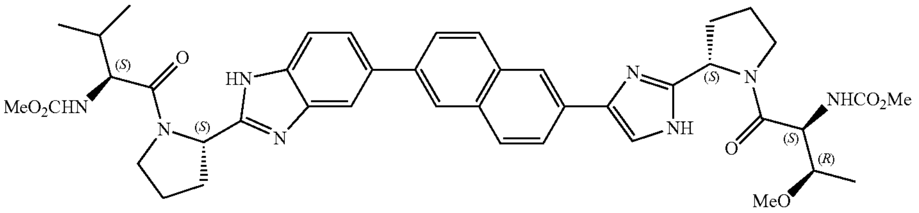

The title compound was synthesized from the compound of step 463a using procedures similar to that described in Example 448. ESIMS m/z=779.33 $[M+H]^+$.

Example 465

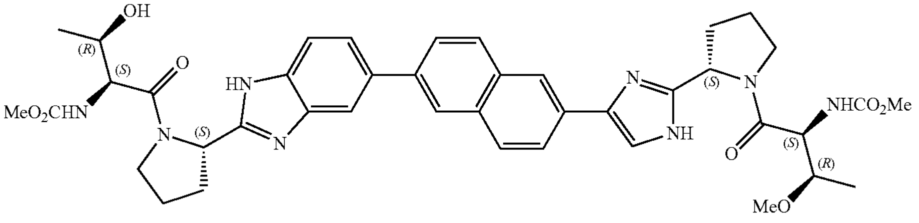

A mixture of the crude compound from step 463a (0.104 mmol at most) and (2S,3R)-3-hydroxy-2-(methoxycarbonylamino)butanoic acid (prepared according to WO 2008/021927, 20.2 mg, 0.114 mmol) in DMF (3 mL) was treated with HATU (35.5 mg, 93.5 μmol) in the presence of DIPEA (0.13 mL, 1.04 mmol) for 2 hours at rt and the volatiles were evaporated off to provide a brown syrup. It was purified by flash column chromatography (silica, $CH_2Cl_2$-MeOH) to give the title compound as a yellow white solid (12.8 mg, 2 steps 16%). ESIMS m/z=781.30 $[M+H]^+$.

Example 466

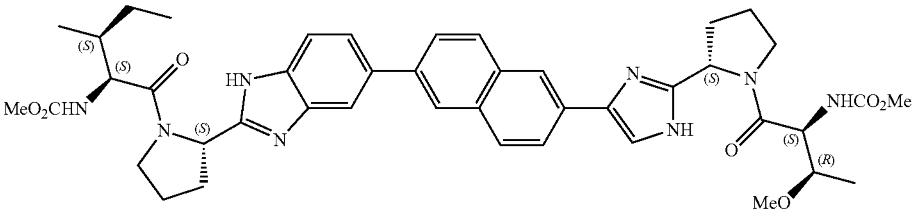

A mixture of the crude compound from step 463a (0.104 mmol at most) and (2S,3S)-2-(methoxycarbonylamino)-3-methylpentanoic acid (prepared according to WO 2008/021927, 21.6 mg, 0.114 mmol) in DMF (3 mL) was treated with HATU (35.5 mg, 93.5 μmol) in the presence of DIPEA (0.13 mL, 1.04 mmol) for 2 hours at rt and the volatiles were evaporated off to provide a brown syrup. It was purified by flash column chromatography (silica, $CH_2Cl_2$-MeOH) to give the title compound as a light yellow solid (15.6 mg, 2 steps 19%). ESIMS m/z=793.33 $[M+H]^+$.

Example 467

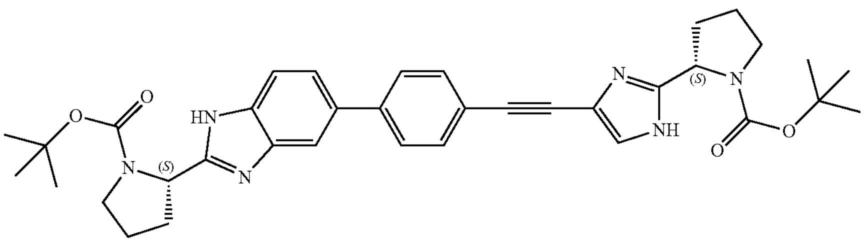

Step 467a. (S)-tert-butyl 2-(5-bromo-1H-imidazol-2-yl)pyrrolidine-1-carboxylate (prepared according to WO 2008/021927, 0.500 g, 1.58 mmol) in $CH_2Cl_2$ (16 mL) was treated with triethyl amine (0.66 mL, 4.75 mmol), di-tert-butyl dicarbonate (0.518 g, 0.237 mmol) and DMAP (38.7 mg, 0.316 mmol) for 1 hours before being evaporated to dryness. The residue was purified by flash column chromatography (silica, hexanes-ethyl acetate) to give the desired compound as a white solid (0.650 g, 98%). ESIMS m/z=416.11, 418.11 $[M+H]^+$.

Step 467b. A mixture of the compound from step 467a (0.650 g, 1.56 mmol), ethynyl-trimethylsilane (2.16 mL, 15.6 mmol), CuI (8.9 mg, 46.8 μmol) and $Pd(PPh_3)_4$ (90.3 mg, 78.1 μmol) in $CH_3CN$ (5 mL) and triethylamine (10 mL) was degassed and heated at 80° C. under Na overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow oil (0.560 g, 83%). ESIMS m/z=434.22 $[M+H]^+$.

Step 467c. The compound from step 467b (0.560 g, 1.29 mmol) in MeOH (30 mL) was treated with potassium carbonate (0.535 g, 3.88 mmol) for 30 minutes before being evaporated to dryness. The residue was partitioned (EtOAc—water), and the organics were washed with brine, dried ($Na_2SO_4$), filtered and evaporated. The residue was purified by flash column chromatography (silica, hexanes-ethyl acetate) to give the desired compound as a light yellow solid (0.312 g, 92%). ESIMS m/z=262.15 $[M+H]^+$.

Step 467d. A mixture of the compound from step 467c (0.103 g, 0.395 mmol), 1,4-diiodo-benzene (62.0 mg, 0.188 mmol), CuI (2.1 mg, 11.2 μmol) and $Pd(PPh_3)_4$ (21.6 mg, 18.7 μmol) in $CH_3CN$ (1 mL) and triethylamine (4 mL) was degassed and heated to 60° C. under Na for 4 hours. The volatiles were evaporated and the residue was partitioned (EtOAc—water).

The organics were washed with brine, dried ($Na_2SO_4$), filtered and evaporated. The residue was purified by flash column chromatography (silica, hexanes-ethyl acetate) to give the desired compound as a very light yellow solid (20.0 mg, 23%). ESIMS m/z=464.06 $[M+H]^+$.

Step 467e. A mixture of the compound from step 467d (20.0 mg, 43.1 μmol), the compound from step 458e (17.8 mg, 43.1 μmol), $Pd(PPh_3)_4$, (9.9 mg, 8.6 μmol) and $NaHCO_3$ (14.5 mg, 0.172 mmol) in DME (3 mL) and $H_2O$ (1 mL) was degassed and heated at 90° C. under Na for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (26.1 mg, 86%). ESIMS m/z=623.28 $[M+H]^+$.

Example 468

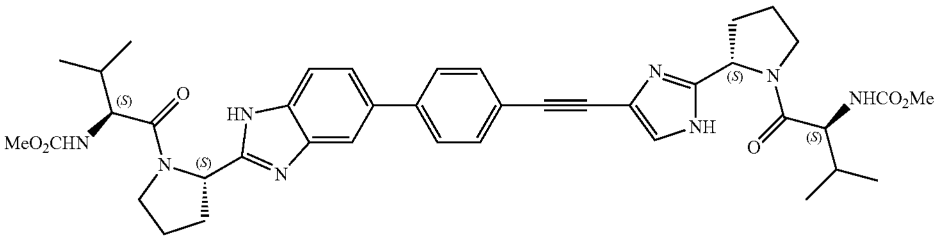

The title compound was synthesized from the compound of Example 467 using procedures similar to that described in Example 448. ESIMS m/z=737.26 $[M+H]^+$.

Example 469

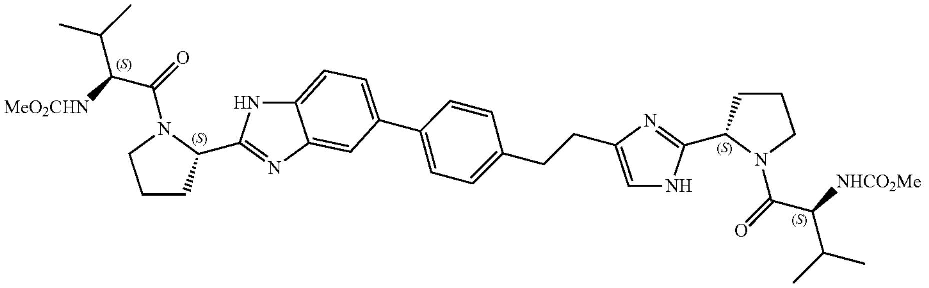

The title compound was synthesized from the compound of Example 468 using procedures similar to that described in Example 443. ESIMS m/z=741.23 $[M+H]^+$.

Example 470

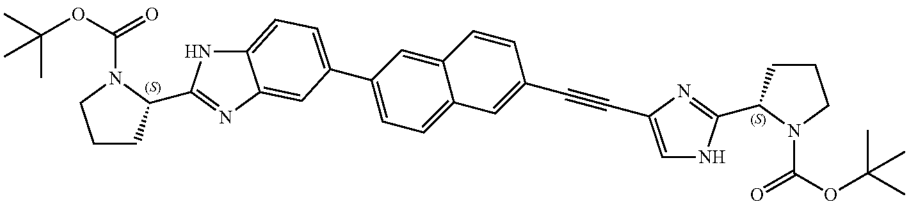

Step 470a. A mixture of the compound of step 467c (0.150 g, 0.575 mmol), 2,6-dibromonaphthalene (98.6 mg, 0.345 mmol), CuI (3.3 mg, 17.2 μmol) and $Pd(PPh_3)_4$ (33.2 mg, 28.7 μmol) in $CH_3CN$ (1 mL) and triethylamine (4 mL) was degassed and heated to 90° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a very light yellow oil (67.6 mg, 25%). ESIMS m/z=466.00, 467.99 $[M+H]^+$.

Step 470b. A mixture of the compound from step 470a (67.6 mg, 0.145 mmol), the compound from step 458e (59.9 mg, 0.145 mmol), $Pd(PPh_3)_4$, (16.8 mg, 14.5 μmol) and $NaHCO_3$ (48.7 mg, 0.580 mmol) in DME (6 mL) and $H_2O$ (2 mL) was degassed and heated at 90° C. under $N_2$ for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (78.8 mg, 81%). ESIMS m/z=673.14 $[M+H]^+$.

Example 471

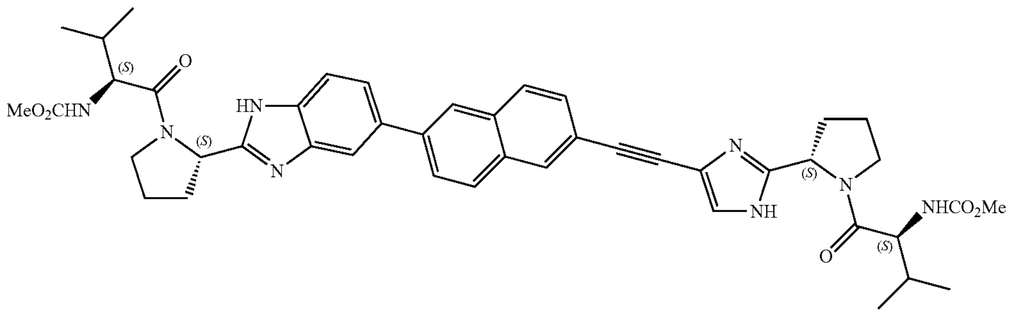

The title compound was synthesized from the compound of Example 470 using procedures similar to that described in Example 448. ESIMS m/z=787.26 $[M+H]^+$.

Example 472

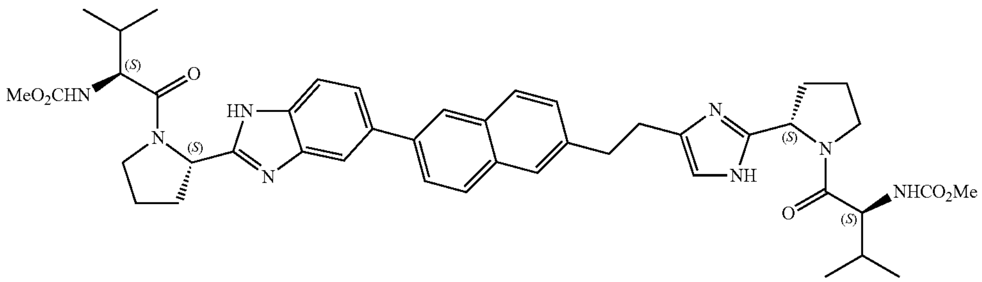

The title compound was synthesized from the compound of Example 471 using procedures similar to that described in Example 443. ESIMS m/z=791.23 $[M+H]^+$.

Example 473

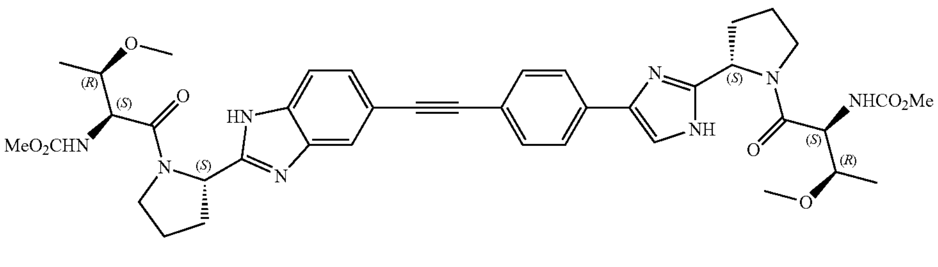

The title compound was synthesized from the compound of Example 1-1 using procedures similar to that described in Example 460. ESIMS m/z=769.37 $[M+H]^+$.

Example 474

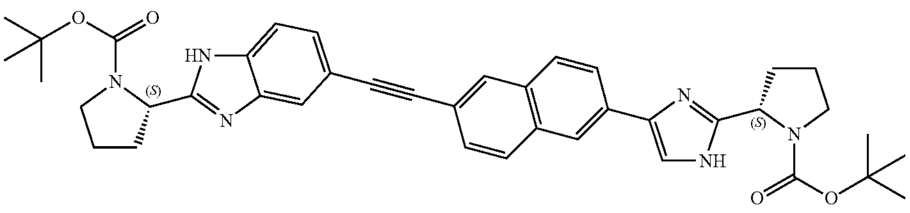

Step 474a. A mixture of the compound from step 515d (0.200 g, 0.643 mmol), 2,6-dibromonaphthalene (0.368 g, 1.29 mmol), CuI (3.6 mg, 19.2 μmol) and $Pd(PPh_3)_4$ (37.1 mg, 32.1 μmol) in $CH_3CN$ (6 mL) and triethylamine (6 mL) was degassed and heated at 90° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow oil (214 mg, 65%). ESIMS m/z=516.08, 518.08 $[M+H]^+$.

Step 474b. A mixture of the compound from step 474a (0.214 g, 0.415 mmol), bis-(pinacolato) diboron (0.211 g, 0.829 mmol) and potassium acetate (0.102 g, 1.04 mmol) in 1,4-dioxane (8 mL) was added $Pd(PPh_3)_4$ (23.9 mg, 20.7 μmol). The resultant mixture were degassed and heated up at 85° C. under $N_2$ for 14 hours. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow oil (0.163 g, 60% purity). ESIMS m/z=564.17 $[M+H]^+$.

Step 474c. A mixture of the compound from step 474b (0.163 g, 0.290 mmol), (S)-tert-butyl 2-(5-bromo-1H-imidazol-2-yl)pyrrolidine-1-carboxylate (prepared according to WO 2008/021927, 0.137 g, 0.434 mmol), $Pd(PPh_3)_4$, (33.4 mg, 28.9 μmol) and $NaHCO_3$ (97.2 mg, 1.16 mmol) in DME (6 mL) and $H_2O$ (2 mL) was degassed and heated at 90° C. under $N_2$ for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a light yellow solid (0.122 g, 60% purity). ESIMS m/z=673.29 $[M+H]^+$.

Example 475

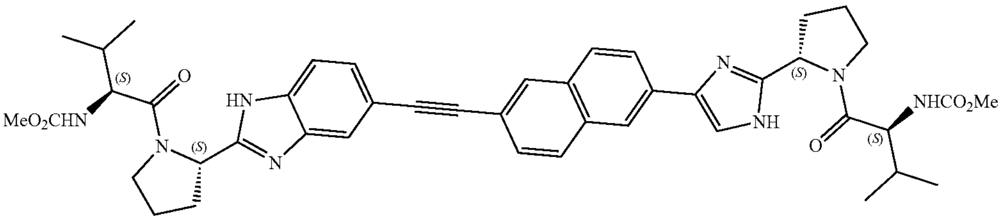

The title compound was synthesized from the compound from Example 474 using procedures similar to that described in Example 448 after HPLC purification. ESIMS m/z=787.20 $[M+H]^+$.

Example 476

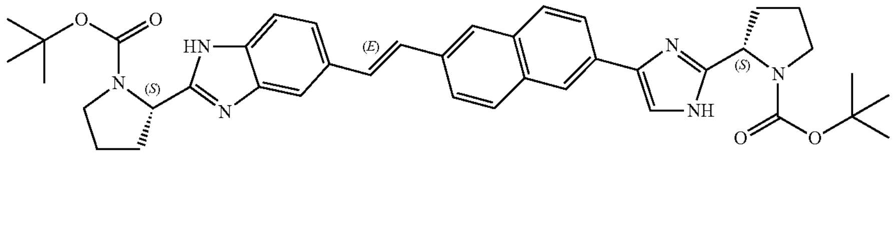

The title compound was obtained as an impurity in the compound of example 474. ESIMS m/z=675.30 $[M+H]^+$.

Example 477

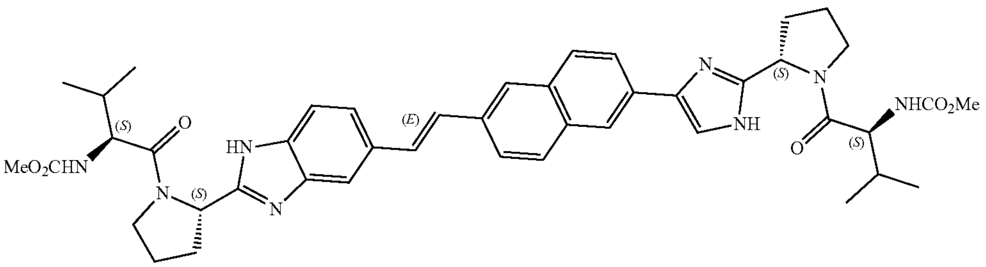

The title compound was synthesized and purified as a minor product in example 475. ESIMS m/z=789.21 $[M+H]^+$.

Example 478

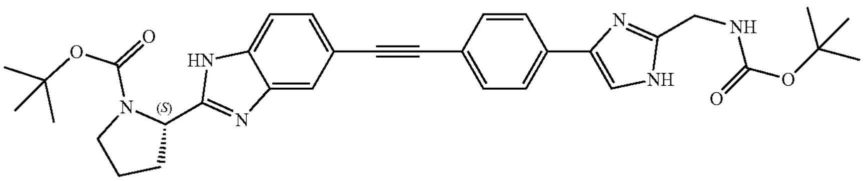

Step 478a. A mixture of 2,4'-dibromoacetophenone (1.59 g, 5.71 mmol) and N-Boc-glycine (1.00 g, 5.71 mmol) in $CH_3CN$ (20 mL) was added DIPEA (1.42 mL, 11.4 mmol) slowly. The mixture was stirred at rt until the disappearance of the starting material. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a light yellow solid (2.02 g, 95%). ESIMS m/z=394.15, 396.15 $[M+Na]^+$.

Step 478b. A solution of the compound from step 478a (2.02 g, 5.43 mmol) in toluene (30 mL) was added ammonium acetate (8.35 g, 0.108 mol) and the resultant mixture was heated up at 100° C. for 20 hours. The volatiles were evaporated and the residue was partitioned (EtOAc—aq. $NaHCO_3$). The organics were washed with brine, dried ($Na_2SO_4$), filtered and evaporated. The residue was purified by flash column chromatography (silica, hexanes-ethyl acetate) to the desired compound as a yellow brown solid (1.62 g, 85%). ESIMS m/z=352.14, 354.14 $[M+H]^+$.

Step 478c. A mixture of the compound from step 478b (80.0 mg, 0.227 mmol), the compound from step 515d (77.8 mg, 0.250 mmol), CuI (1.3 mg, 6.8 μmol) and $Pd(PPh_3)_4$ (26.2 mg, 22.7 μmol) in triethylamine (6 mL) was degassed and heated at 85° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the title compound as a light yellow solid (50.9 mg, 39%). ESIMS m/z=583.37 $[M+H]^+$.

Example 479

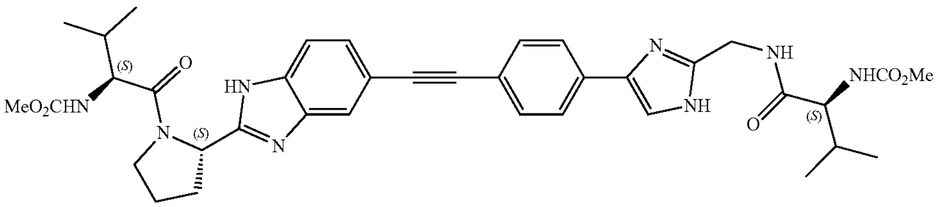

The title compound was synthesized from the compound of Example 478 using procedures similar to that described in Example 448. ESIMS m/z=697.64 $[M+H]^+$.

Example 480

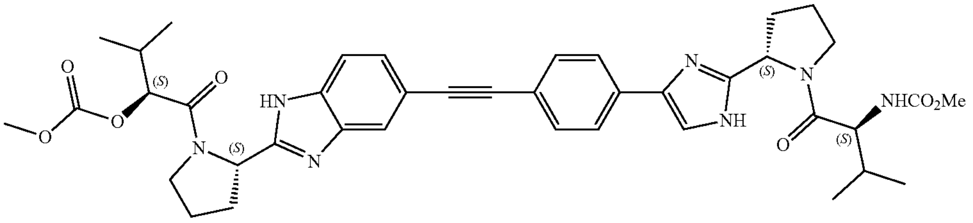

Step 480a. A solution of the compound of example 500 (10.0 mg, 14.7 μmol) in 1,4-dioxane (1 mL) was treated with HCl in 1,4-dioxane (4 M, 4 mL) rt for 30 min. The volatiles were evaporated off to give the crude desired compound as a yellow solid which was directly used in the next step. ESIMS m/z=580.55 $[M+H]^+$.

Step 480b. A mixture of the crude compound from step 480a (14.7 μmol at most) and (S)-2-(methoxycarbonyloxy)-3-methylbutanoic acid (prepared according to *Chemical & Pharmaceutical Bulletin,* 1985, 33, 3922-3928, 2.8 mg, 16.1 μmol) in DMF (3 mL) was treated with HATU (5.6 mg, 14.7 μmol) in the presence of DIPEA (37.0 μL, 0.294 mmol) for 2 hours at rt and the volatiles were evaporated off to provide a brown syrup. It was purified by flash column chromatography (silica, $CH_2Cl_2$-MeOH) to give the title compound as a yellow solid (8.3 mg, 2 steps 76%). ESIMS m/z=738.64 $[M+H]^+$.

Example 481

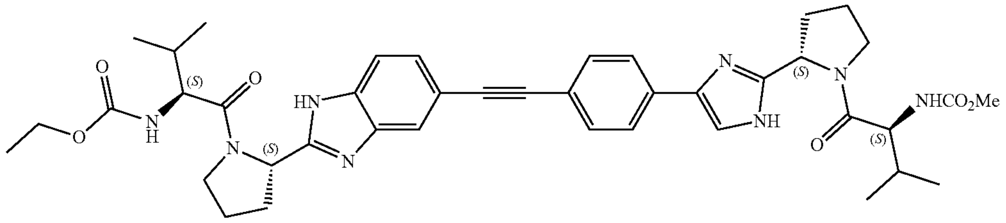

A mixture of the crude compound from step 480a (14.7 μmol at most) and (S)-2-(ethoxy-carbonylamino)-3-methylbutanoic acid (prepared according to WO 2008/021927, 3.0 mg, 16.1 μmol) in DMF (3 mL) was treated with HATU (5.6 mg, 14.7 μmol) in the presence of DIPEA (37.0 μL, 0.294 mmol) for 2 hours at rt and the volatiles were evaporated off to provide a brown syrup. It was purified by flash column chromatography (silica, $CH_2Cl_2$-MeOH) to give the title compound as a very yellow solid (10.2 mg, 2 steps 91%). ESIMS m/z=751.67 $[M+H]^+$.

Example 482

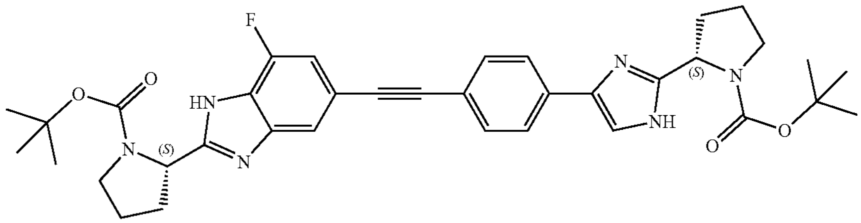

Step 482a. A mixture of N-Boc-L-proline (0.210 g, 0.976 mmol) and TEA (0.14 mL, 0.976 mmol) in THF (10 mL) at −20° C. was treated with iso-butyl chloroformate (0.13 mL, 0.976 mmol) for 30 minutes before a slow addition of 5-bromo-3-fluorobenzene-1,2-diamine (0.200 g, 0.976 mmol) in THF (2 mL). It was then kept at −20° C. for 1 hour and then slowly warmed up to rt and stirred at rt overnight. The volatiles were evaporated and the residue was partitioned (EtOAc—water). The organics were washed with brine, dried ($Na_2SO_4$), filtered and evaporated to give the crude desired compound as a brown foam (0.436 g). ESIMS m/z=402.23, 404.23 $[M+H]^+$.

Step 482b. A solution of the crude compound from step 482a (0.976 mmol at most) in glacial acetic acid (10 mL) was heated at 65° C. for 24 hours. The volatiles were evaporated off and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the desired compound as a light yellow oil (0.327 g, 2 steps 87%). ESIMS m/z=384.16, 386.16 $[M+H]^+$.

Step 482c. A mixture of the compound from step 482b (60.0 mg, 0.156 mmol), the compound from step 1-1b (58.0 mg, 0.172 mmol), CuI (0.9 mg, 4.6 μmol) and $Pd(PPh_3)_4$ (9.0 mg, 7.8 μmol) in triethylamine (4 mL) and $CH_3CN$ (4 mL) was degassed and heated to 90° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the title compound as a light yellow solid (54.2 mg, 54%). ESIMS m/z=641.22 $[M+H]^+$.

Example 483

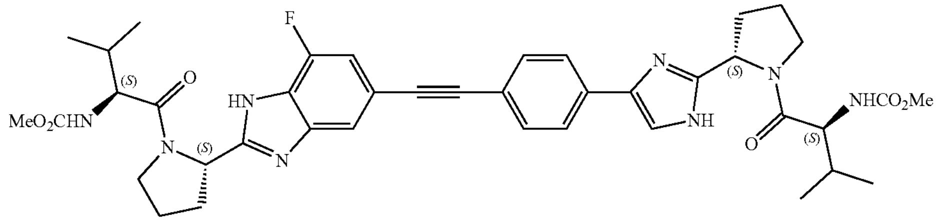

The title compound was synthesized from the compound of Example 482 using procedures similar to that described in Example 448. ESIMS m/z=755.55 $[M+H]^+$.

Example 484

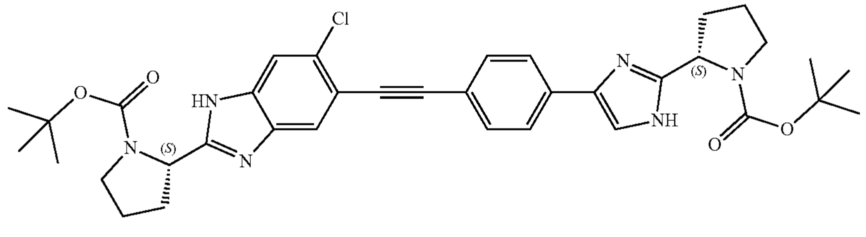

Step 484a. A mixture of 4-bromo-5-chlorobenzene-1,2-diamine (0.3 g, 1.19 mmol) and tin(II) chloride dihydrate (1.08 g, 4.77 mmol) in DMF (10 mL) was heated at 80° C. for 2 hours. The reaction was cooled and then neutralized by the addition of aqueous 2N NaOH. The resultant mixture were partitioned (EtOAc—water) and the organics were washed with brine, dried ($Na_2SO_4$), filtered and evaporated. The residue was purified by flash column chromatography (silica, hexanes-ethyl acetate) to give the desired compound as a light yellow brown solid (0.256 g, 96%).

Step 484b. The compound from step 484a (0.250 g, 1.13 mmol) in DMF (10 mL) was treated with N-Boc-L-proline (0.243 g, 1.13 mmol), EDC.HCl (0.281 g, 1.47 mmol) and DMAP (27.6 mg, 0.226 mmol) for 12 hours before being partitioned (EtOAc—water). The organics were washed with aqueous 1N HCl, brine, dried ($Na_2SO_4$), filtered and evaporated to give the crude desired compound as a light red brown foam (0.401 g). ESIMS m/z=418.20, 420.20 $[M+H]^+$.

Step 484c. A solution of the crude compound from step 484b (1.13 mmol at most) in glacial acetic acid (10 mL) was heated at 50° C. for 2 hours. The volatiles were evaporated off and the residue was partitioned (EtOAc—saturated aqueous $NaHCO_3$). The organics were washed with brine, dried ($Na_2SO_4$), filtered and evaporated. The residue was purified by flash column chromatography (silica, hexanes-ethyl acetate) to give the desired compound as a yellow brown solid (0.326 g, 2 steps 85%). ESIMS m/z=400.21, 402.21 $[M+H]^+$.

Step 484d. A mixture of the compound from step 484c (55.0 mg, 0.140 mmol), the compound from step 1-1b (56.5 mg, 0.168 mmol), CuI (0.8 mg, 4.1 μmol) and $Pd(PPh_3)_4$ (8.0 mg, 6.9 μmol) in triethylamine (3 mL) and $CH_3CN$ (3 mL) was degassed and heated to 95° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the title compound as a light yellow solid (49.7 mg, 55%). ESIMS m/z=657.40 $[M+H]^+$.

Example 485

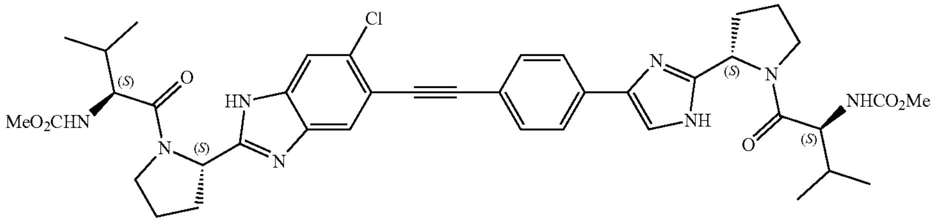

The title compound was synthesized from the compound of Example 484 using procedures similar to that described in Example 448. ESIMS m/z=771.63 $[M+H]^+$.

Example 486

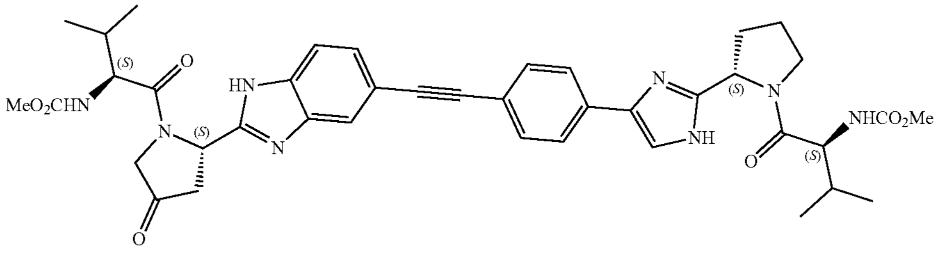

A solution the compound of example 517 (38.6 mg, 51.3 μmol) in $CH_2Cl_2$ (3 mL) was treated with camphorsulfonic acid (23.8 mg, 0.103 mmol) and Dess-Martin periodinane (0.131 mg, 0.308 mmol) for 5 hours before being quenched with saturated aqueous $NsS_2O_3$ and $NaHCO_3$. The mixture was partitioned (EtOAc—water) and the organics were washed with brine, dried ($Na_2SO_4$), filtered and evaporated. The residue was purified by flash column chromatography (silica, MeOH—$CH_2Cl_2$) to give the title compound as a yellow brown solid (33.2 mg, 86%). ESIMS m/z=751.54 $[M+H]^+$.

Example 487

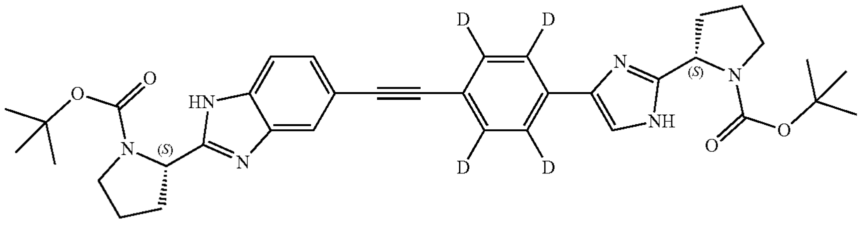

each D is deuterium

Step 487a. A solution of 4'-bromoacetophenone-$d_7$ (0.500 g, 2.43 mmol) in AcOH (10 mL) was treated with bromine (0.12 mL, 2.43 mmol) for 24 hours before being evaporated to dryness. The residue was partitioned (EtOAc—aqueous saturated $NaHCO_3$) and the organics were washed with brine, dried ($Na_2SO_4$), filtered and evaporated to give the desired compound as a white crystal (0.672 g, 98%).

Step 487b. A mixture of the compound from step 487a (0.670 g, 2.38 mmol) and N-Boc-L-proline (0.511 g, 2.38 mmol) in $CH_3CN$ (20 mL) was added DIPEA (0.59 mL, 4.75 mmol) slowly. The mixture was stirred at rt until the disappearance of the starting material. The volatiles were evaporated and the residue was partitioned (EtOAc—water). The organics were washed with brine, dried ($Na_2SO_4$), filtered and evaporated to give the crude desired compound as a yellow brown oil (1.06 g). ESIMS m/z=416.32, 418.32 $[M+H]^+$.

Step 487c. A solution of the compound from step 487b (at most 2.38 mmol) in toluene (24 mL) was added ammonium acetate (3.66 g, 47.5 mmol) and the resultant mixture was heated up at 100° C. for 14 hours. The volatiles were evaporated and the residue was partitioned (EtOAc—aq. $NaHCO_3$). The organics were washed with brine, dried ($Na_2SO_4$), filtered and evaporated. The residue was purified by flash column chromatography (silica, hexanes-ethyl acetate) to give the desired compound as a yellow brown powder (0.749 g, 2 steps, 78%). ESIMS m/z=396.20, 398.20 $[M+H]^+$.

Step 487d. A mixture of the compound from step 487c (200 mg, 0.505 mmol), the compound from step 515d (0.188 g, 0.606 mmol), CuI (2.9 mg, 15.1 μmol) and $Pd(PPh_3)_4$ (29.1 mg, 25.2 μmol) in triethylamine (5 mL) and $CH_3CN$ (5 mL) was degassed and heated at 95° C. under $N_2$ overnight. The volatiles were evaporated and the residue was partitioned (EtOAc—water).

The organics were washed with brine, dried ($Na_2SO_4$), filtered and evaporated. The residue was purified by flash column chromatography (silica, hexanes-ethyl acetate) to give the title compound as a light yellow solid (0.151 g, 48%). ESIMS m/z=627.58 $[M+H]^+$.

Example 488

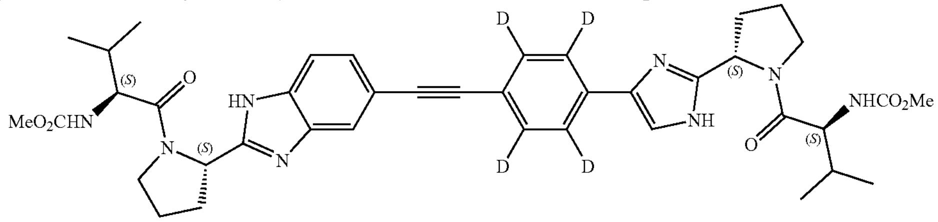

each D is deuterium

The title compound was synthesized from the compound from Example 487 using procedures similar to that described in Example 448. ESIMS m/z=741.70 $[M+H]^+$.

Example 489

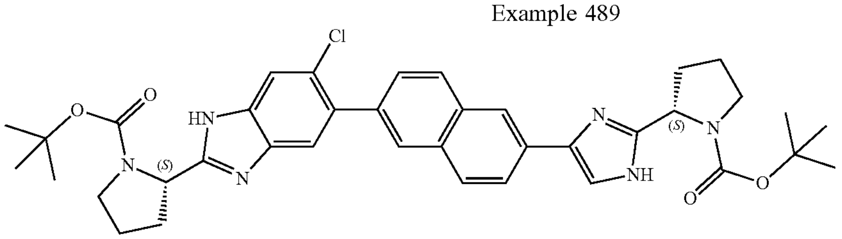

Step 489a. A mixture of the compound from step 458d (0.200 g, 0.452 mmol), bis(pinacolato)diboron (0.144 g, 0.565 mmol), $PdCl_2(dppf)_2$ (36.9 mg, 0.0452 mmol) and potassium acetate (88.7 mg, 0.904 mmol) in DMSO (5 mL) was degassed and heated at 80° C. under $N_2$ for 17 hours. The reaction mixture was allowed to cool down and partitioned (EtOAc—water). The organic layer was washed with brine, dried ($Na_2SO_4$), filtered and evaporated. The residue was purified by chromatography (silica, hexanes-ethyl acetate) to give the desired compound as a yellow solid (0.188 g, 85%). ESIMS m/z=490.12 $[M+H]^+$.

Step 489b. A mixture of the compound from step 484c (50.0 mg, 0.125 mmol), the compound from step 489a (73.2 mg, 0.150 mmol), $Pd(PPh_3)_4$, (7.2 mg, 6.2 μmol) and $NaHCO_3$ (41.9 mg, 0.499 mmol) in DME (6 mL) and $H_2O$ (2 mL) was degassed and heated at 95° C. under $N_2$ for 14 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate) to give the title compound as a white solid (21.3 mg, 25%). ESIMS m/z=683.52 $[M+H]^+$.

Example 490

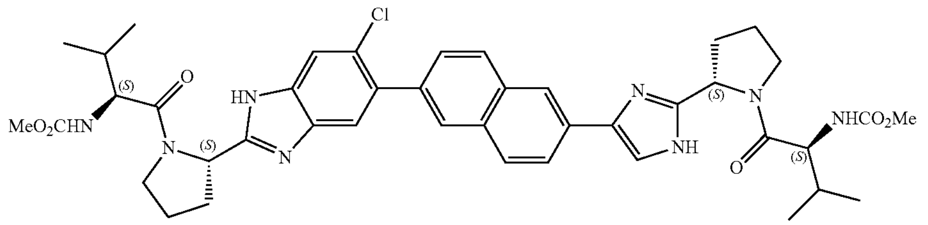

The title compound was synthesized from the compound from Example 489 using procedures similar to that described in Example 448. ESIMS m/z=797.62 $[M+H]^+$.

Example 491

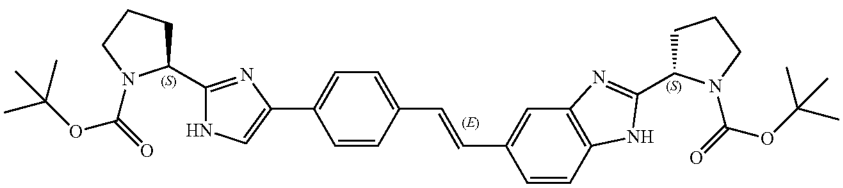

Step 491a. A mixture of the compound of step 1b (1.600 g, 4.369 mmol), tributyl(vinyl)tin (1.53 ml, 5.242 mmol) and $Pd(PPh_3)_4$ (5 mol %, 0.250 g, 0.218 mmol) in toluene (20 mL) was degassed and then refluxed under $N_2$ for 18 h before being allowed to cool to rt. The mixture was directly purified by flash column chromatography (silica, hexanes-ethyl acetate with 1% $Et_3N$ in ethyl acetate) to give the desired compound as a pink foam (0.912 g, 67%). ESIMS m/z=314.18 $[M+H]^+$.

Step 491b. A mixture of the compound from step 491a (1.251 g, 3.191 mmol), the compound of step 1d (1.000 g, 3.191 mmol), $Pd(OAc)_2$ (5 mol %, 35.8 mg, 0.160 mmol) and $P(o\text{-tolyl})_3$ (0.121 g, 0.399 mmol) in $Et_3N$ (4.45 mL) and $CH_3CN$ (30 mL) was degassed and refluxed under $N_2$ gas for 20 hours before being evaporated. The residue was taken up in dichloromethane and filtered through a short pad of Celite. The filtrate was purified by chromatography (silica, hexanes-ethyl acetate with 1% $Et_3N$ in ethyl acetate) to give the title compound as a yellow solid (1.471 g, 74%). ESIMS m/z=625.05 $[M+H]^+$.

Example 492

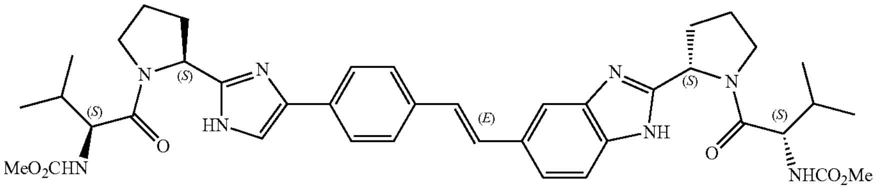

The title compound was prepared from the compound of example 491 using procedures similar to that described in example 448. ESIMS m/z=739.15 $[M+H]^+$.

Example 493

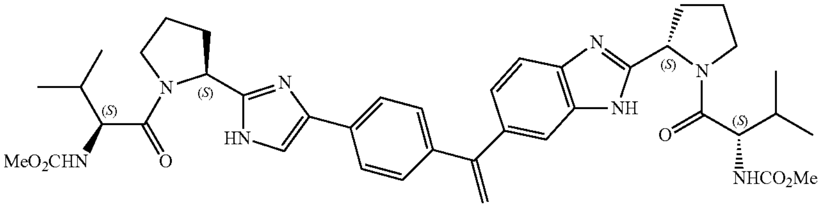

The title compound was obtained as a minor product (~2%) in example 492. ESIMS m/z=739.03 $[M+H]^+$.

Example 494

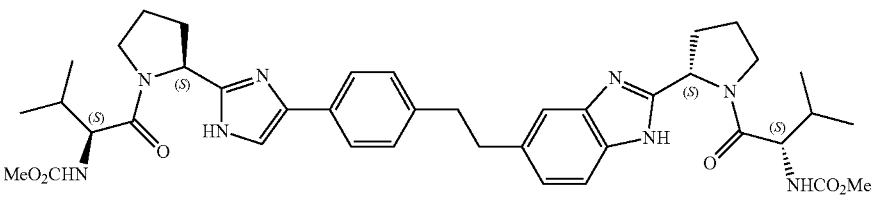

$Pd(OH)_2$ (20% on carbon, 10.8 mg) was added into a solution of the compound from example 492 (10.8 mg, 0.0146 mmol) in EtOH (1.5 mL). The suspension was purged with $H_2$ 3 times and stirred at rt for 6 h under $H_2$ (60 psi) before being filtered through a short pad of Celite. The filtrate was concentrated. The crude was purified by flash column chromatography (silica, $CH_2Cl_2$-MeOH) to give the title compound as a white solid (7.2 mg, 59%). ESIMS m/z=741.13 $[M+H]^+$.

Example 495

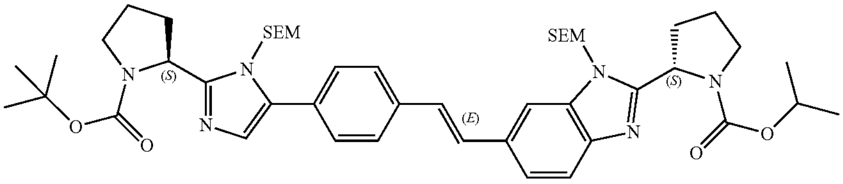

To a solution of the compound from example 491 (0.268 g, 0.430 mmol) in DMF (6 mL) was added NaH (60% in mineral oil, 36.0 mg, 0.902 mmol) at rt. The suspension was stirred at rt for 1 hour. SEMCl (0.154 mL, 0.868 mmol) was added dropwise at rt. After 1.5 hour at rt, the reaction was quenched with saturated $NH_4Cl$ solution and extracted with EtOAc. The organic layer was washed with saturated $NaHCO_3$, brine, dried ($Na_2SO_4$), filtered and concentrated. The crude was purified by flash column chromatography (silica, hexanes-ethyl acetate) to give the title compound as a yellow foam (0.290 g, 76%). The regiochemistry of the SEM groups was not determined. ESIMS m/z=885.25 $[M+H]^+$.

Example 496

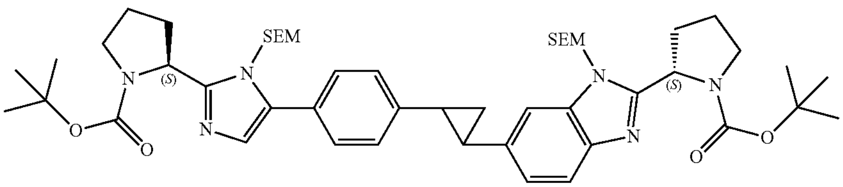

To a solution of the compound from example 495 (0.150 g, 0.169 mmol) in THF (1.5 mL) was added $Pd(OAc)_2$ (3.8 mg, 0.0169 mmol) at 0° C. Excess diazomethane (solution in ether) was added with a plastic pipette until the starting material was consumed. The suspension was concentrated. The residue was taken up in dichloromethane and filtered through a short pad of celite. The filtrate was purified by flash column chromatography (silica, hexanes-ethyl acetate) to give the title compounds as a colorless oil (0.106 g, 70%). The regiochemistry of the SEM group and the stereochemistry of the cyclopropyl ring were not determined. ESIMS m/z=899.07 $[M+H]^+$.

Example 497

497-a

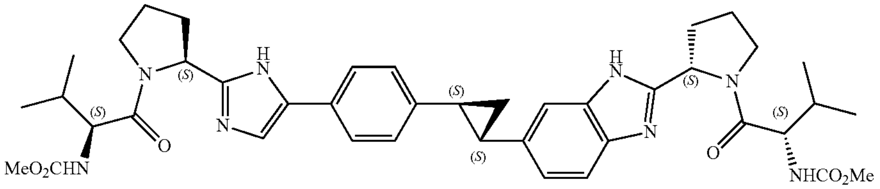

tentative 497-b

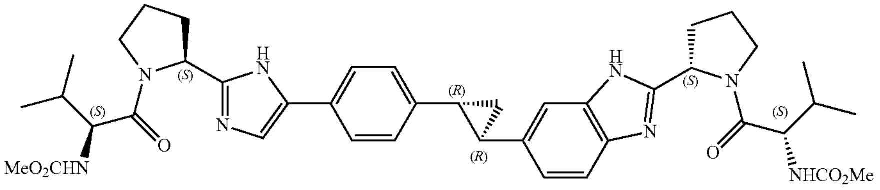

tentative

Step 497a. A solution of the compound of example 496 (0.106 g, 0.118 mmol) in 1,4-dioxane (2 mL) was treated with HCl in 1,4-dioxane (4 M, 12 mL) at 50° C. for 4 hour. The volatiles were evaporated off to give the crude desired compounds as a yellow solid which was used directly in the next step.

Step 497b. A mixture of the crude compound from step 497a (0.118 mmol at most) and (5)-2-(methoxycarbonylamino)-3-methylbutanoic acid (41.3 mg, 0.236 mmol) in DMF (3 mL) was treated with HATU (85.2 mg, 0.224 mmol) in the presence of DIPEA (0.41 mL, 2.360 mmol) for 1 hours at rt and the volatiles were evaporated off to provide a brown syrup. The residue was partitioned (EtOAc—$H_2O$). The organic layer was washed with brine, dried ($Na_2SO_4$), filtered and concentrated. The residue was purified by RP-HPLC ($NH_4HCO_3$ buffer-MeOH) to give the title compounds: the major diastereomer (497-a, tentative) as a yellow solid (19.4 mg), ESIMS m/z=753.12 $[M+H]^+$; and the minor diastereomer (497-b, tentative) as a yellow solid (3.1 mg), ESIMS m/z=753.12 $[M+H]^+$. The stereochemistry of the cyclopropyl rings was not determined.

Example 498

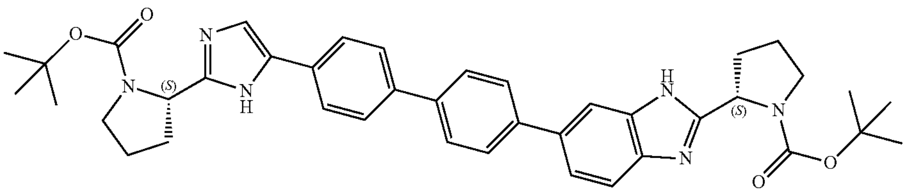

Step 498a. A mixture of the compound from step 458e (0.250 g, 0.605 mmol), 1-bromo-4-iodobenzene (0.257 g, 0.908 mmol), $NaHCO_3$ (0.203 g, 2.42 mmol) and $Pd(PPh_3)_4$ (34.9 mg, 30.2 μmol) in DME (12 mL) and water (4 mL) was degassed and heated to 85° C. under $N_2$ overnight. The volatiles were evaporated and the residue was partitioned (EtOAc—water). The organics were washed with brine, dried ($Na_2SO_4$), filtered and evaporated. The residue was purified by flash column chromatography (silica, hexanes-ethyl acetate) to give the desired compound as a very light yellow solid (0.246 g, 92%). ESIMS m/z=442.00, 444.00 $[M+H]^+$.

Step 498b. A mixture of the compound from step 1e (81.1 mg, 0.185 mmol), the compound from step 498a (85.8 mg, 0.194 mmol), $Pd(PPh_3)_4$, (21.4 mg, 18.5 μmol) and $NaHCO_3$ (62.1 mg, 0.739 mmol) in DME (3 mL) and $H_2O$ (1 mL) was degassed and heated at 80° C. under $N_2$ for 22 hours. The volatiles were evaporated and the residue was partitioned (EtOAc—$H_2O$). The organics were washed with brine, dried ($Na_2SO_4$), filtered and evaporated. The residue was purified by chromatography (silica, hexanes-ethyl acetate with 1% $Et_3N$ in ethyl acetate) to give the title compound as a yellow solid (0.100 g, 81%). ESIMS m/z=675.17 $[M+H]^+$.

Example 499

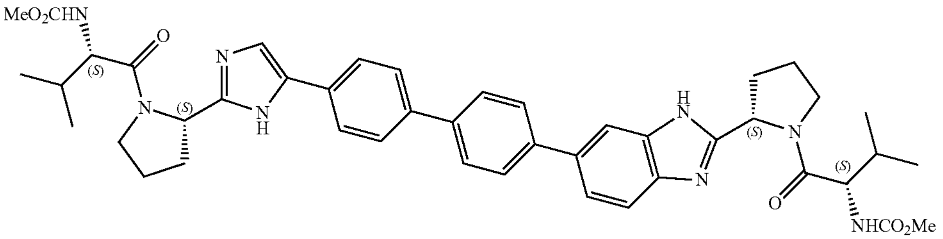

The title compound was prepared from the compound of example 498 using procedures similar to that described in example 448. ESIMS m/z=789.06 $[M+H]^+$.

Example 500

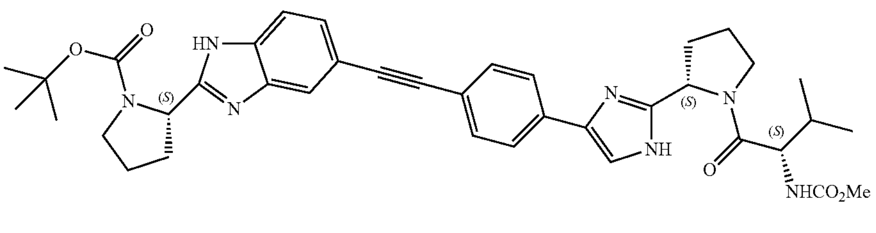

Step 500a. A solution of the compound from step 515b (2.000 g, 4.553 mmol) in 1,4-dioxane (25 mL) was treated with HCl in 1,4-dioxane (4 M, 50 mL) at rt for 1.5 hours. The volatiles were evaporated off to give the crude desired compound as a yellow solid which was used directly in the next step. ESIMS m/z=339.89 $[M+H]^+$.

Step 500b. A mixture of the crude compound from step 500a (4.553 mmol at most) and (5)-2-(methoxycarbonylamino)-3-methylbutanoic acid (0.798 g, 4.553 mmol) in DMF (15 mL) was treated with HATU (1.644 g, 4.325 mmol) in the presence of DIPEA (7.93 mL, 45.53 mmol) for 1.5 hours at rt and the volatiles were evaporated off. The residue was partitioned (EtOAc—$H_2O$). The organics were washed with brine, dried ($Na_2SO_4$), filtered and evaporated. The residue was purified by chromatography (silica, hexanes-ethyl acetate with 1% $Et_3N$ in ethyl acetate) to give the title compound as a yellow foam (2.026 g, 90% over 2 steps). ESIMS m/z=496.90 $[M+H]^+$.

Step 500c. A mixture of compound from step 500b (0.800 g, 1.612 mmol), the compound from step 515d (0.501 g, 1.612 mmol), $Pd(PPh_3)_4$, (5 mol %, 93.1 mg, 80.6 μmol) and CuI (3 mol %, 9.2 mg, 48.3 μmol) in $Et_3N$ (4 mL) and THF (12 mL) was degassed and stirred at 40° C. under $N_2$ for 18 hours. The volatiles were evaporated. The residue was purified by chromatography (silica, hexanes-ethyl acetate with 1% $Et_3N$ in ethyl acetate) to give the title compound as a yellow solid (0.705 g, 64%). ESIMS m/z=680.09 $[M+H]^+$.

Example 501

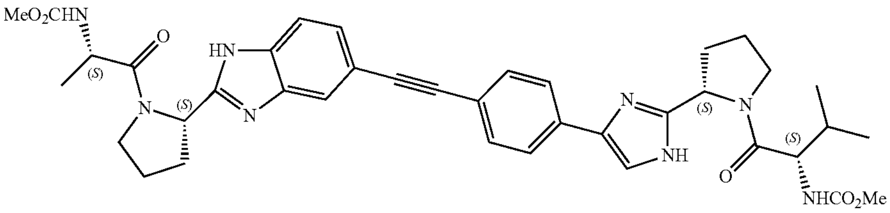

The title compound was prepared from the compound of example 500 and (S)-2-(methoxy-carbonylamino)propanoic acid using procedures similar to that described in steps 500a and 500b. ESIMS m/z=709.05 $[M+H]^+$.

Example 502

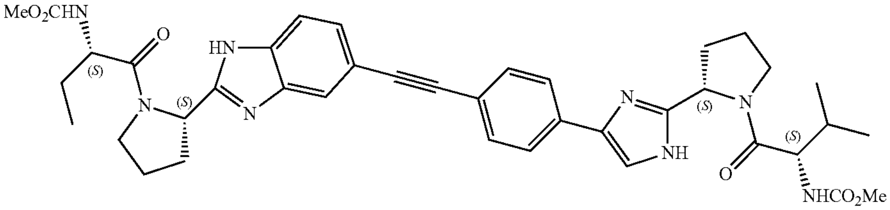

The title compound was prepared from the compound of example 500 and (S)-2-(methoxycarbonylamino)butanoic acid using procedures similar to that described in steps 500a and 500b. ESIMS m/z=723.05 $[M+H]^+$.

Example 503

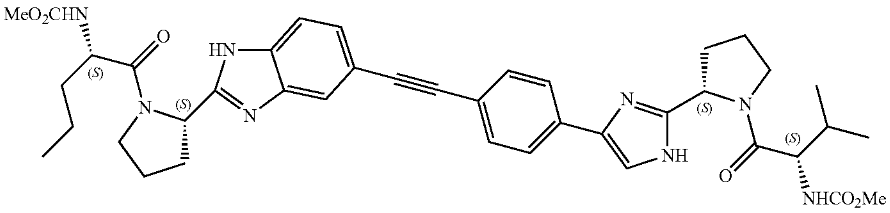

The title compound was prepared from the compound of example 500 and (S)-2-(methoxycarbonylamino)pentanoic acid using procedures similar to that described in steps 500a and 500b. ESIMS m/z=737.09 $[M+H]^+$.

Example 504

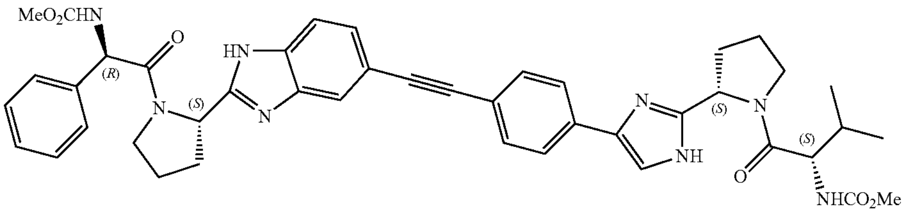

The title compound was prepared from the compound of example 500 and (R)-(methoxycarbonyl)amino phenyl acetic acid using procedures similar to that described in steps 500a and 500b. ESIMS m/z=771.06 $[M+H]^+$.

Example 505

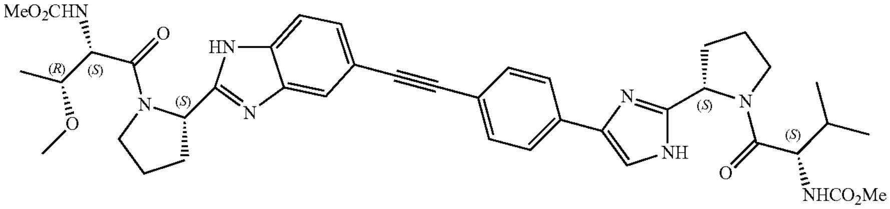

The title compound was prepared from the compound of example 500 and (2S,3R)-3-methoxy-2-(methoxycarbonylamino)butanoic acid using procedures similar to that described in steps 500a and 500b. ESIMS m/z=753.05 $[M+H]^+$.

Example 506

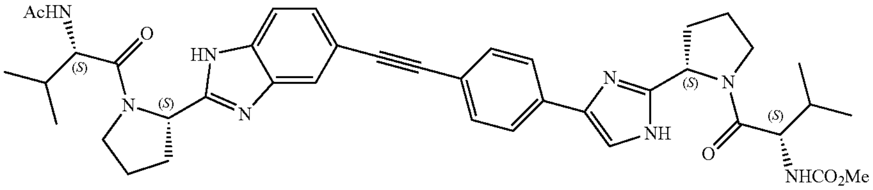

The title compound was prepared from the compound of example 500 and (S)-2-acetamido-3-methylbutanoic acid using procedures similar to that described in steps 500a and 500b. ESIMS m/z=721.48 $[M+H]^+$.

Example 507

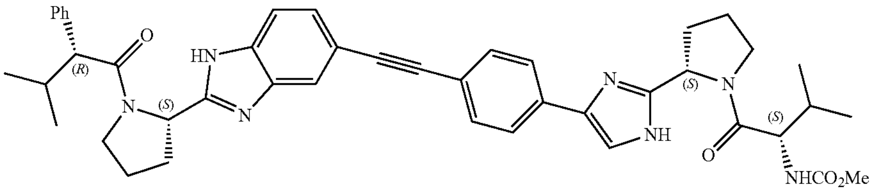

The title compound was prepared from the compound of example 500 and (R)-3-methyl-2-phenylbutanoic acid using procedures similar to that described in steps 500a and 500b. ESIMS m/z=740.50 $[M+H]^+$.

Example 508

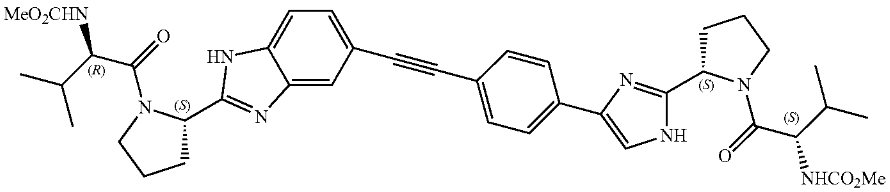

The title compound was prepared from the compound of example 500 and (R)-2-(methoxy-carbonylamino)-3-methylbutanoic acid using procedures similar to that described in steps 500a and 500b. ESIMS m/z=737.49 $[M+H]^+$.

Example 509

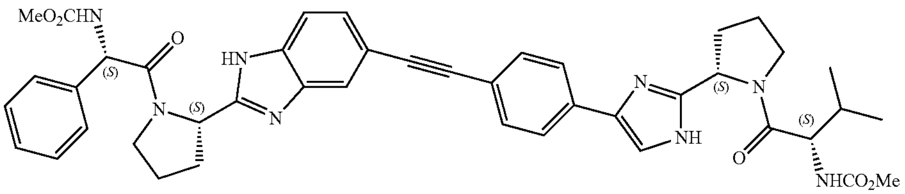

The title compound was prepared from the compound of example 500 and (S)-2-(methoxy-carbonylamino)-2-phenylacetic acid using procedures similar to that described in steps 500a and 500b. ESIMS m/z=771.40 $[M+H]^+$.

Example 510

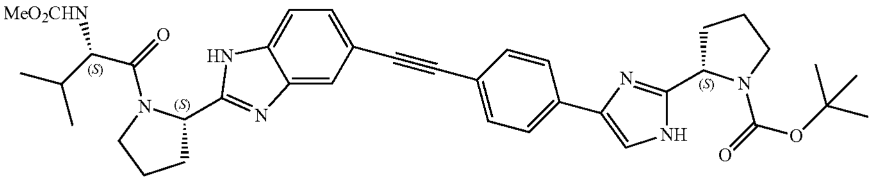

Step 510a. A solution of the compound from the compound from step 515d (1 g, 3.21 mmol) in dichloromethane (20 mL) was treated with HCl in 1,4-dioxane (4 M, 12 mL) at room temperature for 1 hour. The volatiles were evaporated off to give the crude desired compound as a yellow solid which was used directly in the next step.

Step 510b. The mixture of compounds from step 510a (3.21 mml at most) and the compound from step 515g (562 mg, 3.21 mmol) in DMF (12 mL) was added diisopropylethylamine (4.56 mL, 32 mmol) and HATU (1.22 g, 3.21 mmol). The resulting solution was stirred at room temperature for 1 hour before all volatiles were removed to provide a brown slurry, which was partitioned between EtOAc and aqueous NaOH (0.5M). The organic phase was separated, dried ($Na_2SO_4$) and concentrated to afford a brown oil, which was purified by flash column chromatography (silica, EtOAc-methanol) to give the desired compound.

Step 510c. The title compound was prepared from the compound from step 510b and 515b using procedures similar to that described in step 500c. ESIMS m/z=680.36 $[M+H]^+$.

Example 511

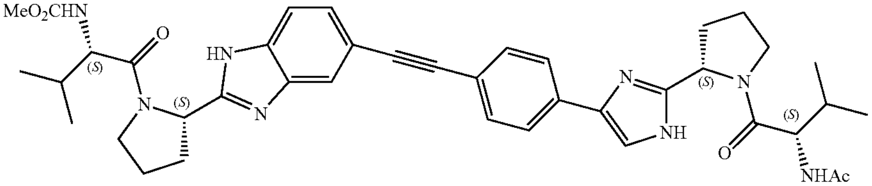

The title compound was prepared from the compound of example 510 and (S)-2-acetamido-3-methylbutanoic acid using procedures similar to that described in steps 500a and 500b. ESIMS m/z=721.49 $[M+H]^+$.

Example 512

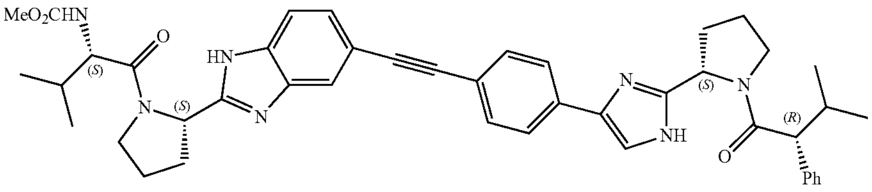

The title compound was prepared from the compound of example 510 and (R)-3-methyl-2-phenylbutanoic acid using procedures similar to that described in steps 500a and 500b. ESIMS m/z=740.51 [M+H]$^+$.

Example 513

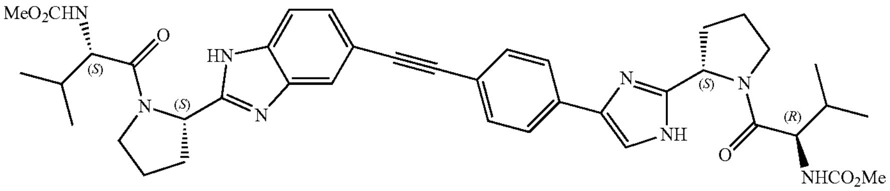

The title compound was prepared from the compound of example 510 and (R)-2-(methoxycarbonylamino)-3-methylbutanoic acid using procedures similar to that described in steps 500a and 500b. ESIMS m/z=737.50 [M+H]$^+$.

Example 514

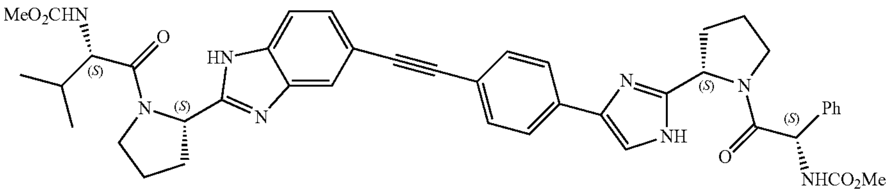

The title compound was prepared from the compound of example 510 and (S)-2-(methoxycarbonylamino)-2-phenylacetic acid using procedures similar to that described in steps 500a and 500b. ESIMS m/z=771.49 [M+H]$^+$.

Example 515

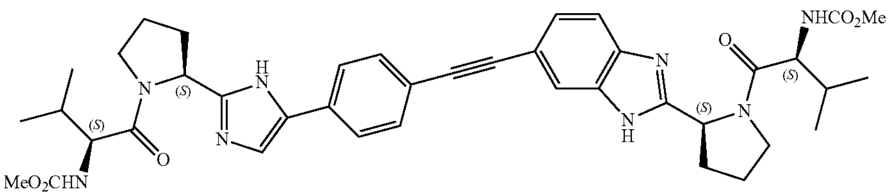

Step 515a. Into a mixture of 2-bromo-1-(4-iodophenyl) ethanone (5 g, 15.4 mmol) and (S)-1-(tert-butoxycarbonyl) pyrrolidine-2-carboxylic acid (3.48 g, 16.1 mmol) in acetonitrile (40 mL) was added diisopropylethylamine (2.4 mL, 17 mmol). The resulting mixture was stirred at rt for 3 hours before being partitioned between EtOAc and aqueous $NaHCO_3$. The organic phase was separated, dried ($Na_2SO_4$) and concentrated to afford a brown oil. It was purified by flash column chromatography (silica, hexane-EtOAc) to give the desired product as light yellow oil (6.0 g, 86%). ESIMS m/z=481.94 [M+Na]$^+$.

Step 515b. The mixture of compound from step 515a (6.0 g, 12.5 mmol) and ammonium acetate (15.1 g, 196 mmol) in toluene (80 mL) was stirred at 80° C. for 3 hours before being partitioned between water and aqueous $NaHCO_3$. The organic phase was separated, dried ($Na_2SO_4$) and concentrated to afford a deep red oil. It was purified by flash column chromatography (silica, hexane-EtOAc) to give the desired product as light yellow solid (5.34 g, 93%). ESIMS m/z=439.83 [M+H]$^+$.

Step 515c. A mixture of the compound from step 1b (2.010 g, 5.488 mmol), trimethylsilylacetylene (2.33 ml, 16.46 mmol), CuI (0.110 g, 0.576 mmol) and $Pd(PPh_3)_2Cl_2$ (0.308 g, 0.439 mmol) in $Et_3N$ (50 mL) was degassed and then heated at 80° C. under $N_2$ overnight before being evaporated. The residue was purified by chromatography (silica, hexanes-ethyl acetate with 1% $Et_3N$ in ethyl acetate) to give the desired compound as a yellow foam (1.140 g, 54%). ESIMS m/z=384.22 $[M+H]^+$.

Step 515d. A suspension of the compound from step 515c (1.140 g, 2.972 mmol) and $K_2CO_3$ (1.027 g, 7.430 mmol) in methanol (30 ml) was stirred at rt for 2 hour. The volatiles were evaporated off. The residue was partitioned (EtOAc—$H_2O$). The organic layer was washed with brine, dried ($Na_2SO_4$), filtered and concentrated. The residue was purified by chromatography (silica, hexanes-ethyl acetate with 1% $Et_3N$ in ethyl acetate) to give the desired compound as a yellow foam (0.792 g, 86%). ESIMS m/z=312.18 $[M+H]^+$.

Step 515e. The mixture of compounds from step 515b (9.1 g, 20.7 mmol) and step 515d (6.45 g, 20.7 mmol) in THF (200 mL), triethylamine (60 mL) and acetonitrile (200 mL) was added tetrakis(triphenylphosphine)palladium(0) (1.15 g, 1 mmol) and copper(I) iodide (119 mg, 0.62 mmol). The resulting mixture was purged with nitrogen before being stirred at room temperature for 12 hours, at 50° C. for 2 hours and at 60° C. for 1 hour. After addition of aqueous NaOH (1M, 100 mL), the organic phase was separated, dried ($Na_2SO_4$) and concentrated to afford a brown slurry, which was absorbed with silica and purified by flash column chromatography (silica, EtOAc-methanol) to give the desired compound as light yellow solid (10.8 g, 84%). ESIMS m/z=623.07 $[M+H]^+$.

Step 515f. A solution of the compound from step 515e (3 g, 4.58 mmol) in dichloromethane (50 mL) and MeOH (5 mL) was treated with HCl in 1,4-dioxane (4 M, 40 mL) at rt for 2 hours. The volatiles were evaporated off to give the crude desired compound as a yellow solid which was used directly in the next step. ESIMS m/z=423.06 $[M+H]^+$.

Step 515g. The mixture of L-valine (50 g, 0.427 mol) in 1,4-dioxane (140 mL) was added water (630 mL), NaOH (54.7 g, 1.4 mol) and methyl chloroformate (65.7 mL, 0.85 mol). The resulting solution was stirred at 60° C. for 22 hours before being added dichloromethane (400 mL). The aqueous phase was separated and extracted with dichloromethane (400 mL) before acidification with hydrochloric acid (37% in water, 90 mL). The cloudy suspension was extracted with EtOAc (500 mL) twice and the combined organic phases were dried ($Na_2SO_4$) and concentrated to afford a white solid, which was recrystalized with hexane and EtOAc to afford the desired product as colorless needle like crystals (54 g, 72%). $^1H$ NMR ($d^6$-DMSO) 12.52 (s, 1H), 7.33 (d, 1H), 3.85 (dd, 1H), 3.56 (s, 3H), 2.06 (m, 1H), 0.98 (m, 6H).

Step 515h. The mixture of compounds from step 515f (4.58 mml at most) and step 515g (1.61 g, 9.16 mmol) in acetonitrile (50 mL) was added diisopropylethylamine (5.21 mL, 39 mmol) and HATU (3.31 g, 8.7 mmol). The resulting solution was stirred at room temperature for 35 minutes before being partitioned between EtOAc (500 mL) and aqueous NaOH (0.5M, 50 mL). The organic phase was separated, dried ($Na_2SO_4$) and concentrated to afford a brown slurry, which was purified by flash column chromatography (silica, EtOAc-methanol) to give the title compound as light yellow solid (2.31 g, 65% over 2 steps). ESIMS m/z=737.12 $[M+H]^+$.

Example 516

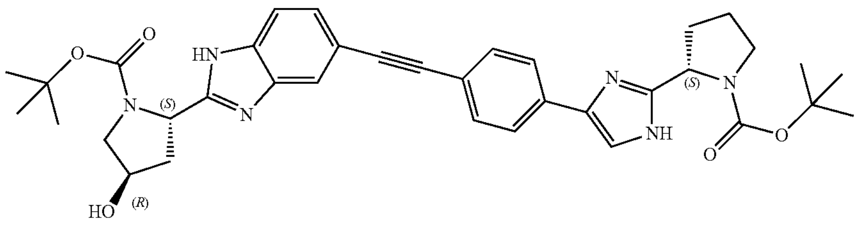

The title compound was prepared from (2S, 4R)-1-(tert-butoxycarbonyl)-4-hydroxy-pyrrolidine-2-carboxylic acid using procedures similar to that described in steps 515a to 515e. ESIMS m/z=639.36 $[M+H]^+$.

Example 517

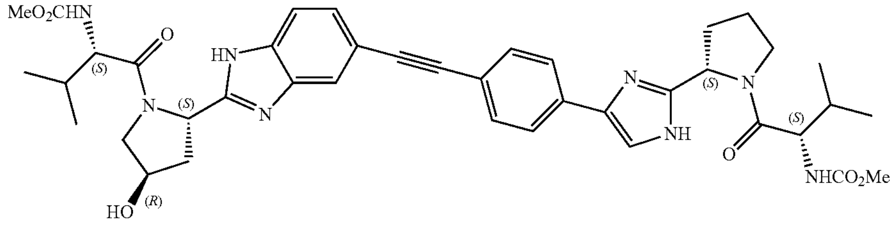

The title compound was prepared from the compound of example 516 using procedures similar to that described in example 448. ESIMS m/z=753.46 $[M+H]^+$.

Example 518

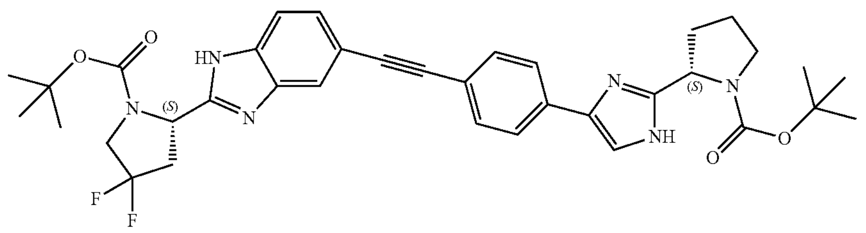

The title compound was prepared from (2S)-1-(tert-butoxycarbonyl)-4,4-difluoropyrrolidine-2-carboxylic acid using procedures similar to that described in steps 515a to 515e. ESIMS m/z=659.35 $[M+H]^+$.

Example 519

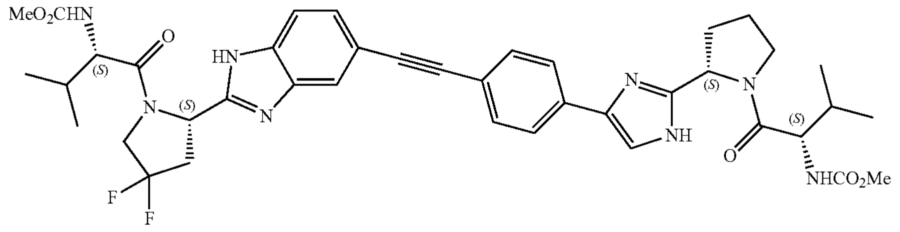

The title compound was prepared from the compound of example 518 using procedures similar to that described in example 448. ESIMS m/z=773.34 $[M+H]^+$.

Example 520

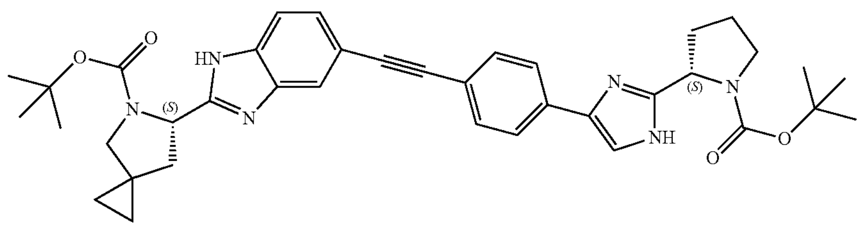

The title compound was prepared from the compound from step 1-1b, 4-bromo-1,2-diaminobenzene and (6S)-5-[(tert-butoxy)carbonyl]-5-azaspiro[2.4]heptane-6-carboxylic acid (prepared according to WO 2009/102325) using procedures similar to that described in examples 1 and 1-1. ESIMS m/z=649.30 $[M+H]^+$.

Example 521

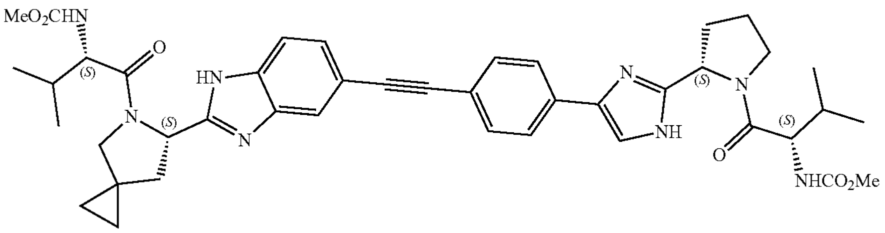

The title compound was prepared from the compound of Example 521 using procedures similar to that described in example 448. ESIMS m/z=763.30 [M+H]$^+$.

Example 522

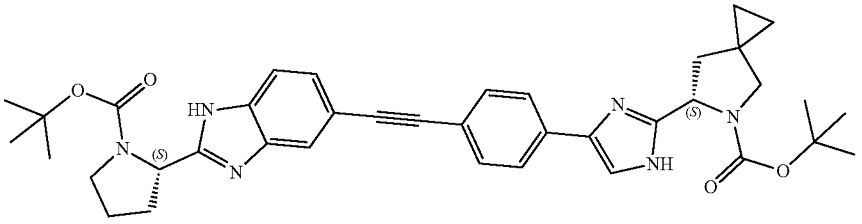

The title compound was prepared from 2,4'-dibromoacetophenone, the compound from step 515d and (6S)-5-[(tert-butoxy)carbonyl]-5-azaspiro[2.4]heptane-6-carboxylic acid (prepared according to WO 2009/102325) using procedures similar to that described in examples 1 and 515. ESIMS m/z=649.35 [M+H]$^+$.

Example 523

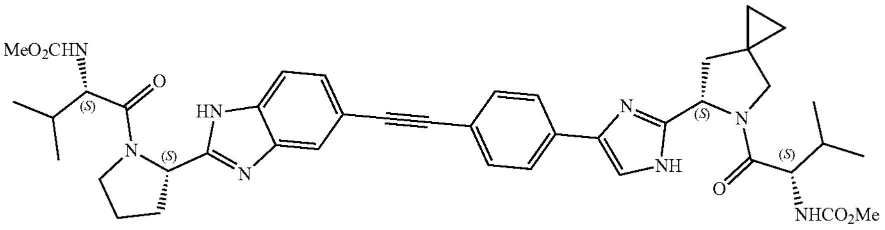

The title compound was prepared from the compound of Example 522 using procedures similar to that described in example 448. ESIMS m/z=763.44 [M+H]$^+$.

Example 524

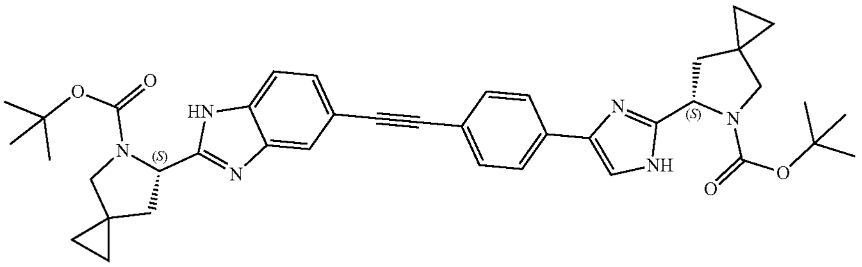

The title compound was prepared from 2,4'-dibromoacetophenone, 4-bromo-1,2-diaminobenzene and (6S)-5-[(tert-butoxy)carbonyl]-5-azaspiro[2.4]heptane-6-carboxylic acid (prepared according to WO 2009/102325) using procedures similar to that described in examples 1 and 515. ESIMS m/z=675.35 [M+H]$^+$.

Example 525

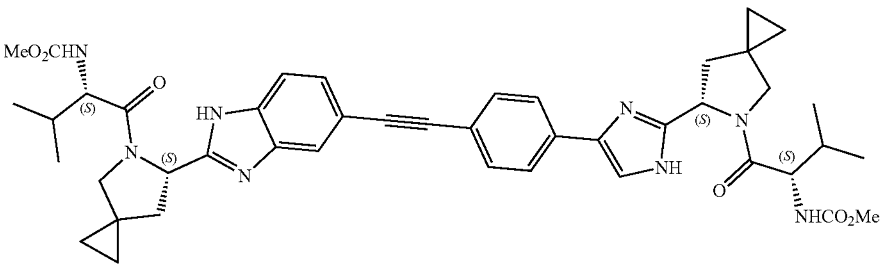

The title compound was prepared from the compound of Example 524 using procedures similar to that described in example 448. ESIMS m/z=789.47 [M+H]$^+$.

Example 526

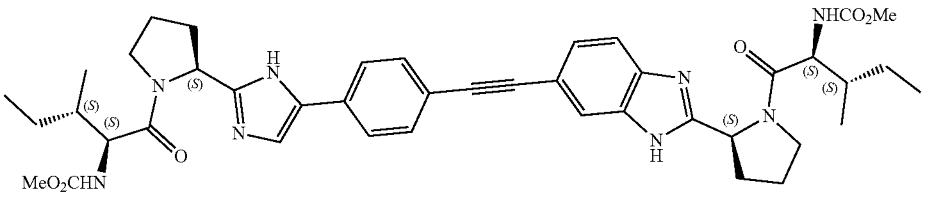

A mixture of the crude compound from step 515f (0.105 mmol at most) and (2S,3S)-2-(methoxycarbonylamino)-3-methylpentanoic acid (prepared by procedure similar to that in step 515g, 35 mg, 0.21 mmol) in acetonitrile (2 mL) was treated with HATU (79 mg, 0.21 mmol) in the presence of DIPEA (0.15 mL, 1.05 mmol) for 2 hours at rt and the volatiles were evaporated off to provide a brown oil. It was purified by flash column chromatography (silica, $CH_2Cl_2$-MeOH) to give the title compound as a yellow solid (60 mg, 2 steps 75%). ESIMS m/z=765.14 [M+H]$^+$.

Example 527

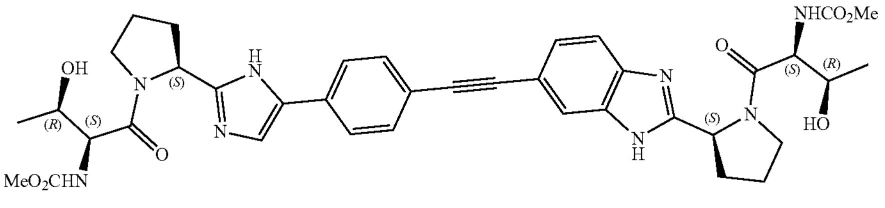

A mixture of the crude compound from step 515f (0.10 mmol at most) and (2S,3R)-3-hydroxy-2-(methoxycarbonylamino)butanoic acid (prepared by procedure similar to that described in step 515g, 35 mg, 0.20 mmol) in DMF (2 mL) was treated with HATU (76 mg, 0.20 mmol) in the presence of DIPEA (0.12 mL, 0.80 mmol) for 2 hours at rt and the volatiles were evaporated off to provide a brown oil. It was purified by flash column chromatography (silica, $CH_2Cl_2$-MeOH) to give the title compound as a yellow solid (64 mg, 2 steps 86%). ESIMS m/z=741.07 $[M+H]^+$.

Example 528

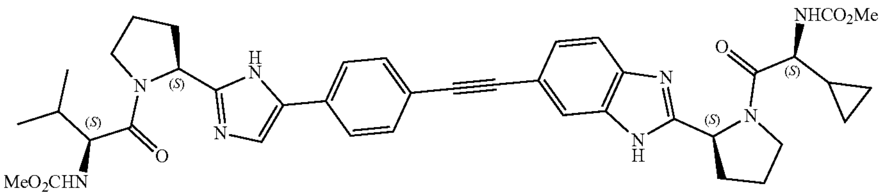

A mixture of the crude compound from step 480a (0.015 mmol at most) and (S)-2-cyclopropyl-2-(methoxycarbonylamino) acetic acid (prepared by procedure similar to that described in step 515g, 2.6 mg, 0.015 mmol) in acetonitrile (2 mL) was treated with HATU (5.7 mg, 0.015 mmol) in the presence of DIPEA (0.03 mL, 0.15 mmol) for 2 hours at rt and the volatiles were evaporated off to provide a brown oil. It was purified by flash column chromatography (silica, $CH_2Cl_2$-MeOH) to give the title compound as a yellow solid (7.6 mg, 2 steps 69%). ESIMS m/z=735.22 $[M+H]^+$.

Example 529

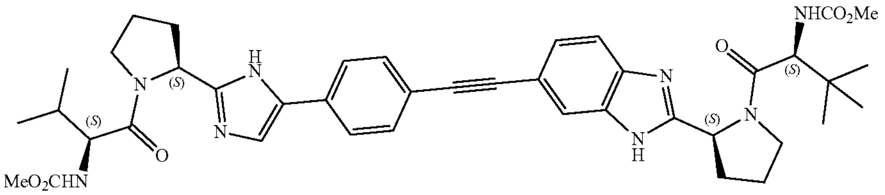

The title compound as a yellow solid (7.9 mg, 2 steps 71%) was prepared from the crude compound from step 480a (0.015 mmol at most) and (S)-2-(methoxycarbonylamino)-3,3-dimethylbutanoic acid (2.8 mg, 0.015 mmol) using the procedures similar to that described in example 528. ESIMS m/z=751.55 $[M+H]^+$.

Example 530

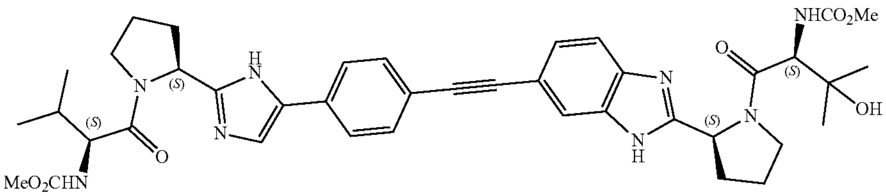

The title compound as a yellow solid (7.3 mg, 2 steps 65%) was prepared from the crude compound from step 480a (0.015 mmol at most) and (S)-3-hydroxy-2-(methoxy-carbonyl-amino)-3-methylbutanoic acid (2.8 mg, 0.015 mmol) using the procedures similar to that described in example 528. ESIMS m/z=753.36 $[M+H]^+$.

Example 531

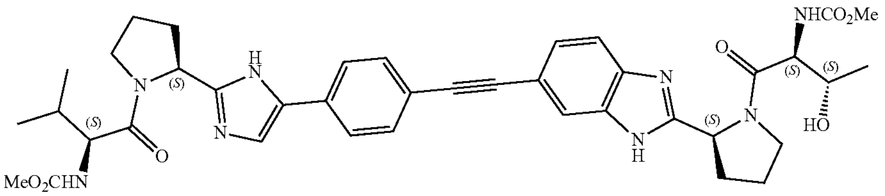

The title compound as a yellow solid (4.0 mg, 2 steps 36%) was prepared from the crude compound from step 480a (0.015 mmol at most) and (2S,3S)-3-hydroxy-2-(methoxycarbonyl-amino)butanoic acid (2.6 mg, 0.015 mmol) using the procedures similar to that described in example 528. ESIMS m/z=739.26 $[M+H]^+$.

Example 532

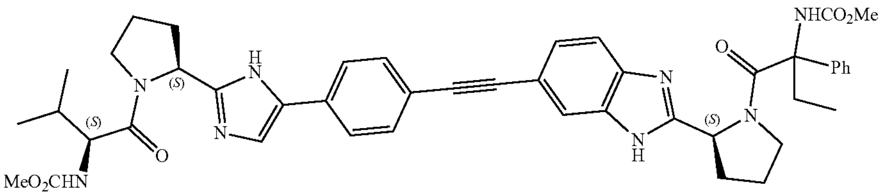

The title compounds as a yellow solid (5.5 mg, 2 steps 46%) was prepared from the crude compound from step 480a (0.015 mmol at most) and 2-(methoxycarbonylamino)-2-phenylbutanoic acid (2.6 mg, 0.015 mmol) using the procedures similar to that described in example 528. ESIMS m/z=799.46 $[M+H]^+$.

Example 533

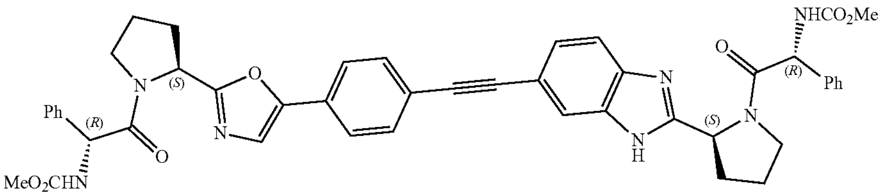

Step 533a. A mixture of (S)-tert-butyl 2-(5-(4-bromophenyl)oxazol-2-yl)pyrrolidine-1-carboxylate (prepared according to US2008/311075A1, 47.5 mg, 0.12 mmol) and the compound from step 515d (38 mg, 0.12 mg) in triethylamine (10 mL) was added tetrakis(triphenylphosphine) palladium(O) (14 mg, 0.012 mmol) and copper(I) iodide (2 mg, 0.01 mmol). The resulting mixture was purged with nitrogen before being stirred at 100° C. for 12 hours. The mixture was partitioned between water and EtOAc and the organic phase was separated, dried ($Na_2SO_4$) and concentrated to afford a brown slurry, which was purified by flash column chromatography (silica, hexane-EtOAc) to give the desired product as a light yellow solid (56 mg, 59%). ESIMS m/z=623.95 $[M+H]^+$.

Step 533b. The desired product was prepared from the compound of step 533a using procedures similar to that described in step 2-1a. ESIMS m/z=424.02 $[M+H]^+$.

Step 533c. The title compound was prepared from the compound of step 533b using procedures similar to that described in step 2-1b. ESIMS m/z=805.92 $[M+H]^+$.

Example 534

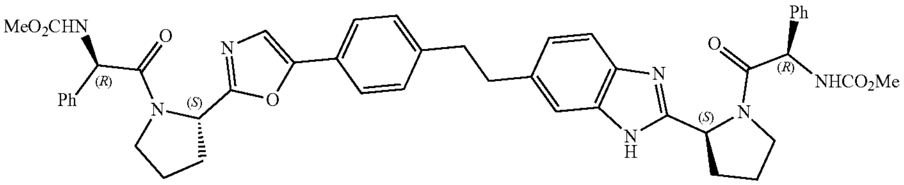

The title compound was prepared from the compound of example 533 using procedures similar to that described in example 2-2. ESIMS m/z=810.10 $[M+H]^+$.

Example 535

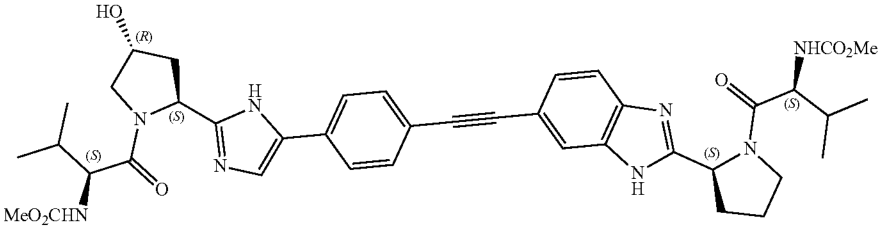

Step 535a. The desired product was prepared from (2S, 4R)-1-(tert-butoxycarbonyl)-4-hydroxypyrrolidine-2-carboxylic acid using procedures similar to that described in step 515a. ESIMS m/z=476.14 $[M+H]^+$.

Step 535b. The desired product was prepared from the compound of step 535a using procedures similar to that described in step 515b. ESIMS m/z=455.99 $[M+H]^+$.

Step 535c. The desired product was prepared from the compound of step 535b and the compound of step 515d using procedures similar to that described in step 515e. ESIMS m/z=639.30 $[M+H]^+$.

Step 535d. The desired product was prepared from the compound of step 535c using procedures similar to that described in step 515f. ESIMS m/z=439.26 $[M+H]^+$.

Step 535e. The title compound was prepared from the compound of step 535d and the compound of step 515g using procedures similar to that described in step 515h. ESIMS m/z=753.40 $[M+H]^+$.

Example 536

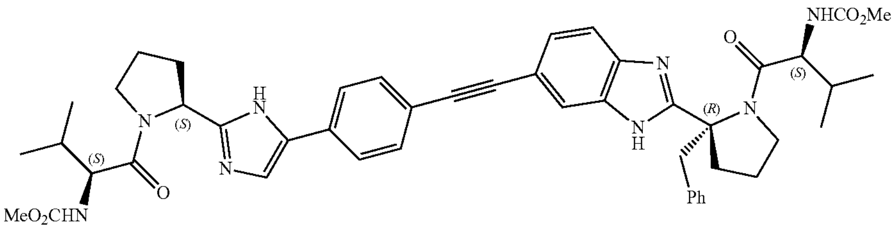

Step 536a. The mixture of (R)-2-benzyl-1-(tert-butoxycarbonyl)pyrrolidine-2-carboxylic acid (200 mg, 0.66 mmol) and 4-bromo-1,2-diaminobenzene (135 mg, 0.73 mmol) in acetonitrile (2 mL) was added EDC (138 mg, 0.73 mmol) and 4-dimethylaminopyridine (40 mg, 0.2 mmol). The resulting mixture was stirred at room temperature for 1 hour before being partitioned between water and EtOAc. The organic phase was separated, dried ($Na_2SO_4$) and concentrated to afford a brown slurry, which was purified by flash column chromatography (silica, hexane-EtOAc) to give the desired product as a light yellow solid (190 mg, 61%). ESIMS m/z=474.18 $[M+H]^+$.

Step 536b. The desired product was prepared from the compound of step 536a using procedures similar to that described in step 1b. ESIMS m/z=456.17 $[M+H]^+$.

Step 536c. The desired product was prepared from the compound of step 536b and the compound from step 1-1b using procedures similar to that described in step 1-1c. ESIMS m/z=713.46 $[M+H]^+$.

Step 536d. The desired product was prepared from the compound of step 536c using procedures similar to that described in step 515f ESIMS m/z=513.30 $[M+H]^+$.

Step 536e. The title compound was prepared from the compound of step 536d and the compound from step 515g using procedures similar to that described in step 515h. ESIMS m/z=827.49 $[M+H]^+$.

Example 537

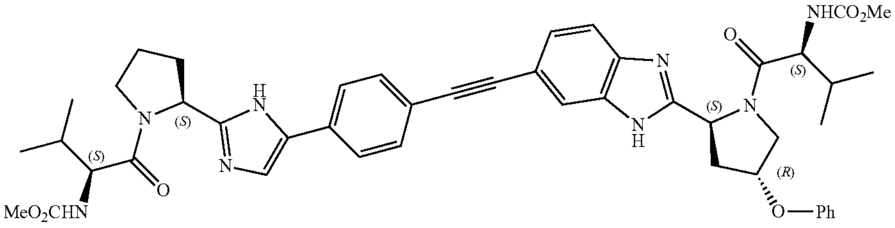

Step 537a. The desired product was prepared from (2S, 4R)-1-(tert-butoxycarbonyl)-4-phenoxypyrrolidine-2-carboxylic acid using procedures similar to that described in step 536a. ESIMS m/z=476.14 $[M+H]^+$.

Step 537b. The desired product was prepared from the compound of step 537a using procedures similar to that described in step 1b. ESIMS m/z=458.16 $[M+H]^+$.

Step 537c. The desired product was prepared from the compound of step 537b and the compound of step 1-1b using procedures similar to that described in step 1-1c. ESIMS m/z=715.36 $[M+H]^+$.

Step 537d. The desired product was prepared from the compound of step 537c using procedures similar to that described in step 515f. ESIMS m/z=515.19 $[M+H]^+$.

Step 537e. The title compound was prepared from the compound from step 537d and the compound from step 515g using procedures similar to that described in step 515h. ESIMS m/z=829.35 $[M+H]^+$.

Example 538

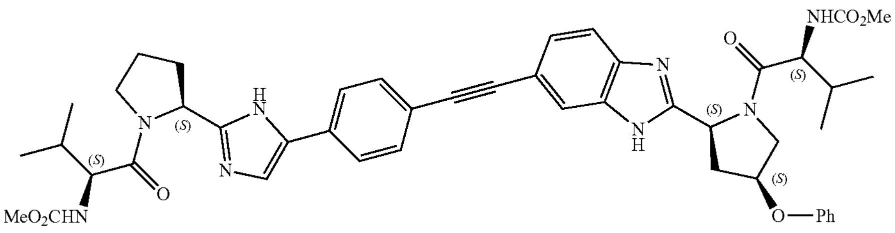

The title compound was prepared from (2S,4S)-1-(tert-butoxycarbonyl)-4-phenoxypyrroli-dine-2-carboxylic acid using procedures similar procedures similar to that described in example 537. ESIMS m/z=829.42 $[M+H]^+$.

Example 539

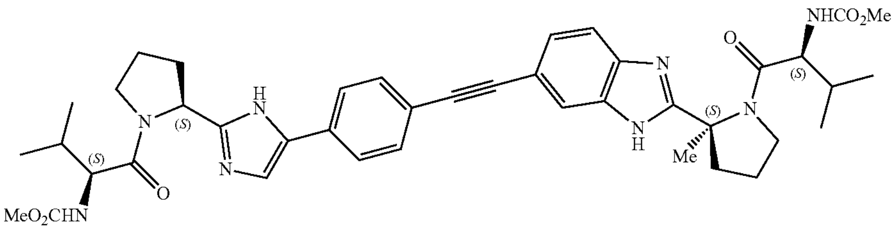

The title compound was prepared from (S)-1-(tert-butoxycarbonyl)-2-methylpyrrolidine-2-carboxylic acid using procedures similar procedures similar to that described in example 536. ESIMS m/z=751.34 $[M+H]^+$.

Example 540

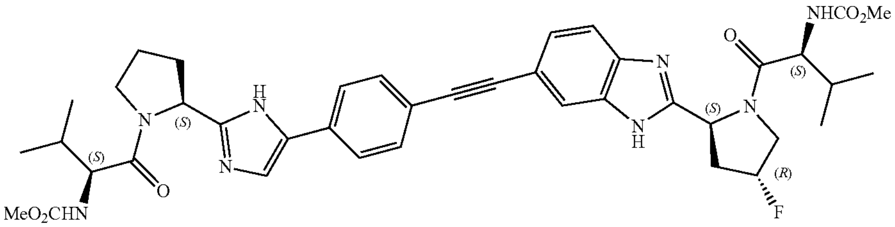

Step 540a. The desired product was prepared from (2S,4R)-1-(tert-butoxycarbonyl)-4-fluoropyrrolidine-2-carboxylic acid using procedures similar to that described in step 536a. ESIMS m/z=402.07 $[M+H]^+$.

Step 540b. The desired product was prepared from the compound from step 540a using procedures similar to that described in step 1b. ESIMS m/z=384.09 $[M+H]^+$.

Step 540c. The desired product was prepared from the compound from step 540b and the compound from step 1-1b using procedures similar to that described in step 1-1c. ESIMS m/z=641.32 $[M+H]^+$.

Step 540d. The desired product was prepared from the compound from step 540c using procedures similar to that described in step 515f. ESIMS m/z=441.13 $[M+H]^+$.

Step 540e. The title compound was prepared from the compound from step 540d and the compound from step 515g using procedures similar to that described in step 515h. ESIMS m/z=755.31 $[M+H]^+$.

Example 541

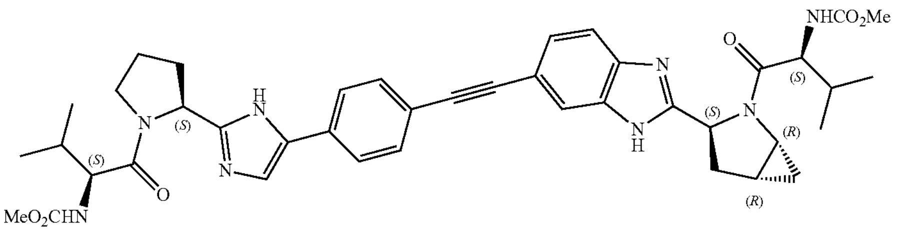

Step 541a. The desired product was prepared from (1R, 3S,5R)-2-(tert-butoxycarbonyl)-2-azabicyclo[3.1.0]hexane-3-carboxylic acid (prepared according to WO2009/102325) using procedures similar to that described in step 536a. ESIMS m/z=396.13 $[M+H]^+$.

Step 541b. The desired product was prepared from compound 541a using procedures similar to that described in step 1b. ESIMS m/z=378.11 $[M+H]^+$.

Step 541c. The desired product was prepared from the compound from step 541b and the compound from step 1-1b using procedures similar to that described in step 1-1c. ESIMS m/z=635.43 $[M+H]^+$.

Step 541d. The desired product was prepared from the compound from step 541c using procedures similar to that described in step 515f ESIMS m/z=435.31 $[M+H]^+$.

Step 541e. The title compound was prepared from the compound from step 541d and the compound from step 515g using procedures similar to that described in step 515h. ESIMS m/z=749.45 $[M+H]^+$.

Example 542

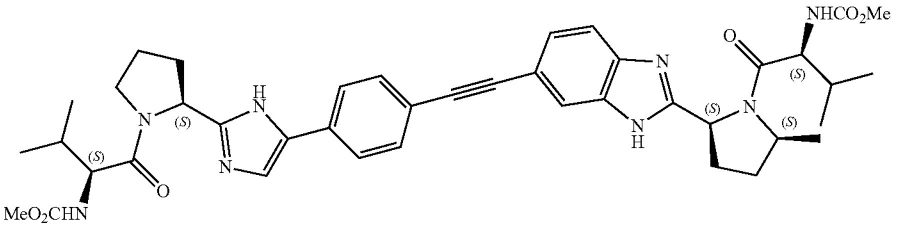

Step 542a. The desired product was prepared from (2S, 5S)-1-(tert-butoxycarbonyl)-5-methylpyrrolidine-2-carboxylic acid (prepared according to *Journal of Medicinal Chemistry* 2009, 49, 3250) using procedures similar to that described in step 536a. ESIMS m/z=398.07 $[M+H]^+$.

Step 542b. The desired product was prepared from the compound from step 542a using procedures similar to that described in step 1b. ESIMS m/z=380.01 $[M+H]^+$.

Step 542c. The desired product was prepared from the compound from step 542b and the compound from step 1-1b using procedures similar to that described in step 1-1c. ESIMS m/z=637.39 $[M+H]^+$.

Step 542d. The desired product was prepared from the compound from step 542c using procedures similar to that described in step 515f. ESIMS m/z=437.26 $[M+H]^+$.

Step 542e. The title compound was prepared from the compound from step 542d and the compound from step 515g using procedures similar to that described in step 515h. ESIMS m/z=751.44 $[M+H]^+$.

Example 543

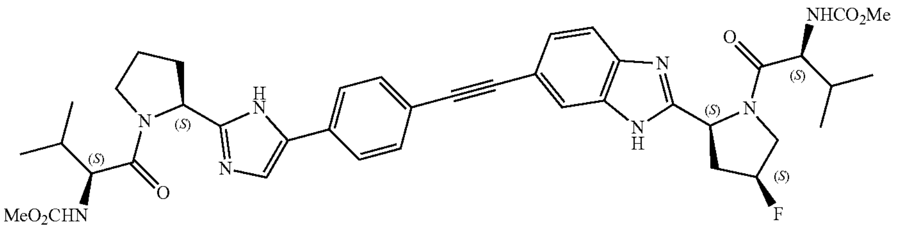

The title compound was prepared from (2S,4S)-1-(tert-butoxycarbonyl)-4-fluoropyrrolidine-2-carboxylic acid using procedures similar procedures similar to that described in example 540. ESIMS m/z=755.42 $[M+H]^+$.

Example 544

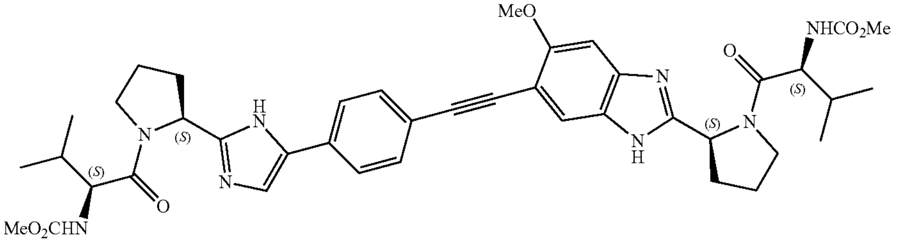

Step 544a. The desired product was prepared from (S)-1-(tert-butoxycarbonyl)pyrrolidine-2-carboxylic acid and 4-bromo-5-methoxybenzene-1,2-diamine (prepared according to *Journal of Medicinal Chemistry* 1997, 40, 730) using procedures similar procedures similar to that described in step 536a. ESIMS m/z=414.10 $[M+H]^+$.

Step 544b. The desired product was prepared from the compound from step 544a using procedures similar procedures similar to that described in step 1b. ESIMS m/z=396.06 $[M+H]^+$.

Step 544c. The desired product was prepared from the compound from step 544b and the compound from step 1-1b using procedures similar procedures similar to that described in step 1-1c. ESIMS m/z=653.39 $[M+H]^+$.

Step 544d. The desired product was prepared from the compound from step 544c using procedures similar procedures similar to that described in step 515f. ESIMS m/z=453.27 $[M+H]^+$.

Step 544e. The title compound was prepared from the compound from step 544d and the compound from step 515g using procedures similar procedures similar to that described in step 515h. ESIMS m/z=767.47 $[M+H]^+$.

Example 545

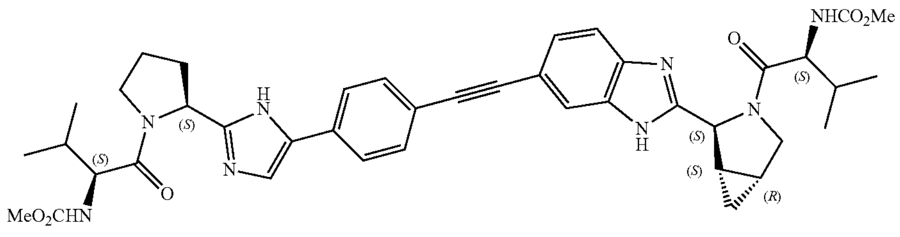

Step 545a. The desired product was prepared from (1S, 2S,5R)-3-(tert-butoxycarbonyl)-3-azabicyclo[3.1.0]hexane-2-carboxylic acid (prepared according to *J. Org. Chem,* 1999, 64, 547) using procedures similar to that described in step 536a. ESIMS m/z=396.25 $[M+H]^+$.

Step 545b. The desired product was prepared from the compound from step 545a using procedures similar to that described in step 1b. ESIMS m/z=378.21 $[M+H]^+$.

Step 545c. The desired product was prepared from the compound from step 545b and the compound from step 1-1b using procedures similar to that described in step 1-1c. ESIMS m/z=635.33 $[M+H]^+$.

Step 545d. The desired product was prepared from the compound from step 545c using procedures similar to that described in step 1f. ESIMS m/z=435.28 $[M+H]^+$.

Step 545e. The title compound was prepared from the compound from step 545d and the compound from step 515g using procedures similar to that described in step 515h. ESIMS m/z=749.44 $[M+H]^+$.

BIOLOGICAL ACTIVITY

1. HCV Replicon Cell Lines

HCV replicon cell lines (kindly provided by R. Bartenschlager) isolated from colonies as described by Lohman et. al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), (iii) the IRES from encephalomyocarditis virus (EMCV), and (iv) HCV NS2 to NSSB genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), (v) the IRES from encephalomyocarditis virus (EMCV), and (vi) HCV NS3 to NS5B genes that harbor cell culture adaptive mutations (E1202G, T1280I, K1846T) and the HCV 3'UTR.

These cell lines were maintained at 37° C., 5% $CO_2$, 100% relative humidity in DMEM (Cat #11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat #15140-122, Invitrogen) and Geneticin (Cat #10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds and combinations were determined by HCV RNA detection using quantitative RT-PCR, according to the manufacturer's instructions, with a TAQMAN® One-Step RT-PCR Master Mix Reagents Kit (Cat # AB 4309169, Applied Biosystems) on an ABI Model 7500 thermocycler. The TaqMan primers used for detecting and quantifying HCV RNA were obtained from Integrated DNA Technologies. HCV RNA was normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat # AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We used the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the $EC_{50}$ of each drug. Briefly, replicon cells are seeded at 7,000 cells per well in 90 ul DMEM (without phenol red, Invitrogen Cat. #31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat. #31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention may inhibit HCV by mechanisms in addition to or other than NSSA inhibition. In one embodiment, the compounds of the present invention inhibit HCV replicon and in another embodiment the compounds of the present invention inhibit NSSA.

The compounds of the present invention can be effective against the HCV 1b genotype. It should also be understood that the compounds of the present invention can inhibit multiple genotypes of HCV. In one embodiment compound of the present invention are active against the 1a, 1b, 2a, 2b, 3a, 4a, and 5a genotypes. Table 10 shows the $EC_{50}$ values of representative compounds of the present invention against the HCV 1b genotype from the above described qRT-PCR or luciferase assay. $EC_{50}$ ranges against HCV 1b are as follows: A>10 nM; B 1-10 nM; C<1 nM.

TABLE 10

| Genotype-1b replicon $EC_{50}$ | | | | | |
|---|---|---|---|---|---|
| Example | Range | Example | Range | Example | Range |
| 2 | C | 2-1 | C | 2-2 | C |
| 357 | C | 442 | C | 443 | C |

TABLE 10-continued

| Genotype-1b replicon $EC_{50}$ | | | | | |
|---|---|---|---|---|---|
| Example | Range | Example | Range | Example | Range |
| 445 | C | 446 | C | 448 | C |
| 449 | C | 451 | C | 453 | C |
| 454 | C | 456 | C | 457 | C |
| 459 | C | 460 | C | 463 | C |
| 464 | C | 465 | C | 466 | C |
| 468 | C | 469 | C | 471 | C |
| 472 | C | 473 | C | 475 | C |
| 477 | C | 479 | C | 480 | C |
| 481 | C | 483 | C | 485 | C |
| 486 | C | 488 | C | 490 | C |
| 492 | C | 493 | C | 494 | C |
| 497-a | C | 497-b | C | 499 | C |
| 500 | B | 501 | C | 502 | C |
| 503 | C | 504 | C | 505 | C |
| 506 | C | 507 | C | 508 | C |
| 509 | C | 510 | C | 511 | C |
| 512 | C | 513 | C | 514 | C |
| 515 | C | 517 | C | 519 | C |
| 521 | C | 523 | C | 525 | C |
| 526 | C | 527 | C | 528 | C |
| 529 | C | 530 | C | 531 | C |
| 532 | C | 533 | C | 534 | C |
| 535 | C | 536 | C | 537 | C |
| 538 | C | 539 | C | 540 | C |
| 541 | C | 542 | C | | |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a hepatitis C virus infection in a subject in need thereof, comprising administering to the subject a therapeutically effective amount of a compound selected from:

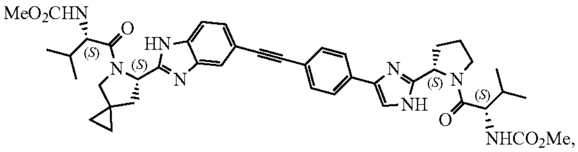

,

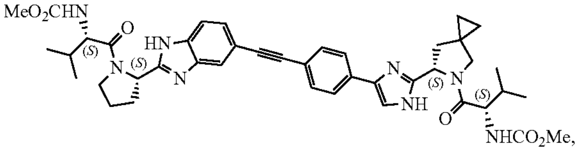

, and

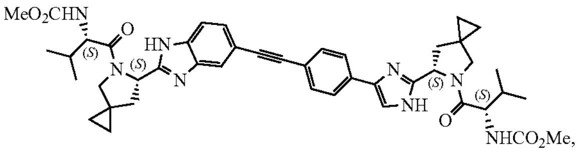

, or a pharmaceutically acceptable salt thereof.

2. The method of claim 1, further comprising the step of administering to the subject an agent which is a host immune modulator or an antiviral agent.

3. The method of claim 2, wherein the host immune modulator is selected from the group consisting of interferon-alpha, pegylated interferon-alpha, interferon-beta, interferon-gamma, consensus interferon, a cytokine and a vaccine.

4. The method of claim 2, wherein the antiviral agent is an inhibitor of a hepatitis C virus protein or replication process, wherein the protein is selected from the group consisting of helicase, protease, polymerase, metalloprotease, NS4A, NS4B, and NS5A, and the replication process is selected from IRES, assembly and entry.

5. The method of claim 1, wherein the compound is:

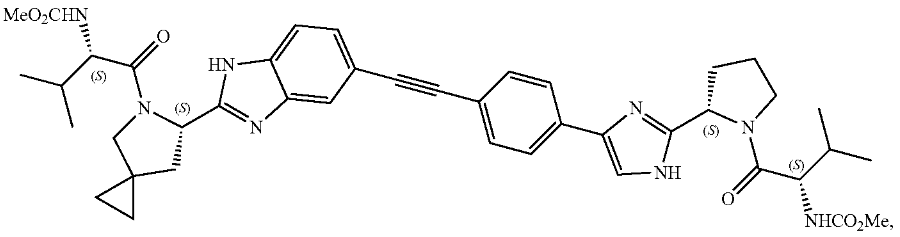

, or a pharmaceutically acceptable salt thereof.

6. The method of claim 1, wherein the compound is:

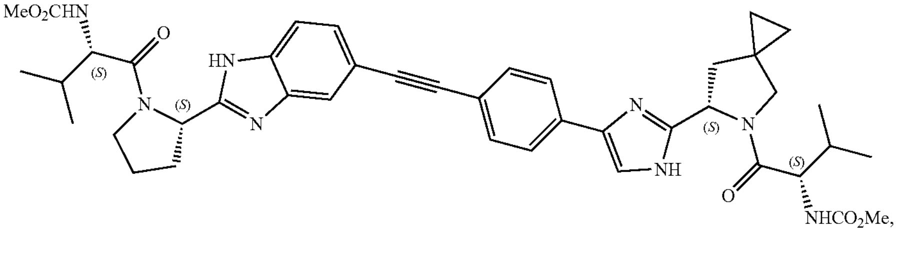

, or a pharmaceutically acceptable salt thereof.

7. The method of claim 1, wherein the compound is:
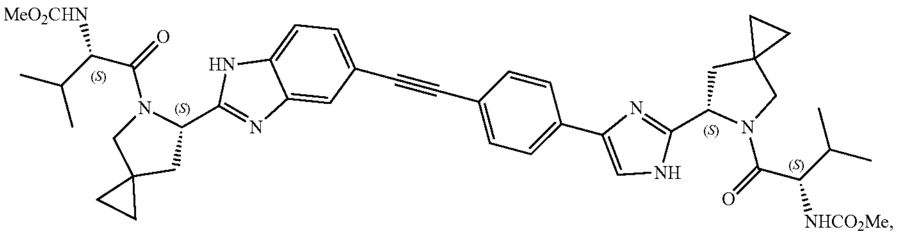
or a pharmaceutically acceptable salt thereof.
* * * * *